(12) United States Patent
Lockman et al.

(10) Patent No.: US 10,138,207 B2
(45) Date of Patent: *Nov. 27, 2018

(54) BENZOMORPHAN ANALOGS AND THE USE THEREOF

(71) Applicant: Purdue Pharma L.P., Stamford, CT (US)

(72) Inventors: Jeffrey Lockman, Princeton Junction, NJ (US); Laykea Tafesse, Robbinsville, NJ (US); Jiangchao Yao, Princeton, NJ (US); Jianming Yu, Plainsboro, NJ (US)

(73) Assignee: Purdue Pharma, L.P., Stamford, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/075,176

(22) Filed: Nov. 8, 2013

(65) Prior Publication Data

US 2014/0135351 A1    May 15, 2014

Related U.S. Application Data

(60) Provisional application No. 61/724,786, filed on Nov. 9, 2012, provisional application No. 61/788,618, filed on Mar. 15, 2013, provisional application No. 61/899,002, filed on Nov. 1, 2013.

(51) Int. Cl.
*A61K 31/4353* (2006.01)
*C07D 417/12* (2006.01)
(Continued)

(52) U.S. Cl.
CPC ......... *C07D 221/26* (2013.01); *C07D 401/04* (2013.01); *C07D 401/12* (2013.01);
(Continued)

(58) Field of Classification Search
CPC .. C07D 417/12; C07D 221/26; C07D 401/04; C07D 405/12
(Continued)

(56) References Cited

U.S. PATENT DOCUMENTS 3,956,336 A    5/1976  Montzka et al.
3,966,747 A    6/1976  Monkovic et al.
(Continued)

FOREIGN PATENT DOCUMENTS

EP    0028717    5/1981
GB    1431705    4/1976
(Continued)

OTHER PUBLICATIONS

May Everette et al. Structures related to Morphine, Further Synthesis in the Morphine Series., 1957.*
(Continued)

*Primary Examiner* — Rita J Desai
(74) *Attorney, Agent, or Firm* — Purdue Pharma L.P.; Alan L. Koller; Weiying Yang

(57) ABSTRACT

The present invention is directed to Benzomorphan Analog compounds of the Formula I″, Formula IA″, Formula IB″, Formula IC″, or Formula ID″ as shown below; and related Formula I′, Formula IA′, Formula IB′, Formula IC′, or Formula ID′; Formula I, Formula IA, Formula IB, Formula IC, or Formula ID; wherein $R^1$, $R^{2a}$, $R^{2b}$, $R^3$ and $R^4$ are as defined herein.

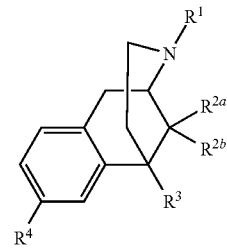

I″

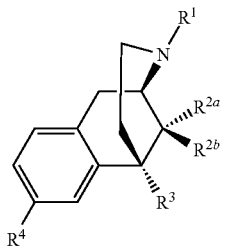

IA″

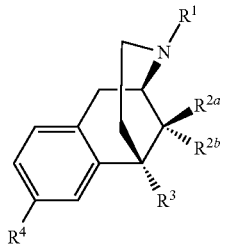

IB″

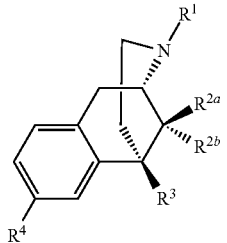

IC″

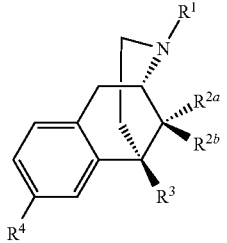

ID″

Compounds of the Invention are useful for treating pain, constipation, and other conditions modulated by activity of opioid and ORL-1 receptors.

43 Claims, No Drawings

(51) Int. Cl.
  *C07D 221/26* (2006.01)
  *C07D 401/04* (2006.01)
  *C07D 401/12* (2006.01)
  *C07D 405/12* (2006.01)
  *C07D 409/12* (2006.01)

(52) U.S. Cl.
  CPC ......... *C07D 405/12* (2013.01); *C07D 409/12* (2013.01); *C07D 417/12* (2013.01)

(58) Field of Classification Search
  USPC ..................................... 546/97; 514/266.22
  See application file for complete search history.

(56) References Cited

U.S. PATENT DOCUMENTS

| | | | |
|---|---|---|---|
| 4,016,167 A | 4/1977 | Montzka et al. | |
| 4,100,164 A | 7/1978 | Michne | |
| 4,119,628 A | 10/1978 | Lewis et al. | |
| 4,214,085 A | 7/1980 | Lewis et al. | |
| 4,288,444 A | 9/1981 | Akkerman et al. | |
| 4,366,325 A | 12/1982 | Wedemeyer et al. | |
| 4,406,904 A | 9/1983 | Welle et al. | |
| 4,425,353 A * | 1/1984 | Akkerman et al. | 514/295 |
| 6,740,641 B2 | 5/2004 | Gao et al. | |
| 6,825,205 B2 | 11/2004 | Kyle | |
| 6,958,398 B1 | 10/2005 | Kupper et al. | |
| 7,084,150 B2 | 8/2006 | Boer et al. | |
| 7,125,884 B2 | 10/2006 | Reidenberg et al. | |
| 7,202,259 B2 | 4/2007 | Chen | |
| 7,687,518 B2 | 3/2010 | Chen | |
| 8,026,254 B2 | 9/2011 | Chen | |
| 8,426,594 B2 | 4/2013 | Kyle | |
| 8,481,743 B2 | 7/2013 | Zhou | |
| 8,530,494 B2 | 9/2013 | Kyle et al. | |
| 8,937,084 B2 | 1/2015 | Park et al. | |
| 8,946,255 B2 | 1/2015 | Kassick et al. | |
| 8,957,084 B2 | 2/2015 | Kyle | |
| 8,969,358 B2 | 3/2015 | Goehring et al. | |
| 8,980,906 B2 | 3/2015 | Tafesse | |
| 8,987,287 B2 | 3/2015 | Goehring et al. | |
| 9,096,606 B2 | 8/2015 | Kyle | |
| 9,168,255 B2 | 10/2015 | Goehring et al. | |
| 9,340,504 B2 | 5/2016 | Park | |
| 2014/0057931 A1 | 2/2014 | Kyle et al. | |
| 2014/0057932 A1 | 2/2014 | Reisch | |
| 2014/0163058 A1 | 6/2014 | Youngman | |
| 2014/0221419 A1 | 8/2014 | Lockman et al. | |
| 2014/0275117 A1 | 9/2014 | Goehring et al. | |
| 2014/0364448 A1 | 12/2014 | Kyle | |
| 2015/0175569 A1 | 6/2015 | Lynch et al. | |
| 2015/0183787 A1 | 7/2015 | Lockman | |
| 2015/0259293 A1 | 9/2015 | Ni et al. | |
| 2015/0284383 A1 | 10/2015 | Lynch et al. | |
| 2015/0335642 A1 | 11/2015 | Shao | |
| 2015/0336974 A1 | 11/2015 | Youngman | |
| 2015/0353512 A1 | 12/2015 | Tadesse et al. | |
| 2016/0009659 A1 | 1/2016 | Lockman et al. | |
| 2016/0024022 A1 | 1/2016 | Ni et al. | |
| 2016/0031873 A1 | 2/2016 | Yao et al. | |
| 2016/0052911 A1 | 2/2016 | Yao et al. | |
| 2016/0318872 A1 | 11/2016 | Lockman et al. | |
| 2016/0318932 A1 | 11/2016 | Youngman | |
| 2016/0333020 A1 | 11/2016 | Kyle et al. | |
| 2017/0037046 A1 | 2/2017 | Tafesse | |
| 2017/0073313 A1 * | 3/2017 | Tafesse | C07D 221/26 |

FOREIGN PATENT DOCUMENTS

| | | |
|---|---|---|
| GB | 1575009 | 9/1980 |
| WO | WO/1998/054168 | 12/1998 |
| WO | WO-2009068989 | 6/2009 |
| WO | WO-2013167963 | 11/2013 |
| WO | WO-2015/094443 | 6/2015 |
| WO | WO-2015/099841 | 7/2015 |
| WO | WO-2015/112801 | 7/2015 |
| WO | WO-2015097545 | 7/2015 |
| WO | WO-2015097547 | 7/2015 |
| WO | WO-2015097548 | 7/2015 |
| WO | WO-2015099863 | 7/2015 |
| WO | WO-2015100092 | 7/2015 |
| WO | WO-2015102682 | 7/2015 |
| WO | WO-2015123398 | 8/2015 |
| WO | WO/2015/183780 | 12/2015 |
| WO | WO/2015/192039 | 12/2015 |
| WO | WO/2015/192053 | 12/2015 |
| WO | WO/2016/044546 | 3/2016 |

OTHER PUBLICATIONS

Hiroshi Kugita et al . 1963.*
Everette May, 1961 Structures realated to Morphine, XV. Stereochemical Control of Methyl-Mettalo Additions to 9-Oxobenzomorphans.*
K.M. Foley, Pain, in Cecil Textbook of Medicine 100-107, J.C. Bennett and F. Plum eds., 20th ed. 1996.
Gutstein, Howard B., Akil, Huda, "Chapter 21. Opioid Analgesics" (Chapter 21), Brunton, LL, Lazo, JS, Parker, KI: Goodman & Gilman's The Pharmacological Basis of Therapeutics, 11th Edition: http://www.accessmedicine.com/content.aspx?aID=940653.
C. Altier et al., "ORL-1 receptor-mediated internalization of N-type calcium channelsm." Nature Neuroscience, 2005, 9:31.
D. Barlocco et al., "The opioid-receptor-like 1 (ORL-1) as a potential target for new analgesics." Eur. J. Med. Chem., 2000, 35:275.
J.S. Mogil et al., "Orphanin FQ is a functional anti-opioid peptide." Neurosci., 1996, 75:333.
K. Lutfy et al., "Tolerance develops to the inhibitory effect of orphanin FQ on morphine-induced antinociception in the rat," NeuroReport, 1999, 10:103.
M.M. Morgan et al., "Antinociception mediated by the periaqueductal gray is attenuated by orphanin FQ." NeuroReport, 1997, 8:3431.
J. Tian et al., "Involvement of endogenous Orphanin FQ in electroacupuncture-induced analgesia," NeuroReport, 1997, 8:497.
J. Tian et al., "Functional studies using antibodies against orphanin FQ/nociceptin," Peptides, 2000, 21:1047.
H. Ueda et al., "Enhanced Spinal Nociceptin Receptor Expression Develops Morphine Tolerance and Dependence," J. Neurosci., 2000, 20:7640.
Wood & Galligan, "Function of opioids in the enteric nervous system," Neurogastroenterology & Motility 16 (Suppl.2): 17-28, 2004.
Chignell et al., Structures Related to Morphine. XXVII. Alternatives Syntheses of a- and b-2,9-Dimethyl-2'-hydroxy-5-propyl-6,7-benzomorphan,Journal of Medical Chemistry, American Chemical Society, V. 8 , p. 235-238, Jan. 1965.
Iddon et al., Acetamides of 1,2,3,4,5,6-Hexahydro-2,6-methano-3-benzazocine (Benzomorphan) . . . as Potential Selective Opioid Analgesics, J.Chem.Soc, Perkin Trans, vol. 4, 1091-1095, 1990.
International Search Report dated Jul. 28, 2014 in Corresponding International Application No. PCT/IB2013/002511 with Written Opinion.
Kugita et al., Syntheses of Morphin-like Structures. II 2'-Methoxy-9-hydroxymethyl-2,5-dimethyl-6,7-benzormorphan Chem. & Pharm Bull. 12(10), 1163-1166, 1964.
Kugita et al., Syntheses of Morphin-like Structures. III Sterochemical Control of Addition of Borante to 9-Methykebenzomorphan, Chem. & Pharm Bull.,12(10), 1166-1171, 1964.

* cited by examiner

BENZOMORPHAN ANALOGS AND THE USE THEREOF

CROSS REFERENCE TO RELATED APPLICATIONS

This application claims the benefit under 35 U.S.C. § 119(e) of provisional application Ser. No. 61/724,786, filed Nov. 9, 2012, provisional application Ser. No. 61/788,618, filed Mar. 15, 2013, and provisional application Ser. No. 61/899,002, filed Nov. 1, 2013, the contents of all of which are incorporated herein by reference.

FIELD OF THE INVENTION

The invention is in the field of medicinal chemistry. It relates to novel benzomorphan analogs having activity as opioid receptor agonists and/or antagonists. In certain embodiments compounds of the invention have dual activity as opioid agonists and ORL-1 receptor antagonists.

BACKGROUND OF THE INVENTION

Pain is the most common symptom for which patients seek medical advice and treatment. While acute pain is usually self-limited, chronic pain can persist for 3 months or longer and lead to significant changes in a patient's personality, lifestyle, functional ability and overall quality of life (K. M. Foley, Pain, in *Cecil Textbook of Medicine* 100-107, J. C. Bennett and F. Plum eds., 20th ed. 1996).

Pain has traditionally been managed by administering either a non-opioid analgesic (such as acetylsalicylic acid, choline magnesium trisalicylate, acetaminophen, ibuprofen, fenoprofen, diflunisal or naproxen), or an opioid analgesic (such as morphine, hydromorphone, methadone, levorphanol, fentanyl, oxycodone or oxymorphone).

Although the term "narcotic" is often used to refer to opioids, the term is not specifically applicable to opioids. The term "narcotic", derived from the Greek word for "stupor", originally referred to any drug that induced sleep, only later being associated with opioids (Gutstein, Howard B., Akil, Huda, "Chapter 21. Opioid Analgesics" (Chapter 21), Brunton, L L, Lazo, J S, Parker, Kl: Goodman & Gilman's The Pharmacological Basis of Therapeutics, 11$^{th}$ Edition: http://www.accessmedicine.com/content.aspx?aID=940653). In the legal context, the term "narcotic" refers to a variety of mechanistically unrelated substances with abuse or addictive potential (Gutstein, Howard B., Akil, Huda, "Chapter 21. Opioid Analgesics" (Chapter 21), Brunton L L, Lazo J S, Parker Kl: Goodman & Gilman's The Pharmacological Basis of Therapeutics, 11$^{th}$ Edition: http://www.accessmedicine.com/content.aspx?aID=940653). Thus, the term "narcotic" not only refers to opioids, but also refers to such drugs as cocaine, methamphetamine, ecstasy, etc., which exert their pharmacological effects via different receptors than opioids. Furthermore, because the term "narcotic" refers to such a wide variety of unrelated drugs, many of which do not possess analgesic properties, it cannot be assumed that a drug that has "narcotic" properties is necessarily analgesic. For example, drugs such as ecstasy and methamphetamine are not analgesic, and are not used to treat pain.

Until recently, there was evidence of three major classes of opioid receptors in the central nervous system (CNS), with each class having subtype receptors. These receptor classes are known as $\mu$, $\delta$ and $\kappa$. As opiates have a high affinity to these receptors while not being endogenous to the body, research followed in order to identify and isolate the endogenous ligands to these receptors. These ligands were identified as endorphins, enkephalins, and dynorphins, respectively. Additional experimentation has led to the identification of the opioid receptor-like (ORL-1) receptor, which has a high degree of homology to the known opioid receptor classes. This newly discovered receptor was classified as an opioid receptor based only on structural grounds, as the receptor did not exhibit pharmacological homology. It was initially demonstrated that non-selective ligands having a high affinity for $\mu$, $\delta$ and $\kappa$ receptors had low affinity for the ORL-1 receptor. This characteristic, along with the fact that an endogenous ligand had not yet been discovered, led to the ORL-1 receptor being designated as an "orphan receptor".

Subsequent research led to the isolation and structure of the endogenous ligand of the ORL-1 receptor. This ligand, nociceptin (also known as orphanin FQ (OFQ)), is a seventeen amino acid peptide structurally similar to members of the opioid peptide family. (C. Altier et al., "ORL-1 receptor-mediated internalization of N-type calcium channels." *Nature Neuroscience*, 2005, 9:31).

The discovery of the ORL-1 receptor and its endogenous ligand, presents an opportunity for the discovery of novel compounds that can be administered for pain management or other syndromes influenced by this receptor.

Many publications in the ORL-1/nociceptin field provide evidence that activation of ORL-1 receptors in the brain can inhibit opioid-mediated analgesia (e.g., D. Barlocco et al., "The opioid-receptor-like 1 (ORL-1) as a potential target for new analgesics." *Eur. J. Med. Chem.*, 2000, 35:275; J. S. Mogil et al., "Orphanin FQ is a functional anti-opioid peptide." *Neurosci.*, 1996, 75:333; K. Lutfy et al., "Tolerance develops to the inhibitory effect of orphanin FQ on morphine-induced antinociception in the rat." *NeuroReport*, 1999, 10:103; M. M. Morgan et al., "Antinociception mediated by the periaqueductal gray is attenuated by orphanin FQ." *NeuroReport*, 1997, 8:3431; and J. Tian et al., "Involvement of endogenous Orphanin FQ in electroacupuncture-induced analgesia." *NeuroReport*, 1997, 8:497).

A growing body of evidence supports a more generalized regulatory role for ORL-1 against the actions of the $\mu$ receptor, possibly contributing to the development of $\mu$-agonist tolerance in patients being treated with classical opiates (e.g., J. Tian et al., "Functional studies using antibodies against orphanin FQ/nociceptin." *Peptides*, 2000, 21:1047; and H. Ueda et al., "Enhanced Spinal Nociceptin Receptor Expression Develops Morphine Tolerance and Dependence." *J. Neurosci.*, 2000, 20:7640). Moreover, ORL-1 activation appears to have an inhibitory effect on the rewarding properties of several drugs of abuse, including $\mu$ agonists. Use of opioid analgesics often leads to constipation as a side effect. Constipation associated with the use of opioid analgesics is presumed to occur primarily and mechanistically as a result of the action of mu opioid agonists directly upon mu opioid receptors located in the bowel (Wood & Galligan (2004), Function of opioids in the enteric nervous system. *Neurogastroenterology & Motility* 16 (Suppl. 2): 17-28.). Stimulation of the mu opioid receptors in the bowel causes inhibition of normal gastrointestinal (GI) motility, leading to constipation. The effect of $\mu$ opioid agonism on $\mu$ opioid receptors in the bowel can be observed via the action of loperamide (Imodium™) in treating diarrhea. Loperamide is a potent $\mu$ opioid agonist that is administered orally, but which has little to no absorption into the blood stream. As a result, loperamide exerts its action locally upon the $\mu$ opioid receptors in the bowel, and this results in inhibition of GI motility, which treats diarrhea.

There has been recent interest in developing combinations of μ receptor agonists and antagonists having defined biodistribution properties that might serve to limit opioid-induced constipation. For example, the co-administration of an orally bio-available μ opioid receptor agonist (such as morphine, codeine, oxycodone or hydromorphone) together with a potent μ opioid receptor antagonist (such as N-methylnaloxone or N-methylnaltrexone) that is not orally bio-available may serve to prevent or reduce the constipation otherwise associated with mu opioid receptor agonist therapy. The rationale is that the agonist component will be absorbed and distributed throughout the periphery and the central nervous system (CNS), resulting in the desired analgesia, while the antagonist component will remain in the bowel where it will prevent or reduce any agonist-induced constipation that might otherwise occur.

Benzomorphan analog compounds, such as 3,11,11-trimethyl-1,2,3,4,5,6-hexahydro-2,6-methanobenzo[d]azocine-6,8-diol and 8-methoxy-3,11,11-trimethyl-1,2,3,4,5,6-hexahydro-2,6-methanobenzo[d]azocin-6-ol, having analgesic activity have been described (see, e.g. U.S. Pat. No. 4,425,353; U.S. Pat. No. 4,406,904; and U.S. Pat. No. 4,366,325).

BRIEF SUMMARY OF THE INVENTION

The present invention provides novel benzomorphan analog compounds useful for treating a variety of conditions, including pain, in particular chronic pain, and constipation. More specifically, the present invention provides compounds of Formula I'', Formula I', and Formula I below, and the pharmaceutically acceptable salts, prodrugs and solvates thereof, that exhibit affinity for one or more of the ORL-1, μ, δ, and κ opioid receptors. Such compounds, salts, prodrugs and solvates are collectively referred to hereinafter as "Compounds of the Invention" (each is individually referred to hereinafter as a "Compound of the Invention").

The present invention provides novel compounds of Formula I'':

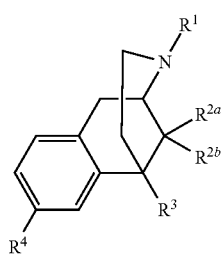

I'' wherein
$R^1$ is selected from the group consisting of —($C_1$-$C_{10}$)alkyl, —($C_2$-$C_{10}$)alkenyl, —($C_2$-$C_{10}$)alkynyl, —($C_3$-$C_{12}$)cycloalkyl, ($C_3$-$C_{12}$)cycloalkyl-($C_1$-$C_6$)alkyl-, —($C_3$-$C_{12}$)cycloalkenyl, ($C_3$-$C_{12}$)cycloalkenyl-($C_1$-$C_6$)alkyl-, -(6- to 14-membered)aryl, ((6- to 14-membered)aryl)-($C_1$-$C_6$)alkyl-, diphenyl($C_1$-$C_6$)alkyl-, -(3- to 12-membered)heterocycle, ((3- to 12 membered)heterocycle)-($C_1$-$C_6$)alkyl-, —(OCH$_2$CH$_2$)$_s$—O—($C_1$-$C_6$)alkyl, —(CH$_2$CH$_2$O)$_s$—($C_1$-$C_6$)alkyl, ($C_1$-$C_{10}$)alkoxy, C(halo)$_3$, CH(halo)$_2$, CH$_2$(halo), C(O)$R^5$, —C(O)O—($C_1$-$C_{10}$)alkyl, and —(CH$_2$)$_n$—N($R^6$)$_2$, each of which is optionally substituted by 1, 2 or 3 independently selected $R^9$ groups;

$R^{2a}$ is hydrogen, OH, or absent;
$R^{2b}$ is
  a) ((6- to 14-membered)aryl), -((5- to 12-membered)heteroaryl), or ((3- to 12-membered)heterocycle), each of which is optionally substituted with one, two, or three independently selected $R^{30}$ groups; or
  b) —Z-G-$R^{10}$, provided that —Z-G-$R^{10}$ is other than hydrogen;
or $R^{2a}$ and $R^{2b}$ together form =O;
Z is absent or —(CH$_2$)$_m$—, optionally substituted with 1 or 2-($C_1$-$C_6$)alkyl;
G is selected from the group consisting of:
  a) a bond, —($C_1$-$C_6$)alkylene, —($C_2$-$C_6$)alkenylene;
  b) O, —OCO—, —C(=O), =CH;
  c) NR$^8$, =N—O, =N—NH;
  d) S, SO, SO$_2$; and
  e) —NH—SO$_2$;
and when Z is absent and G is =CH, =N—O, or =N—NH, then $R^{2a}$ is absent;
$R^{10}$ is selected from the group consisting of hydrogen, —($C_1$-$C_{10}$)alkyl, —($C_2$-$C_{12}$)alkenyl, —C(=O), —C(=O)—($C_1$-$C_6$)alkyl, —C(=O)—($C_2$-$C_6$)alkenyl, —C(=O)-(6- to 14-membered)aryl, —C(=O)—($C_1$-$C_6$)alkyl-(6- to 14-membered)aryl, —($C_2$-$C_{12}$)alkynyl, —($C_1$-$C_{10}$)alkoxy, —(OCH$_2$CH$_2$)$_s$—O($C_1$-$C_6$)alkyl, —(CH$_2$CH$_2$O)$_s$—($C_1$-$C_6$)alkyl, —NH$_2$, —NH($C_1$-$C_6$)alkyl, CN, NR$^5$R$^6$, —($C_1$-$C_6$)alkyl-NR$^5$R$^6$, —CONR$^5$R$^6$, —($C_1$-$C_6$)alkyl-CO—NR$^5$R$^6$, —COOR$^7$, —($C_1$-$C_6$)alkyl-CO—OR$^7$, —($C_1$-$C_6$)alkoxy-COOR$^7$, —CO—(CH$_2$)$_n$—COOR$^7$, —CO—(CH$_2$)$_n$—CO—NR$^5$R$^6$, —($C_3$-$C_{12}$)cycloalkyl, (($C_3$-$C_{12}$)cycloalkyl)-($C_1$-$C_6$)alkyl-, —($C_4$-$C_{12}$)cycloalkenyl, (($C_4$-$C_{12}$)cycloalkenyl)-($C_1$-$C_6$)alkyl-, —($C_6$-$C_{14}$)bicycloalkyl, (($C_6$-$C_{14}$)bicycloalkyl)-($C_1$-$C_6$)alkyl-, —($C_8$-$C_{20}$)tricycloalkyl, (($C_8$-$C_{20}$)tricycloalkyl)-($C_1$-$C_6$)alkyl-, —($C_7$-$C_{14}$)bicycloalkenyl, (($C_7$-$C_{14}$)bicycloalkenyl)-($C_1$-$C_6$)alkyl-, —($C_8$-$C_{20}$)tricycloalkenyl, (($C_8$-$C_{20}$)tricycloalkenyl)-($C_1$-$C_6$)alkyl-, -(6- to 14-membered)aryl, ((6- to 14-membered)aryl)-($C_1$-$C_6$)alkyl-, —SO$_2$—($C_1$-$C_6$)alkyl, —SO$_2$(($C_3$-$C_{12}$)cycloalkyl), —SO$_2$—(($C_3$-$C_{12}$)cycloalkyl)-($C_1$-$C_6$)alkyl, —SO$_2$-((5- to 12-membered)heteroaryl), —SO$_2$-((5- to 12-membered)heteroaryl)-($C_1$-$C_6$)alkyl, —C(=O)—NH-((5- to 12-membered)heteroaryl), —C(=O)—NH-((5- to 12-membered)heteroaryl)-($C_1$-$C_6$)alkyl, —C(=O)—NH-((3- to 12-membered)heterocycle), —C(=O)—NH-((3- to 12-membered)heterocycle)-($C_1$-$C_6$)alkyl, —SO$_2$-((6- to 14-membered)aryl), —SO$_2$-((6- to 14 membered)aryl)-($C_1$-$C_6$)alkyl, -(7- to 12-membered)bicyclic ring system, ((7- to 12-membered)bicyclic ring system)-($C_1$-$C_6$)alkyl-, -(7- to 12-membered)bicyclic aryl, ((7- to 12-membered)bicyclic aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12 membered)heterocycle)-($C_1$-$C_6$)alkyl-, -(7- to 12-membered)bicycloheterocycle, ((7- to 12-membered)bicycloheterocycle)-($C_1$-$C_6$)alkyl-, phenyl, benzyl and naphthyl; each of which is optionally substituted with one, two, or three substituents independently selected from the group consisting of —OH, (=O), halo, —C(halo)$_3$, —CH(halo)$_2$, —CH$_2$(halo), —($C_1$-$C_6$)alkyl, halo($C_1$-$C_6$)alkyl-, —($C_2$-$C_6$)alkenyl, —($C_2$-$C_6$)alkynyl, hydroxy($C_1$-$C_6$)alkyl-, dihydroxy($C_1$-$C_6$)alkyl-, —($C_1$-$C_6$)alkoxy, (($C_1$-$C_6$)alkoxy)CO($C_1$-$C_6$)alkoxy-, phenyl, benzyl, —NH$_2$, —NH($C_1$-$C_6$)alkyl, —($C_1$-$C_6$)alkyl-NH($C_1$-$C_6$)alkyl-$R^{14}$, —CN, —SH, —OR$^{11}$, —CONR$^5$R$^6$, —($C_1$-$C_6$)alkyl)-CO—NR$^5$R$^6$, —COOR$^7$, —($C_1$-$C_6$)alkyl-CO—OR$^7$, —($C_1$-$C_6$)alkoxy-COOR$^7$, —(OCH$_2$CH$_2$)$_s$—O($C_1$-$C_6$)alkyl, —(CH$_2$CH$_2$O)$_s$—($C_1$-$C_6$)alkyl, —SO$_2$—NR$^{5a}$R$^{6a}$, ($C_1$-$C_6$)alkyl)

sulfonyl, $((C_1-C_6)alkyl)sulfonyl(C_1-C_6)alkyl-$, $—NH—SO_2(C_1-C_6)alkyl$, $NH_2—SO_2(C_1-C_6)alkyl-$, $—N(SO_2(C_1-C_6)alkyl)_2$, $—C(=NH)NH_2$, $—NH—CO—(C_1-C_6)alkyl$, $—NH—CO—NH_2$, $—NH—C(=O)—NH—(C_1-C_6)alkyl$, $—NH—C(=O)-(6-$ to 14-membered)aryl, $—NH—C(=O)—(C_1-C_6)alkyl-(6-$ to 14-membered)aryl, $—NH—(C_1-C_6)alkyl-CO—OR^7$, $—NH—C(=O)—(C_1-C_6)alkyl-CO—OR^7$, $—NH—C(=O)—CH(NH_2)—(C_1-C_6)alkyl-CO—OR^7$, $—(C_3-C_{12})cycloalkyl$, $((C_3-C_{12})cycloalkyl)-(C_1-C_6)alkyl-$, -(6- to 14-membered)aryl, -(6- to 14-membered)aryloxy, $—(C_1-C_6)alkoxy-C(O)NR^5R^6$, $—NH—(C_1-C_6)alkyl-C(O)—NR^5R^6$, $—C(O)NH—(C_1-C_6)alkyl-COOR^7$, $((6-$ to 14-membered)aryl$)-(C_1-C_6)alkyl-$, -(5- to 12-membered)heteroaryl, ((5- to 12-membered)heteroaryl$)-(C_1-C_6)alkyl-$, -(3- to 12-membered)heterocycle, ((3- to 12-membered)heterocycle$)-(C_1-C_6)alkyl-$, -(7- to 12-membered)bicycloheterocycle, and ((7- to 12-membered)bicycloheterocycle$)-(C_1-C_6)alkyl-$;

$R^3$ is selected from:
  a) —H; or
  b) $—(C_1-C_6)alkyl$, $—(C_2-C_6)alkenyl$, or $—(C_2-C_6)alkynyl$;

$R^4$ is selected from
  a) —H, —OH, halo, $—C(halo)_3$, $—CH(halo)_2$, $—CH_2(halo)$, COOH, or $CONH_2$; or
  b) $—(C_1-C_5)alkyl$, $—(C_2-C_5)alkenyl$, $—(C_2-C_5)alkynyl$, $—(CH_2)_n—O—(CH_2)_n—CH_3$, or $—(C_1-C_5)alkoxy$, each of which is optionally substituted with 1, 2, or 3 independently selected $R^9$ groups;

$R^5$ and $R^6$ are each independently selected from
  a) hydrogen, —OH, halo, $—C(halo)_3$, $—CH(halo)_2$, $—CH_2(halo)$;
  b) $—(C_1-C_6)alkyl$, $—(C_2-C_5)alkenyl$, $—(C_2-C_5)alkynyl$, $—(CH_2)_n—O—(CH_2)_n—CH_3$, $—(C_1-C_6)alkoxy$, each of which is optionally substituted with 1, 2, or 3 substituents independently selected from —OH, halo, $—(C_1-C_{10})alkyl$, $—(C_2-C_{10})alkenyl$, $—(C_2-C_{10})alkynyl$, $—(C_1-C_{10})alkoxy$, $—(C_3-C_{12})cycloalkyl$, —CHO, —C(O)OH, $—C(halo)_3$, $—CH(halo)_2$, $CH_2(halo)$, $—(CH_2)_n—O—(CH_2)_n—CH_3$, phenyl, or $CONR^{5a}R^{6a}$;
  c) $—(C_3-C_8)cycloalkyl$, $((C_3-C_8)cycloalkyl)-(C_1-C_6)alkyl-$, $—COOR^7$, $—(C_1-C_6)alkyl-COOR^7$, $—CONH_2$, or $(C_1-C_6)alkyl-CONH—$;
  d) ((6- to 14-membered)aryl) optionally substituted with 1, 2, or 3 independently selected $R^{30}$ groups;
  e) -((5- to 12-membered)heteroaryl) optionally substituted with 1, 2, or 3 independently selected $R^{30}$ groups; or
  f) $R^5$ and $R^6$ together with the nitrogen atom to which they are attached form a (3- to 12-membered)heterocycle optionally substituted with 1, 2, or 3 independently selected $R^{30}$ groups;

$R^{5a}$ and $R^{6a}$ are each independently selected from the group consisting of:
  a) hydrogen, —OH, halo, $—C(halo)_3$, $—CH(halo)_2$, and $—CH_2(halo)$;
  b) $—(C_1-C_6)alkyl$, $—(C_2-C_6)alkenyl$, $—(C_2-C_6)alkynyl$, $—(CH_2)_n—O—(CH_2)_n—CH_3$, and $—(C_1-C_6)alkoxy$, each of which is optionally substituted with 1, 2, or 3 substituents independently selected from —OH, halo, $—(C_1-C_{10})alkyl$, $—(C_2-C_{12})alkenyl$, $—(C_2-C_{12})alkynyl$, $—(C_1-C_{10})alkoxy$, $—(C_3-C_{12})cycloalkyl$, —CHO, —COOH, $—C(halo)_3$, $—CH(halo)_2$, $CH_2(halo)$, $—(CH_2)_n—O—(CH_2)_n—CH_3$, and phenyl;
  c) $—(C_3-C_8)cycloalkyl$, $((C_3-C_8)cycloalkyl)-(C_1-C_6)alkyl-$, $—COOR^7$, $—(C_1-C_6)alkyl-COOR^7$, $—CONH_2$, and $(C_1-C_6)alkyl-CONH—$;
  d) -(6- to 14-membered)aryl optionally substituted with 1, 2, or 3 independently selected $R^{30}$ groups;
  e) -((5- to 12-membered)heteroaryl) optionally substituted with 1, 2, or 3 independently selected $R^{30}$ groups; or
  f) $R^{5a}$ and $R^{6a}$ together with the nitrogen atom to which they are attached form a (3- to 12-membered)heterocycle optionally substituted with 1, 2, or 3 independently selected $R^{30}$ groups;

each $R^7$ is independently selected from the group consisting of hydrogen, $—(C_1-C_6)alkyl$, $—(C_2-C_6)alkenyl$, $—(C_2-C_6)alkynyl$, $—(C_3-C_{12})cycloalkyl$, $—(C_4-C_{12})cycloalkenyl$, $((C_3-C_{12})cycloalkyl)-(C_1-C_6)alkyl-$, and $((C_4-C_{12})cycloalkenyl)-(C_1-C_6)alkyl-$;

each $R^8$ is independently selected from H, $—(C_1-C_6)alkyl$, $—(C_2-C_6)alkenyl$, $—(C_2-C_6)alkynyl$, $—(C_1-C_{10})alkoxy$, $—(C_3-C_{12})cycloalkyl$, $—(C_3-C_{12})cycloalkenyl$, $((C_3-C_{12})cycloalkyl)-(C_1-C_6)alkyl-$, $((C_3-C_{12})cycloalkenyl)-(C_1-C_6)alkyl-$, $—C(=O)(C_1-C_6)alkyl$ or $SO_2(C_1-C_6)alkyl$;

each $R^9$ is independently selected from —OH, halo, $—(C_1-C_{10})alkyl$, $—(C_2-C_{10})alkenyl$, $—(C_2-C_{10})alkynyl$, $—(C_1-C_{10})alkoxy$, $—(C_3-C_{12})cycloalkyl$, —CHO, —C(O)OH, $—C(halo)_3$, $—CH(halo)_2$, $CH_2(halo)$, $—(CH_2)_n—O—(CH_2)_n—CH_3$, phenyl, or $CONR^{5a}R^{6a}$;

each $R^{11}$ is independently selected from $—C(halo)_3$, $—CH(halo)_2$, $—CH_2(halo)$, $—(C_2-C_5)alkenyl$, $—(C_2-C_5)alkynyl$, $—(CH_2)_n—O—(CH_2)_n—CH_3$, (6- to 14-membered)aryl, ((6- to 14-membered)aryl$)-(C_1-C_6)alkyl-$, or (5- to 12-membered)heteroaryl, ((5- to 12-membered)heteroaryl$)-(C_1-C_6)alkyl-$, each of which is optionally substituted with 1, 2, or 3 independently selected $R^9$ groups;

each $R^{14}$ is independently selected from $—COOR^7$, $—(C_1-C_6)alkyl-COOR^7$, $—C(=O)—(C_1-C_6)alkyl-COOR^7$, $—(C_1-C_6)alkyl-C(=O)—(C_1-C_6)alkyl-COOR^7$, $CONH_2$, or $—(C_1-C_6)alkyl-CONH$;

each $R^{30}$ is independently selected from $COOR^7$, $CONR^{5a}R^{6a}$, $—(C_1-C_6)alkyl$, $—C(=O)$, CN, -(3- to 12-membered)heteroaryl, ((3- to 12-membered)heteroaryl$)-(C_1-C_6)alkyl-$, $NH_2$, halo, and ((6- to 14-membered)aryl$)-(C_1-C_6)alkoxy-$;

m is an integer 1, 2, 3, 4, 5, or 6;
n is an integer 0, 1, 2, 3, 4, 5, or 6;
s in an integer 1, 2, 3, 4, 5, or 6;

provided that when $R^4$ is $—(C_1-C_5)alkoxy$ then:
  a) $R^{2a}$ and $R^{2b}$ cannot be taken together to form $=O$; or
  b) $R^{2a}$ cannot be OH when $R^{2b}$ is $—Z-G-R^{10}$, and $—Z-G-R^{10}$ is either:
    a. OH;
    b. $—(C_1-C_6)alkyl$;
    c. 2-propenyl;
    d. 2-propynyl; or
  c) $R^{2a}$ cannot be H when the combination $—Z-G-R^{10}$ is either:
    a. OH;
    b. $—O—C(=O)—(C_1-C_6)alkyl$; or
    c. $—O—C(=O)—(C2-C6)alkenyl$;

and provided that when $R^4$ is OH then:
  a) $R^{2a}$ cannot be OH when $R^{2b}$ is $—Z-G-R^{10}$, and $—Z-G-R^{10}$ is:
    a. methyl;
    b. ethyl;
    c. 2-propenyl; or
    d. 2-propynyl;

b) $R^{2a}$ cannot be H when $R^{2b}$ is —Z-G-$R^{10}$, and —Z-G-$R^{10}$ is either:
   a. OH;
   b. —O—C(=O)—($C_1$-$C_6$)alkyl; or
   c. —O—C(=O)—($C_2$-$C_6$)alkenyl;

and provided that when $R^3$ is ($C_1$-$C_6$)alkyl or ($C_2$-$C_6$)alkenyl, and $R^4$ is H, OH, or ($C_1$-$C_5$)alkoxy, then $R^{2b}$ is not:
   a) optionally substituted (5- to 12-membered)heteroaryl;
   b) optionally substituted (3- to 12-membered)heterocycle; or
   c) unsubstituted phenyl or phenyl substituted with F or Cl, methyl, $CF_3$, hydroxy, methoxy, (3- to 12-membered) heterocycle, or $NH_2$;

and provided that when $R^4$ is OH and $R^1$ is ($C_1$-$C_{10}$)alkyl, then $R^{2a}$ and $R^{2b}$ cannot be together selected =O;

and provided that when $R^4$ is hydrogen and when $R^1$ and $R^3$ are both methyl, then:
   a) $R^{2a}$ and $R^{2b}$ cannot together form =O or =N—OH; or
   b) $R^{2b}$ may not be $NH_2$ or NHC(O)$CH_3$ if $R^{2a}$ is hydrogen;

and provided that when $R^{2a}$ is H, then $R^{2b}$ may not be —Z-G-$R^{10}$, wherein —Z-G-$R^{10}$ is:
   a) —$CH_2$—$CHR^{20}$—C(=O)$R^{21}$, wherein
      $R^{20}$ is H, or —($C_1$-$C_6$)alkyl, and
      $R^{21}$ is selected from the group consisting of H, —($C_1$-$C_{10}$)alkyl, —($C_3$-$C_{12}$)cycloalkyl, (($C_3$-$C_{12}$)cycloalkyl)-($C_1$-$C_6$)alkyl-, phenyl, and phenyl-($C_1$-$C_6$)alkyl; or
   b) —$CH_2$—$CHR^{20}$—$CR^{22}R^{23}$OH, wherein
      $R^{20}$ is defined as above, and
      $R^{22}$ and $R^{23}$ are each independently selected from the group consisting of
         H, —($C_1$-$C_{10}$)alkyl, (($C_3$-$C_{12}$)cycloalkyl)-($C_1$-$C_6$)alkyl-, phenyl, and phenyl-($C_1$-$C_6$)alkyl; or
   c) —$CH_2$—$CR^{20}$=$CR^{23}R^{24}$, wherein
      $R^{20}$ and $R^{23}$ are defined as above, and
      $R^{24}$ is selected from the group consisting of H, and —($C_1$-$C_6$)alkyl;

and the pharmaceutically acceptable salts and solvates thereof.

In one embodiment, the present invention provides novel compounds of Formula IA":

IA"

wherein $R^1$, $R^{2a}$, $R^{2b}$, $R^3$ and $R^4$ are as defined above for Formula I", and the pharmaceutically acceptable salts and solvates thereof.

In another embodiment, the present invention provides novel compounds of Formula IB":

IB"

wherein $R^1$, $R^{2a}$, $R^{2b}$, $R^3$ and $R^4$ are as defined above for Formula I", and the pharmaceutically acceptable salts and solvates thereof.

In another embodiment, the present invention provides novel compounds of Formula IC":

IC"

wherein $R^1$, $R^{2a}$, $R^{2b}$, $R^3$ and $R^4$ are as defined above for Formula I", and the pharmaceutically acceptable salts and solvates thereof.

In another embodiment, the present invention provides novel compounds of Formula ID":

ID"

wherein $R^1$, $R^{2a}$, $R^{2b}$, $R^3$ and $R^4$ are as defined above for Formula I", and the pharmaceutically acceptable salts and solvates thereof.

In one embodiment, the present invention provides novel compounds of Formula I":

I"

wherein
$R^1$ is selected from the group consisting of —($C_1$-$C_{10}$)alkyl, —($C_2$-$C_{10}$)alkenyl, —($C_2$-$C_{10}$)alkynyl, —($C_3$-$C_{12}$)cycloalkyl, $(C_3-C_{12})$cycloalkyl-$(C_1-C_6)$alkyl-, —$(C_3-C_{12})$cycloalkenyl, $(C_3-C_{12})$cycloalkenyl-$(C_1-C_6)$alkyl-, -(6- to 14-membered)aryl, ((6- to 14-membered)aryl)-$(C_1-C_6)$alkyl-, diphenyl$(C_1-C_6)$alkyl-, -(3- to 12-membered)heterocycle, ((3- to 12 membered)heterocycle)-$(C_1-C_6)$alkyl-, —(OCH$_2$CH$_2$)$_s$—O—$(C_1-C_6)$alkyl, —(CH$_2$CH$_2$O)$_s$—$(C_1-C_6)$alkyl, $(C_1-C_{10})$alkoxy, C(halo)$_3$, CH(halo)$_2$, CH$_2$(halo), C(O)R$^5$, —C(O)O—$(C_1-C_{10})$alkyl, and —(CH$_2$)$_n$—N(R$^6$)$_2$, each of which is optionally substituted by 1, 2 or 3 independently selected R$^9$ groups;

R$^{2a}$ is hydrogen, OH, or absent;

R$^{2b}$ is
  a) ((6- to 14-membered)aryl), -((5- to 12-membered)heteroaryl), or ((3- to 12-membered)heterocycle), each of which is optionally substituted with one, two, or three independently selected R$^{30}$ groups; or
  b) —Z-G-R$^{10}$, provided that —Z-G-R$^{10}$ is other than hydrogen;
or R$^{2a}$ and R$^{2b}$ together form =O;

Z is absent or —(CH$_2$)$_m$—, optionally substituted with 1 or 2-$(C_1-C_6)$alkyl;

G is selected from the group consisting of:
  a) a bond, —$(C_1-C_6)$alkylene, —$(C_2-C_6)$alkenylene;
  b) O, —OCO—, —C(=O), =CH;
  c) NR$^8$, =N—O, =N—NH;
  d) S, SO, SO$_2$; and
  e) —NH—SO$_2$;
and when Z is absent and G is =CH, =N—O, or =N—NH, then R$^{2a}$ is absent;

R$^{10}$ is selected from the group consisting of hydrogen, —$(C_1-C_{10})$alkyl, —$(C_2-C_{12})$alkenyl, —C(=O), —C(=O)—$(C_1-C_6)$alkyl, —C(=O)—$(C_2-C_6)$alkenyl, —C(=O)-(6- to 14-membered)aryl, —C(=O)—$(C_1-C_6)$alkyl-(6- to 14-membered)aryl, —$(C_2-C_{12})$alkynyl, —$(C_1-C_{10})$alkoxy, —(OCH$_2$CH$_2$)$_s$—O$(C_1-C_6)$alkyl, —(CH$_2$CH$_2$O)$_s$—$(C_1-C_6)$alkyl, —NH$_2$, —NH$(C_1-C_6)$alkyl, CN, NR$^5$R$^6$, —$(C_1-C_6)$alkyl-NR$^5$R$^6$, —CONR$^5$R$^6$, —$(C_1-C_6)$alkyl-CO—NR$^5$R$^6$, —COOR$^7$, —$(C_1-C_6)$alkyl-CO—OR$^7$, —$(C_1-C_6)$alkoxy-COOR$^7$, —CO—(CH$_2$)$_n$—COOR$^7$, —CO—(CH$_2$)$_n$—CO—NR$^5$R$^6$, —$(C_3-C_{12})$cycloalkyl, $((C_3-C_{12})$cycloalkyl)-$(C_1-C_6)$alkyl-, —$(C_4-C_{12})$cycloalkenyl, $((C_4-C_{12})$cycloalkenyl)-$(C_1-C_6)$alkyl-, —$(C_6-C_{14})$bicycloalkyl, $((C_6-C_{14})$bicycloalkyl)-$(C_1-C_6)$alkyl-, —$(C_8-C_{20})$tricycloalkyl, $((C_8-C_{20})$tricycloalkyl)-$(C_1-C_6)$alkyl-, —$(C_7-C_{14})$bicycloalkenyl, $((C_7-C_{14})$bicycloalkenyl)-$(C_1-C_6)$alkyl-, —$(C_8-C_{20})$tricycloalkenyl, $((C_8-C_{20})$tricycloalkenyl)-$(C_1-C_6)$alkyl-, -(6- to 14-membered)aryl, ((6- to 14-membered)aryl)-$(C_1-C_6)$alkyl-, —SO$_2$—$(C_1-C_6)$alkyl, —SO$_2$($(C_3-C_{12})$cycloalkyl), —SO$_2$—$((C_3-C_{12})$cycloalkyl)-$(C_1-C_6)$alkyl, —SO$_2$-((5- to 12-membered)heteroaryl), —SO$_2$-((5- to 12-membered)heteroaryl)-$(C_1-C_6)$alkyl, —C(=O)—NH-((5- to 12-membered)heteroaryl), —C(=O)—NH-((5- to 12-membered)heteroaryl)-$(C_1-C_6)$alkyl, —C(=O)—NH-((3- to 12-membered)heterocycle), —C(=O)—NH-((3- to 12-membered)heterocycle)-$(C_1-C_6)$alkyl, SO$_2$-((6- to 14-membered)aryl), SO$_2$-((6- to 14 membered)aryl)-$(C_1-C_6)$alkyl, -(7- to 12-membered)bicyclic ring system, ((7- to 12-membered)bicyclic ring system)-$(C_1-C_6)$alkyl-, -(7- to 12-membered)bicyclic aryl, ((7- to 12-membered)bicyclic aryl)-$(C_1-C_6)$alkyl-, -(5- to 12-membered)heteroaryl, ((5- to 12-membered)heteroaryl)-$(C_1-C_6)$alkyl-, -(3- to 12-membered)heterocycle, ((3- to 12 membered)heterocycle)-$(C_1-C_6)$alkyl-, -(7- to 12-membered)bicycloheterocycle, ((7- to 12-membered)bicycloheterocycle)-$(C_1-C_6)$alkyl-, phenyl, benzyl and naphthyl; each of which is optionally substituted with one, two, or three substituents independently selected from the group consisting of —OH, (=O), halo, —C(halo)$_3$, —CH(halo)$_2$, —CH$_2$(halo), —$(C_1-C_6)$alkyl, halo$(C_1-C_6)$alkyl-, —$(C_2-C_6)$alkenyl, —$(C_2-C_6)$alkynyl, hydroxy$(C_1-C_6)$alkyl-, dihydroxy$(C_1-C_6)$alkyl-, —$(C_1-C_6)$alkoxy, $((C_1-C_6)$alkoxy)CO$(C_1-C_6)$alkoxy-, phenyl, benzyl, —NH$_2$, —NH$(C_1-C_6)$alkyl, —$(C_1-C_6)$alkyl-NH$(C_1-C_6)$alkyl-R$^{14}$, —CN, —SH, —OR$^{11}$, —CONR$^5$R$^6$, —$(C_1-C_6$alkyl)-CO—NR$^5$R$^6$, —COOR$^7$, —$(C_1-C_6)$alkyl-CO—OR$^7$, —$(C_1-C_6)$alkoxy-COOR$^7$, —(OCH$_2$CH$_2$)$_s$—O$(C_1-C_6)$alkyl, —(CH$_2$CH$_2$O)$_s$—$(C_1-C_6)$alkyl, —SO$_2$—NR$^{5a}$R$^{6a}$, $(C_1-C_6)$alkyl)sulfonyl, $((C_1-C_6)$alkyl)sulfonyl$(C_1-C_6)$alkyl-, —NH—SO$_2$$(C_1-C_6)$alkyl, NH$_2$—SO$_2$$(C_1-C_6)$alkyl-, —N(SO$_2$$(C_1-C_6)$alkyl)$_2$, —C(=NH)NH$_2$, —NH—CO—$(C_1-C_6)$alkyl, —NH—CO—NH$_2$, —NH—C(=O)—NH—$(C_1-C_6)$alkyl, —NH—C(=O)-(6- to 14-membered)aryl, —NH—C(=O)—$(C_1-C_6)$alkyl-(6- to 14-membered)aryl, —NH—$(C_1-C_6)$alkyl-CO—OR$^7$, —NH—C(=O)—$(C_1-C_6)$alkyl-CO—OR$^7$, —NH—C(=O)—CH(NH$_2$)—$(C_1-C_6)$alkyl-CO—OR$^7$, —$(C_3-C_{12})$cycloalkyl, $((C_3-C_{12})$cycloalkyl)-$(C_1-C_6)$alkyl-, -(6- to 14-membered)aryl, -(6- to 14-membered)aryloxy, —$(C_1-C_6)$alkoxy-C(O)NR$^5$R$^6$, —NH—$(C_1-C_6)$alkyl-C(O)—NR$^5$R$^6$, —C(O)NH—$(C_1-C_6)$alkyl-COOR$^7$, ((6- to 14-membered)aryl)-$(C_1-C_6)$alkyl-, -(5- to 12-membered)heteroaryl, ((5- to 12-membered)heteroaryl)-$(C_1-C_6)$alkyl-, -(3- to 12-membered)heterocycle, ((3- to 12-membered)heterocycle)-$(C_1-C_6)$alkyl-, -(7- to 12-membered)bicycloheterocycle, and ((7- to 12-membered)bicycloheterocycle)-$(C_1-C_6)$alkyl-;

R$^3$ is selected from:
  a) —H; or
  b) —$(C_1-C_6)$alkyl, —$(C_2-C_6)$alkenyl, or —$(C_2-C_6)$alkynyl;

R$^4$ is selected from
  a) —H, —OH, halo, —C(halo)$_3$, —CH(halo)$_2$, —CH$_2$(halo), COOH, or CONH$_2$; or
  b) —$(C_1-C_5)$alkyl, —$(C_2-C_5)$alkenyl, —$(C_2-C_5)$alkynyl, —(CH$_2$)$_n$—O—(CH$_2$)$_n$—CH$_3$, or —$(C_1-C_5)$alkoxy, each of which is optionally substituted with 1, 2, or 3 independently selected R$^9$ groups;

R$^5$ and R$^6$ are each independently selected from
  a) hydrogen, —OH, halo, —C(halo)$_3$, —CH(halo)$_2$, —CH$_2$(halo);
  b) —$(C_1-C_6)$alkyl, —$(C_2-C_5)$alkenyl, —$(C_2-C_5)$alkynyl, —(CH$_2$)$_n$—O—(CH$_2$)$_n$—CH$_3$, —$(C_1-C_6)$alkoxy, each of which is optionally substituted with 1, 2, or 3 substituents independently selected from —OH, halo, —$(C_1-C_{10})$alkyl, —$(C_2-C_{10})$alkenyl, —$(C_2-C_{10})$alkynyl, —$(C_1-C_{10})$alkoxy, —$(C_3-C_{12})$cycloalkyl, —CHO, —C(O)OH, —C(halo)$_3$, —CH(halo)$_2$, CH$_2$(halo), —(CH$_2$)$_n$—O—(CH$_2$)$_n$—CH$_3$, phenyl, or CONR$^{5a}$R$^{6a}$;
  c) —$(C_3-C_8)$cycloalkyl, $((C_3-C_8)$cycloalkyl)-$(C_1-C_6)$alkyl-, —COOR$^7$, —$(C_1-C_6)$alkyl-COOR$^7$, —CONH$_2$, or $(C_1-C_6)$alkyl-CONH—;
  d) ((6- to 14-membered)aryl) optionally substituted with 1, 2, or 3 independently selected R$^{30}$ groups;
  e) -((5- to 12-membered)heteroaryl) optionally substituted with 1, 2, or 3 independently selected R$^{30}$ groups; or
  f) R$^5$ and R$^6$ together with the nitrogen atom to which they are attached form a (3- to 12-membered)heterocycle optionally substituted with 1, 2, or 3 independently selected R$^{30}$ groups;

R$^{5a}$ and R$^{6a}$ are each independently selected from the group consisting of:
  a) hydrogen, —OH, halo, —C(halo)$_3$, —CH(halo)$_2$, and —CH$_2$(halo);

b) —$(C_1$-$C_6)$alkyl, —$(C_2$-$C_6)$alkenyl, —$(C_2$-$C_6)$alkynyl, —$(CH_2)_n$—O—$(CH_2)_n$—$CH_3$, and —$(C_1$-$C_6)$alkoxy, each of which is optionally substituted with 1, 2, or 3 substituents independently selected from —OH, halo, —$(C_1$-$C_{10})$alkyl, —$(C_2$-$C_{12})$alkenyl, —$(C_2$-$C_{12})$alkynyl, —$(C_1$-$C_{10})$alkoxy, —$(C_3$-$C_{12})$cycloalkyl, —CHO, —COOH, —C(halo)$_3$, —CH(halo)$_2$, $CH_2$(halo), —$(CH_2)_n$—O—$(CH_2)_n$—$CH_3$, and phenyl;

c) —$(C_3$-$C_8)$cycloalkyl, $((C_3$-$C_8)$cycloalkyl)-$(C_1$-$C_6)$alkyl-, —COOR$^7$, —$(C_1$-$C_6)$alkyl-COOR$^7$, —CONH$_2$, and $(C_1$-$C_6)$alkyl-CONH—;

d) -(6- to 14-membered)aryl optionally substituted with 1, 2, or 3 independently selected R$^{30}$ groups;

e) -((5- to 12-membered)heteroaryl) optionally substituted with 1, 2, or 3 independently selected R$^{30}$ groups; or f) R$^{5a}$ and R$^{6a}$ together with the nitrogen atom to which they are attached form a (3- to 12-membered)heterocycle optionally substituted with 1, 2, or 3 independently selected R$^{30}$ groups;

each R$^7$ is independently selected from the group consisting of hydrogen, —$(C_1$-$C_6)$alkyl, —$(C_2$-$C_6)$alkenyl, —$(C_2$-$C_6)$alkynyl, —$(C_3$-$C_{12})$cycloalkyl, —$(C_4$-$C_{12})$cycloalkenyl, $((C_3$-$C_{12})$cycloalkyl)-$(C_1$-$C_6)$alkyl-, and $((C_4$-$C_{12})$cycloalkenyl)-$(C_1$-$C_6)$alkyl-;

each R$^8$ is independently selected from H, —$(C_1$-$C_6)$alkyl, —$(C_2$-$C_6)$alkenyl, —$(C_2$-$C_6)$alkynyl, —$(C_1$-$C_{10})$alkoxy, —$(C_3$-$C_{12})$cycloalkyl, —$(C_3$-$C_{12})$cycloalkenyl, $((C_3$-$C_{12})$cycloalkyl)-$(C_1$-$C_6)$alkyl-, $((C_3$-$C_{12})$cycloalkenyl)-$(C_1$-$C_6)$alkyl-, —C(=O)$(C_1$-$C_6)$alkyl or SO$_2$$(C_1$-$C_6)$alkyl;

each R$^9$ is independently selected from —OH, halo, —$(C_1$-$C_{10})$alkyl, —$(C_2$-$C_{10})$alkenyl, —$(C_2$-$C_{10})$alkynyl, —$(C_1$-$C_{10})$alkoxy, —$(C_3$-$C_{12})$cycloalkyl, —CHO, —C(O)OH, —C(halo)$_3$, —CH(halo)$_2$, CH$_2$(halo), —$(CH_2)_n$—O—$(CH_2)_n$—$CH_3$, phenyl, or CONR$^{5a}$R$^{6a}$;

each R$^{11}$ is independently selected from —C(halo)$_3$, —CH(halo)$_2$, —CH$_2$(halo), —$(C_2$-$C_5)$alkenyl, —$(C_2$-$C_5)$alkynyl, —$(CH_2)_n$—O—$(CH_2)_n$—$CH_3$, (6- to 14-membered)aryl, ((6- to 14-membered)aryl)-$(C_1$-$C_6)$alkyl-, or (5- to 12-membered)heteroaryl, ((5- to 12-membered)heteroaryl)-$(C_1$-$C_6)$alkyl-, each of which is optionally substituted with 1, 2, or 3 independently selected R$^9$ groups;

each R$^{14}$ is independently selected from —COOR$^7$, —$(C_1$-$C_6)$alkyl-COOR$^7$, —C(=O)—$(C_1$-$C_6)$alkyl-COOR$^7$, —$(C_1$-$C_6)$alkyl-C(=O)—$(C_1$-$C_6)$alkyl-COOR$^7$, CONH$_2$, or —$(C_1$-$C_6)$alkyl-CONH;

each R$^{30}$ is independently selected from COOR$^7$, CONR$^{5a}$R$^{6a}$, —$(C_1$-$C_6)$alkyl, —C(=O), CN, -(3- to 12-membered)heteroaryl, ((3- to 12-membered)heteroaryl)-$(C_1$-$C_6)$alkyl-, NH$_2$, halo, and ((6- to 14-membered)aryl)-$(C_1$-$C_6)$alkoxy-;

m is an integer 1, 2, 3, 4, 5, or 6;
n is an integer 0, 1, 2, 3, 4, 5, or 6;
s in an integer 1, 2, 3, 4, 5, or 6;

provided that when R$^4$ is —$(C_1$-$C_5)$alkoxy then:
a) R$^{2a}$ and R$^{2b}$ cannot be taken together to form =O; or
b) R$^{2a}$ cannot be OH when R$^{2b}$ is —Z-G-R$^{10}$, and —Z-G-R$^{10}$ is either:
   a. OH;
   b. —$(C_1$-$C_6)$alkyl;
   c. —$(C_2$-$C_6)$alkenyl; or
   d. —$(C_2$-$C_6)$alkynyl; or
c) R$^{2a}$ cannot be H when the combination —Z-G-R$^{10}$ is either:
   a. OH;
   b. —O—C(=O)—$(C_1$-$C_6)$alkyl; or
   c. —O—C(=O)—$(C_2$-$C_6)$alkenyl;

and provided that when R$^4$ is OH then:
a) R$^{2a}$ cannot be OH when R$^{2b}$ is —Z-G-R$^{10}$, and —Z-G-R$^{10}$ is:
   a. —$(C_1$-$C_6)$alkyl;
   b. —$(C_2$-$C_6)$alkenyl;
   c. or —$(C_2$-$C_6)$alkynyl;
b) R$^{2a}$ cannot be H when R$^{2b}$ is —Z-G-R$^{10}$, and —Z-G-R$^{10}$ is:
   a. OH
   b. —O—C(=O)—$(C_1$-$C_6)$alkyl; or
   c. —O—C(=O)—$(C_2$-$C_6)$alkenyl;

and provided that when R$^3$ is $(C_1$-$C_6)$alkyl or $(C_2$-$C_6)$alkenyl, and R$^4$ is H, OH, or $(C_1$-$C_5)$alkoxy, then R$^{2b}$ is not
a) optionally substituted (5- to 12-membered)heteroaryl,
b) optionally substituted (3- to 12-membered)heterocycle, or
c) unsubstituted phenyl or phenyl substituted with halo, $(C_1$-$C_6)$alkyl, C(halo)$_3$, hydroxy, $(C_1$-$C_6)$alkoxy, (3- to 12-membered)heterocycle, or NH$_2$ and provided that when R$^4$ is OH and R$^1$ is $(C_1$-$C_{10})$alkyl, then R$^{2a}$ and R$^{2b}$ cannot be together selected =O.

and provided that when R$^4$ is hydrogen and when R$^1$ and R$^3$ are both methyl, then
a) R$^{2a}$ and R$^{2b}$ cannot together form =O or =N—OH; or
b) R$^{2b}$ may not be NH$_2$ or NHC(O)CH$_3$ if R$^{2a}$ is hydrogen.

and provided that when R$^{2a}$ is H, then R$^{2b}$ may not be —Z-G-R$^{10}$, wherein —Z-G-R$^{10}$ is:
a) —CH$_2$—CHR$^{20}$—C(=O)R$^{21}$, wherein
   R$^{20}$ is H, or —$(C_1$-$C_6)$alkyl, and
   R$^{21}$ is selected from the group consisting of H, —$(C_1$-$C_{10})$alkyl, —$(C_3$-$C_{12})$cycloalkyl, $((C_3$-$C_{12})$cycloalkyl)-$(C_1$-$C_6)$alkyl-, -(6- to 14-membered)aryl, and ((6- to 14-membered)aryl)-$(C_1$-$C_6)$alkyl-; or
b) —CH$_2$—CHR$^{20}$—CR$^{22}$R$^{23}$OH, wherein
   R$^{20}$ is defined as above, and
   R$^{22}$ and R$^{23}$ are each independently selected from the group consisting of
   H, —$(C_1$-$C_{10})$alkyl, $((C_3$-$C_{12})$cycloalkyl)-$(C_1$-$C_6)$alkyl-, -(6- to 14-membered)aryl, and ((6- to 14-membered)aryl)-$(C_1$-$C_6)$alkyl-; or
c) —CH$_2$—CR$^{20}$=CR$^{23}$R$^{24}$, wherein
   R$^{20}$ and R$^{23}$ are defined as above, and
   R$^{24}$ is selected from the group consisting of H, and —$(C_1$-$C_6)$alkyl.

and the pharmaceutically acceptable salts and solvates thereof.

In another aspect, the present invention provides novel compounds of Formula I':

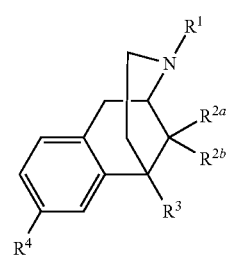

wherein
R$^1$ is selected from the group consisting of —$(C_1$-$C_{10})$alkyl, —$(C_2$-$C_{10})$alkenyl, —$(C_2$-$C_{10})$alkynyl, —$(C_3$-$C_{12})$cycloalkyl, $(C_3$-$C_{12})$cycloalkyl-$(C_1$-$C_6)$alkyl-, —$(C_3$-$C_{12})$cycloalkenyl, $(C_3$-$C_{12})$cycloalkenyl-$(C_1$-$C_6)$alkyl-, -(6- to 14-membered)aryl, ((6- to 14-membered)aryl)-($C_1$-$C_6$)alkyl-, diphenyl($C_1$-$C_6$)alkyl-, -(3- to 12-membered)heterocycle, ((3- to 12 membered)heterocycle)-($C_1$-$C_6$)alkyl-, —(OCH$_2$CH$_2$)$_s$—O($C_1$-$C_6$)alkyl, —(CH$_2$CH$_2$O)$_s$—($C_1$-$C_6$)alkyl, ($C_1$-$C_{10}$)alkoxy, C(halo)$_3$, CH(halo)$_2$, CH$_2$(halo), C(O)R$^5$, —C(O)O—($C_1$-$C_{10}$)alkyl, and —(CH$_2$)$_n$—N(R$^6$)$_2$, each of which is optionally substituted by 1, 2 or 3 independently selected R$^9$ groups;

R$^{2a}$ is absent or OH;

R$^{2b}$ is
  a) ((6- to 14-membered)aryl) or ((3- to 12-membered)heterocycle), each of which is optionally substituted with one, two, or three independently selected R$^{30}$ groups; or
  b) —Z-G-R$^{10}$, provided that —Z-G-R$^{10}$ is other than hydrogen;

or R$^{2a}$ and R$^{2b}$ together form =O;

Z is absent or —(CH$_2$)$_m$—, optionally substituted with 1 or 2-($C_1$-$C_6$)alkyl;

G is selected from the group consisting of:
  a) a bond, —($C_1$-$C_6$)alkylene, —($C_2$-$C_6$)alkenylene;
  b) O, —OCO—, —C(=O), =CH;
  c) NR$^8$, =N—O, =N—NH;
  d) S, SO, and SO$_2$;

R$^{10}$ is selected from the group consisting of hydrogen, —($C_1$-$C_{10}$)alkyl, —($C_2$-$C_{12}$)alkenyl, —C(=O), —C(=O)—($C_1$-$C_6$)alkyl, —C(=O)—($C_2$-$C_6$)alkenyl, —C(=O)-(6- to 14-membered)aryl, —C(=O)—($C_1$-$C_6$)alkyl-(6- to 14-membered)aryl, —($C_2$-$C_{12}$)alkynyl, —($C_1$-$C_{10}$)alkoxy, —(OCH$_2$CH$_2$)$_s$—O($C_1$-$C_6$)alkyl, —(CH$_2$CH$_2$O)$_s$—($C_1$-$C_6$)alkyl, —NH$_2$, —NH($C_1$-$C_6$)alkyl, CN, NR$^5$R$^6$, —($C_1$-$C_6$)alkyl-NR$^5$R$^6$, —CONR$^5$R$^6$, —($C_1$-$C_6$)alkyl-CO—NR$^5$R$^6$, —COOR$^7$, —($C_1$-$C_6$)alkyl-CO—OR$^7$, —($C_1$-$C_6$)alkoxy-COOR$^7$, —CO—(CH$_2$)$_n$—COOR$^7$, —CO—(CH$_2$)$_n$—CO—NR$^5$R$^6$, —($C_3$-$C_{12}$)cycloalkyl, (($C_3$-$C_{12}$)cycloalkyl)-($C_1$-$C_6$)alkyl, —($C_4$-$C_{12}$)cycloalkenyl, (($C_4$-$C_{12}$)cycloalkenyl)-($C_1$-$C_6$)alkyl-, —($C_6$-$C_{14}$)bicycloalkyl, (($C_6$-$C_{14}$)bicycloalkyl)-($C_1$-$C_6$)alkyl-, —($C_8$-$C_{20}$)tricycloalkyl, (($C_8$-$C_{20}$)tricycloalkyl)-($C_1$-$C_6$)alkyl-, —($C_7$-$C_{14}$)bicycloalkenyl, (($C_7$-$C_{14}$)bicycloalkenyl)-($C_1$-$C_6$)alkyl-, —($C_8$-$C_{20}$)tricycloalkenyl, (($C_8$-$C_{20}$)tricycloalkenyl)-($C_1$-$C_6$)alkyl-, -(6- to 14-membered)aryl, ((6- to 14-membered)aryl)-($C_1$-$C_6$)alkyl-, -(7- to 12-membered)bicyclic ring system, ((7- to 12-membered)bicyclic ring system)-($C_1$-$C_6$)alkyl-, -(7- to 12-membered)bicyclic aryl, ((7- to 12-membered)bicyclic aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12 membered)heterocycle)-($C_1$-$C_6$)alkyl-, -(7- to 12-membered)bicycloheterocycle, ((7- to 12-membered)bicycloheterocycle)-($C_1$-$C_6$)alkyl-, phenyl, benzyl and naphthyl; each of which is optionally substituted with one, two, or three substituents independently selected from the group consisting of —OH, (=O), halo, —C(halo)$_3$, —CH(halo)$_2$, —CH$_2$(halo), —($C_1$-$C_6$)alkyl, halo($C_1$-$C_6$)alkyl-, —($C_2$-$C_6$)alkenyl, —($C_2$-$C_6$)alkynyl, hydroxy($C_1$-$C_6$)alkyl-, dihydroxy($C_1$-$C_6$)alkyl-, —($C_1$-$C_6$)alkoxy, (($C_1$-$C_6$)alkoxy)CO($C_1$-$C_6$)alkoxy-, phenyl, benzyl, —NH$_2$, —NH($C_1$-$C_6$)alkyl, —($C_1$-$C_6$)alkyl-NH($C_1$-$C_6$)alkyl-R$^{14}$, —CN, —SH, —OR$^{11}$, —CONR$^5$R$^6$, —($C_1$-$C_6$alkyl)-CO—NR$^5$R$^6$, —COOR$^7$, —($C_1$-$C_6$)alkyl-CO—OR$^7$, —($C_1$-$C_6$)alkoxy-COOR$^7$, —(OCH$_2$CH$_2$)$_s$—O($C_1$-$C_6$)alkyl, —(CH$_2$CH$_2$O)$_s$—($C_1$-$C_6$)alkyl, ($C_1$-$C_6$)alkyl)sulfonyl, (($C_1$-$C_6$)alkyl)sulfonyl($C_1$-$C_6$)alkyl-, —NH—SO$_2$($C_1$-$C_6$)alkyl, NH$_2$—SO$_2$($C_1$-$C_6$)alkyl-, —N(SO$_2$($C_1$-$C_6$)alkyl)$_2$, —C(=NH)NH$_2$, —NH—CO—($C_1$-$C_6$)alkyl, —NH—CO—NH$_2$, —NH—C(=O)—NH—($C_1$-$C_6$)alkyl, —NH—C(=O)-(6- to 14-membered)aryl, —NH—C(=O)—($C_1$-$C_6$)alkyl-(6- to 14-membered)aryl, —NH—($C_1$-$C_6$)alkyl-CO—OR$^7$, —NH—C(=O)—($C_1$-$C_6$)alkyl-CO—OR$^7$, —NH—C(=O)—CH(NH$_2$)—($C_1$-$C_6$)alkyl-CO—OR$^7$, —($C_3$-$C_{12}$)cycloalkyl, (($C_3$-$C_{12}$)cycloalkyl)-($C_1$-$C_6$)alkyl-, -(6- to 14-membered)aryl, -(6- to 14-membered)aryloxy, —($C_1$-$C_6$)alkoxy-C(O)NR$^5$R$^6$, —NH—($C_1$-$C_6$)alkyl-C(O)—NR$^5$R$^6$, —C(O)NH—($C_1$-$C_6$)alkyl-COOR$^7$, ((6- to 14-membered)aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12-membered)heterocycle)-($C_1$-$C_6$)alkyl-, -(7- to 12-membered)bicycloheterocycle, and ((7- to 12-membered)bicycloheterocycle)-($C_1$-$C_6$)alkyl-;

R$^3$ is selected from:
  a) —H; or
  b) —($C_1$-$C_6$)alkyl, —($C_2$-$C_6$)alkenyl, or —($C_2$-$C_6$)alkynyl;

R$^4$ is selected from
  a) —H, —OH, halo, —C(halo)$_3$, —CH(halo)$_2$, —CH$_2$(halo), COOH, or CONH$_2$; or
  b) —($C_1$-$C_5$)alkyl, —($C_2$-$C_5$)alkenyl, —($C_2$-$C_5$)alkynyl, —(CH$_2$)$_n$—O—(CH$_2$)$_n$—CH$_3$, or —($C_1$-$C_5$)alkoxy, each of which is optionally substituted with 1, 2, or 3 independently selected R$^9$ groups;

R$^5$ and R$^6$ are each independently selected from
  a) hydrogen, —OH, halo, —C(halo)$_3$, —CH(halo)$_2$, —CH$_2$(halo);
  b) —($C_1$-$C_6$)alkyl, —($C_2$-$C_5$)alkenyl, —($C_2$-$C_5$)alkynyl, —(CH$_2$)$_n$—O—(CH$_2$)$_n$—CH$_3$, —($C_1$-$C_6$)alkoxy, each of which is optionally substituted with 1, 2, or 3 substituents independently selected from —OH, halo, —($C_1$-$C_{10}$)alkyl, —($C_2$-$C_{10}$)alkenyl, —($C_1$-$C_{10}$)alkynyl, —($C_1$-$C_{10}$)alkoxy, —($C_3$-$C_{12}$)cycloalkyl, —CHO, —C(O)OH, —C(halo)$_3$, —CH(halo)$_2$, CH$_2$(halo), —(CH$_2$)$_n$—O—(CH$_2$)$_n$—CH$_3$, phenyl, or CONR$^5$R$^6$;
  c) —($C_3$-$C_8$)cycloalkyl, (($C_3$-$C_8$)cycloalkyl)-($C_1$-$C_6$)alkyl-, —COOR$^7$, —($C_1$-$C_6$)alkyl-COOR$^7$, —CONH$_2$, or ($C_1$-$C_6$)alkyl-CONH—;
  d) ((6- to 14-membered)aryl) optionally substituted with 1, 2, or 3 independently selected R$^{30}$ groups; or
  e) R$^5$ and R$^6$ together with the nitrogen atom to which they are attached form a (4- to 8-membered)heterocycle optionally substituted with 1, 2, or 3 independently selected R$^{30}$ groups;

R$^{5a}$ and R$^{6a}$ are each independently selected from the group consisting of:
  a) hydrogen, —OH, halo, —C(halo)$_3$, —CH(halo)$_2$, and —CH$_2$(halo);
  b) —($C_1$-$C_6$)alkyl, —($C_2$-$C_6$)alkenyl, —($C_2$-$C_6$)alkynyl, —(CH$_2$)$_n$—O—(CH$_2$)$_n$—CH$_3$, and —($C_1$-$C_6$)alkoxy, each of which is optionally substituted with 1, 2, or 3 substituents independently selected from —OH, halo, —($C_1$-$C_{10}$)alkyl, —($C_2$-$C_{12}$)alkenyl, —($C_2$-$C_{12}$)alkynyl, —($C_1$-$C_{10}$)alkoxy, —($C_3$-$C_{12}$)cycloalkyl, —CHO, —COOH, —C(halo)$_3$, —CH(halo)$_2$, CH$_2$(halo), —(CH$_2$)$_n$—O—(CH$_2$)$_n$—CH$_3$, and phenyl;
  c) —($C_3$-$C_8$)cycloalkyl, (($C_3$-$C_8$)cycloalkyl)-($C_1$-$C_6$)alkyl-, —COOR$^7$, —($C_1$-$C_6$)alkyl-COOR$^7$, —CONH$_2$, and ($C_1$-$C_6$)alkyl-CONH—;
  d) -(6- to 14-membered)aryl optionally substituted with 1, 2, or 3 independently selected R$^{30}$ groups; or
  e) R$^{5a}$ and R$^{6a}$ together with the nitrogen atom to which they are attached form a (4- to 8-membered)heterocycle optionally substituted with 1, 2, or 3 independently selected R$^{30}$ groups;

each $R^7$ is independently selected from the group consisting of hydrogen, —$(C_1-C_6)$alkyl, —$(C_2-C_6)$alkenyl, —$(C_2-C_6)$alkynyl, —$(C_3-C_{12})$cycloalkyl, —$(C_4-C_{12})$cycloalkenyl, $((C_3-C_{12})$cycloalkyl)-$(C_1-C_6)$alkyl-, and $((C_4-C_{12})$cycloalkenyl)-$(C_1-C_6)$alkyl-;

each $R^8$ is independently selected from H, —$(C_1-C_6)$alkyl, —$(C_2-C_6)$alkenyl, —$(C_2-C_6)$alkynyl, —$(C_1-C_{10})$alkoxy, —$(C_3-C_{12})$cycloalkyl, —$(C_3-C_{12})$cycloalkenyl, $((C_3-C_{12})$cycloalkyl)-$(C_1-C_6)$alkyl-, $((C_3-C_{12})$cycloalkenyl)-$(C_1-C_6)$alkyl-, —$C(=O)(C_1-C_6)$alkyl or $SO_2(C_1-C_6)$alkyl;

each $R^9$ is independently selected from —OH, halo, —$(C_1-C_{10})$alkyl, —$(C_2-C_{10})$alkenyl, —$(C_2-C_{10})$alkynyl, —$(C_1-C_{10})$alkoxy, —$(C_3-C_{12})$cycloalkyl, —CHO, —C(O)OH, —C(halo)$_3$, —CH(halo)$_2$, CH$_2$(halo), —(CH$_2$)$_n$—O—(CH$_2$)$_n$—CH$_3$, phenyl, or CONR$^{5a}$R$^{6a}$;

each $R^{11}$ is independently selected from —C(halo)$_3$, —CH(halo)$_2$, —CH$_2$(halo), —$(C_2-C_5)$alkenyl, —$(C_2-C_5)$alkynyl, —(CH$_2$)$_n$—O—(CH$_2$)$_n$—CH$_3$, (6- to 14-membered)aryl, ((6- to 14-membered)aryl)-$(C_1-C_6)$alkyl-, or (5- to 12-membered)heteroaryl, ((5- to 12-membered)heteroaryl)-$(C_1-C_6)$alkyl-, each of which is optionally substituted with 1, 2, or 3 independently selected $R^9$ groups;

each $R^{14}$ is independently selected from —COOR$^7$, —$(C_1-C_6)$alkyl-COOR$^7$, —C(=O)—$(C_1-C_6)$alkyl-COOR$^7$, —$(C_1-C_6)$alkyl-C(=O)—$(C_1-C_6)$alkyl-COOR$^7$, CONH$_2$, or —$(C_1-C_6)$alkyl-CONH;

each $R^{30}$ is independently selected from COOR$^7$, CONR$^{5a}$R$^{6a}$, —$(C_1-C_6)$alkyl, —C(=O), CN, -(3- to 12-membered)heteroaryl, ((3- to 12-membered)heteroaryl)-$(C_1-C_6)$alkyl-, NH$_2$, halo, and ((6- to 14-membered)aryl)-$(C_1-C_6)$alkoxy-;

m is an integer 1, 2, 3, 4, 5, or 6;
n is an integer 0, 1, 2, 3, 4, 5, or 6;
s in an integer 1, 2, 3, 4, 5, or 6;
provided that when $R^4$ is —$(C_1-C_5)$alkoxy then:
  a) $R^{2a}$ and $R^{2b}$ cannot be taken together to form =O; or
  b) $R^{2a}$ cannot be OH when $R^{2b}$ is —Z-G-R$^{10}$, and —Z-G-R$^{10}$ is either:
    a. OH; or
    b. —$(C_1-C_6)$alkyl; or
  c) $R^{2a}$ cannot be H when the combination —Z-G-R$^{10}$ is OH;

and the pharmaceutically acceptable salts and solvates thereof.

In one embodiment, the present invention provides novel compounds of Formula IA':

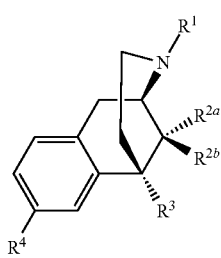

IA' wherein $R^1$, $R^{2a}$, $R^{2b}$, $R^3$ and $R^4$ are as defined above for Formula I', and the pharmaceutically acceptable salts and solvates thereof.

In another embodiment, the present invention provides novel compounds of Formula IB':

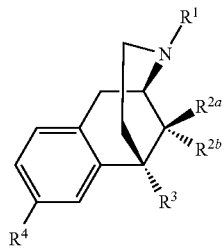

IB' wherein $R^1$, $R^{2a}$, $R^{2b}$, $R^3$ and $R^4$ are as defined above for Formula I', and the pharmaceutically acceptable salts and solvates thereof.

In another embodiment, the present invention provides novel compounds of Formula IC':

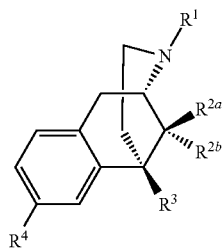

IC' wherein $R^1$, $R^{2a}$, $R^{2b}$, $R^3$ and $R^4$ are as defined above for Formula I', and the pharmaceutically acceptable salts and solvates thereof.

In another embodiment, the present invention provides novel compounds of Formula ID':

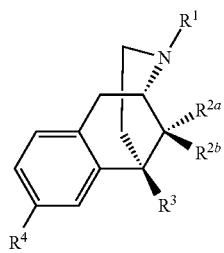

ID' wherein $R^1$, $R^{2a}$, $R^{2b}$, $R^3$ and $R^4$ are as defined above for Formula I', and the pharmaceutically acceptable salts and solvates thereof.

The present invention further provides novel compounds of Formula I:

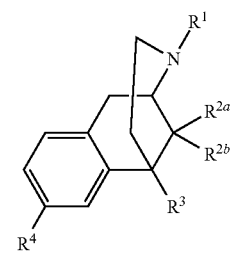

I wherein
$R^1$ is selected from the group consisting of —$(C_1-C_{10})$alkyl, —$(C_2-C_{10})$alkenyl, —$(C_2-C_{10})$alkynyl, —$(C_3-C_{12})$cycloalkyl, $(C_3-C_{12})$cycloalkyl-$(C_1-C_6)$alkyl-, —$(C_3-C_{12})$cycloalkenyl, $(C_3-C_{12})$cycloalkenyl-$(C_1-C_6)$alkyl-, -(6- to 14-membered)aryl, ((6- to 14-membered)aryl)-$(C_1-C_6)$alkyl-, diphenyl$(C_1-C_6)$alkyl-, —(OCH$_2$CH$_2$)$_s$—O—$(C_1-C_6)$alkyl, —(CH$_2$CH$_2$O)$_s$—$(C_1-C_6)$alkyl, $(C_1-C_{10})$alkoxy, C(halo)$_3$, CH(halo)$_2$, CH$_2$(halo), C(O)R$^5$, —C(O)O—$(C_1-C_{10})$alkyl, and —(CH$_2$)$_n$—N(R$^6$)$_2$, each of which is optionally substituted by 1, 2 or 3 independently selected R$^9$ groups;

R$^{2a}$ is hydrogen or OH;

R$^{2b}$ is
a) ((6- to 14-membered)aryl) or ((3- to 12-membered)heterocycle), each of which is optionally substituted with one, two, or three independently selected R$^{30}$ groups; or
b) —Z-G-R$^{10}$, provided that —Z-G-R$^{10}$ is other than hydrogen;

or R$^{2a}$ and R$^{2b}$ together form =O;

Z is absent or —(CH$_2$)$_m$—, optionally substituted with 1 or 2-$(C_1-C_6)$alkyl;

G is selected from the group consisting of:
a) a bond, —$(C_1-C_6)$alkylene, —$(C_2-C_6)$alkenylene;
b) O, —OCO—, —C(=O), =CH;
c) NR$^8$, =N—O, =N—NH;
d) S, SO, and SO$_2$;

R$^{10}$ is selected from the group consisting of hydrogen, —$(C_1-C_{10})$alkyl, —$(C_2-C_{12})$alkenyl, —C(=O), —C(=O)—$(C_1-C_6)$alkyl, —C(=O)—$(C_2-C_6)$alkenyl, —C(=O)-(6- to 14-membered)aryl, —C(=O)—$(C_1-C_6)$alkyl-(6- to 14-membered)aryl, —$(C_2-C_{12})$alkynyl, —$(C_1-C_{10})$alkoxy, —(OCH$_2$CH$_2$)$_s$—O$(C_1-C_6)$alkyl, —(CH$_2$CH$_2$O)$_s$—$(C_1-C_6)$alkyl, —NH$_2$, —NH$(C_1-C_6)$alkyl, CN, NR$^5$R$^6$, —$(C_1-C_6)$alkyl-NR$^5$R$^6$, —CONR$^5$R$^6$, —$(C_1-C_6)$alkyl-CO—NR$^5$R$^6$, —COOR$^7$, —$(C_1-C_6)$alkyl-CO—OR$^7$, —$(C_1-C_6)$alkoxy-COOR$^7$, —CO—(CH$_2$)$_n$—COOR$^7$, —CO—(CH$_2$)$_n$—CO—NR$^5$R$^6$, —$(C_3-C_{12})$cycloalkyl, (($C_3-C_{12}$)cycloalkyl)-$(C_1-C_6)$alkyl, —$(C_4-C_{12})$cycloalkenyl, (($C_4-C_{12}$)cycloalkenyl)-$(C_1-C_6)$alkyl-, —$(C_6-C_{14})$bicycloalkyl, (($C_6-C_{14}$)bicycloalkyl)-$(C_1-C_6)$alkyl-, —$(C_8-C_{20})$tricycloalkyl, (($C_8-C_{20}$)tricycloalkyl)-$(C_1-C_6)$alkyl-, —$(C_7-C_{14})$bicycloalkenyl, (($C_7-C_{14}$)bicycloalkenyl)-$(C_1-C_6)$alkyl-, —$(C_8-C_{20})$tricycloalkenyl, (($C_8-C_{20}$)tricycloalkenyl)-$(C_1-C_6)$alkyl-, -(6- to 14-membered)aryl, ((6- to 14-membered)aryl)-$(C_1-C_6)$alkyl-, -(7- to 12-membered)bicyclic ring system, ((7- to 12-membered)bicyclic ring system)-$(C_1-C_6)$alkyl-, -(7- to 12-membered)bicyclic aryl, ((7- to 12-membered)bicyclic aryl)-$(C_1-C_6)$alkyl-, -(5- to 12-membered)heteroaryl, ((5- to 12-membered)heteroaryl)-$(C_1-C_6)$alkyl-, -(3- to 12-membered)heterocycle, ((3- to 12 membered)heterocycle)-$(C_1-C_6)$alkyl-, -(7- to 12-membered)bicycloheterocycle, ((7- to 12-membered)bicycloheterocycle)-$(C_1-C_6)$alkyl-, phenyl, benzyl and naphthyl; each of which is optionally substituted with one, two, or three substituents independently selected from the group consisting of —OH, (=O), halo, —C(halo)$_3$, —CH(halo)$_2$, —CH$_2$(halo), —$(C_1-C_6)$alkyl, halo$(C_1-C_6)$alkyl-, —$(C_2-C_6)$alkenyl, —$(C_2-C_6)$alkynyl, hydroxy$(C_1-C_6)$alkyl-, dihydroxy$(C_1-C_6)$alkyl-, —$(C_1-C_6)$alkoxy, (($C_1-C_6$)alkoxy)CO$(C_1-C_6)$alkoxy-, phenyl, benzyl, —NH$_2$, —NH$(C_1-C_6)$alkyl, —$(C_1-C_6)$alkyl-NH$(C_1-C_6)$alkyl-R$^{14}$, —CN, —SH, —OR$^{11}$, —CONR$^5$R$^6$, —$(C_1-C_6$alkyl)-CO—NR$^5$R$^6$, —COOR$^7$, —$(C_1-C_6)$alkyl-CO—OR$^7$, —$(C_1-C_6)$alkoxy-COOR$^7$, —(OCH$_2$CH$_2$)$_s$—O$(C_1-C_6)$alkyl, —(CH$_2$CH$_2$O)$_s$—$(C_1-C_6)$alkyl, ($C_1-C_6)$alkyl)sulfonyl, (($C_1-C_6)$alkyl)sulfonyl$(C_1-C_6)$alkyl-, —NH—SO$_2$$(C_1-C_6)$alkyl, NH$_2$—SO$_2$$(C_1-C_6)$alkyl-, —N(SO$_2$$(C_1-C_6)$alkyl)$_2$, —C(=NH)NH$_2$, —NH—CO—$(C_1-C_6)$alkyl, —NH—CO—NH$_2$, —NH—C(=O)—NH—$(C_1-C_6)$alkyl, —NH—C(=O)-(6- to 14-membered)aryl, —NH—C(=O)—$(C_1-C_6)$alkyl-(6- to 14-membered)aryl, —NH—$(C_1-C_6)$alkyl-CO—OR$^7$, —NH—C(=O)—$(C_1-C_6)$alkyl-CO—OR$^7$, —NH—C(=O)—CH(NH$_2$)—$(C_1-C_6)$alkyl-CO—OR$^7$, —$(C_3-C_{12})$cycloalkyl, (($C_3-C_{12}$)cycloalkyl)-$(C_1-C_6)$alkyl-, -(6- to 14-membered)aryl, -(6- to 14-membered)aryloxy, —$(C_1-C_6)$alkoxy-C(O)NR$^5$R$^6$, —NH—$(C_1-C_6)$alkyl-C(O)—NR$^5$R$^6$, —C(O)NH—$(C_1-C_6)$alkyl-COOR$^7$, ((6- to 14-membered)aryl)-$(C_1-C_6)$alkyl-, -(5- to 12-membered)heteroaryl, ((5- to 12-membered)heteroaryl)-$(C_1-C_6)$alkyl-, -(3- to 12-membered)heterocycle, ((3- to 12-membered)heterocycle)-$(C_1-C_6)$alkyl-, -(7- to 12-membered)bicycloheterocycle, and ((7- to 12-membered)bicycloheterocycle)-$(C_1-C_6)$alkyl-;

R$^3$ is selected from:
a) —H; or
b) —$(C_1-C_6)$alkyl, —$(C_2-C_6)$alkenyl, or —$(C_2-C_6)$alkynyl;

R$^4$ is selected from
a) —H, —OH, halo, —C(halo)$_3$, —CH(halo)$_2$, —CH$_2$(halo), COOH, or CONH$_2$; or
b) —$(C_1-C_5)$alkyl, —$(C_2-C_5)$alkenyl, —$(C_2-C_5)$alkynyl, —(CH$_2$)$_n$—O—(CH$_2$)$_n$—CH$_3$, or —$(C_1-C_5)$alkoxy, each of which is optionally substituted with 1, 2, or 3 independently selected R$^9$ groups;

R$^5$ and R$^6$ are each independently selected from
a) hydrogen, —OH, halo, —C(halo)$_3$, —CH(halo)$_2$, —CH$_2$(halo);
b) —$(C_1-C_6)$alkyl, —$(C_2-C_5)$alkenyl, —$(C_2-C_5)$alkynyl, —(CH$_2$)$_n$—O—(CH$_2$)$_n$—CH$_3$, —$(C_1-C_6)$alkoxy, each of which is optionally substituted with 1, 2, or 3 substituents independently selected from —OH, halo, —$(C_1-C_{10})$alkyl, —$(C_2-C_{10})$alkenyl, —$(C_2-C_{10})$alkynyl, —$(C_1-C_{10})$alkoxy, —$(C_3-C_{12})$cycloalkyl, —CHO, —C(O)OH, —C(halo)$_3$, —CH(halo)$_2$, CH$_2$(halo), —(CH$_2$)$_n$—O—(CH$_2$)$_n$—CH$_3$, phenyl, or CONR$^5$R$^6$;
c) —$(C_3-C_8)$cycloalkyl, (($C_3-C_8$)cycloalkyl)-$(C_1-C_6)$alkyl-, —COOR$^7$, —$(C_1-C_6)$alkyl-COOR$^7$, —CONH$_2$, or $(C_1-C_6)$alkyl-CONH—;
d) ((6- to 14-membered)aryl) optionally substituted with 1, 2, or 3 independently selected R$^{30}$ groups; or
e) R$^5$ and R$^6$ together with the nitrogen atom to which they are attached form a (4- to 8-membered)heterocycle optionally substituted with 1, 2, or 3 independently selected R$^{30}$ groups;

each R$^7$ is independently selected from the group consisting of hydrogen, —$(C_1-C_6)$alkyl, —$(C_2-C_6)$alkenyl, —$(C_2-C_6)$alkynyl, —$(C_3-C_{12})$cycloalkyl, —$(C_4-C_{12})$cycloalkenyl, (($C_3-C_{12}$)cycloalkyl)-$(C_1-C_6)$alkyl-, and (($C_4-C_{12}$)cycloalkenyl)-$(C_1-C_6)$alkyl-;

each R$^8$ is independently selected from H, —$(C_1-C_6)$alkyl, —$(C_2-C_6)$alkenyl, —$(C_2-C_6)$alkynyl, —$(C_1-C_{10})$alkoxy, —$(C_3-C_{12})$cycloalkyl, —$(C_3-C_{12})$cycloalkenyl, (($C_3-C_{12}$)cycloalkyl)-$(C_1-C_6)$alkyl-, (($C_3-C_{12}$)cycloalkenyl)-$(C_1-C_6)$alkyl-, —C(=O)$(C_1-C_6)$alkyl or SO$_2$$(C_1-C_6)$alkyl;

each R$^9$ is independently selected from —OH, halo, —$(C_1-C_{10})$alkyl, —$(C_2-C_{10})$alkenyl, —$(C_2-C_{10})$alkynyl, —$(C_1-C_{10})$alkoxy, —$(C_3-C_{12})$cycloalkyl, —CHO, —C(O)OH, —C(halo)$_3$, —CH(halo)$_2$, CH$_2$(halo), —(CH$_2$)$_n$—O—(CH$_2$)$_n$—CH$_3$, phenyl, or CONR$^5$R$^6$;

each R$^{11}$ is independently selected from —C(halo)$_3$, —CH(halo)$_2$, —CH$_2$(halo), —$(C_2-C_5)$alkenyl, —$(C_2-C_5)$alkynyl, —(CH$_2$)$_n$—O—(CH$_2$)$_n$—CH$_3$, (6- to 14-membered)aryl, ((6- to 14-membered)aryl)-$(C_1-C_6)$alkyl-, or (5- to 12-membered)heteroaryl, ((5- to 12-membered)heteroaryl)-$(C_1-C_6)$ alkyl-, each of which is optionally substituted with 1, 2, or 3 independently selected $R^9$ groups;

each $R^{14}$ is independently selected from —COOR$^7$, —(C$_1$-C$_6$)alkyl-COOR$^7$, —C(=O)—(C$_1$-C$_6$)alkyl-COOR$^7$, —(C$_1$-C$_6$)alkyl-C(=O)—(C$_1$-C$_6$)alkyl-COOR$^7$, CONH$_2$, or —(C$_1$-C$_6$)alkyl-CONH;

each $R^{30}$ is independently selected from COOR$^7$, CONR$^5$R$^6$, —(C$_1$-C$_6$)alkyl, CN, -(3- to 12-membered)heteroaryl, ((3- to 12-membered)heteroaryl)-(C$_1$-C$_6$)alkyl-, NH$_2$, halo, and ((6- to 14-membered)aryl)-(C$_1$-C$_6$)alkoxy-;

m is an integer 1, 2, 3, 4, 5, or 6;

n is an integer 0, 1, 2, 3, 4, 5, or 6;

s in an integer 1, 2, 3, 4, 5, or 6;

provided that when $R^4$ is —(C$_1$-C$_5$)alkoxy then:
  a) $R^{2a}$ and $R^{2b}$ cannot be taken together to form =O; or
  b) $R^{2a}$ cannot be OH when $R^{2b}$ is —Z-G-R$^{10}$, and —Z-G-R$^{10}$ is either:
    a. OH; or
    b. —(C$_1$-C$_6$)alkyl; or
  c) $R^{2a}$ cannot be H when the combination —Z-G-R$^{10}$ is OH;

and the pharmaceutically acceptable salts, prodrugs and solvates thereof.

In one embodiment, the present invention provides novel compounds of Formula IA:

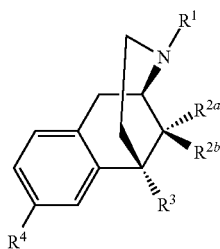

IA wherein $R^1$, $R^{2a}$, $R^{2b}$, $R^3$ and $R^4$ are as defined above for Formula I, and the pharmaceutically acceptable salts, prodrugs and solvates thereof.

In another embodiment, the present invention provides novel compounds of Formula IB:

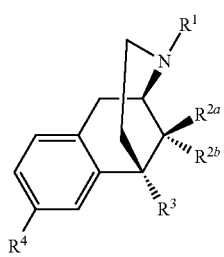

IB wherein $R^1$, $R^{2a}$, $R^{2b}$, $R^3$ and $R^4$ are as defined above for Formula I, and the pharmaceutically acceptable salts, prodrugs and solvates thereof.

In another embodiment, the present invention provides novel compounds of Formula IC:

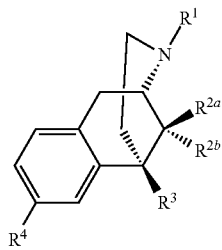

IC wherein $R^1$, $R^{2a}$, $R^{2b}$, $R^3$ and $R^4$ are as defined above for Formula I, and the pharmaceutically acceptable salts, prodrugs and solvates thereof.

In another embodiment, the present invention provides novel compounds of Formula ID:

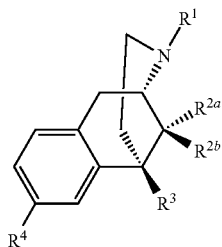

ID wherein $R^1$, $R^{2a}$, $R^{2b}$, $R^3$ and $R^4$ are as defined above for Formula I, and the pharmaceutically acceptable salts, prodrugs and solvates thereof.

It is an object of certain embodiments of the present invention to provide new Compounds of the Invention that have antagonist activity at the ORL-1 receptor which is greater than compounds currently available, e.g., JTC-801 (described in WO 99/48492; and Shinkai et al., "4-aminoquinolines: Novel nociceptin antagonists with analgesic activity", *J. Med. Chem.*, 2000, 43:4667-4677) and J-113397 (described in WO 98/54168; and Kawamoto et al., "Discovery of the first potent and selective small molecule opioid receptor-like (ORL-1) antagonist: 1-[(3R,4R)-1-cyclooctylmethyl-3-hydroxymethyl-4-piperidyl]-3-ethyl-1,3-dihydro-2H-benzimidazol-2-one (J-113397)", *J. Med. Chem.*, 1999, 42:5061-6063).

Certain Compounds of the Invention have agonist activity at the μ, δ and/or κ receptors which is greater than currently available compounds, e.g., morphine.

Certain Compounds of the Invention have both: (i) antagonist activity at the ORL-1 receptor; and (ii) agonist activity at one or more of the μ, δ and/or κ opioid receptors. Certain Compounds of the Invention have both: (i) antagonist activity at the ORL-1 receptor; and (ii) agonist activity at the μ opioid receptor. Certain compounds of the invention have both: (i) antagonist activity at the μ opioid receptor; and (ii) agonist activity at the κ opioid receptor. Certain compounds of the invention have: (i) antagonist activity at the ORL-1 receptor; (ii) agonist activity at the μ opioid receptor; and (iii) agonist activity at the κ opioid receptor. Certain compounds of the invention have: (i) antagonist activity at the μ opioid receptor; (ii) agonist activity at the κ opioid receptor; and (iii) antagonist activity at the δ opioid receptor.

Compounds of the Invention may be useful as analgesics; anti-inflammatories; diuretics; anesthetics; neuroprotective agents; anti-hypertensives; anxiolytics; agents for appetite control; hearing regulators; anti-tussives; anti-asthmatics; anti-epileptics; anti-convulsants; modulators of locomotor activity; modulators of learning and memory; regulators of neurotransmitter release; modulators of hormone release; kidney function modulators; anti-depressants; agents to treat memory loss due to Alzheimer's disease or other dementias; agents to treat withdrawal from alcohol and/or drugs of addiction; agents to control water balance or sodium excretion; agents to treat arterial blood pressure disorders, or any of the following: UI, ulcers, IBD, IBS, diarrhea, constipation, addictive disorders, Parkinson's disease, parkinsonism, anxiety, epilepsy, stroke, a seizure, pruritic conditions, psychosis, cognitive disorders, memory deficits, restricted brain function, Huntington's chorea, ALS, dementia, retinopathy, muscle spasms, migraines, vomiting, dyskinesia, and/or depression (each being a "Condition").

The present invention further provides methods for treating a Condition, comprising administering to a subject in need thereof a therapeutically effective amount of a Compound of the Invention. In certain embodiments, the Condition is pain (chronic or acute pain). The Compounds of the Invention are particularly useful for treating chronic pain. In certain embodiments, the Compound of the Invention is an ORL-1 receptor antagonist. In other embodiments, the Compound of the Invention is an agonist at one or more of the $\mu$, $\delta$ and/or $\kappa$ opioid receptors. In other embodiments, the Compound of the Invention is both an ORL-1 receptor antagonist and an agonist at one or more of the $\mu$, $\delta$ and/or $\kappa$ opioid receptors. In other embodiments, the Compound of the Invention is both an ORL-1 receptor antagonist and an agonist at the $\mu$ opioid receptor. In certain non-limiting embodiments, the Compound of the Invention produces fewer side effects and/or less severe side effects than currently available analgesic opioid compounds when administered at doses producing equivalent levels of analgesia and/or anti-hyperalgesia.

In certain non-limiting embodiments, the Compound of the Invention exhibits a substantially linear dose response curve, such that the bell-shaped dose response curve observed for most opioid analgesics (i.e. low and high doses do not produce significant analgesia, whereas mid-range doses produce analgesia) is not observed for the Compound of the Invention. It is expected, therefore, that it will be easier to titrate to an effective dose of the Compound of the Invention in a patient than it is for conventional opioid analgesics. It is further expected that the Compound of the Invention will produce effective analgesia and/or anti-hyperalgesia in a patient who has become tolerant to conventional opioids, and for whom a conventional opioid is no longer an effective treatment. It is further expected that a Compound of the Invention will produce effective analgesia and/or anti-hyperalgesia at doses that do not induce side effects such as respiratory depression in patients for whom a dose of a conventional opioid that is high enough to be an effective treatment also induces significant side effects such as respiratory depression.

The present invention further provides methods for preventing a Condition, comprising administering to s a subject in need thereof a Condition-preventing effective amount of a Compound of the Invention.

Another object of the invention is to provide benzomorphan analog compounds useful for treating or preventing constipation, preferably $\mu$ opioid receptor-induced constipation. More specifically, the present invention provides Compounds of the Invention having activity as $\mu$ opioid receptor antagonists. In certain embodiments, Compounds of the Invention are expected to have dual activity as both $\mu$ opioid receptor antagonists and $\kappa$ opioid receptor agonists. In other embodiments, Compounds of the Invention are expected to be $\mu$ opioid receptor antagonists, $\kappa$ opioid receptor agonists, $\delta$ opioid receptor antagonists, and inactive at ORL-1 receptors. In yet other embodiments, certain Compounds of the Invention are expected to be $\mu$ opioid receptor antagonists, $\kappa$ opioid receptor agonists, $\delta$ opioid receptor antagonists, and ORL-1 receptor antagonists. In other embodiments, certain Compounds of the Invention are expected to be $\mu$ opioid receptor antagonists, $\kappa$ opioid receptor agonists, $\delta$ opioid receptor antagonists, and ORL-1 receptor partial agonists. In certain embodiments, Compounds of the Invention will be inactive at $\delta$ opioid receptors. Certain Compounds of the Invention are expected to be substantially restricted to the GI tract.

Compounds of the Invention that have $\mu$ opioid receptor antagonist activity and are substantially restricted to the GI tract will significantly reduce or prevent constipation that would otherwise occur in a patient as a result of treatment with a $\mu$ opioid receptor agonist. In one embodiment, the reduction or prevention of constipation is obtained without reducing the desired analgesic effect of the $\mu$ agonist. Compounds of the Invention that also exhibit $\kappa$ opioid receptor agonist activity should additionally stimulate GI motility via a non-$\mu$ receptor mediated mechanism.

The present invention provides a method for treating or preventing a Condition in a subject. In certain embodiments, the Condition treated will be pain (acute or chronic pain). The present invention further provides a method for treating or preventing constipation, preferably constipation associated with $\mu$-opioid agonist therapy, by administering an effective amount of a Compound of the Invention to a patient in need of such treatment or prevention. In one embodiment, the Compound of the Invention is a $\mu$ antagonist that is substantially restricted to the GI tract. In another embodiment, the Compound of the Invention is both a $\mu$ antagonist and a $\kappa$ agonist, and is substantially restricted to the GI tract. In another embodiment, the method comprises co-administering to a patient both an effective amount of a Compound of the Invention that is a $\mu$ antagonist and is substantially restricted to the GI tract, and an analgesically effective amount of a $\mu$ agonist. In another embodiment, the method comprises co-administration to a patient of both an effective amount of a Compound of the Invention that is both a $\mu$ antagonist and a $\kappa$ agonist, and which is substantially restricted to the GI tract, and an analgesically effective amount of a $\mu$ agonist.

The present invention further provides pharmaceutical compositions comprising a therapeutically effective amount of a Compound of the Invention admixed with a pharmaceutically acceptable carrier or excipient. Such compositions are useful for treating or preventing a Condition in a subject. The pharmaceutical compositions of the present invention may be formulated as immediate release formulations, or as controlled or sustained release formulations. Pharmaceutical compositions of the present invention may be formulated for administration by any of a number of different routes known in the art, including but not limited to, oral, intradermal, intramuscular, intraperitoneal, parenteral, intravenous, subcutaneous, intranasal, epidural, sublingual, intracerebral, intravaginal, transdermal, transmucosal, rectal, by inhalation, or topical (particularly to the ears, nose, eyes, or skin).

The present invention further provides methods for preparing a composition, comprising the step of admixing a Compound of the Invention and a pharmaceutically acceptable carrier or excipient to form a pharmaceutical composition.

The present invention further provides the use of a Compound of the Invention in the manufacturing of a medicament useful to treat or prevent a Condition in a subject.

The invention still further relates to a kit comprising a container (preferably sterile) containing an effective amount of a Compound of the Invention.

DETAILED DESCRIPTION OF THE INVENTION

The Compounds of the Invention are novel benzomorphan analogs. They are useful for treating or preventing one or more Conditions, such as pain or constipation. Compounds of the Invention may provide a reduced liability for developing analgesic tolerance and physical dependence.

Compounds of the Invention are useful for modulating a pharmacodynamic response from ORL-1 receptors either centrally or peripherally, or both. Compounds of the Invention may also be useful for modulating a pharmacodynamic response from one or more opioid receptors (μ, δ, κ) either centrally or peripherally, or both. The pharmacodynamic response may be attributed to the compound stimulating (agonizing) or inhibiting (antagonizing) the one or more receptors. Certain Compounds of the Invention may inhibit (or antagonize) the ORL-1 receptor, while also stimulating (or agonizing) one or more other opioid receptors (e.g. as a μ, δ and/or κ agonist). Compounds of the Invention having agonist activity may be either full or partial agonists.

In certain embodiments, Compounds of the Invention can be used in combination with at least one other therapeutic agent. The other therapeutic agent can be, but is not limited to, a μ-opioid agonist, a non-opioid analgesic, a non-steroidal anti-inflammatory agent, a Cox-II inhibitor, an antiemetic, β-adrenergic blocker, an anticonvulsant, an antidepressant, a $Ca^{2+}$-channel blocker, an anticancer agent, or a mixture thereof.

Various objects and advantages of the present invention will become apparent from the following detailed description.

The present invention provides novel compounds of Formula I":

I"

wherein
$R^1$ is selected from the group consisting of —$(C_1$-$C_{10})$alkyl, $(C_2$-$C_{10})$alkenyl, $(C_2$-$C_{10})$alkynyl, —$(C_3$-$C_{12})$cycloalkyl, $(C_3$-$C_{12})$cycloalkyl-$(C_1$-$C_6)$alkyl-, $(C_3$-$C_{12})$cycloalkenyl, $(C_3$-$C_{12})$cycloalkenyl-$(C_1$-$C_6)$alkyl-, -(6- to 14-membered)aryl, ((6- to 14-membered)aryl)-$(C_1$-$C_6)$alkyl-, diphenyl$(C_1$-$C_6)$alkyl-, -(3- to 12-membered)heterocycle, ((3- to 12 membered)heterocycle)-$(C_1$-$C_6)$alkyl-, —$(OCH_2CH_2)_s$—O$(C_1$-$C_6)$alkyl, —$(CH_2CH_2O)_s$—$(C_1$-$C_6)$alkyl, $(C_1$-$C_{10})$alkoxy, C(halo)$_3$, CH(halo)$_2$, CH$_2$(halo), C(O)$R^5$, —C(O)O—$(C_1$-$C_{10})$alkyl, and —$(CH_2)_n$—N$(R^6)_2$, each of which is optionally substituted by 1, 2 or 3 independently selected $R^9$ groups;
$R^{2a}$ is hydrogen, OH, or absent;
$R^{2b}$ is
  a) ((6- to 14-membered)aryl), -((5- to 12-membered)heteroaryl), or ((3- to 12-membered)heterocycle), each of which is optionally substituted with one, two, or three independently selected $R^{30}$ groups; or
  b) —Z-G-$R^{10}$, provided that —Z-G-$R^{10}$ is other than hydrogen;
or $R^{2a}$ and $R^{2b}$ together form =O;
Z is absent or —$(CH_2)_m$—, optionally substituted with 1 or 2 $(C_1$-$C_6)$alkyl;
G is selected from the group consisting of:
  a) a bond, —$(C_1$-$C_6)$alkylene, —$(C_2$-$C_6)$alkenylene;
  b) O, —OCO—, —C(=O), =CH;
  c) $NR^8$, =N—O, =N—NH;
  d) S, SO, $SO_2$; and
  e) —NH—$SO_2$;
and when Z is absent and G is =CH, =N—O, or =N—NH, then $R^{2a}$ is absent;
$R^{10}$ is selected from the group consisting of hydrogen, —$(C_1$-$C_{10})$alkyl, —$(C_2$-$C_{12})$alkenyl, —C(=O), —C(=O)—$(C_1$-$C_6)$alkyl, —C(=O)—$(C_2$-$C_6)$alkenyl, —C(=O)-(6- to 14-membered)aryl, —C(=O)—$(C_1$-$C_6)$alkyl-(6- to 14-membered)aryl, —$(C_2$-$C_{12})$alkynyl, —$(C_1$-$C_{10})$alkoxy, —$(OCH_2CH_2)_s$—O(C)—$C_6$)alkyl, —$(CH_2CH_2O)_s$—$(C_1$-$C_6)$alkyl, —$NH_2$, —NH$(C_1$-$C_6)$alkyl, CN, $NR^5R^6$, —$(C_1$-$C_6)$alkyl-$NR^5R^6$, —CON$R^5R^6$, —$(C_1$-$C_6)$alkyl-CO—$NR^5R^6$, —$COOR^7$, —$(C_1$-$C_6)$alkyl-CO—$OR^7$, —$(C_1$-$C_6)$alkoxy-$COOR^7$, —CO—$(CH_2)_n$—$COOR^7$, —CO—$(CH_2)_n$—CO—$NR^5R^6$, —$(C_3$-$C_{12})$cycloalkyl, $((C_3$-$C_{12})$cycloalkyl)-$(C_1$-$C_6)$alkyl, —$(C_4$-$C_{12})$cycloalkenyl, $((C_4$-$C_{12})$cycloalkenyl)-$(C_1$-$C_6)$alkyl-, —$(C_6$-$C_{14})$bicycloalkyl, $((C_6$-$C_{14})$bicycloalkyl)-$(C_1$-$C_6)$alkyl-, —$(C_8$-$C_{20})$tricycloalkyl, $((C_8$-$C_{20})$tricycloalkyl)-$(C_1$-$C_6)$alkyl-, —$(C_7$-$C_{14})$bicycloalkenyl, $((C_7$-$C_{14})$bicycloalkenyl)-$(C_1$-$C_6)$alkyl-, —$(C_8$-$C_{20})$tricycloalkenyl, $((C_8$-$C_{20})$tricycloalkenyl)-$(C_1$-$C_6)$alkyl-, -(6- to 14-membered)aryl, ((6- to 14-membered)aryl)-$(C_1$-$C_6)$alkyl-, —$SO_2$—$(C_1$-$C_6)$alkyl, —$SO_2$—$((C_3$-$C_{12})$cycloalkyl), —$SO_2$—$((C_3$-$C_{12})$cycloalkyl)-$(C_1$-$C_6)$alkyl, —$SO_2$-((5- to 12-membered)heteroaryl), —$SO_2$-((5- to 12-membered)heteroaryl)-$(C_1$-$C_6)$alkyl, —C(=O)—NH-((5- to 12-membered)heteroaryl), —C(=O)—NH-((5- to 12-membered)heteroaryl)-$(C_1$-$C_6)$alkyl, —C(=O)—NH-((3- to 12-membered)heterocycle), —C(=O)—NH-((3- to 12-membered)heterocycle)-$(C_1$-$C_6)$alkyl, $SO_2$— ((6- to 14-membered)aryl), $SO_2$-((6- to 14 membered)aryl)-$(C_1$-$C_6)$alkyl, -(7- to 12-membered)bicyclic ring system, ((7- to 12-membered)bicyclic ring system)-$(C_1$-$C_6)$alkyl-, -(7- to 12-membered)bicyclic aryl, ((7- to 12-membered)bicyclic aryl)-$(C_1$-$C_6)$alkyl-, -(5- to 12-membered)heteroaryl, ((5- to 12-membered)heteroaryl)-$(C_1$-$C_6)$alkyl-, -(3- to 12-membered)heterocycle, ((3- to 12 membered)heterocycle)-$(C_1$-$C_6)$alkyl-, -(7- to 12-membered)bicycloheterocycle, ((7- to 12-membered) bicycloheterocycle)-$(C_1$-$C_6)$alkyl-, phenyl, benzyl and naphthyl; each of which is optionally substituted with one, two, or three substituents independently selected from the group consisting of —OH, (=O), halo, —C(halo)$_3$, —CH(halo)$_2$, —CH$_2$(halo), —$(C_1$-$C_6)$alkyl, halo$(C_1$-$C_6)$alkyl-, —$(C_2$-$C_6)$alkenyl, —$(C_2$-$C_6)$alkynyl, hydroxy$(C_1$-$C_6)$alkyl-, dihydroxy$(C_1$-$C_6)$alkyl-, —$(C_1$-$C_6)$alkoxy, $((C_1$-$C_6)$alkoxy)CO$(C_1$-$C_6)$alkoxy-, phenyl, benzyl, —$NH_2$, —NH (C$_1$-C$_6$)alkyl, —(C$_1$-C$_6$)alkyl-NH(C$_1$-C$_6$)alkyl-R$^{14}$, —CN, —SH, —OR$^{11}$, —CONR$^5$R$^6$, —(C$_1$-C$_6$alkyl)-CO—NR$^5$R$^6$, —COOR$^7$, —(C$_1$-C$_6$)alkyl-CO—OR$^7$, —(C$_1$-C$_6$)alkyl-COOR$^7$, —(OCH$_2$CH$_2$)$_s$—O(C$_1$-C$_6$)alkyl, —(CH$_2$CH$_2$O)$_s$—(C$_1$-C$_6$)alkyl, —SO$_2$—NR$^{5a}$R$^{6a}$, (C$_1$-C$_6$)alkyl sulfonyl, ((C$_1$-C$_6$)alkyl)sulfonyl(C$_1$-C$_6$)alkyl-, —NH—SO$_2$(C$_1$-C$_6$)alkyl, NH$_2$—SO$_2$(C$_1$-C$_6$)alkyl-, —N(SO$_2$(C$_1$-C$_6$)alkyl)$_2$, —C(=NH)NH$_2$, —NH—CO—(C$_1$-C$_6$)alkyl, —NH—CO—NH$_2$, —NH—C(=O)—NH—(C$_1$-C$_6$)alkyl, —NH—C(=O)-(6- to 14-membered)aryl, —NH—C(=O)— (C$_1$-C$_6$)alkyl-(6- to 14-membered)aryl, —NH—(C$_1$-C$_6$)alkyl-CO—OR$^7$, —NH—C(=O)—(C$_1$-C$_6$)alkyl-CO—OR$^7$, —NH—C(=O)—CH(NH$_2$)—(C$_1$-C$_6$)alkyl-CO—OR$^7$, —(C$_3$-C$_{12}$)cycloalkyl, ((C$_3$-C$_{12}$)cycloalkyl)-(C$_1$-C$_6$)alkyl-, -(6- to 14-membered)aryl, -(6- to 14-membered)aryloxy, —(C$_1$-C$_6$)alkoxy-C(O)NR$^5$R$^6$, —NH—(C$_1$-C$_6$)alkyl-C(O)—NR$^5$R$^6$, —C(O)NH—(C$_1$-C$_6$)alkyl-COOR$^7$, ((6- to 14-membered)aryl)-(C$_1$-C$_6$)alkyl-, -(5- to 12-membered)heteroaryl, ((5- to 12-membered)heteroaryl)-(C$_1$-C$_6$)alkyl-, -(3- to 12-membered)heterocycle, ((3- to 12-membered)heterocycle)-(C$_1$-C$_6$)alkyl-, -(7- to 12-membered)bicycloheterocycle, and ((7- to 12-membered)bicycloheterocycle)-(C$_1$-C$_6$)alkyl-;

R$^3$ is selected from:
a) —H; or
b) —(C$_1$-C$_6$)alkyl, —(C$_2$-C$_6$)alkenyl, or —(C$_2$-C$_6$)alkynyl;

R$^4$ is selected from
a) —H, —OH, halo, —C(halo)$_3$, —CH(halo)$_2$, —CH$_2$(halo), COOH, or CONH$_2$; or
b) —(C$_1$-C$_5$)alkyl, —(C$_2$-C$_5$)alkenyl, —(C$_2$-C$_5$)alkynyl, —(CH$_2$)$_n$—O—(CH$_2$)$_n$—CH$_3$, or —(C$_1$-C$_5$)alkoxy, each of which is optionally substituted with 1, 2, or 3 independently selected R$^9$ groups;

R$^5$ and R$^6$ are each independently selected from
a) hydrogen, —OH, halo, —C(halo)$_3$, —CH(halo)$_2$, —CH$_2$(halo);
b) —(C$_1$-C$_6$)alkyl, —(C$_2$-C$_5$)alkenyl, —(C$_2$-C$_5$)alkynyl, —(CH$_2$)$_n$—O—(CH$_2$)$_n$—CH$_3$, —(C$_1$-C$_6$)alkoxy, each of which is optionally substituted with 1, 2, or 3 substituents independently selected from —OH, halo, —(C$_1$-C$_{10}$)alkyl, —(C$_2$-C$_{10}$)alkenyl, —(C$_2$-C$_{10}$)alkynyl, —(C$_1$-C$_{10}$)alkoxy, —(C$_3$-C$_{12}$)cycloalkyl, —CHO, —C(O)OH, —C(halo)$_3$, —CH(halo)$_2$, CH$_2$(halo), —(CH$_2$)$_n$—O—(CH$_2$)$_n$—CH$_3$, phenyl, or CONR$^{5a}$R$^{6a}$;
c) —(C$_3$-C$_8$)cycloalkyl, ((C$_3$-C$_8$)cycloalkyl)-(C$_1$-C$_6$)alkyl-, —COOR$^7$, —(C$_1$-C$_6$)alkyl-COOR$^7$, —CONH$_2$, or (C$_1$-C$_6$)alkyl-CONH—;
d) ((6- to 14-membered)aryl) optionally substituted with 1, 2, or 3 independently selected R$^{30}$ groups;
e) -((5- to 12-membered)heteroaryl) optionally substituted with 1, 2, or 3 independently selected R$^{30}$ groups; or
f) R$^5$ and R$^6$ together with the nitrogen atom to which they are attached form a (3- to 12-membered)heterocycle optionally substituted with 1, 2, or 3 independently selected R$^{30}$ groups;

R$^{5a}$ and R$^{6a}$ are each independently selected from the group consisting of:
a) hydrogen, —OH, halo, —C(halo)$_3$, —CH(halo)$_2$, and —CH$_2$(halo);
b) —(C$_1$-C$_6$)alkyl, —(C$_2$-C$_6$)alkenyl, —(C$_2$-C$_6$)alkynyl, —(CH$_2$)$_n$—O—(CH$_2$)$_n$—CH$_3$, and —(C$_1$-C$_6$)alkoxy, each of which is optionally substituted with 1, 2, or 3 substituents independently selected from —OH, halo, —(C$_1$-C$_{10}$)alkyl, —(C$_2$-C$_{12}$)alkenyl, —(C$_2$-C$_{12}$)alkynyl, —(C$_1$-C$_{10}$)alkoxy, —(C$_3$-C$_{12}$)cycloalkyl, —CHO, —COOH, —C(halo)$_3$, —CH(halo)$_2$, CH$_2$(halo), —(CH$_2$)$_n$—O—(CH$_2$)$_n$—CH$_3$, and phenyl;
c) —(C$_3$-C$_8$)cycloalkyl, ((C$_3$-C$_8$)cycloalkyl)-(C$_1$-C$_6$)alkyl-, —COOR$^7$, —(C$_1$-C$_6$)alkyl-COOR$^7$, —CONH$_2$, and (C$_1$-C$_6$)alkyl-CONH—;
d) -(6- to 14-membered)aryl optionally substituted with 1, 2, or 3 independently selected R$^{30}$ groups;
e) -((5- to 12-membered)heteroaryl) optionally substituted with 1, 2, or 3 independently selected R$^{30}$ groups; or
f) R$^{5a}$ and R$^{6a}$ together with the nitrogen atom to which they are attached form a (3- to 12-membered)heterocycle optionally substituted with 1, 2, or 3 independently selected R$^{30}$ groups;

each R$^7$ is independently selected from the group consisting of hydrogen, —(C$_1$-C$_6$)alkyl, —(C$_2$-C$_6$)alkenyl, —(C$_2$-C$_6$)alkynyl, —(C$_3$-C$_{12}$)cycloalkyl, —(C$_4$-C$_{12}$)cycloalkenyl, ((C$_3$-C$_{12}$)cycloalkyl)-(C$_1$-C$_6$)alkyl-, and ((C$_4$-C$_{12}$)cycloalkenyl)-(C$_1$-C$_6$)alkyl-;

each R$^8$ is independently selected from H, —(C$_1$-C$_6$)alkyl, —(C$_2$-C$_6$)alkenyl, —(C$_2$-C$_6$)alkynyl, —(C$_1$-C$_{10}$)alkoxy, —(C$_3$-C$_{12}$)cycloalkyl, —(C$_3$-C$_{12}$)cycloalkenyl, ((C$_3$-C$_{12}$)cycloalkyl)-(C$_1$-C$_6$)alkyl-, ((C$_3$-C$_{12}$)cycloalkenyl)-(C$_1$-C$_6$)alkyl-, —C(=O)(C$_1$-C$_6$)alkyl or SO$_2$(C$_1$-C$_6$)alkyl;

each R$^9$ is independently selected from —OH, halo, —(C$_1$-C$_{10}$)alkyl, —(C$_2$-C$_{10}$)alkenyl, —(C$_2$-C$_{10}$)alkynyl, —(C$_1$-C$_{10}$)alkoxy, —(C$_3$-C$_{12}$)cycloalkyl, —CHO, —C(O)OH, —C(halo)$_3$, —CH(halo)$_2$, CH$_2$(halo), —(CH$_2$)$_n$—O—(CH$_2$)$_n$—CH$_3$, phenyl, or CONR$^{5a}$R$^{6a}$;

each R$^{11}$ is independently selected from —C(halo)$_3$, —CH(halo)$_2$, —CH$_2$(halo), —(C$_2$-C$_5$)alkenyl, —(C$_2$-C$_5$)alkynyl, —(CH$_2$)$_n$—O—(CH$_2$)$_n$—CH$_3$, (6- to 14-membered)aryl, ((6- to 14-membered)aryl)-(C$_1$-C$_6$)alkyl-, or (5- to 12-membered)heteroaryl, ((5- to 12-membered)heteroaryl)-(C$_1$-C$_6$)alkyl-, each of which is optionally substituted with 1, 2, or 3 independently selected R$^9$ groups;

each R$^{14}$ is independently selected from —COOR$^7$, —(C$_1$-C$_6$)alkyl-COOR$^7$, —C(=O)—(C$_1$-C$_6$)alkyl-COOR$^7$, —(C$_1$-C$_6$)alkyl-C(=O)—(C$_1$-C$_6$)alkyl-COOR$^7$, CONH$_2$, or —(C$_1$-C$_6$)alkyl-CONH;

each R$^{30}$ is independently selected from COOR$^7$, CONR$^{5a}$R$^{6a}$, —(C$_1$-C$_6$)alkyl, —C(=O), CN, -(3- to 12-membered)heteroaryl, ((3- to 12-membered)heteroaryl)-(C$_1$-C$_6$)alkyl-, NH$_2$, halo, and ((6- to 14-membered)aryl)-(C$_1$-C$_6$)alkoxy-;

m is an integer 1, 2, 3, 4, 5, or 6;
n is an integer 0, 1, 2, 3, 4, 5, or 6;
s in an integer 1, 2, 3, 4, 5, or 6;

provided that when R$^4$ is —(C$_1$-C$_5$)alkoxy then:
a) R$^{2a}$ and R$^{2b}$ cannot be taken together to form =O; or
b) R$^{2a}$ cannot be OH when R$^{2b}$ is —Z-G-R$^{10}$, and —Z-G-R$^{10}$ is either:
a. OH;
b. —(C$_1$-C$_6$)alkyl;
c. 2-propenyl;
d. 2-propynyl; or
c) R$^{2a}$ cannot be H when the combination —Z-G-R$^{10}$ is either: OH;
a. OH;
b. O—C(=O)—(C$_1$-C$_6$)alkyl; or
c. O—C(=O)—(C2-C6)alkenyl;

and provided that when R$^4$ is OH then:
a) R$^{2a}$ cannot be OH when R$^{2b}$ is —Z-G-R$^{10}$, and —Z-G-R$^{10}$ is:
e. methyl;
f. ethyl;

g. 2-propenyl; or h. 2-propynyl;

b) $R^{2a}$ cannot be H when $R^{2b}$ is —Z-G-$R^{10}$, and —Z-G-$R^{10}$ is either:

a. OH;

b. —O—C(=O)—($C_1$-$C_6$)alkyl; or c. —O—C(=O)—($C_2$-$C_6$)alkenyl;

and provided that when $R^3$ is ($C_1$-$C_6$)alkyl or ($C_2$-$C_6$)alkenyl, and $R^4$ is H, OH, or ($C_1$-$C_5$)alkoxy, then $R^{2b}$ is not:

a) optionally substituted (5- to 12-membered)heteroaryl;

b) optionally substituted (3- to 12-membered)heterocycle; or c) unsubstituted phenyl or phenyl substituted with F or Cl, methyl, $CF_3$, hydroxy, methoxy, (3- to 12-membered) heterocycle, or $NH_2$;

and provided that when $R^4$ is OH and $R^1$ is ($C_1$-$C_{10}$)alkyl, then $R^{2a}$ and $R^{2b}$ cannot be together selected =O;

and provided that when $R^4$ is hydrogen and when $R^1$ and $R^3$ are both methyl, then:

a) $R^{2a}$ and $R^{2b}$ cannot together form =O or =N—OH; or b) $R^{2b}$ may not be $NH_2$ or NHC(O)$CH_3$ if $R^{2a}$ is hydrogen;

and provided that when $R^{2a}$ is H, then $R^{2b}$ may not be —Z-G-$R^{10}$, wherein —Z-G-$R^{10}$ is:

a) —$CH_2$—CHR$^{20}$—C(=O)R$^{21}$, wherein $R^{20}$ is H, or —($C_1$-$C_6$)alkyl, and $R^{21}$ is selected from the group consisting of H, —($C_1$-$C_{10}$)alkyl, —($C_3$-$C_{12}$)cycloalkyl, (($C_3$-$C_{12}$)cycloalkyl)-($C_1$-$C_6$)alkyl-, phenyl, and phenyl-($C_1$-$C_6$)alkyl; or b) —$CH_2$—CHR$^{20}$—CR$^{22}$R$^{23}$OH, wherein $R^{20}$ is defined as above, and $R^{22}$ and $R^{23}$ are each independently selected from the group consisting of H, —($C_1$-$C_{10}$)alkyl, (($C_3$-$C_{12}$)cycloalkyl)-($C_1$-$C_6$)alkyl-, phenyl, and phenyl-($C_1$-$C_6$)alkyl; or c) —$CH_2$—CR$^{20}$=CR$^{23}$R$^{24}$, wherein $R^{20}$ and $R^{23}$ are defined as above, and $R^{24}$ is selected from the group consisting of H, and —($C_1$-$C_6$)alkyl;

and the pharmaceutically acceptable salts and solvates thereof.

In one embodiment, the present invention provides novel compounds of Formula IA":

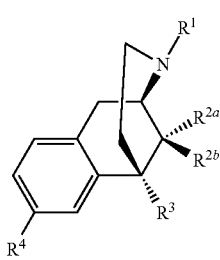

IA"

wherein $R^1$, $R^{2a}$, $R^{2b}$, $R^3$ and $R^4$ are as defined above for Formula I", and the pharmaceutically acceptable salts and solvates thereof.

In another embodiment, the present invention provides novel compounds of Formula IB":

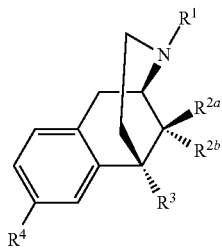

IB"

wherein $R^1$, $R^{2a}$, $R^{2b}$, $R^3$ and $R^4$ are as defined above for Formula I", and the pharmaceutically acceptable salts and solvates thereof.

In another embodiment, the present invention provides novel compounds of Formula IC":

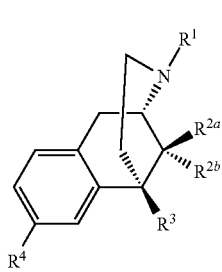

IC"

wherein $R^1$, $R^{2a}$, $R^{2b}$, $R^3$ and $R^4$ are as defined above for Formula I", and the pharmaceutically acceptable salts and solvates thereof.

In another embodiment, the present invention provides novel compounds of Formula ID":

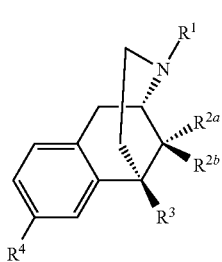

ID"

wherein $R^1$, $R^{2a}$, $R^{2b}$, $R^3$ and $R^4$ are as defined above for Formula I", and the pharmaceutically acceptable salts and solvates thereof.

In one embodiment, the present invention provides novel compounds of Formula I":

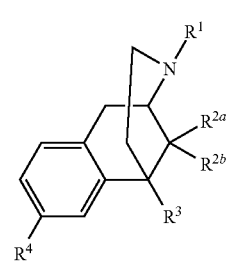

I"

wherein $R^1$ is selected from the group consisting of —($C_1$-$C_{10}$)alkyl, —($C_2$-$C_{10}$)alkenyl, —($C_2$-$C_{10}$)alkynyl, —($C_3$-$C_{12}$)cycloalkyl, $(C_3-C_{12})$cycloalkyl-$(C_1-C_6)$alkyl-, —$(C_3-C_{12})$cycloalkenyl, $(C_3-C_{12})$cycloalkenyl-$(C_1-C_6)$alkyl-, -(6- to 14-membered)aryl, ((6- to 14-membered)aryl)-$(C_1-C_6)$alkyl-, diphenyl$(C_1-C_6)$alkyl-, -(3- to 12-membered)heterocycle, ((3- to 12 membered)heterocycle)-$(C_1-C_6)$alkyl-, —$(OCH_2CH_2)_s$—O—$(C_1-C_6)$alkyl, —$(CH_2CH_2O)_s$—$(C_1-C_6)$alkyl, $(C_1-C_{10})$alkoxy, $C(halo)_3$, $CH(halo)_2$, $CH_2(halo)$, $C(O)R^5$, —$C(O)O$—$(C_1-C_{10})$alkyl, and —$(CH_2)_n$—$N(R^6)_2$, each of which is optionally substituted by 1, 2 or 3 independently selected $R^9$ groups;

$R^{2a}$ is hydrogen, OH, or absent;

$R^{2b}$ is
  a) ((6- to 14-membered)aryl), -((5- to 12-membered)heteroaryl), or ((3- to 12-membered)heterocycle), each of which is optionally substituted with one, two, or three independently selected $R^{30}$ groups; or
  b) —Z-G-$R^{10}$, provided that —Z-G-$R^{10}$ is other than hydrogen;
or $R^{2a}$ and $R^{2b}$ together form =O;

Z is absent or —$(CH_2)_m$—, optionally substituted with 1 or 2 $(C_1-C_6)$alkyl;

G is selected from the group consisting of:
  a) a bond, —$(C_1-C_6)$alkylene, —$(C_2-C_6)$alkenylene;
  b) O, —OCO—, —C(=O), =CH;
  c) $NR^8$, =N—O, =N—NH;
  d) S, SO, $SO_2$; and
  e) —NH—$SO_2$;
and when Z is absent and G is =CH, =N—O, or =N—NH, then $R^{2a}$ is absent;

$R^{10}$ is selected from the group consisting of hydrogen, —$(C_1-C_{10})$alkyl, —$(C_2-C_{12})$alkenyl, —C(=O), —C(=O)—$(C_1-C_6)$alkyl, —C(=O)—$(C_2-C_6)$alkenyl, —C(=O)-(6- to 14-membered)aryl, —C(=O)—$(C_1-C_6)$alkyl-(6- to 14-membered)aryl, —$(C_2-C_{12})$alkynyl, —$(C_1-C_{10})$alkoxy, —$(OCH_2CH_2)_s$—$O(C_1-C_6)$alkyl, —$(CH_2CH_2O)_s$—$(C_1-C_6)$alkyl, —$NH_2$, —$NH(C_1-C_6)$alkyl, CN, $NR^5R^6$, —$(C_1-C_6)$alkyl-$NR^5R^6$, —$CONR^5R^6$, —$(C_1-C_6)$alkyl-CO—$NR^5R^6$, —$COOR^7$, —$(C_1-C_6)$alkyl-CO—$OR^7$, —$(C_1-C_6)$alkoxy-$COOR^7$, —CO—$(CH_2)_n$—$COOR^7$, —CO—$(CH_2)_n$—CO—$NR^5R^6$, —$(C_3-C_{12})$cycloalkyl, $((C_3-C_{12})$cycloalkyl)-$(C_1-C_6)$alkyl, —$(C_4-C_{12})$cycloalkenyl, $((C_4-C_{12})$cycloalkenyl)-$(C_1-C_6)$alkyl-, —$(C_6-C_{14})$bicycloalkyl, $((C_6-C_{14})$bicycloalkyl)-$(C_1-C_6)$alkyl-, —$(C_8-C_{20})$tricycloalkyl, $((C_8-C_{20})$tricycloalkyl)-$(C_1-C_6)$alkyl-, —$(C_7-C_{14})$bicycloalkenyl, $((C_7-C_{14})$bicycloalkenyl)-$(C_1-C_6)$alkyl-, —$(C_8-C_{20})$tricycloalkenyl, $((C_8-C_{20})$tricycloalkenyl)-$(C_1-C_6)$alkyl-, -(6- to 14-membered)aryl, ((6- to 14-membered)aryl)-$(C_1-C_6)$alkyl-, —$SO_2$—$(C_1-C_6)$alkyl, —$SO_2((C_3-C_{12})$cycloalkyl), —$SO_2$—$((C_3-C_{12})$cycloalkyl)-$(C_1-C_6)$alkyl, —$SO_2$-((5- to 12-membered)heteroaryl), —$SO_2$-((5- to 12-membered)heteroaryl)-$(C_1-C_6)$alkyl, —C(=O)—NH-((5- to 12-membered)heteroaryl), —C(=O)—NH-((5- to 12-membered)heteroaryl)-$(C_1-C_6)$alkyl, —C(=O)—NH-((3- to 12-membered)heterocycle), —C(=O)—NH-((3- to 12-membered)heterocycle)-$(C_1-C_6)$alkyl, $SO_2$-((6- to 14-membered)aryl), $SO_2$-((6- to 14 membered)aryl)-$(C_1-C_6)$alkyl, -(7- to 12-membered)bicyclic ring system, ((7- to 12-membered)bicyclic ring system)-$(C_1-C_6)$alkyl-, -(7- to 12-membered)bicyclic aryl, ((7- to 12-membered)bicyclic aryl)-$(C_1-C_6)$alkyl-, -(5- to 12-membered)heteroaryl, ((5- to 12-membered)heteroaryl)-$(C_1-C_6)$alkyl-, -(3- to 12-membered)heterocycle, ((3- to 12 membered)heterocycle)-$(C_1-C_6)$alkyl-, -(7- to 12-membered)bicycloheterocycle, ((7- to 12-membered)bicycloheterocycle)-$(C_1-C_6)$alkyl-, phenyl, benzyl and naphthyl; each of which is optionally substituted with one, two, or three substituents independently selected from the group consisting of —OH, (=O), halo, —$C(halo)_3$, —$CH(halo)_2$, —$CH_2(halo)$, —$(C_1-C_6)$alkyl, halo$(C_1-C_6)$alkyl-, —$(C_2-C_6)$alkenyl, —$(C_2-C_6)$alkynyl, hydroxy$(C_1-C_6)$alkyl-, dihydroxy$(C_1-C_6)$alkyl-, —$(C_1-C_6)$alkoxy, $((C_1-C_6)$alkoxy)$CO(C_1-C_6)$alkoxy-, phenyl, benzyl, —$NH_2$, —$NH(C_1-C_6)$alkyl, —$(C_1-C_6)$alkyl-$NH(C_1-C_6)$alkyl-$R^{14}$, —CN, —SH, —$OR^{11}$, —$CONR^5R^6$, —$(C_1-C_6$alkyl)-CO—$NR^5R^6$, —$COOR^7$, —$(C_1-C_6)$alkyl-CO—$OR^7$, —$(C_1-C_6)$alkoxy-$COOR^7$, —$(OCH_2CH_2)_s$—O$(C_1-C_6)$alkyl, —$(CH_2CH_2O)_s$—$(C_1-C_6)$alkyl, —$SO_2$—$NR^{5a}R^{6a}$, $(C_1-C_6)$alkyl)sulfonyl, $((C_1-C_6)$alkyl)sulfonyl$(C_1-C_6)$alkyl-, —NH—$SO_2(C_1-C_6)$alkyl, $NH_2$—$SO_2(C_1-C_6)$alkyl-, —$N(SO_2(C_1-C_6)$alkyl$)_2$, —C(=NH)$NH_2$, —NH—CO—$(C_1-C_6)$alkyl, —NH—CO—$NH_2$, —NH—C(=O)—NH—$(C_1-C_6)$alkyl, —NH—C(=O)-(6- to 14-membered)aryl, —NH—C(=O)—$(C_1-C_6)$alkyl-(6- to 14-membered)aryl, —NH—$(C_1-C_6)$alkyl-CO—$OR^7$, —NH—C(=O)—$(C_1-C_6)$alkyl-CO—$OR^7$, —NH—C(=O)—$CH(NH_2)$—$(C_1-C_6)$alkyl-CO—$OR^7$, —$(C_3-C_{12})$cycloalkyl, $((C_3-C_{12})$cycloalkyl)-$(C_1-C_6)$alkyl-, -(6- to 14-membered)aryl, -(6- to 14-membered)aryloxy, —$(C_1-C_6)$alkoxy-$C(O)NR^5R^6$, —NH—$(C_1-C_6)$alkyl-$C(O)$—$NR^5R^6$, —$C(O)NH$—$(C_1-C_6)$alkyl-$COOR^7$, ((6- to 14-membered)aryl)-$(C_1-C_6)$alkyl-, -(5- to 12-membered)heteroaryl, ((5- to 12-membered)heteroaryl)-$(C_1-C_6)$alkyl-, -(3- to 12-membered)heterocycle, ((3- to 12-membered)heterocycle)-$(C_1-C_6)$alkyl-, -(7- to 12-membered)bicycloheterocycle, and ((7- to 12-membered)bicycloheterocycle)-$(C_1-C_6)$alkyl-;

$R^3$ is selected from:
  a) —H; or
  b) —$(C_1-C_6)$alkyl, —$(C_2-C_6)$alkenyl, or —$(C_2-C_6)$alkynyl;

$R^4$ is selected from
  a) —H, —OH, halo, —$C(halo)_3$, —$CH(halo)_2$, —$CH_2(halo)$, COOH, or $CONH_2$; or
  b) —$(C_1-C_5)$alkyl, —$(C_2-C_5)$alkenyl, —$(C_2-C_5)$alkynyl, —$(CH_2)_n$—O—$(CH_2)_n$—$CH_3$, or —$(C_1-C_5)$alkoxy, each of which is optionally substituted with 1, 2, or 3 independently selected $R^9$ groups;

$R^5$ and $R^6$ are each independently selected from
  a) hydrogen, —OH, halo, —$C(halo)_3$, —$CH(halo)_2$, —$CH_2(halo)$;
  b) —$(C_1-C_6)$alkyl, —$(C_2-C_5)$alkenyl, —$(C_2-C_5)$alkynyl, —$(CH_2)_n$—O—$(CH_2)_n$—$CH_3$, —$(C_1-C_6)$alkoxy, each of which is optionally substituted with 1, 2, or 3 substituents independently selected from —OH, halo, —$(C_1-C_{10})$alkyl, —$(C_2-C_{10})$alkenyl, —$(C_1-C_{10})$alkynyl, —$(C_1-C_{10})$alkoxy, —$(C_3-C_{12})$cycloalkyl, —CHO, —C(O)OH, —$C(halo)_3$, —$CH(halo)_2$, $CH_2(halo)$, —$(CH_2)_n$—O—$(CH_2)_n$—$CH_3$, phenyl, or $CONR^{5a}R^{6a}$;
  c) —$(C_3-C_8)$cycloalkyl, $((C_3-C_8)$cycloalkyl)-$(C_1-C_6)$alkyl-, —$COOR^7$, —$(C_1-C_6)$alkyl-$COOR^7$, —$CONH_2$, or $(C_1-C_6)$alkyl-CONH—;
  d) ((6- to 14-membered)aryl) optionally substituted with 1, 2, or 3 independently selected $R^{30}$ groups;
  e) -((5- to 12-membered)heteroaryl) optionally substituted with 1, 2, or 3 independently selected $R^{30}$ groups; or
  f) $R^5$ and $R^6$ together with the nitrogen atom to which they are attached form a (3- to 12-membered)heterocycle optionally substituted with 1, 2, or 3 independently selected $R^{30}$ groups;

$R^{5a}$ and $R^{6a}$ are each independently selected from the group consisting of:
  a) hydrogen, —OH, halo, —$C(halo)_3$, —$CH(halo)_2$, and —$CH_2(halo)$;

b) —(C$_1$-C$_6$)alkyl, —(C$_2$-C$_6$)alkenyl, —(C$_2$-C$_6$)alkynyl, —(CH$_2$)$_n$—O—(CH$_2$)$_n$—CH$_3$, and —(C$_1$-C$_6$)alkoxy, each of which is optionally substituted with 1, 2, or 3 substituents independently selected from —OH, halo, —(C$_1$-C$_{10}$)alkyl, —(C$_2$-C$_{12}$)alkenyl, —(C$_2$-C$_{12}$)alkynyl, —(C$_1$-C$_{10}$)alkoxy, —(C$_3$-C$_{12}$)cycloalkyl, —CHO, —COOH, —C(halo)$_3$, —CH(halo)$_2$, CH$_2$(halo), —(CH$_2$)$_n$—O—(CH$_2$)$_n$—CH$_3$, and phenyl;

c) —(C$_3$-C$_8$)cycloalkyl, ((C$_3$-C$_8$)cycloalkyl)-(C$_1$-C$_6$)alkyl-, —COOR$^7$, —(C$_1$-C$_6$)alkyl-COOR$^7$, —CONH$_2$, and (C$_1$-C$_6$)alkyl-CONH—;

d) -(6- to 14-membered)aryl optionally substituted with 1, 2, or 3 independently selected R$^{30}$ groups;

e) -((5- to 12-membered)heteroaryl) optionally substituted with 1, 2, or 3 independently selected R$^{30}$ groups; or f) R$^{5a}$ and R$^{6a}$ together with the nitrogen atom to which they are attached form a (3- to 12-membered)heterocycle optionally substituted with 1, 2, or 3 independently selected R$^{30}$ groups;

each R$^7$ is independently selected from the group consisting of hydrogen, —(C$_1$-C$_6$)alkyl, —(C$_2$-C$_6$)alkenyl, —(C$_2$-C$_6$)alkynyl, —(C$_3$-C$_{12}$)cycloalkyl, —(C$_4$-C$_{12}$)cycloalkenyl, ((C$_3$-C$_{12}$)cycloalkyl)-(C$_1$-C$_6$)alkyl-, and ((C$_4$-C$_{12}$)cycloalkenyl)-(C$_1$-C$_6$)alkyl-;

each R$^8$ is independently selected from H, —(C$_1$-C$_6$)alkyl, —(C$_2$-C$_6$)alkenyl, —(C$_2$-C$_6$)alkynyl, —(C$_1$-C$_{10}$)alkoxy, —(C$_3$-C$_{12}$)cycloalkyl, —(C$_3$-C$_{12}$)cycloalkenyl, ((C$_3$-C$_{12}$)cycloalkyl)-(C$_1$-C$_6$)alkyl-, ((C$_3$-C$_{12}$)cycloalkenyl)-(C$_1$-C$_6$)alkyl-, —C(=O)(C$_1$-C$_6$)alkyl or SO$_2$(C$_1$-C$_6$)alkyl;

each R$^9$ is independently selected from —OH, halo, —(C$_1$-C$_{10}$)alkyl, —(C$_2$-C$_{10}$)alkenyl, —(C$_2$-C$_{10}$)alkynyl, —(C$_1$-C$_{10}$)alkoxy, —(C$_3$-C$_{12}$)cycloalkyl, —CHO, —C(O)OH, —C(halo)$_3$, —CH(halo)$_2$, CH$_2$(halo), —(CH$_2$)$_n$—O—(CH$_2$)$_n$—CH$_3$, phenyl, or CONR$^{5a}$R$^{6a}$;

each R$^{11}$ is independently selected from —C(halo)$_3$, —CH(halo)$_2$, —CH$_2$(halo), —(C$_2$-C$_5$)alkenyl, —(C$_2$-C$_5$)alkynyl, —(CH$_2$)$_n$—O—(CH$_2$)$_n$—CH$_3$, (6- to 14-membered)aryl, ((6- to 14-membered)aryl)-(C$_1$-C$_6$)alkyl-, or (5- to 12-membered)heteroaryl, ((5- to 12-membered)heteroaryl)-(C$_1$-C$_6$)alkyl-, each of which is optionally substituted with 1, 2, or 3 independently selected R$^9$ groups;

each R$^{14}$ is independently selected from —COOR$^7$, —(C$_1$-C$_6$)alkyl-COOR$^7$, —C(=O)—(C$_1$-C$_6$)alkyl-COOR$^7$, —(C$_1$-C$_6$)alkyl-C(=O)—(C$_1$-C$_6$)alkyl-COOR$^7$, CONH$_2$, or —(C$_1$-C$_6$)alkyl-CONH;

each R$^{30}$ is independently selected from COOR$^7$, CONR$^{5a}$R$^{6a}$, —(C$_1$-C$_6$)alkyl, —C(=O), CN, -(3- to 12-membered)heteroaryl, ((3- to 12-membered)heteroaryl)-(C$_1$-C$_6$)alkyl-, NH$_2$, halo, and ((6- to 14-membered)aryl)-(C$_1$-C$_6$)alkoxy-;

m is an integer 1, 2, 3, 4, 5, or 6;
n is an integer 0, 1, 2, 3, 4, 5, or 6;
s in an integer 1, 2, 3, 4, 5, or 6;

provided that when R$^4$ is —(C$_1$-C$_5$)alkoxy then:
a) R$^{2a}$ and R$^{2b}$ cannot be taken together to form =O; or
b) R$^{2a}$ cannot be OH when R$^{2b}$ is —Z-G-R$^{10}$, and —Z-G-R$^{10}$ is either:
a. OH;
b. —(C$_1$-C$_6$)alkyl;
c. —(C$_2$-C$_6$)alkenyl; or
d. —(C$_2$-C$_6$)alkynyl; or
c) R$^{2a}$ cannot be H when the combination —Z-G-R$^{10}$ is either:
a. OH;
b. —O—C(=O)—(C$_1$-C$_6$)alkyl; or
c. —O—C(=O)—(C$_2$-C$_6$)alkenyl;

and provided that when R$^4$ is OH then:
a) R$^{2a}$ cannot be OH when R$^{2b}$ is —Z-G-R$^{10}$, and —Z-G-R$^{10}$ is:
a. —(C$_1$-C$_6$)alkyl;
b. —(C$_2$-C$_6$)alkenyl;
c. or —(C$_2$-C$_6$)alkynyl;
b) R$^{2a}$ cannot be H when R$^{2b}$ is —Z-G-R$^{10}$, and —Z-G-R$^{10}$ is
a. OH
b. —O—C(=O)—(C$_1$-C$_6$)alkyl; or
c. —O—C(=O)—(C$_2$-C$_6$)alkenyl;

and provided that when R$^3$ is (C$_1$-C$_6$)alkyl or (C$_2$-C$_6$)alkenyl, and R$^4$ is H, OH, or (C$_1$-C$_5$)alkoxy, then R$^{2b}$ is not:
a) optionally substituted (5- to 12-membered)heteroaryl,
b) optionally substituted (3- to 12-membered)heterocycle; or
c) unsubstituted phenyl or phenyl substituted with halo, (C$_1$-C$_6$)alkyl, C(halo)$_3$, hydroxy, (C$_1$-C$_6$)alkoxy, (3- to 12-membered)heterocycle, or NH$_2$;

and provided that when R$^4$ is OH and R$^1$ is (C$_1$-C$_{10}$)alkyl, then R$^{2a}$ and R$^{2b}$ cannot be together selected =O;

and provided that when R$^4$ is hydrogen and when R$^1$ and R$^3$ are both methyl, then:
a) R$^{2a}$ and R$^{2b}$ cannot together form =O or =N—OH; or
b) R$^{2b}$ may not be NH$_2$ or NHC(O)CH$_3$ if R$^{2a}$ is hydrogen.

and provided that when R$^{2a}$ is H, then R$^{2b}$ may not be —Z-G-R$^{10}$, wherein —Z-G-R$^{10}$ is:
a) —CH$_2$—CHR$^{20}$—C(=O)R$^{21}$, wherein
R$^{20}$ is H, or —(C$_1$-C$_6$)alkyl, and
R$^{21}$ is selected from the group consisting of H, —(C$_1$-C$_{10}$)alkyl, —(C$_3$-C$_{12}$)cycloalkyl, ((C$_3$-C$_{12}$)cycloalkyl)-(C$_1$-C$_6$)alkyl-, -(6- to 14-membered)aryl, and ((6- to 14-membered)aryl)-(C$_1$-C$_6$)alkyl-; or
b) —CH$_2$—CHR$^{20}$—CR$^{22}$R$^{23}$OH, wherein
R$^{20}$ is defined as above, and
R$^{22}$ and R$^{23}$ are each independently selected from the group consisting of
H, —(C$_1$-C$_{10}$)alkyl, ((C$_3$-C$_{12}$)cycloalkyl)-(C$_1$-C$_6$)alkyl-, -(6- to 14-membered)aryl, and ((6- to 14-membered)aryl)-(C$_1$-C$_6$)alkyl-; or
c) —CH$_2$—CR$^{20}$=CR$^{23}$R$^{24}$, wherein
R$^{20}$ and R$^{23}$ are defined as above, and
R$^{24}$ is selected from the group consisting of H, and —(C$_1$-C$_6$)alkyl;

and the pharmaceutically acceptable salts and solvates thereof.

The present invention provides novel compounds of Formula I':

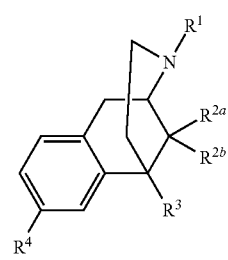

wherein
R$^1$ is selected from the group consisting of —(C$_1$-C$_{10}$)alkyl, —(C$_2$-C$_{10}$)alkenyl, —(C$_2$-C$_{10}$)alkynyl, —(C$_3$-C$_{12}$)cycloalkyl, (C$_3$-C$_{12}$)cycloalkyl-(C$_1$-C$_6$)alkyl-, —(C$_3$-C$_{12}$)cycloalkenyl, (C$_3$-C$_{12}$)cycloalkenyl-(C$_1$-C$_6$)alkyl-, -(6- to 14-membered)aryl, ((6- to 14-membered)aryl)-($C_1$-$C_6$)alkyl-, diphenyl($C_1$-$C_6$)alkyl-, -(3- to 12-membered)heterocycle, ((3- to 12 membered)heterocycle)-($C_1$-$C_6$)alkyl-, —(OCH$_2$CH$_2$)$_s$—O($C_1$-$C_6$)alkyl, —(CH$_2$CH$_2$O)$_s$—($C_1$-$C_6$) alkyl, ($C_1$-$C_{10}$)alkoxy, C(halo)$_3$, CH(halo)$_2$, CH$_2$(halo), C(O)R$^5$, —C(O)O—($C_1$-$C_{10}$)alkyl, and —(CH$_2$)$_n$—N(R$^6$)$_2$, each of which is optionally substituted by 1, 2 or 3 independently selected R$^9$ groups;

R$^{2a}$ is absent or OH;

R$^{2b}$ is
  a) ((6- to 14-membered)aryl) or ((3- to 12-membered)heterocycle), each of which is optionally substituted with one, two, or three independently selected R$^{30}$ groups; or
  b) —Z-G-R$^{10}$, provided that —Z-G-R$^{10}$ is other than hydrogen;

or R$^{2a}$ and R$^{2b}$ together form =O;

Z is absent or —(CH$_2$)$_m$—, optionally substituted with 1 or 2-($C_1$-$C_6$)alkyl;

G is selected from the group consisting of:
  a) a bond, —($C_1$-$C_6$)alkylene, —($C_2$-$C_6$)alkenylene;
  b) O, —OCO—, —C(=O), =CH;
  c) NR$^8$, =N—O, =N—NH;
  d) S, SO, and SO$_2$;

R$^{10}$ is selected from the group consisting of hydrogen, —($C_1$-$C_{10}$)alkyl, —($C_2$-$C_{12}$)alkenyl, —C(=O), —C(=O)—($C_1$-$C_6$)alkyl, —C(=O)—($C_2$-$C_6$)alkenyl, —C(=O)-(6- to 14-membered)aryl, —C(=O)—($C_1$-$C_6$)alkyl-(6- to 14-membered)aryl, —($C_2$-$C_{12}$)alkynyl, —($C_1$-$C_{10}$)alkoxy, —(OCH$_2$CH$_2$)$_s$—O($C_1$-$C_6$)alkyl, —(CH$_2$CH$_2$O)$_s$—($C_1$-$C_6$)alkyl, —NH$_2$, —NH($C_1$-$C_6$)alkyl, CN, NR$^5$R$^6$, —($C_1$-$C_6$)alkyl-NR$^5$R$^6$, —CONR$^5$R$^6$, —($C_1$-$C_6$)alkyl-CO—NR$^5$R$^6$, —COOR$^7$, —($C_1$-$C_6$)alkyl-CO—OR$^7$, —($C_1$-$C_6$)alkoxy-COOR$^7$, —CO—(CH$_2$)$_n$—COOR$^7$, —CO—(CH$_2$)$_n$—CO—NR$^5$R$^6$, —($C_3$-$C_{12}$)cycloalkyl, (($C_3$-$C_{12}$)cycloalkyl)-($C_1$-$C_6$)alkyl, —($C_4$-$C_{12}$)cycloalkenyl, (($C_4$-$C_{12}$)cycloalkenyl)-($C_1$-$C_6$)alkyl-, —($C_6$-$C_{14}$)bicycloalkyl, (($C_6$-$C_{14}$)bicycloalkyl)-($C_1$-$C_6$)alkyl-, —($C_8$-$C_{20}$)tricycloalkyl, (($C_8$-$C_{20}$)tricycloalkyl)-($C_1$-$C_6$)alkyl-, —($C_7$-$C_{14}$)bicycloalkenyl, (($C_7$-$C_{14}$)bicycloalkenyl)-($C_1$-$C_6$)alkyl-, —($C_8$-$C_{20}$)tricycloalkenyl, (($C_8$-$C_{20}$)tricycloalkenyl)-($C_1$-$C_6$)alkyl-, -(6- to 14-membered)aryl, ((6- to 14-membered)aryl)-($C_1$-$C_6$)alkyl-, -(7- to 12-membered)bicyclic ring system, ((7- to 12-membered)bicyclic ring system)-($C_1$-$C_6$)alkyl-, -(7- to 12-membered)bicyclic aryl, ((7- to 12-membered)bicyclic aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12 membered)heterocycle)-($C_1$-$C_6$)alkyl-, -(7- to 12-membered)bicycloheterocycle, ((7- to 12-membered)bicycloheterocycle)-($C_1$-$C_6$)alkyl-, phenyl, benzyl and naphthyl; each of which is optionally substituted with one, two, or three substituents independently selected from the group consisting of —OH, (=O), halo, —C(halo)$_3$, —CH(halo)$_2$, —CH$_2$(halo), —($C_1$-$C_6$)alkyl, halo($C_1$-$C_6$)alkyl-, —($C_2$-$C_6$)alkenyl, —($C_2$-$C_6$)alkynyl, hydroxy($C_1$-$C_6$)alkyl-, dihydroxy($C_1$-$C_6$)alkyl-, —($C_1$-$C_6$)alkoxy, (($C_1$-$C_6$)alkoxy)CO($C_1$-$C_6$)alkoxy-, phenyl, benzyl, —NH$_2$, —NH($C_1$-$C_6$)alkyl, —($C_1$-$C_6$)alkyl-NH($C_1$-$C_6$)alkyl-R$^{14}$, —CN, —SH, —OR$^{11}$, —CONR$^5$R$^6$, —($C_1$-$C_6$alkyl)-CO—NR$^5$R$^6$, —COOR$^7$, —($C_1$-$C_6$)alkyl-CO—OR$^7$, —($C_1$-$C_6$)alkoxy-COOR$^7$, —(OCH$_2$CH$_2$)$_s$—O($C_1$-$C_6$)alkyl, —(CH$_2$CH$_2$O)$_s$—($C_1$-$C_6$)alkyl, ($C_1$-$C_6$alkyl)sulfonyl, (($C_1$-$C_6$alkyl)sulfonyl($C_1$-$C_6$)alkyl-, —NH—SO$_2$($C_1$-$C_6$)alkyl, NH$_2$—SO$_2$($C_1$-$C_6$)alkyl-, —N(SO$_2$($C_1$-$C_6$)alkyl)$_2$, —C(=NH)NH$_2$, —NH—CO—($C_1$-$C_6$)alkyl, —NH—CO—NH$_2$, —NH—C(=O)—NH—($C_1$-$C_6$)alkyl, —NH—C(=O)-(6- to 14-membered)aryl, —NH—C(=O)—($C_1$-$C_6$)alkyl-(6- to 14-membered)aryl, —NH—($C_1$-$C_6$)alkyl-CO—OR$^7$, —NH—C(=O)—($C_1$-$C_6$)alkyl-CO—OR$^7$, —NH—C(=O)—CH(NH$_2$)—($C_1$-$C_6$)alkyl-CO—OR$^7$, —($C_3$-$C_{12}$)cycloalkyl, (($C_3$-$C_{12}$)cycloalkyl)-($C_1$-$C_6$)alkyl-, -(6- to 14-membered)aryl, -(6- to 14-membered)aryloxy, —($C_1$-$C_6$)alkoxy-C(O)NR$^5$R$^6$, —NH—($C_1$-$C_6$)alkyl-C(O)—NR$^5$R$^6$, —C(O)NH—($C_1$-$C_6$)alkyl-COOR$^7$, ((6- to 14-membered)aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12-membered)heterocycle)-($C_1$-$C_6$)alkyl-, -(7- to 12-membered)bicycloheterocycle, and ((7- to 12-membered)bicycloheterocycle)-($C_1$-$C_6$)alkyl-;

R$^3$ is selected from:
  a) —H; or
  b) —($C_1$-$C_6$)alkyl, —($C_2$-$C_6$)alkenyl, or —($C_2$-$C_6$)alkynyl;

R$^4$ is selected from
  a) —H, —OH, halo, —C(halo)$_3$, —CH(halo)$_2$, —CH$_2$(halo), COOH, or CONH$_2$; or
  b) —($C_1$-$C_5$)alkyl, —($C_2$-$C_5$)alkenyl, —($C_2$-$C_5$)alkynyl, —(CH$_2$)$_n$—O—(CH$_2$)$_n$—CH$_3$, or —($C_1$-$C_5$)alkoxy, each of which is optionally substituted with 1, 2, or 3 independently selected R$^9$ groups;

R$^5$ and R$^6$ are each independently selected from
  a) hydrogen, —OH, halo, —C(halo)$_3$, —CH(halo)$_2$, —CH$_2$(halo);
  b) —($C_1$-$C_6$)alkyl, —($C_2$-$C_5$)alkenyl, —($C_2$-$C_5$)alkynyl, —(CH$_2$)$_n$—O—(CH$_2$)$_n$—CH$_3$, —($C_1$-$C_6$)alkoxy, each of which is optionally substituted with 1, 2, or 3 substituents independently selected from —OH, halo, —($C_1$-$C_{10}$)alkyl, —($C_2$-$C_{10}$)alkenyl, —($C_2$-$C_{10}$)alkynyl, —($C_1$-$C_{10}$)alkoxy, —($C_3$-$C_{12}$)cycloalkyl, —CHO, —C(O)OH, —C(halo)$_3$, —CH(halo)$_2$, CH$_2$(halo), —(CH$_2$)$_n$—O—(CH$_2$)$_n$—CH$_3$, phenyl, or CONR$^5$R$^6$;
  c) —($C_3$-$C_8$)cycloalkyl, (($C_3$-$C_8$)cycloalkyl)-($C_1$-$C_6$)alkyl-, —COOR$^7$, —($C_1$-$C_6$)alkyl-COOR$^7$, —CONH$_2$, or ($C_1$-$C_6$)alkyl-CONH—;
  d) ((6- to 14-membered)aryl) optionally substituted with 1, 2, or 3 independently selected R$^{30}$ groups; or
  e) R$^5$ and R$^6$ together with the nitrogen atom to which they are attached form a (4- to 8-membered)heterocycle optionally substituted with 1, 2, or 3 independently selected R$^{30}$ groups;

R$^{5a}$ and R$^{6a}$ are each independently selected from the group consisting of:
  a) hydrogen, —OH, halo, —C(halo)$_3$, —CH(halo)$_2$, and —CH$_2$(halo);
  b) —($C_1$-$C_6$)alkyl, —($C_2$-$C_6$)alkenyl, —($C_2$-$C_6$)alkynyl, —(CH$_2$)$_n$—O—(CH$_2$)$_n$—CH$_3$, and —($C_1$-$C_6$)alkoxy, each of which is optionally substituted with 1, 2, or 3 substituents independently selected from —OH, halo, —($C_1$-$C_{10}$)alkyl, —($C_2$-$C_{12}$)alkenyl, —($C_2$-$C_{12}$)alkynyl, —($C_1$-$C_{10}$)alkoxy, —($C_3$-$C_{12}$)cycloalkyl, —CHO, —COOH, —C(halo)$_3$, —CH(halo)$_2$, CH$_2$(halo), —(CH$_2$)$_n$—O—(CH$_2$)$_n$—CH$_3$, and phenyl;
  c) —($C_3$-$C_8$)cycloalkyl, (($C_3$-$C_8$)cycloalkyl)-($C_1$-$C_6$)alkyl-, —COOR$^7$, —($C_1$-$C_6$)alkyl-COOR$^7$, —CONH$_2$, and ($C_1$-$C_6$)alkyl-CONH—;
  d) -(6- to 14-membered)aryl optionally substituted with 1, 2, or 3 independently selected R$^{30}$ groups; or
  e) R$^{5a}$ and R$^{6a}$ together with the nitrogen atom to which they are attached form a (4- to 8-membered)heterocycle optionally substituted with 1, 2, or 3 independently selected R$^{30}$ groups;

each R$^7$ is independently selected from the group consisting of hydrogen, —($C_1$-$C_6$)alkyl, —($C_2$-$C_6$)alkenyl, —($C_2$-$C_6$)

alkynyl, —(C₃-C₁₂)cycloalkyl, —(C₄-C₁₂)cycloalkenyl, ((C₃-C₁₂)cycloalkyl)-(C₁-C₆)alkyl-, and ((C₄-C₁₂)cycloalkenyl)-(C₁-C₆)alkyl-;

each $R^8$ is independently selected from H, —(C₁-C₆)alkyl, —(C₂-C₆)alkenyl, —(C₂-C₆)alkynyl, —(C₁-C₁₀)alkoxy, —(C₃-C₁₂)cycloalkyl, —(C₃-C₁₂)cycloalkenyl, ((C₃-C₁₂)cycloalkyl)-(C₁-C₆)alkyl-, ((C₃-C₁₂)cycloalkenyl)-(C₁-C₆)alkyl-, —C(=O)(C₁-C₆)alkyl or SO₂(C₁-C₆)alkyl;

each $R^9$ is independently selected from —OH, halo, —(C₁-C₁₀)alkyl, —(C₂-C₁₀)alkenyl, —(C₂-C₁₀)alkynyl, —(C₁-C₁₀)alkoxy, —(C₃-C₁₂)cycloalkyl, —CHO, —C(O)OH, —C(halo)₃, —CH(halo)₂, —CH₂(halo), —(CH₂)ₙ—O—(CH₂)ₙ—CH₃, phenyl, or CONR⁵ᵃR⁶ᵃ;

each $R^{11}$ is independently selected from —C(halo)₃, —CH(halo)₂, —CH₂(halo), —(C₂-C₅)alkenyl, —(C₂-C₅)alkynyl, —(CH₂)ₙ—O—(CH₂)ₙ—CH₃, (6- to 14-membered)aryl, ((6- to 14-membered)aryl)-(C₁-C₆)alkyl-, or (5- to 12-membered)heteroaryl, ((5- to 12-membered)heteroaryl)-(C₁-C₆)alkyl-, each of which is optionally substituted with 1, 2, or 3 independently selected $R^9$ groups;

each $R^{14}$ is independently selected from —COOR⁷, —(C₁-C₆)alkyl-COOR⁷, —C(=O)—(C₁-C₆)alkyl-COOR⁷, —(C₁-C₆)alkyl-C(=O)—(C₁-C₆)alkyl-COOR⁷, CONH₂, or —(C₁-C₆)alkyl-CONH;

each $R^{30}$ is independently selected from COOR⁷, CONR⁵ᵃR⁶ᵃ, —(C₁-C₆)alkyl, —C(=O), CN, -(3- to 12-membered)heteroaryl, ((3- to 12-membered)heteroaryl)-(C₁-C₆)alkyl-, NH₂, halo, and ((6- to 14-membered)aryl)-(C₁-C₆)alkoxy-;

m is an integer 1, 2, 3, 4, 5, or 6;
n is an integer 0, 1, 2, 3, 4, 5, or 6;
s in an integer 1, 2, 3, 4, 5, or 6;
provided that when $R^4$ is —(C₁-C₅)alkoxy then:
  a) $R^{2a}$ and $R^{2b}$ cannot be taken together to form =O; or
  b) $R^{2a}$ cannot be OH when $R^{2b}$ is —Z-G-R¹⁰, and —Z-G-R¹⁰ is either:
    a. OH; or
    b. —(C₁-C₆)alkyl; or
  c) $R^{2a}$ cannot be H when the combination —Z-G-R¹⁰ is OH;

and the pharmaceutically acceptable salts and solvates thereof.

In one embodiment, the present invention provides novel compounds of Formula IA':

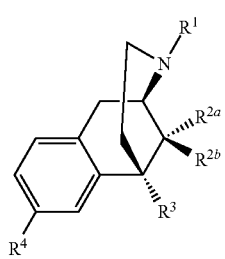

wherein $R^1$, $R^{2a}$, $R^{2b}$, $R^3$ and $R^4$ are as defined above for Formula I', and the pharmaceutically acceptable salts and solvates thereof.

In another embodiment, the present invention provides novel compounds of Formula IB':

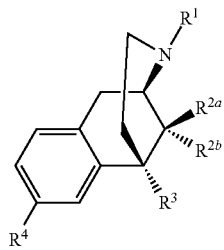

wherein $R^1$, $R^{2a}$, $R^{2b}$, $R^3$ and $R^4$ are as defined above for Formula I', and the pharmaceutically acceptable salts and solvates thereof.

In another embodiment, the present invention provides novel compounds of Formula IC':

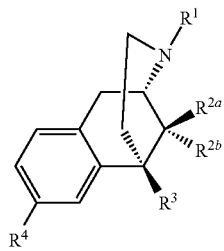

wherein $R^1$, $R^{2a}$, $R^{2b}$, $R^3$ and $R^4$ are as defined above for Formula I', and the pharmaceutically acceptable salts and solvates thereof.

In another embodiment, the present invention provides novel compounds of Formula ID':

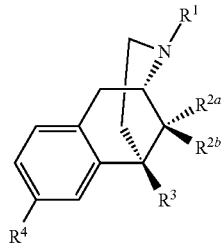

wherein $R^1$, $R^{2a}$, $R^{2b}$, $R^3$ and $R^4$ are as defined above for Formula I', and the pharmaceutically acceptable salts and solvates thereof.

The present invention further provides novel compounds of Formula I:

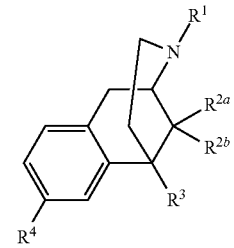

wherein
$R^1$ is selected from the group consisting of —(C₁-C₁₀)alkyl, —(C₂-C₁₀)alkenyl, —(C₂-C₁₀)alkynyl, —(C₃-C₁₂)cycloalkyl, $(C_3-C_{12})$cycloalkyl-$(C_1-C_6)$alkyl-, —$(C_3-C_{12})$cycloalkenyl, $(C_3-C_{12})$cycloalkenyl-$(C_1-C_6)$alkyl-, -(6- to 14-membered)aryl, ((6- to 14-membered)aryl)-$(C_1-C_6)$alkyl-, diphenyl$(C_1-C_6)$alkyl-, —$(OCH_2CH_2)_s$—O—$(C_1-C_6)$alkyl, —$(CH_2CH_2O)_s$—$(C_1-C_6)$alkyl, $(C_1-C_6)$alkoxy, C(halo)$_3$, CH(halo)$_2$, CH$_2$(halo), C(O)R$^5$, —C(O)O—$C_1-C_{10}$)alkyl, and —$(CH_2)_n$—N(R$^6$)$_2$, each of which is optionally substituted by 1, 2 or 3 independently selected R$^9$ groups;

R$^{2a}$ is hydrogen or OH;
R$^{2b}$ is
  a) ((6- to 14-membered)aryl) or ((3- to 12-membered)heterocycle), each of which is optionally substituted with one, two, or three independently selected R$^{30}$ groups; or
  b) —Z-G-R$^{10}$, provided that —Z-G-R$^{10}$ is other than hydrogen;
or R$^{2a}$ and R$^{2b}$ together form =O;

Z is absent or —$(CH_2)_m$—, optionally substituted with 1 or 2-$(C_1-C_6)$alkyl;

G is selected from the group consisting of:
  a) a bond, —$(C_1-C_6)$alkylene, —$(C_2-C_6)$alkenylene;
  b) O, —OCO—, —C(=O), =CH;
  c) NR$^8$, =N—O, =N—NH;
  d) S, SO, and SO$_2$;

R$^{10}$ is selected from the group consisting of hydrogen, —$(C_1-C_{10})$alkyl, —$(C_2-C_{12})$alkenyl, —C(=O), —C(=O)—$(C_1-C_6)$alkyl, —C(=O)—$(C_2-C_6)$alkenyl, —C(=O)-(6- to 14-membered)aryl, —C(=O)—$(C_1-C_6)$alkyl-(6- to 14-membered)aryl, —$(C_2-C_{12})$alkynyl, —$(C_1-C_{10})$alkoxy, —$(OCH_2CH_2)_s$—O$(C_1-C_6)$alkyl, —$(CH_2CH_2O)_s$—$(C_1-C_6)$alkyl, —NH$_2$, —NH$(C_1-C_6)$alkyl, CN, NR$^5$R$^6$, —$(C_1-C_6)$alkyl-NR$^5$R$^6$, —CONR$^5$R$^6$, —$(C_1-C_6)$alkyl-CO—NR$^5$R$^6$, —COOR$^7$, —$(C_1-C_6)$alkyl-CO—OR$^7$, —$(C_1-C_6)$alkoxy-COOR$^7$, —CO—$(CH_2)_n$—COOR$^7$, —CO—$(CH_2)_n$—CO—NR$^5$R$^6$, —$(C_3-C_{12})$cycloalkyl, $((C_3-C_{12})$cycloalkyl)-$(C_1-C_6)$alkyl, —$(C_4-C_{12})$cycloalkenyl, $((C_4-C_{12})$cycloalkenyl)-$(C_1-C_6)$alkyl-, —$(C_6-C_{14})$bicycloalkyl, $((C_6-C_{14})$bicycloalkyl)-$(C_1-C_6)$alkyl-, —$(C_8-C_{20})$tricycloalkyl, $((C_8-C_{20})$tricycloalkyl)-$(C_1-C_6)$alkyl-, —$(C_7-C_{14})$bicycloalkenyl, $((C_7-C_{14})$bicycloalkenyl)-$(C_1-C_6)$alkyl-, —$(C_8-C_{20})$tricycloalkenyl, $((C_8-C_{20})$tricycloalkenyl)-$(C_1-C_6)$alkyl-, -(6- to 14-membered)aryl, ((6- to 14-membered)aryl)-$(C_1-C_6)$alkyl-, -(7- to 12-membered)bicyclic ring system, ((7- to 12-membered)bicyclic ring system)-$(C_1-C_6)$alkyl-, -(7- to 12-membered)bicyclic aryl, ((7- to 12-membered)bicyclic aryl)-$(C_1-C_6)$alkyl-, -(5- to 12-membered)heteroaryl, ((5- to 12-membered)heteroaryl)-$(C_1-C_6)$alkyl-, -(3- to 12-membered)heterocycle, ((3- to 12 membered)heterocycle)-$(C_1-C_6)$alkyl-, -(7- to 12-membered)bicycloheterocycle, ((7- to 12-membered)bicycloheterocycle)-$(C_1-C_6)$alkyl-, phenyl, benzyl and naphthyl; each of which is optionally substituted with one, two, or three substituents independently selected from the group consisting of —OH, (=O), halo, —C(halo)$_3$, —CH(halo)$_2$, —CH$_2$(halo), —$(C_1-C_6)$alkyl, halo$(C_1-C_6)$alkyl-, —$(C_2-C_6)$alkenyl, —$(C_2-C_6)$alkynyl, hydroxy$(C_1-C_6)$alkyl-, dihydroxy$(C_1-C_6)$alkyl-, —$(C_1-C_6)$alkoxy, $((C_1-C_6)$alkoxy)CO$(C_1-C_6)$alkoxy-, phenyl, benzyl, —NH$_2$, —NH$(C_1-C_6)$alkyl, —$(C_1-C_6)$alkyl-NH$(C_1-C_6)$alkyl-R$^{14}$, —CN, —SH, —OR$^{11}$, —CONR$^5$R$^6$, —$(C_1-C_6$alkyl)-CO—NR$^5$R$^6$, —COOR$^7$, —$(C_1-C_6)$alkyl-CO—OR$^7$, —$(C_1-C_6)$alkoxy-COOR$^7$, —$(OCH_2CH_2)_s$—O$(C_1-C_6)$alkyl, —$(CH_2CH_2O)_s$—$(C_1-C_6)$alkyl, $(C_1-C_6)$alkyl)sulfonyl, $((C_1-C_6)$alkyl)sulfonyl$(C_1-C_6)$alkyl-, —NH—SO$_2(C_1-C_6)$alkyl, NH$_2$—SO$_2(C_1-C_6)$alkyl-, —N(SO$_2(C_1-C_6)$alkyl)$_2$, —C(=NH)NH$_2$, —NH—CO—$(C_1-C_6)$alkyl, —NH—CO—NH$_2$, —NH—C(=O)—NH—$(C_1-C_6)$alkyl, —NH—C(=O)-(6- to 14-membered)aryl, —NH—C(=O)—$(C_1-C_6)$alkyl-(6- to 14-membered)aryl, —NH—$(C_1-C_6)$alkyl-CO—OR$^7$, —NH—C(=O)—$(C_1-C_6)$alkyl-CO—OR$^7$, —NH—C(=O)—CH(NH$_2$)—$(C_1-C_6)$alkyl-CO—OR$^7$, —$(C_3-C_{12})$cycloalkyl, $((C_3-C_{12})$cycloalkyl)-$(C_1-C_6)$alkyl-, -(6- to 14-membered)aryl, -(6- to 14-membered)aryloxy, —$(C_1-C_6)$alkoxy-C(O)NR$^5$R$^6$, —NH—$(C_1-C_6)$alkyl-C(O)—NR$^5$R$^6$, —C(O)NH—$(C_1-C_6)$alkyl-COOR$^7$, ((6- to 14-membered)aryl)-$(C_1-C_6)$alkyl-, -(5- to 12-membered)heteroaryl, ((5- to 12-membered)heteroaryl)-$(C_1-C_6)$alkyl-, -(3- to 12-membered)heterocycle, ((3- to 12-membered)heterocycle)-$(C_1-C_6)$alkyl-, -(7- to 12-membered)bicycloheterocycle, and ((7- to 12-membered)bicycloheterocycle)-$(C_1-C_6)$alkyl-;

R$^3$ is selected from:
  a) —H; or
  b) —$(C_1-C_5)$alkyl, —$(C_2-C_5)$alkenyl, or —$(C_2-C_5)$alkynyl;

R$^4$ is selected from
  a) —H, —OH, halo, —C(halo)$_3$, —CH(halo)$_2$, —CH$_2$(halo), COOH, or CONH$_2$; or
  b) —$(C_1-C_5)$alkyl, —$(C_2-C_5)$alkenyl, —$(C_2-C_5)$alkynyl, —$(CH_2)_n$—O—$(CH_2)_n$—CH$_3$, or —$(C_1-C_5)$alkoxy, each of which is optionally substituted with 1, 2, or 3 independently selected R$^9$ groups;

R$^5$ and R$^6$ are each independently selected from
  a) hydrogen, —OH, halo, —C(halo)$_3$, —CH(halo)$_2$, —CH$_2$(halo);
  b) —$(C_1-C_6)$alkyl, —$(C_2-C_5)$alkenyl, —$(C_2-C_5)$alkynyl, —$(CH_2)_n$—O—$(CH_2)_n$—CH$_3$, —$(C_1-C_6)$alkoxy, each of which is optionally substituted with 1, 2, or 3 substituents independently selected from —OH, halo, —$(C_1-C_{10})$alkyl, —$(C_1-C_{10})$alkenyl, —$(C_1-C_{10})$alkynyl, —$(C_1-C_{10})$alkoxy, —$(C_3-C_{12})$cycloalkyl, —CHO, —C(O)OH, —C(halo)$_3$, —CH(halo)$_2$, CH$_2$(halo), —$(CH_2)_n$—O—$(CH_2)_n$—CH$_3$, phenyl, or CONR$^5$R$^6$;
  c) —$(C_3-C_8)$cycloalkyl, $((C_3-C_8)$cycloalkyl)-$(C_1-C_6)$alkyl-, —COOR$^7$, —$(C_1-C_6)$alkyl-COOR$^7$, —CONH$_2$, or $(C_1-C_6)$alkyl-CONH—;
  d) ((6- to 14-membered)aryl) optionally substituted with 1, 2, or 3 independently selected R$^{30}$ groups; or
  e) R$^5$ and R$^6$ together with the nitrogen atom to which they are attached form a (4- to 8-membered)heterocycle optionally substituted with 1, 2, or 3 independently selected R$^{30}$ groups;

each R$^7$ is independently selected from the group consisting of hydrogen, —$(C_1-C_6)$alkyl, —$(C_2-C_6)$alkenyl, $(C_2-C_6)$alkynyl, —$(C_3-C_{12})$cycloalkyl, —$(C_4-C_{12})$cycloalkenyl, $((C_3-C_{12})$cycloalkyl)-$(C_1-C_6)$alkyl-, and $((C_4-C_{12})$cycloalkenyl)-$(C_1-C_6)$alkyl-;

each R$^8$ is independently selected from H, —$(C_1-C_6)$alkyl, —$(C_2-C_6)$alkenyl, —$(C_2-C_6)$alkynyl, —$(C_1-C_{10})$alkoxy, —$(C_3-C_{12})$cycloalkyl, —$(C_3-C_{12})$cycloalkenyl, $((C_3-C_{12})$cycloalkyl)-$(C_1-C_6)$alkyl-, $((C_3-C_{12})$cycloalkenyl)-$(C_1-C_6)$alkyl-, —C(=O)$(C_1-C_6)$alkyl or SO$_2(C_1-C_6)$alkyl;

each R$^9$ is independently selected from —OH, halo, —$(C_1-C_{10})$alkyl, —$(C_2-C_{10})$alkenyl, —$(C_2-C_{10})$alkynyl, —$(C_1-C_{10})$alkoxy, —$(C_3-C_{12})$cycloalkyl, —CHO, —C(O)OH, —C(halo)$_3$, —CH(halo)$_2$, CH$_2$(halo), —$(CH_2)_n$—O—$(CH_2)_n$—CH$_3$, phenyl, or CONR$^5$R$^6$;

each R$^{11}$ is independently selected from —C(halo)$_3$, —CH(halo)$_2$, —CH$_2$(halo), —$(C_2-C_5)$alkenyl, —$(C_2-C_5)$alkynyl, —$(CH_2)_n$—O—$(CH_2)_n$—CH$_3$, (6- to 14-membered)aryl, ((6- to 14-membered)aryl)-$(C_1-C_6)$alkyl-, (5- to 12-membered)heteroaryl, or ((5- to 12-membered)heteroaryl)-$(C_1-$ $C_6$)alkyl, each of which is optionally substituted with 1, 2, or 3 independently selected $R^9$ groups;

each $R^{14}$ is independently selected from —COOR$^7$, —($C_1$-$C_6$)alkyl-COOR$^7$, —C(=O)—($C_1$-$C_6$)alkyl-COOR$^7$, —($C_1$-$C_6$)alkyl-C(=O)—($C_1$-$C_6$)alkyl-COOR$^7$, CONH$_2$, or —($C_1$-$C_6$)alkyl-CONH;

each $R^{30}$ is independently selected from COOR$^7$, CONR$^5$R$^6$, —($C_1$-$C_6$)alkyl, CN, -(3- to 12-membered)heteroaryl, ((3- to 12-membered)heteroaryl)-($C_1$-$C_6$)alkyl-, NH$_2$, halo, and ((6- to 14-membered)aryl)-($C_1$-$C_6$)alkoxy-;

m is an integer 1, 2, 3, 4, 5, or 6;

n is an integer 0, 1, 2, 3, 4, 5, or 6;

s in an integer 1, 2, 3, 4, 5, or 6;

provided that when $R^4$ is —($C_1$-$C_5$)alkoxy then:

a) $R^{2a}$ and $R^{2b}$ cannot be taken together to form =O; or b) $R^{2a}$ cannot be OH when $R^{2b}$ is —Z-G-R$^{10}$, and —Z-G-R$^{10}$ is either:

a. OH; or b. —($C_1$-$C_6$)alkyl; or c) $R^{2a}$ cannot be H when the combination —Z-G-R$^{10}$ is OH;

and the pharmaceutically acceptable salts, prodrugs and solvates thereof.

In one embodiment, the present invention provides novel compounds of Formula IA:

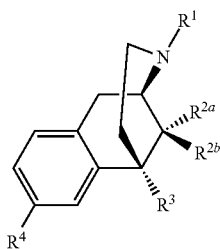

IA wherein $R^1$, $R^{2a}$, $R^{2b}$, $R^3$ and $R^4$ are as defined above for Formula I, and the pharmaceutically acceptable salts, prodrugs, and solvates thereof.

In another embodiment, the present invention provides novel compounds of Formula IB:

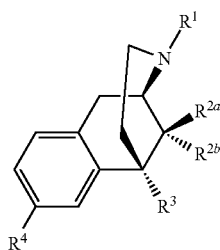

IB wherein $R^1$, $R^{2a}$, $R^{2b}$, $R^3$ and $R^4$ are as defined above for Formula I, and the pharmaceutically acceptable salts, prodrugs and solvates thereof.

In another embodiment, the present invention provides novel compounds of Formula IC:

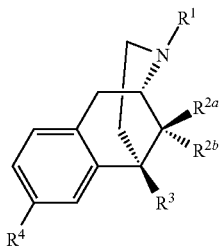

IC wherein $R^1$, $R^{2a}$, $R^{2b}$, $R^3$ and $R^4$ are as defined above for Formula I, and the pharmaceutically acceptable salts, prodrugs and solvates thereof.

In another embodiment, the present invention provides novel compounds of Formula ID:

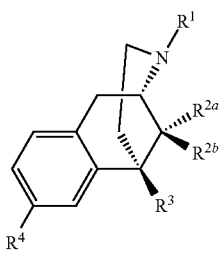

ID wherein $R^1$, $R^{2a}$, $R^{2b}$, $R^3$ and $R^4$ are as defined above for Formula I, and the pharmaceutically acceptable salts, prodrugs and solvates thereof.

The following embodiments may be selected for any of the formulae shown above

Item 1. In certain embodiments, $R^{2a}$ is absent.

Item 2. In certain embodiments, $R^{2a}$ is hydrogen.

Item 3. In certain embodiments, $R^{2a}$ is OH.

Item 4. In certain embodiments $R^{2a}$ and $R^{2b}$ together form =O.

Item 5. In certain embodiments of any one of Items 1 to 3, $R^{2b}$ is ((6- to 14-membered)aryl) or ((3- to 12-membered) heterocycle), each of which is optionally substituted with one or more $R^{30}$.

Item 6. In certain embodiments of any one of Items 1 to 3, $R^{2b}$ is —Z-G-R$^{10}$, provided that —Z-G-R$^{10}$ is other than hydrogen.

Item 7. In certain embodiments of any one of Items 1 to 6, Z is absent.

Item 8. In certain embodiments, of any one of Items 1 to 3, or 6 Z is CH$_2$.

Item 9. In certain embodiments of any one of Items 1 to 3, or 6 to 7, G is NR$^8$.

Item 10. In certain embodiments of Item 9, G is NR$^8$, wherein R$^8$ is hydrogen.

Item 11. In other embodiments of Item 9, G is NR$^8$, wherein R$^8$ is ($C_1$-$C_6$)alkyl.

Item 12. In other embodiments of Item 11, G is NR$^8$, wherein R$^8$ is methyl or ethyl.

Item 13. In certain embodiments of any one of Items 1 to 3, or 6 to 8, G is a bond.

Item 14. In certain embodiments of any one of Items 1 to 3, or 6 to 8, G is O.

Item 15. In certain embodiments of any one of Items 1 to 3, or 6 to 8, G is —OCO—.

Item 16. In certain embodiments of any one of Items 1 to 3, or 6 to 8, G is C(=O).

Item 17. In certain embodiments of any one of Items 1 to 3, or 6 to 8, G is =CH.

Item 18. In certain embodiments of any one of Items 1 to 3, or 6 to 8, G is =N—O.

Item 19. In certain embodiments of any one of Items 1 to 3, or 6 to 8, G is S.

Item 20. In certain embodiments of any one of Items 1 to 3, or 6 to 8, G is SO.

Item 21. In certain embodiments of any one of Items 1 to 3, or 6 to 8, G is $SO_2$.

Item 22. In certain embodiments of any of Items 1 to 3, or 6 to 21, $R^{10}$ is a (6- to 14-membered)aryl or ((6- to 14-membered)aryl)-($C_1$-$C_6$)alkyl-, optionally substituted with one, two or three substituents independently selected from ($C_1$-$C_6$)alkyl, halo, C(halo)$_3$, CH(halo)$_2$, CH$_2$(halo), —($C_1$-$C_6$)alkyl-CO—NR$^5$R$^6$, NH$_2$—SO$_2$($C_1$-$C_6$)alkyl-, or SO$_2$—NR$^{5a}$R$^{6a}$. In certain embodiments, $R^{10}$ is substituted with ($C_1$-$C_6$)alkyl.

Item 23. In certain embodiments of Item 22, $R^{10}$ is substituted with SO$_2$—NR$^{5a}$R$^{6a}$.

Item 24. In certain embodiments of Item 23, at least one of $R^{5a}$ or $R^{6a}$ is hydrogen.

Item 25. In certain embodiments of any of Items 22 or 23, both $R^{5a}$ and $R^{6a}$ are hydrogen.

Item 26. In certain embodiments of Item 22, $R^{10}$ is optionally substituted phenyl or benzyl.

Item 27. In certain embodiments, $R^{10}$ is -(5- to 12-membered)heteroaryl, ((5- to 12-membered)heteroaryl-($C_1$-$C_6$)alkyl-, -(3- to 12-membered)heterocycle, ((3- to 12-membered)heterocycle)-($C_1$-$C_6$)alkyl-, (7- to 12-membered)bicycloheterocycle, or ((7- to 12-membered)bicycloheterocycle)-($C_1$-$C_6$)alkyl-, each of which is optionally substituted.

Item 28. In certain embodiments of Item 27, $R^{10}$ is optionally substituted with one, two or three substituents independently selected from the group consisting of —($C_1$-$C_6$)alkyl, —($C_{3-12}$)cycloalkyl, -(6- to 14-membered)aryl, and (5- to 12-membered)heteroaryl.

Item 29. In certain embodiments of Item 27, $R^{10}$ is substituted with COOR$^7$.

Item 30. In certain embodiments of Item 27, $R^7$ is —($C_1$-$C_6$)alkyl.

Item 31. In certain embodiments of Item 27, $R^{10}$ is piperidinyl optionally substituted with COOR$^7$ or NH$_2$.

Item 32. In certain embodiments of Item 27, $R^{10}$ is pyrrolidinyl.

Item 33. In certain embodiments of Item 27, $R^{10}$ is optionally substituted pyridinyl.

Item 34. In other embodiments of Item 27, $R^{10}$ is furanyl.

Item 35. In certain embodiments, $R^{10}$ is optionally substituted C(=O)-((6- to 14-membered)aryl).

Item 36. In certain embodiments, $R^{10}$ is optionally substituted C(=O)—NH-(4- to 12-membered)heteroaryl.

Item 37. In other embodiments, $R^{10}$ is C(=O) or C(=O)—($C_2$-$C_6$)alkenyl, optionally substituted with ($C_3$-$C_{12}$)cycloalkyl, (6- to 14-membered)aryl or (5- to 12-membered)heteroaryl.

Item 38. In certain embodiments of Item 37, $R^{10}$ is substituted with ($C_3$-$C_{12}$)cycloalkyl.

Item 39. In certain embodiments, $R^{10}$ is C(=O)—($C_1$-$C_6$)alkyl-(6- to 14-membered)aryl, optionally substituted with halo.

Item 40. In certain embodiments, $R^{10}$ is NR$^5$R$^6$ or ($C_1$-$C_6$)alkyl-NR$^5$NR$^6$, each of which is optionally substituted.

Item 41. In certain embodiments of Item 40, at least one of $R^5$ or $R^6$ is hydrogen.

Item 42. In certain embodiments of any one of Items 40 or 41, at least one of $R^5$ or $R^6$ is ($C_1$-$C_6$)alkyl.

Item 43. In certain embodiments of Item 40, at least one of $R^5$ or $R^6$ is -(6- to 14-membered)aryl.

Item 44. In certain embodiments of Item 40, at least one of $R^5$ or $R^6$ is -(5- to 12-membered)heteroaryl.

Item 45. In other embodiments of any one of Items 40 or 41, at least one of $R^5$ or $R^6$ is hydrogen, and the other is —($C_1$-$C_6$)alkyl-COOR$^7$.

Item 46. In certain embodiments of Item 45, $R^7$ is hydrogen.

Item 47. In certain embodiments of Item 45, $R^7$ is —($C_1$-$C_6$)alkyl.

Item 48. In certain embodiments, $R^{10}$ is CONR$^5$R$^6$.

Item 49. In certain embodiments of Item 48, at least one of $R^5$ or $R^6$ is optionally substituted ($C_1$-$C_6$)alkyl.

Item 50. In certain embodiments of any one of Items 48 or 49, at least one of $R^5$ or $R^6$ is substituted with phenyl.

Item 51. In other embodiments of Item 48, at least one of $R^5$ or $R^6$ is -(6- to 14-membered)aryl optionally substituted with one, two or three independently selected $R^{30}$ groups.

Item 52. In other embodiments of Item 48, at least one of $R^5$ or $R^6$ is -(6- to 14-membered)aryl substituted with one $R^{30}$ group.

Item 53. In certain embodiments of Item 52, $R^{30}$ is —($C_1$-$C_6$)alkyl.

Item 54. In certain embodiments of Item 52, $R^{30}$ is COOR$^7$.

Item 55. In other embodiments of Item 54, $R^7$ is hydrogen.

Item 56. In certain embodiments of Item 48, at least one of $R^5$ or $R^6$ is -(5- to 12-membered)heteroaryl or (3- to 12-membered)heterocycle.

Item 57. In certain embodiments of Item 48, $R^5$ and $R^6$ together with the nitrogen to which they are attached, form an optionally substituted -(3- to 12-membered)heterocycle.

Item 58. In certain embodiments of Item 57, the (3- to 12-membered) heterocycle is substituted with one, two or three independently selected halo, C(halo)$_3$, CH(halo)$_2$, or CH$_2$(halo).

Item 59. In certain embodiments, $R^{10}$ is optionally substituted SO$_2$—($C_1$-$C_6$)alkyl.

Item 60. In certain embodiments, $R^{10}$ is optionally substituted SO$_2$—($C_3$-$C_{12}$)cycloalkyl.

Item 61. In certain embodiments, $R^{10}$ is optionally substituted SO$_2$-(5- to 12-membered)heteroaryl.

Item 62. In certain embodiments, $R^{10}$ is optionally substituted SO$_2$-((6- to 14-membered)aryl) or SO$_2$-((6- to 14-membered)aryl)-($C_1$-$C_6$)alkyl.

Item 63. In certain embodiments of Item 60, $R^{10}$ is substituted with one, two or three independently selected halo, C(halo)$_3$, CH(halo)$_2$, or CH$_2$(halo).

Item 64. In certain embodiments, $R^{10}$ is optionally substituted ($C_1$-$C_6$)alkyl-NR$^5$R$^6$.

Item 65. In certain embodiments of Item 64, at least one of $R^5$ and $R^6$ is hydrogen.

Item 66. In certain embodiments of any one of Items 64 or 65, at least one of $R^5$ and $R^6$ is COOR$^7$.

Item 67. In certain embodiments of Item 66, $R^7$ is —($C_1$-$C_6$)alkyl.

Item 68. In certain embodiments, $R^{2a}$ is hydrogen, and $R^{2b}$ is —Z-G-R$^{10}$, wherein Z is absent, G is NR$^8$ where $R^8$ is hydrogen, and $R^{10}$ is C(=O)—($C_2$-$C_6$)alkenyl substituted with a (5- to 12-membered)heteroaryl.

Item 69. In other embodiments, $R^{2a}$ is hydrogen, and $R^{2b}$ is —Z-G-$R^{10}$, wherein Z is absent, G is $NR^8$ wherein $R^8$ is $(C_1-C_6)$alkyl, and $R^{10}$ is ((6- to 14-membered)aryl)-$(C_1-C_6)$alkyl-.

Item 70. In other embodiments, $R^{2a}$ is hydrogen, and $R^{2b}$ is —Z-G-$R^{10}$, wherein Z is $CH_2$, G is a bond, and $R^{10}$ is $CONR^5R^6$, wherein one of $R^5$ or $R^6$ is hydrogen, and the other is (6- to 14-membered)aryl substituted with one $R^{30}$ wherein $R^{30}$ is $COOR^7$ wherein $R^7$ is hydrogen.

Item 71. In other embodiments, $R^{2a}$ is hydrogen, and $R^{2b}$ is —Z-G-$R^{10}$, wherein Z is absent, G is $NR^8$ wherein $R^8$ is $(C_1-C_6)$alkyl, and $R^{10}$ is C(=O) substituted with a (6- to 14-membered)aryl.

Item 72. In certain embodiments, $R^{2a}$ is hydrogen, and $R^{2b}$ is —Z-G-$R^{10}$, wherein Z is $CH_2$, G is O, and $R^{10}$ is (6-14-membered)aryl substituted with a —$(C_1-C_6)$alkyl-CO—$NR^5R^6$, wherein $R^5$ and $R^6$ are both hydrogen.

Item 73. In other embodiments, $R^{2a}$ is hydrogen, and $R^{2b}$ is —Z-G-$R^{10}$, wherein Z is absent, G is $NR^8$ wherein $R^8$ is hydrogen, and $R^{10}$ is (6-14-membered)aryl substituted with $NH_2$—$SO_2(C_1-C_6)$alkyl-.

Item 74. In other embodiments, $R^{2a}$ is hydrogen, and $R^{2b}$ is —Z-G-$R^{10}$, wherein Z is absent, G is $NR^8$ wherein $R^8$ is $(C_1-C_6)$alkyl, and $R^{10}$ is -(6- to 14-membered)aryl substituted with $NH_2$—$SO_2(C_1-C_6)$alkyl-.

Item 75. In other embodiments, $R^{2a}$ is hydrogen, and $R^{2b}$ is —Z-G-$R^{10}$, wherein Z is absent, G is $NR^8$ wherein $R^8$ is $(C_1-C_6)$alkyl, and $R^{10}$ is C(=O)—$(C_2-C_6)$alkenyl substituted with (5- to 12-membered)heteroaryl or (3- to -12-membered)heterocycle.

Item 76. In other embodiments, $R^{2a}$ is hydrogen, and $R^{2b}$ is —Z-G-$R^{10}$, wherein Z is absent, G is $NR^8$ wherein $R^8$ is hydrogen, and $R^{10}$ is -(6- to 14-membered)aryl substituted with $NH_2$—$SO_2(C_1-C_6)$alkyl-.

Item 77. In other embodiments, $R^{2a}$ is hydrogen, and $R^{2b}$ is —Z-G-$R^{10}$, wherein Z is absent, G is $NR^8$ wherein $R^8$ is $(C_1-C_6)$alkyl, and $R^{10}$ is $CONR^5R^6$ wherein one of $R^5$ or $R^6$ is hydrogen and the other is —$(C_1-C_6)$alkyl-$COOR^7$.

Item 78. In other embodiments, $R^{2a}$ is hydrogen, and $R^{2b}$ is —Z-G-$R^{10}$, wherein Z is absent, G is a bond, and $R^{10}$ is (3- to 12-membered)heterocycle substituted with $COOR^7$ wherein $R^7$ is hydrogen.

Item 79. In other embodiments, $R^{2a}$ is hydrogen, and $R^{2b}$ is —Z-G-$R^{10}$, wherein Z is $CH_2$, G is $NR^8$ wherein $R^8$ is hydrogen, and $R^{10}$ is C(=O)—$(C_1-C_6)$alkyl-(6- to 14-membered)aryl substituted with two halo.

Item 80. In other embodiments, $R^{2a}$ is hydrogen, and $R^{2b}$ is —Z-G-$R^{10}$, wherein Z is absent, G is $NR^8$ wherein $R^8$ is $(C_1-C_6)$alkyl, and $R^{10}$ is $CONR^5R^6$ wherein one of $R^5$ or $R^6$ is hydrogen and the other is —$(C_1-C_6)$alkyl-$COOR^7$.

Item 81. In other embodiments, $R^{2a}$ is hydrogen, and $R^{2b}$ is —Z-G-$R^{10}$, wherein Z is absent, G is $NR^8$ wherein $R^8$ is —$(C_1-C_6)$alkyl, and $R^{10}$ is C(=O)—$(C_2-C_6)$alkenyl substituted with (3- to 12-membered)heterocycle.

Item 82. In one embodiment, $R^{2a}$ is hydrogen, and $R^{2b}$ is —Z-G-$R^{10}$, wherein Z is absent, G is $NR^8$ wherein $R^8$ is —$(C_1-C_6)$alkyl, and $R^{10}$ is ((3- to 12-membered)heterocycle)-$(C_1-C_6)$alkyl-substituted with $COOR^7$.

Item 83. In one embodiment of Item 82, $R^7$ is —$(C_1-C_6)$alkyl.

Item 84. In certain embodiments, $R^{2a}$ is hydrogen, and $R^{2b}$ is —Z-G-$R^{10}$, wherein Z is absent, G is $NR^8$ where $R^8$ is hydrogen, and $R^{10}$ is optionally substituted $SO_2$-((6- to 14-membered)aryl).

Item 85. In certain embodiments, $R^{2a}$ is hydrogen, and $R^{2b}$ is —Z-G-$R^{10}$, wherein Z is absent, G is N—$SO_2$, and $R^{10}$ is -(6- to 14-membered)aryl or ((6- to 14-membered)aryl)-$(C_1-C_6)$alkyl-, each of which is optionally substituted.

Item 86. In certain embodiments, $R^{2a}$ is hydrogen, and $R^{2b}$ is —Z-G-$R^{10}$, wherein Z is absent, G is $NR^8$ where $R^8$ is —$(C_1-C_6)$alkyl, and $R^{10}$ is -(6- to 14-membered)aryl substituted with $SO_2$—$NR^{5a}R^{6a}$.

Item 87. In one embodiment, $R^{2a}$ is hydrogen, and $R^{2b}$ is —Z-G-$R^{10}$, wherein Z is absent, G is $NR^8$ where $R^8$ is hydrogen, and $R^{10}$ is —$(C_1-C_6)$alkyl-$NR^5R^6$.

Item 88. In one embodiment of Item 87, at least one of $R^5$ and $R^6$ is hydrogen.

Item 89. In one embodiment of any one of Items 87 or 88 at least one of $R^5$ and $R^6$ is $COOR^7$.

Item 90. In one embodiment of Item 89, $R^7$ is —$(C_1-C_6)$alkyl.

Item 91. In one embodiment, $R^{2a}$ is hydrogen, and $R^{2b}$ is —Z-G-$R^{10}$, wherein Z is absent, G is $NR^8$ where $R^8$ is —$(C_1-C_6)$alkyl, and $R^{10}$ is $CONR^5R^6$.

Item 92. In one embodiment of Item 91, $R^5$ and $R^6$ taken together with the nitrogen atom to which they are attached form an optionally substituted (3- to 12-membered)heterocycle.

Item 93. In one embodiment of Item 92, the (3- to 12-membered) heterocycle is substituted with one $R^{30}$ group.

Item 94. In one embodiment of Item 93, $R^{30}$ is selected from the group consisting of halo, C(halo)$_3$, CH(halo)$_2$, and $CH_2$(halo).

Item 95. In one embodiment, $R^{2a}$ is hydrogen, and $R^{2b}$ is —Z-G-$R^{10}$, wherein Z is absent, G is $NR^8$ where $R^8$ is hydrogen, and $R^{10}$ is optionally substituted $SO_2$-((6- to 14-membered)aryl).

Item 96. In one embodiment of Item 95, $R^{10}$ is substituted with one, two or three substituents independently selected from the group consisting of halo, C(halo)$_3$, CH(halo)$_2$, and $CH_2$(halo).

Item 97. In one embodiment, $R^{2a}$ is hydrogen, and $R^{2b}$ is —Z-G-$R^{10}$, wherein Z is absent, G is N—$SO_2$, and $R^{10}$ is optionally substituted (6- to 14-membered)aryl.

Item 98. In one embodiment of Item 97, $R^{10}$ is optionally substituted with one, two or three substituents independently selected from the group consisting of halo, C(halo)$_3$, CH(halo)$_2$, and $CH_2$(halo).

Item 99. In one embodiment, $R^{2a}$ is hydrogen, and $R^{2b}$ is —Z-G-$R^{10}$, wherein Z is absent, G is $NR^8$, and $R^{10}$ is $CONR^5R^6$.

Item 100. In one embodiment of Item 99, $R^8$ is —$(C_1-C_6)$alkyl.

Item 101. In one embodiment of any one of Items 99 or 100 at least one of $R^5$ and $R^6$ is hydrogen.

Item 102. In one embodiment of any one of Items 99 to 101, at least one of $R^5$ and $R^6$ is optionally substituted (6- to 14-membered)aryl.

Item 103. In one embodiment of Item 102, the (6 to 14-membered)aryl is substituted with one $R^{30}$ group.

Item 104. In one embodiment of Item 103, $R^{30}$ is —$(C_1-C_6)$alkyl.

Item 105. In one embodiment, $R^{2a}$ is hydrogen, and $R^{2b}$ is —Z-G-$R^{10}$, wherein Z is absent, G is $NR^8$, and $R^{10}$ is optionally substituted ((6- to 14-membered)aryl)-$(C_1-C_6)$alkyl-.

Item 106. In one embodiment of Item 105, $R^8$ is hydrogen.

Item 107. In one embodiment of any one of Items 105 or 106, $R^{10}$ is substituted with $(C_1-C_6)$alkyl.

Item 108. In one embodiment, $R^{2a}$ is hydrogen, and $R^{2b}$ is —Z-G-$R^{10}$, wherein Z is absent, G is $NR^8$, and $R^{10}$ is (3- to 12-membered)heterocycle, ((3- to 12-membered)heterocycle)-($C_1$-$C_6$)alkyl-, (7- to 12-membered)bicycloheterocycle, or ((7- to 12-membered)bicycloheterocycle)-($C_1$-$C_6$)alkyl-, each of which is optionally substituted.

Item 109. In one embodiment of Item 108, $R^8$ is hydrogen.

Item 110. In one embodiment of any one of Items 108 or 109, $R^{10}$ is substituted with $COOR^7$.

Item 111. In one embodiment of Item 110, $R^7$ is —($C_1$-$C_6$)alkyl.

Item 112. In one embodiment, $R^{2a}$ is hydrogen, and $R^{2b}$ is —Z-G-$R^{10}$, wherein Z is absent, G is $NR^8$, and $R^{10}$ is optionally substituted C(=O)—NH-((3- to 12-membered)heterocycle).

Item 113. In one embodiment of Item 112, $R^8$ is —($C_1$-$C_6$)alkyl.

Item 114. In one embodiment of any one of Items 112 or 113, $R^{10}$ is substituted with one, two or three independently selected halo, C(halo)$_3$, CH(halo)$_2$, and CH$_2$(halo).

Item 115. In one embodiment, $R^{2a}$ is hydrogen, and $R^{2b}$ is —Z-G-$R^{10}$, wherein Z is absent, G is $NR^8$, and $R^{10}$ is optionally substituted ((6- to 14-membered)aryl)-($C_1$-$C_6$)alkyl-.

Item 116. In one embodiment of Item 115, $R^8$ is hydrogen.

Item 117. In one embodiment of any one of Items 115 or 116, $R^{10}$ is substituted with —SO$_2$—$NR^{5a}R^{6a}$.

Item 118. In one embodiment of Item 117, at least one of $R^{5a}$ and $R^{6a}$ is hydrogen.

Item 119. In one embodiment of any one of Items 117 or 118, both $R^{5a}$ and $R^{6a}$ are hydrogen.

Item 120. In one embodiment, $R^{2a}$ is hydrogen, and $R^{2b}$ is —Z-G-$R^{10}$, wherein Z is absent, G is $NR^8$, and $R^{10}$ is optionally substituted C(=O).

Item 121. In one embodiment of Item 120, $R^8$ is —($C_1$-$C_6$)alkyl.

Item 122. In one embodiment of any one of Items 120 or 121, $R^{10}$ is substituted with (6- to 14-membered)aryl.

Item 123. In one embodiment of Item 122, $R^{10}$ is substituted with phenyl or benzyl.

Item 124. In any one of Items 120 or 121, $R^{10}$ is substituted with (3- to 12-membered)heterocycle or (5- to 12-membered)heteroaryl.

Item 125. In one embodiment, $R^{2a}$ is hydrogen, and $R^{2b}$ is —Z-G-$R^{10}$, wherein Z is absent, G is $NR^8$, and $R^{10}$ is (6- to 14-membered)aryl or ((6- to 14-membered)aryl)-($C_1$-$C_6$)alkyl-, each of which is optionally substituted.

Item 126. In one embodiment of Item 125, $R^8$ is hydrogen.

Item 127. In one embodiment of any one of Items 125 or 126, $R^{10}$ is substituted by one, two or three independently selected halo, C(halo)$_3$, CH(halo)$_2$, or CH$_2$(halo).

Item 128. In one embodiment, $R^{2a}$ is hydrogen, and $R^{2b}$ is —Z-G-$R^{10}$, wherein Z is absent, G is $NR^8$, and $R^{10}$ is optionally substituted C(=O)—(C1-C6)alkyl.

Item 129. In one embodiment, $R^{2a}$ is hydrogen, and $R^{2b}$ is —Z-G-$R^{10}$, wherein Z is absent, G is $NR^8$, and $R^{10}$ is $NR^5R^6$.

Item 130. In one embodiment of Item 129, $R^8$ is hydrogen.

Item 131. In any one of Items 129 or 130, at least one of $R^5$ or $R^6$ is hydrogen.

Item 132. In any one of Items 129 to 131, at least one of $R^5$ or $R^6$ is $COOR^7$.

Item 133. In one embodiment of Item 132, $R^7$ is —($C_1$-$C_6$)alkyl.

Item 134. In one embodiment $R^{2a}$ is hydrogen, and $R^{2b}$ is —Z-G-$R^{10}$, wherein Z is absent, G is $NR^8$, and $R^{10}$ is optionally substituted SO$_2$-((6- to 14-membered)aryl).

Item 135. In one embodiment of Item 134, $R^8$ is hydrogen.

Item 136. In one embodiment of any one of Items 134 or 135, $R^{10}$ is substituted with one, two or three independently selected halo, C(halo)$_3$, CH(halo)$_2$, or CH$_2$(halo).

Item 137. In one embodiment, $R^{2a}$ is hydrogen, and $R^{2b}$ is —Z-G-$R^{10}$, wherein Z is absent, G is $NR^8$, and $R^{10}$ is optionally substituted ((6- to 14-membered)aryl)-($C_1$-$C_6$)alkyl.

Item 138. In one embodiment of Item 137, $R^8$ is —($C_1$-$C_6$)alkyl.

Item 139. In one embodiment of any one of Items 137 or 138, $R^{10}$ is substituted with —SO$_2$—$NR^{5a}R^{6a}$.

Item 140. In one embodiment of Item 139, at least one of $R^{5a}$ and $R^{6a}$ is hydrogen.

Item 141. In one embodiment of any one of Items 139 or 140, both $R^{5a}$ and $R^{6a}$ are hydrogen.

Item 142. In one embodiment, $R^{2a}$ is hydrogen, and $R^{2b}$ is —Z-G-$R^{10}$, wherein Z is absent, G is $NR^8$, and $R^{10}$ is optionally substituted ($C_1$-$C_6$)alkyl-$NR^5R^6$.

Item 143. In one embodiment of Item 142, at least one of $R^5$ and $R^6$ is hydrogen.

Item 144. In one embodiment of anyone of Items 142 or 143, at least one of $R^5$ and $R^6$ is $COOR^7$.

Item 145. In one embodiment of Item 144, $R^7$ is —($C_1$-$C_6$)alkyl.

Specific Compounds of the Invention include:

2-(((8-methoxy-3,6-dimethyl-1,2,3,4,5,6-hexahydro-2,6-methanobenzo[d]azocin-11-ylidene)amino)oxy)acetic acid (Compound 1);

8-methoxy-3,6-dimethyl-1,2,3,4,5,6-hexahydro-2,6-methanobenzo[d]azocin-11-one oxime (Compound 2);

2-(((6R,11R)-8-methoxy-3,6-dimethyl-1,2,3,4,5,6-hexahydro-2,6-methanobenzo[d]azocin-11-yl)oxy)acetamide (Compound 3);

2-(((6R,11S)-8-methoxy-3,6-dimethyl-1,2,3,4,5,6-hexahydro-2,6-methanobenzo[d]azocin-11-yl)oxy)acetamide (Compound 4);

8-methoxy-3,6-dimethyl-1,2,3,4,5,6-hexahydro-2,6-methanobenzo[d]azocin-11-one-O-(2-(diethylamino)ethyl) oxime (Compound 5);

8-methoxy-3,6-dimethyl-11-propylidene-1,2,3,4,5,6-hexahydro-2,6-methanobenzo[d]azocine (Compound 6);

4-(11,11-dihydroxy-8-methoxy-6-methyl-1,2,5,6-tetrahydro-2,6-methanobenzo[d]azocin-3(4H)-yl)-N,N-dimethyl-2,2-diphenylbutanamide (Compound 7);

(6R,11S)-8-methoxy-N,3,6-trimethyl-1,2,3,4,5,6-hexahydro-2,6-methanobenzo[d]azocin-11-amine (Compound 8);

(6R,11R)-8-methoxy-N,3,6-trimethyl-1,2,3,4,5,6-hexahydro-2,6-methanobenzo[d]azocin-11-amine (Compound 9);

3-(cyclopropylmethyl)-8-methoxy-6-methyl-1,2,3,4,5,6-hexahydro-2,6-methanobenzo[d]azocin-11-one O-methyl oxime (Compound 10);

((6S,11R)-8-methoxy-3,6-dimethyl-1,2,3,4,5,6-hexahydro-2,6-methanobenzo[d]azocin-11-yl)methanol (Compound 11);

(4-ethyl 2-(8-methoxy-3,6-dimethyl-1,2,3,4,5,6-hexahydro-2,6-methanobenzo[d]azocin-11-ylidene)acetate (Compound 12);

(Z)-2-(8-methoxy-3,6-dimethyl-1,2,3,4,5,6-hexahydro-2,6-methanobenzo[d]azocin-11-ylidene)acetic acid (Compound 13);

ethyl 2-((6S,11R)-8-methoxy-3,6-dimethyl-1,2,3,4,5,6-hexahydro-2,6-methanobenzo[d]azocin-11-yl)acetate (Compound 14);

2-((6S,11R)-8-methoxy-3,6-dimethyl-1,2,3,4,5,6-hexahydro-2,6-methanobenzo[d]azocin-11-yl)acetic acid (Compound 15);

(E)-3-(furan-3-yl)-N-((6R,11R)-8-methoxy-3,6-dimethyl-1,2,3,4,5,6-hexahydro-2,6-methanobenzo[d]azocin-11-yl)-N-methylacrylamide (Compound 16);

4-((6R,11S)-11-hydroxy-8-methoxy-6-methyl-1,2,5,6-tetrahydro-2,6-methanobenzo[d]azocin-3 (4H)-yl)-N,N-dimethyl-2,2-diphenylbutanamide (Compound 17);

8-hydroxy-3,6-dimethyl-1,2,3,4,5,6-hexahydro-2,6-methanobenzo[d]azocin-11-one oxime (Compound 18);

4-(11-(hydroxyimino)-8-methoxy-6-methyl-1,2,5,6-tetrahydro-2,6-methanobenzo[d]azocin-3 (4H)-yl)-N,N-dimethyl-2,2-diphenylbutanamide (Compound 19);

(E)-3-(furan-3-yl)-N-((6R,11S)-8-methoxy-3,6-dimethyl-1,2,3,4,5,6-hexahydro-2,6-methanobenzo[d]azocin-11-yl)-N-methylacrylamide (Compound 20);

4-((6R,11R)-8,11-dihydroxy-6-methyl-1,2,5,6-tetrahydro-2,6-methanobenzo[d]azocin-3(4H)-yl)-N,N-dimethyl-2,2-diphenylbutanamide (Compound 21);

4-((6R,11S)-8,11-dihydroxy-6-methyl-1,2,5,6-tetrahydro-2,6-methanobenzo[d]azocin-3(4H)-yl)-N,N-dimethyl-2,2-diphenylbutanamide (Compound 22);

(E)-3-(furan-3-yl)-N-((2R,6R,11S)-8-methoxy-3,6-dimethyl-1,2,3,4,5,6-hexahydro-2,6-methanobenzo[d]azocin-11-yl)acrylamide (Compound 23);

(E)-3-(furan-3-yl)-N-((2R,6R,11S)-8-hydroxy-3,6-dimethyl-1,2,3,4,5,6-hexahydro-2,6-methanobenzo[d]azocin-11-yl)-N-methylacrylamide (Compound 24);

(E)-N-ethyl-3-(furan-3-yl)-N-((2R,6R,11S)-8-methoxy-3,6-dimethyl-1,2,3,4,5,6-hexahydro-2,6-methanobenzo[d]azocin-11-yl)acrylamide (Compound 25);

4-fluoro-N'-((2S,6R)-8-methoxy-3,6-dimethyl-1,2,3,4,5,6-hexahydro-2,6-methanobenzo[d]azocin-11-ylidene)benzohydrazide (Compound 26);

N-((2R,6R,11S)-8-hydroxy-3,6-dimethyl-1,2,3,4,5,6-hexahydro-2,6-methanobenzo[d]azocin-11-yl)-N-methyl-2-(4-(methylsulfonyl)phenyl)acetamide (Compound 27);

4-(((2R,6R,11S)-8-hydroxy-3,6-dimethyl-1,2,3,4,5,6-hexahydro-2,6-methanobenzo[d]azocin-11-yl)(methyl)amino)-4-oxobutanoic acid (Compound 28);

(2R,6R,11S)-3,6-dimethyl-11-(methyl(phenethyl)amino)-1,2,3,4,5,6-hexahydro-2,6-methanobenzo[d]azocin-8-ol (Compound 29);

tert-butyl 4-((((2R,6S,11R)-8-hydroxy-3,6-dimethyl-1,2,3,4,5,6-hexahydro-2,6-methanobenzo[d]azocin-11-yl)amino)methyl)piperidine-1-carboxylate (Compound 30);

tert-butyl 4-((((2R,6S,11R)-8-hydroxy-3,6-dimethyl-1,2,3,4,5,6-hexahydro-2,6-methanobenzo[d]azocin-11-yl)(methyl)amino)methyl)piperidine-1-carboxylate (Compound 31);

4-(2-((6S,11R)-8-hydroxy-3,6-dimethyl-1,2,3,4,5,6-hexahydro-2,6-methanobenzo[d]azocin-11-yl)acetamido)benzoic acid (Compound 32);

5-(((2R,6S,11S)-8-hydroxy-3,6-dimethyl-1,2,3,4,5,6-hexahydro-2,6-methanobenzo[d]azocin-11-yl)methoxy)nicotinic acid (Compound 33);

5-(((6S,11S)-8-hydroxy-3,6-dimethyl-1,2,3,4,5,6-hexahydro-2,6-methanobenzo[d]azocin-11-yl)methoxy)nicotinic acid (Compound 34);

2-(2-((6S,11R)-8-hydroxy-3,6-dimethyl-1,2,3,4,5,6-hexahydro-2,6-methanobenzo[d]azocin-11-yl)acetamido)benzoic acid (Compound 35);

3-((6S,11R)-8-methoxy-3,6-dimethyl-1,2,3,4,5,6-hexahydro-2,6-methanobenzo[d]azocin-11-yl)benzonitrile (Compound 36);

3-((6R,11S)-11-hydroxy-8-methoxy-3,6-dimethyl-1,2,3,4,5,6-hexahydro-2,6-methanobenzo[d]azocin-11-yl)benzonitrile (Compound 37);

3-((6S,11R)-8-methoxy-3,6-dimethyl-1,2,3,4,5,6-hexahydro-2,6-methanobenzo[d]azocin-11-yl)benzoic acid (Compound 38);

N-((2R,6R,11R)-8-hydroxy-3,6-dimethyl-1,2,3,4,5,6-hexahydro-2,6-methanobenzo[d]azocin-11-yl)-N-methylbenzamide (Compound 39);

3-(((6S,11R)-8-hydroxy-3,6-dimethyl-1,2,3,4,5,6-hexahydro-2,6-methanobenzo[d]azocin-11-yl)methoxy)benzoic acid (Compound 40);

3-(((2R,6S,11S)-8-hydroxy-3,6-dimethyl-1,2,3,4,5,6-hexahydro-2,6-methanobenzo[d]azocin-11-yl)methoxy)benzoic acid (Compound 41);

(6S,11R)-11-(3-(1H-tetrazol-5-yl)phenyl)-8-methoxy-3,6-dimethyl-1,2,3,4,5,6-hexahydro-2,6-methanobenzo[d]azocine (Compound 42);

(1S)-1-(5-chloro-6-(((6S,11R)-8-hydroxy-3,6-dimethyl-1,2,3,4,5,6-hexahydro-2,6-methanobenzo[d]azocin-11-yl)methoxy)pyridin-3-yl)ethane-1,2-diol (Compound 43);

4-(((6S,11S)-8-hydroxy-3,6-dimethyl-1,2,3,4,5,6-hexahydro-2,6-methanobenzo[d]azocin-11-yl)methoxy)benzamide (Compound 44);

4-(3-((2R,6R,11S)-8-hydroxy-3,6-dimethyl-1,2,3,4,5,6-hexahydro-2,6-methanobenzo[d]azocin-11-yl)-3-methylureido)benzoic acid (Compound 45);

4-(3-((2R,6R,11R)-8-hydroxy-3,6-dimethyl-1,2,3,4,5,6-hexahydro-2,6-methanobenzo[d]azocin-11-yl)-3-methylureido)benzoic acid (Compound 46);

3-(((2R,6R,11S)-8-hydroxy-3,6-dimethyl-1,2,3,4,5,6-hexahydro-2,6-methanobenzo[d]azocin-11-yl)(methyl)carbamoyl)benzoic acid (Compound 47);

3-(((2R,6R,11R)-8-hydroxy-3,6-dimethyl-1,2,3,4,5,6-hexahydro-2,6-methanobenzo[d]azocin-11-yl)(methyl)carbamoyl)benzoic acid (Compound 48);

2-(((2R,6R,11S)-8-hydroxy-3,6-dimethyl-1,2,3,4,5,6-hexahydro-2,6-methanobenzo[d]azocin-11-yl)(methyl)carbamoyl)benzoic acid (Compound 49);

2-(4-(((2R,6R,11S)-8-hydroxy-3,6-dimethyl-1,2,3,4,5,6-hexahydro-2,6-methanobenzo[d]azocin-11-yl)amino)phenyl)ethanesulfonamide (Compound 50);

2-(4-(((2R,6R,11S)-8-hydroxy-3,6-dimethyl-1,2,3,4,5,6-hexahydro-2,6-methanobenzo[d]azocin-11-yl)(methyl)amino)phenyl)ethanesulfonamide (Compound 51);

4-((6S,11R)-8-hydroxy-3,6-dimethyl-1,2,3,4,5,6-hexahydro-2,6-methanobenzo[d]azocine-11-carboxamido)benzoic acid (Compound 52);

2-(((6S,11R)-8-hydroxy-3,6-dimethyl-1,2,3,4,5,6-hexahydro-2,6-methanobenzo[d]azocin-11-yl)methoxy)isonicotinamide (Compound 53);

3-((6S,11R)-8-methoxy-3,6-dimethyl-1,2,3,4,5,6-hexahydro-2,6-methanobenzo[d]azocin-11-yl)benzamide (Compound 54);

(2S)-1-(2-((6S,11R)-8-hydroxy-3,6-dimethyl-1,2,3,4,5,6-hexahydro-2,6-methanobenzo[d]azocin-11-yl)acetyl)pyrrolidine-2-carboxylic acid (Compound 55);

(2R,6R,11S)-3-(cyclopropylmethyl)-8-methoxy-N,6-dimethyl-1,2,3,4,5,6-hexahydro-2,6-methanobenzo[d]azocin-11-amine (Compound 56);

(E)-N-((2R,6R,11S)-3-(cyclopropylmethyl)-8-methoxy-6-methyl-1,2,3,4,5,6-hexahydro-2,6-methanobenzo[d]azocin-11-yl)-3-(furan-3-yl)-N-methylacrylamide (Compound 57);

2-(4-(((2R,6R,11S)-8-hydroxy-3,6-dimethyl-1,2,3,4,5,6-hexahydro-2,6-methanobenzo[d]azocin-11-yl)amino)phenyl)ethanesulfonamide (Compound 58);

4-(((2R,6R,11R)-8-hydroxy-3,6-dimethyl-1,2,3,4,5,6-hexahydro-2,6-methanobenzo[d]azocin-11-yl)(methyl)carbamoyl)benzoic acid (Compound 59);
3-((6R,11R)-11-hydroxy-8-methoxy-3,6-dimethyl-1,2,3,4,5,6-hexahydro-2,6-methanobenzo[d]azocin-11-yl)benzonitrile (Compound 60);
(6S,11R)-11-(3-(benzyloxy)phenyl)-8-methoxy-3,6-dimethyl-1,2,3,4,5,6-hexahydro-2,6-methanobenzo[d]azocine (Compound 61);
methyl 3-((6R,11R)-11-hydroxy-8-methoxy-3,6-dimethyl-1,2,3,4,5,6-hexahydro-2,6-methanobenzo[d]azocin-11-yl)benzoate (Compound 62);
3-((6R,11S)-11-hydroxy-8-methoxy-3,6-dimethyl-1,2,3,4,5,6-hexahydro-2,6-methanobenzo[d]azocin-11-yl)benzamide (Compound 63);
methyl 3-((6R,11S)-11-hydroxy-8-methoxy-3,6-dimethyl-1,2,3,4,5,6-hexahydro-2,6-methanobenzo[d]azocin-11-yl)benzoate (Compound 64);
(6R,11R)-11-(3-(1H-tetrazol-5-yl)phenyl)-8-methoxy-3,6-dimethyl-1,2,3,4,5,6-hexahydro-2,6-methanobenzo[d]azocin-11-ol (Compound 65);
(6R,11S)-11-(3-(1H-tetrazol-5-yl)phenyl)-8-methoxy-3,6-dimethyl-1,2,3,4,5,6-hexahydro-2,6-methanobenzo[d]azocin-11-ol (Compound 66);
3-((6R,11R)-11-hydroxy-8-methoxy-3,6-dimethyl-1,2,3,4,5,6-hexahydro-2,6-methanobenzo[d]azocin-11-yl)benzamide (Compound 67);
3-(3-((2R,6R,11S)-8-hydroxy-3,6-dimethyl-1,2,3,4,5,6-hexahydro-2,6-methanobenzo[d]azocin-11-yl)-3-methylureido)propanoic acid (Compound 68);
(6R)-8-methoxy-3,6-dimethyl-11-(pyrrolidin-1-yl)-1,2,3,4,5,6-hexahydro-2,6-methanobenzo[d]azocine (Compound 69);
1-((6R)-8-methoxy-3,6-dimethyl-1,2,3,4,5,6-hexahydro-2,6-methanobenzo[d]azocin-11-yl)piperidin-4-amine (Compound 70);
3-((6R,11S)-11-hydroxy-8-methoxy-3,6-dimethyl-1,2,3,4,5,6-hexahydro-2,6-methanobenzo[d]azocin-11-yl)benzoic acid (Compound 71);
1-(2-((6S,11S)-8-hydroxy-3,6-dimethyl-1,2,3,4,5,6-hexahydro-2,6-methanobenzo[d]azocin-11-yl)acetyl)piperidine-4-carboxylic acid (Compound 72);
2-(((2R,6R,11S)-3-(cyclopropylmethyl)-8-methoxy-6-methyl-1,2,3,4,5,6-hexahydro-2,6-methanobenzo[d]azocin-11-yl)(methyl)amino)acetic acid (Compound 73);
1-((6R)-8-methoxy-3,6-dimethyl-1,2,3,4,5,6-hexahydro-2,6-methanobenzo[d]azocin-11-yl)piperidine-3-carboxylic acid (Compound 74);
2-(3,4-dichlorophenyl)-N-(((6S,11S)-8-methoxy-3,6-dimethyl-1,2,3,4,5,6-hexahydro-2,6-methanobenzo[d]azocin-11-yl)methyl)acetamide (Compound 75);
2-(3-((2R,6S,11S)-8-hydroxy-3,6-dimethyl-1,2,3,4,5,6-hexahydro-2,6-methanobenzo[d]azocin-11-yl)-3-methylureido)-4-methylpentanoic acid (Compound 76);
(E)-N-((2R,6R,11S)-3-(cyclopropylmethyl)-8-hydroxy-6-methyl-1,2,3,4,5,6-hexahydro-2,6-methanobenzo[d]azocin-11-yl)-3-(furan-3-yl)-N-methylacrylamide (Compound 77);
3-(4-cyanophenyl)-1-((2R,6R,11S)-8-hydroxy-3,6-dimethyl-1,2,3,4,5,6-hexahydro-2,6-methanobenzo[d]azocin-11-yl)-1-methylurea (Compound 78);
3-(4-cyanophenyl)-1-((2R,6R,11S)-8-hydroxy-3,6-dimethyl-1,2,3,4,5,6-hexahydro-2,6-methanobenzo[d]azocin-11-yl)-1-methylurea (Compound 79); and
the pharmaceutically acceptable salts and solvates thereof.

Preferred Compounds of the Invention include:
(E)-3-(furan-3-yl)-N-((2R,6R,11S)-8-hydroxy-3,6-dimethyl-1,2,3,4,5,6-hexahydro-2,6-methanobenzo[d]azocin-11-yl)-N-methylacrylamide (Compound 24);
(2R,6R,11S)-3,6-dimethyl-11-(methyl(phenethyl)amino)-1,2,3,4,5,6-hexahydro-2,6-methanobenzo[d]azocin-8-ol (Compound 29);
4-(2-((6S,11R)-8-hydroxy-3,6-dimethyl-1,2,3,4,5,6-hexahydro-2,6-methanobenzo[d]azocin-11-yl)acetamido)benzoic acid (Compound 32);
N-((2R,6R,11R)-8-hydroxy-3,6-dimethyl-1,2,3,4,5,6-hexahydro-2,6-methanobenzo[d]azocin-11-yl)-N-methylbenzamide (Compound 39);
4-(((6S,11S)-8-hydroxy-3,6-dimethyl-1,2,3,4,5,6-hexahydro-2,6-methanobenzo[d]azocin-11-yl)methoxy)benzamide (Compound 44);
2-(4-(((2R,6R,11S)-8-hydroxy-3,6-dimethyl-1,2,3,4,5,6-hexahydro-2,6-methanobenzo[d]azocin-11-yl)amino)phenyl)ethanesulfonamide (Compound 50);
2-(4-(((2R,6R,11S)-8-hydroxy-3,6-dimethyl-1,2,3,4,5,6-hexahydro-2,6-methanobenzo[d]azocin-11-yl)(methyl)amino)phenyl)ethanesulfonamide (Compound 51);
(E)-N-((2R,6R,11S)-3-(cyclopropylmethyl)-8-methoxy-6-methyl-1,2,3,4,5,6-hexahydro-2,6-methanobenzo[d]azocin-11-yl)-3-(furan-3-yl)-N-methylacrylamide (Compound 57);
2-(4-(((2R,6R,11S)-8-hydroxy-3,6-dimethyl-1,2,3,4,5,6-hexahydro-2,6-methanobenzo[d]azocin-11-yl)amino)phenyl)ethanesulfonamide (Compound 58);
3-(3-((2R,6R,11S)-8-hydroxy-3,6-dimethyl-1,2,3,4,5,6-hexahydro-2,6-methanobenzo[d]azocin-11-yl)-3-methylureido)propanoic acid (Compound 68);
1-((6R)-8-methoxy-3,6-dimethyl-1,2,3,4,5,6-hexahydro-2,6-methanobenzo[d]azocin-11-yl)piperidine-3-carboxylic acid (Compound 74);
2-(3,4-dichlorophenyl)-N-(((6S,11S)-8-methoxy-3,6-dimethyl-1,2,3,4,5,6-hexahydro-2,6-methanobenzo[d]azocin-11-yl)methyl)acetamide (Compound 75);
2-(3-((2R,6S,11S)-8-hydroxy-3,6-dimethyl-1,2,3,4,5,6-hexahydro-2,6-methanobenzo[d]azocin-11-yl)-3-methylureido)-4-methylpentanoic acid (Compound 76);
(E)-N-((2R,6R,11S)-3-(cyclopropylmethyl)-8-hydroxy-6-methyl-1,2,3,4,5,6-hexahydro-2,6-methanobenzo[d]azocin-11-yl)-3-(furan-3-yl)-N-methylacrylamide (Compound 77);
3-(4-cyanophenyl)-1-((2R,6R,11S)-8-hydroxy-3,6-dimethyl-1,2,3,4,5,6-hexahydro-2,6-methanobenzo[d]azocin-11-yl)-1-methylurea (Compound 78);
3-(4-cyanophenyl)-1-((2R,6R,11S)-8-hydroxy-3,6-dimethyl-1,2,3,4,5,6-hexahydro-2,6-methanobenzo[d]azocin-11-yl)-1-methylurea (Compound 79); and the pharmaceutically acceptable salts and solvates thereof.

Specific Compounds of the Invention also include:
3-(4-cyanophenyl)-1-((6R,11R)-3-(cyclopropylmethyl)-8-hydroxy-6-methyl-1,2,3,4,5,6-hexahydro-2,6-methanobenzo[d]azocin-11-yl)-1-methylurea (Compound 80);
3-(4-cyanophenyl)-1-((6R,11S)-3-(cyclopropylmethyl)-8-hydroxy-6-methyl-1,2,3,4,5,6-hexahydro-2,6-methanobenzo[d]azocin-11-yl)-1-methylurea (Compound 81);
4-(3-((6R,11S)-3-(cyclopropylmethyl)-8-methoxy-6-methyl-1,2,3,4,5,6-hexahydro-2,6-methanobenzo[d]azocin-11-yl)-3-methylureido)benzamide (Compound 82);
(E)-N-((6R,11R)-3-(cyclopropylmethyl)-8-hydroxy-6-methyl-1,2,3,4,5,6-hexahydro-2,6-methanobenzo[d]azocin-11-yl)-3-(furan-3-yl)-N-methylacrylamide (Compound 83);

4-((2R,6R,11S)-11-(3-(4-cyanophenyl)-1-methylureido)-8-hydroxy-6-methyl-1,2,5,6-tetrahydro-2,6-methanobenzo[d]azocin-3(4H)-yl)-N,N-dimethyl-2,2-diphenylbutanamide (Compound 84);

(E)-N-((2R,6R,11S)-3-(cyclopropylmethyl)-8-methoxy-6-methyl-1,2,3,4,5,6-hexahydro-2,6-methanobenzo[d]azocin-11-yl)-3-(furan-3-yl)-N-methylacrylamide (Compound 85);

(Z)—N-((2R,6R,11S)-3-(cyclopropylmethyl)-8-methoxy-6-methyl-1,2,3,4,5,6-hexahydro-2,6-methanobenzo[d]azocin-11-yl)-3-(furan-3-yl)-N-methylacrylamide (Compound 86);

3-(4-cyanophenyl)-1-((2R,6R,11S)-8-hydroxy-6-methyl-3-phenethyl-1,2,3,4,5,6-hexahydro-2,6-methanobenzo[d]azocin-11-yl)-1-methylurea (Compound 87);

3-(4-cyanophenyl)-1-((6R,11R)-3-(cyclobutylmethyl)-8-hydroxy-6-methyl-1,2,3,4,5,6-hexahydro-2,6-methanobenzo[d]azocin-11-yl)-1-methylurea (Compound 88);

3-(4-cyanophenyl)-1-((6R,11R)-3-(2,3-difluorobenzyl)-8-hydroxy-6-methyl-1,2,3,4,5,6-hexahydro-2,6-methanobenzo[d]azocin-11-yl)-1-methylurea (Compound 89);

3-(4-cyanophenyl)-1-((2R,6R,11S)-3-(furan-3-ylmethyl)-8-hydroxy-6-methyl-1,2,3,4,5,6-hexahydro-2,6-methanobenzo[d]azocin-11-yl)-1-methylurea (Compound 90);

3-((2R,6R,11S)-8-hydroxy-3,6-dimethyl-1,2,3,4,5,6-hexahydro-2,6-methanobenzo[d]azocin-11-yl)-3,4-dihydroquinazolin-2(1H)-one (Compound 91);

and the pharmaceutically acceptable salts and solvates thereof.

Specific Compounds of the Invention further include:

4-(2-(((2R,6S,11R)-8-hydroxy-3,6-dimethyl-1,2,3,4,5,6-hexahydro-2,6-methanobenzo[d]azocin-11-yl)amino)ethyl)benzenesulfonamide (Compound 92);

4-(2-(((2S,6R,11S)-8-hydroxy-3,6-dimethyl-1,2,3,4,5,6-hexahydro-2,6-methanobenzo[d]azocin-11-yl)amino)ethyl)benzenesulfonamide (Compound 93);

4-(2-(((2R,6S,11S)-8-hydroxy-3,6-dimethyl-1,2,3,4,5,6-hexahydro-2,6-methanobenzo[d]azocin-11-yl)amino)ethyl)benzenesulfonamide (Compound 94);

4-(2-(((2S,6R,11R)-8-hydroxy-3,6-dimethyl-1,2,3,4,5,6-hexahydro-2,6-methanobenzo[d]azocin-11-yl)amino)ethyl)benzenesulfonamide (Compound 95);

4-(2-(((2R,6S,11R)-3-(cyclopropylmethyl)-8-hydroxy-6-methyl-1,2,3,4,5,6-hexahydro-2,6-methanobenzo[d]azocin-11-yl)amino)ethyl)benzenesulfonamide (Compound 96);

4-(2-(((2R,6S,11S)-3-(cyclopropylmethyl)-8-hydroxy-6-methyl-1,2,3,4,5,6-hexahydro-2,6-methanobenzo[d]azocin-11-yl)amino)ethyl)benzenesulfonamide (Compound 97);

(2R,6S,11R)-11-((3,4-dichlorophenethyl)amino)-3,6-dimethyl-1,2,3,4,5,6-hexahydro-2,6-methanobenzo[d]azocin-8-ol (Compound 98);

(2R,6S,11S)-11-((3,4-dichlorophenethyl)amino)-3,6-dimethyl-1,2,3,4,5,6-hexahydro-2,6-methanobenzo[d]azocin-8-ol (Compound 99);

(2R,6S,11R)-11-((4-methoxyphenethyl)amino)-3,6-dimethyl-1,2,3,4,5,6-hexahydro-2,6-methanobenzo[d]azocin-8-ol (Compound 100);

(2R,6S,11R)-11-((4-fluorophenethyl)amino)-3,6-dimethyl-1,2,3,4,5,6-hexahydro-2,6-methanobenzo[d]azocin-8-ol (Compound 101);

(2R,6S,11S)-3-(cyclopropylmethyl)-6-methyl-11-((piperidin-4-ylmethyl)amino)-1,2,3,4,5,6-hexahydro-2,6-methanobenzo[d]azocin-8-ol (Compound 102);

(2R,6S,11S)-3,6-dimethyl-11-((2-(pyridin-4-yl)ethyl)amino)-1,2,3,4,5,6-hexahydro-2,6-methanobenzo[d]azocin-8-ol (Compound 103);

(2R,6S,11R)-3,6-dimethyl-11-((2-(thiophen-2-yl)ethyl)amino)-1,2,3,4,5,6-hexahydro-2,6-methanobenzo[d]azocin-8-ol (Compound 104);

(2R,6S,11S)-11-((4-(tert-butyl)phenethyl)amino)-3,6-dimethyl-1,2,3,4,5,6-hexahydro-2,6-methanobenzo[d]azocin-8-ol (Compound 105);

tert-butyl 4-((((2R,6S,11S)-8-hydroxy-3,6-dimethyl-1,2,3,4,5,6-hexahydro-2,6-methanobenzo[d]azocin-11-yl)amino)methyl)piperidine-1-carboxylate (Compound 106);

tert-butyl 4-((((2R,6S,11R)-8-hydroxy-3,6-dimethyl-1,2,3,4,5,6-hexahydro-2,6-methanobenzo[d]azocin-11-yl)amino)methyl)piperidine-1-carboxylate (Compound 107);

tert-butyl 4-((((2R,6S,11R)-8-hydroxy-3,6-dimethyl-1,2,3,4,5,6-hexahydro-2,6-methanobenzo[d]azocin-11-yl)(methyl)amino)methyl)piperidine-1-carboxylate (Compound 108);

4-(2-(((2R,6S,11S)-8-hydroxy-3,6-dimethyl-1,2,3,4,5,6-hexahydro-2,6-methanobenzo[d]azocin-11-yl)(methyl)amino)ethyl)benzenesulfonamide (Compound 109);

(2R,6S,11S)-11-((2-(1H-indol-3-yl)ethyl)amino)-3,6-dimethyl-1,2,3,4,5,6-hexahydro-2,6-methanobenzo[d]azocin-8-ol (Compound 110);

tert-butyl (3-(((2R,6S,11S)-8-hydroxy-3,6-dimethyl-1,2,3,4,5,6-hexahydro-2,6-methanobenzo[d]azocin-11-yl)amino)propyl)carbamate (Compound 111);

tert-butyl (2-(((2R,6S,11S)-8-hydroxy-3,6-dimethyl-1,2,3,4,5,6-hexahydro-2,6-methanobenzo[d]azocin-11-yl)amino)ethyl)carbamate (Compound 112);

N-((2R,6S,11S)-3-(cyclopropylmethyl)-8-hydroxy-6-methyl-1,2,3,4,5,6-hexahydro-2,6-methanobenzo[d]azocin-11-yl)thiophene-3-carboxamide (Compound 113);

N-((2R,6S,11S)-3-(cyclopropylmethyl)-8-hydroxy-6-methyl-1,2,3,4,5,6-hexahydro-2,6-methanobenzo[d]azocin-11-yl)-N-methylthiophene-3-carboxamide (Compound 114);

N-((2R,6S,11S)-3-(cyclopropylmethyl)-8-hydroxy-6-methyl-1,2,3,4,5,6-hexahydro-2,6-methanobenzo[d]azocin-11-yl)-N-methylbenzamide (Compound 115);

N-((2R,6S,11R)-8-hydroxy-3,6-dimethyl-1,2,3,4,5,6-hexahydro-2,6-methanobenzo[d]azocin-11-yl)-N,4-dimethylpentanamide (Compound 116);

N-((2R,6S,11S)-8-hydroxy-3,6-dimethyl-1,2,3,4,5,6-hexahydro-2,6-methanobenzo[d]azocin-11-yl)-N-methyl-2-phenylacetamide (Compound 117);

N-((2R,6S,11R)-8-hydroxy-3,6-dimethyl-1,2,3,4,5,6-hexahydro-2,6-methanobenzo[d]azocin-11-yl)-N-methyl-2-phenylacetamide (Compound 118);

N-((2R,6S,11R)-8-hydroxy-3,6-dimethyl-1,2,3,4,5,6-hexahydro-2,6-methanobenzo[d]azocin-11-yl)-N-methylbenzamide (Compound 119);

N-((2R,6S,11S)-8-hydroxy-3,6-dimethyl-1,2,3,4,5,6-hexahydro-2,6-methanobenzo[d]azocin-11-yl)-N-methylcyclohexanecarboxamide (Compound 120);

N-((2R,6S,11R)-8-hydroxy-3,6-dimethyl-1,2,3,4,5,6-hexahydro-2,6-methanobenzo[d]azocin-11-yl)-N-methylcyclohexanecarboxamide (Compound 121);

(E)-N-((2R,6S,11R)-8-hydroxy-3,6-dimethyl-1,2,3,4,5,6-hexahydro-2,6-methanobenzo[d]azocin-11-yl)-N-methyl-3-(pyridin-3-yl)acrylamide (Compound 122);

N-((2R,6S,11R)-8-hydroxy-3,6-dimethyl-1,2,3,4,5,6-hexahydro-2,6-methanobenzo[d]azocin-11-yl)-N-methyl-2-(thiophen-3-yl)acetamide (Compound 123);

N-((2R,6S,11R)-8-hydroxy-3,6-dimethyl-1,2,3,4,5,6-hexahydro-2,6-methanobenzo[d]azocin-11-yl)-N-methylthiophene-3-carboxamide (Compound 124);

N-((2R,6S,11S)-8-hydroxy-3,6-dimethyl-1,2,3,4,5,6-hexahydro-2,6-methanobenzo[d]azocin-11-yl)-N-methylthiophene-3-carboxamide (Compound 125);

N-((2R,6S,11S)-8-hydroxy-3,6-dimethyl-1,2,3,4,5,6-hexahydro-2,6-methanobenzo[d]azocin-11-yl)-N-methyl-5-(trifluoromethyl)picolinamide (Compound 126);

N-((2R,6S,11R)-3-(cyclopropylmethyl)-8-hydroxy-6-methyl-1,2,3,4,5,6-hexahydro-2,6-methanobenzo[d]azocin-11-yl)thiophene-3-carboxamide (Compound 127);

N-((2R,6S,11S)-3-(cyclopropylmethyl)-8-hydroxy-6-methyl-1,2,3,4,5,6-hexahydro-2,6-methanobenzo[d]azocin-11-yl)-3-(trifluoromethyl)benzenesulfonamide (Compound 128);

N-((2R,6S,11R)-3-(cyclopropylmethyl)-8-hydroxy-6-methyl-1,2,3,4,5,6-hexahydro-2,6-methanobenzo[d]azocin-11-yl)-3-(trifluoromethyl)benzenesulfonamide (Compound 129);

N-((2R,6S,11S)-3-(cyclopropylmethyl)-8-hydroxy-6-methyl-1,2,3,4,5,6-hexahydro-2,6-methanobenzo[d]azocin-11-yl)-N-methyl-3-(trifluoromethyl)benzenesulfonamide (Compound 130);

N-((2R,6S,11S)-8-hydroxy-3,6-dimethyl-1,2,3,4,5,6-hexahydro-2,6-methanobenzo[d]azocin-11-yl)-N-methyl-3-(trifluoromethyl)benzenesulfonamide (Compound 131);

N-((2R,6S,11R)-8-hydroxy-3,6-dimethyl-1,2,3,4,5,6-hexahydro-2,6-methanobenzo[d]azocin-11-yl)-N-methyl-3-(trifluoromethyl)benzenesulfonamide (Compound 132);

3-(4-(tert-butyl)phenyl)-1-((2R,6S,11S)-3-(cyclopropylmethyl)-8-hydroxy-6-methyl-1,2,3,4,5,6-hexahydro-2,6-methanobenzo[d]azocin-11-yl)-1-methylurea (Compound 133);

1-((2R,6S,11S)-3-(cyclopropylmethyl)-8-hydroxy-6-methyl-1,2,3,4,5,6-hexahydro-2,6-methanobenzo[d]azocin-11-yl)-3-(5-fluorobenzo[d]thiazol-2-yl)-1-methylurea (Compound 134);

1-((6R,11R)-6-allyl-8-methoxy-3-methyl-1,2,3,4,5,6-hexahydro-2,6-methanobenzo[d]azocin-11-yl)-3-(4-cyanophenyl)-1-methylurea (Compound 135);

3-(4-cyanophenyl)-1-((6R,11R)-8-methoxy-3-methyl-6-propyl-1,2,3,4,5,6-hexahydro-2,6-methanobenzo[d]azocin-11-yl)-1-methylurea (Compound 136);

3-(4-cyanophenyl)-1-((6R,11S)-8-hydroxy-3-methyl-6-propyl-1,2,3,4,5,6-hexahydro-2,6-methanobenzo[d]azocin-11-yl)-1-methylurea (Compound 137);

3-(4-(aminomethyl)phenyl)-1-((6R,11S)-8-methoxy-3-methyl-6-propyl-1,2,3,4,5,6-hexahydro-2,6-methanobenzo[d]azocin-11-yl)-1-methylurea (Compound 138);

1-(5-fluorobenzo[d]thiazol-2-yl)-3-((2R,6S,11R)-8-hydroxy-3,6-dimethyl-1,2,3,4,5,6-hexahydro-2,6-methanobenzo[d]azocin-11-yl)urea (Compound 139);

3-(5-fluorobenzo[d]thiazol-2-yl)-1-((2R,6S,11R)-8-hydroxy-3,6-dimethyl-1,2,3,4,5,6-hexahydro-2,6-methanobenzo[d]azocin-11-yl)-1-methylurea (Compound 140);

and the pharmaceutically acceptable salts and solvates thereof.

As used herein, the term "—($C_1$-$C_{10}$)alkyl" refers to straight-chain and branched non-cyclic saturated hydrocarbons having from 1 to 10 carbon atoms. Representative straight chain —($C_1$-$C_{10}$) alkyl groups include methyl, -ethyl, -n-propyl, -n-butyl, -n-pentyl, -n-hexyl, n-heptyl, n-octyl, n-nonyl and n-decyl. Representative branched —($C_1$-$C_{10}$)alkyl groups include isopropyl, sec-butyl, isobutyl, tert-butyl, isopentyl, neopentyl, 1-methylbutyl, 2-methylbutyl, 3-methylbutyl, 1,1-dimethylpropyl, 1,2-dimethylpropyl, 1-methylpentyl, 2-methylpentyl, 3-methylpentyl, 4-methylpentyl, 1-ethylbutyl, 2-ethylbutyl, 3-ethylbutyl, 1,1-dimethylbutyl, 1,2-dimethylbutyl, 1,3-dimethylbutyl, 2,2-dimethylbutyl, 2,3-dimethylbutyl, 3,3-dimethylbutyl, 5-methylhexyl, 6-methylheptyl, and the like.

As used herein, the term "—($C_1$-$C_6$)alkyl" refers to straight-chain and branched non-cyclic saturated hydrocarbons having from 1 to 6 carbon atoms. Representative straight chain —($C_1$-$C_6$)alkyl groups include methyl, -ethyl, -n-propyl, -n-butyl, -n-pentyl, and -n-hexyl. Representative branched-chain —($C_1$-$C_6$)alkyl groups include isopropyl, sec-butyl, isobutyl, tert-butyl, isopentyl, neopentyl, 1-methylbutyl, 2-methylbutyl, 3-methylbutyl, 1,1-dimethylpropyl, and 1,2-dimethylpropyl, methylpentyl, 2-methylpentyl, 3-methylpentyl, 4-methylpentyl, 1-ethylbutyl, 2-ethylbutyl, 3-ethylbutyl, 1,1-dimethylbutyl, 1,2-dimethylbutyl, 1,3-dimethylbutyl, 2,2-dimethylbutyl, 2,3-dimethylbutyl, 3,3-dimethylbutyl, and the like.

As used herein, the term "—($C_2$-$C_{10}$)alkenyl" refers to straight chain and branched non-cyclic hydrocarbons having from 2 to 10 carbon atoms and including at least one carbon-carbon double bond. Representative straight chain and branched —($C_2$-$C_{10}$)alkenyl groups include -vinyl, allyl, -1-butenyl, -2-butenyl, -isobutylenyl, -1-pentenyl, -2-pentenyl, -3-methyl-1-butenyl, -2-methyl-2-butenyl, -2,3-dimethyl-2-butenyl, -1-hexenyl, -2-hexenyl, 3-hexenyl, and the like.

As used herein, the term "—($C_2$-$C_6$)alkenyl" refers to straight chain and branched non-cyclic hydrocarbons having from 2 to 6 carbon atoms and including at least one carbon-carbon double bond. Representative straight chain and branched ($C_2$-$C_6$)alkenyl groups include -vinyl, allyl, -1-butenyl, -2-butenyl, -isobutylenyl, -1-pentenyl, -2-pentenyl, -3-methyl-1-butenyl, -2-methyl-2-butenyl, and the like.

As used herein, the term "—($C_2$-$C_{10}$)alkynyl" refers to straight chain and branched non-cyclic hydrocarbons having from 2 to 10 carbon atoms and including at least one carbon-carbon triple bond. Representative straight chain and branched ($C_2$-$C_{10}$)alkynyl groups include -acetylenyl, -propynyl, -1 butynyl, -2-butynyl, -1-pentynyl, -2-pentynyl, -3-methyl-1-butynyl, -4-pentynyl, -1-hexynyl, -2-hexynyl, -5-hexynyl, and the like.

As used herein, the term "—($C_2$-$C_6$)alkynyl" refers to straight chain and branched non-cyclic hydrocarbons having from 2 to 6 carbon atoms and including at least one carbon-carbon triple bond. Representative straight chain and branched ($C_2$-$C_6$)alkynyl groups include -acetylenyl, -propynyl, -1 butynyl, -2-butynyl, -1-pentynyl, -2-pentynyl, -3-methyl-1-butynyl, -4-pentynyl, and the like.

As used herein, "—($C_1$-$C_{10}$)alkoxy" means a straight chain or branched non-cyclic hydrocarbon having one or more ether groups and from 1 to 10 carbon atoms. Representative straight chain and branched ($C_1$-$C_{10}$)alkoxys include -methoxy, -ethoxy, -propoxy, -butyloxy, -pentyloxy, -hexyloxy, -heptyloxy, -methoxymethyl, -2-methoxyethyl, -5-methoxypentyl, -3-ethoxybutyl and the like.

As used herein, "—($C_1$-$C_6$)alkoxy" means a straight chain or branched non-cyclic hydrocarbon having one or more ether groups and from 1 to 6 carbon atoms. Representative straight chain and branched ($C_1$-$C_5$)alkoxys include -methoxy, -ethoxy, -propoxy, -butyloxy, -pentyloxy, -hexyloxy, -methoxymethyl, -2-methoxyethyl, -5-methoxypentyl, -3-ethoxybutyl and the like.

As used herein, "—($C_1$-$C_5$)alkoxy" means a straight chain or branched non-cyclic hydrocarbon having one or more ether groups and from 1 to 5 carbon atoms. Representative straight chain and branched ($C_1$-$C_5$)alkoxys include -methoxy, -ethoxy, -propoxy, -butyloxy, -pentyloxy, -methoxymethyl, -2-methoxyethyl, -5-methoxypentyl, -3-ethoxybutyl and the like.

As used herein, the term "—($C_3$-$C_{12}$)cycloalkyl" refers to a cyclic saturated hydrocarbon having from 3 to 12 carbon atoms. Representative ($C_3$-$C_{12}$)cycloalkyls include cyclopropyl, cyclobutyl, cyclopentyl, cyclohexyl, cycloheptyl, cyclooctyl, and cyclononyl, cyclodecyl, cycloundecyl, cyclododecyl, and the like.

As used herein, "—($C_6$-$C_{14}$)bicycloalkyl" means a bicyclic hydrocarbon ring system having from 6 to 14 carbon atoms and at least one saturated cyclic alkyl ring. Representative —($C_6$-$C_{14}$)bicycloalkyls include -indanyl, -norbornyl, -1,2,3,4-tetrahydronaphthalenyl, -5,6,7,8-tetrahydronaphthalenyl, -perhydronaphthalenyl, and the like.

As used herein, "—($C_8$-$C_{20}$)tricycloalkyl" means a tricyclic hydrocarbon ring system having from 8 to 20 carbon atoms and at least one saturated cyclic alkyl ring. Representative —($C_8$-$C_{20}$)tricycloalkyls include -pyrenyl, -adamantyl, -1,2,3,4-tetrahydroanthracenyl, -perhydroanthracenyl-aceanthrenyl, -1,2,3,4-tetrahydropenanthrenyl, -5,6,7,8-tetrahydrophenanthrenyl, -perhydrophenanthrenyl, tetradecahydro-1H-cyclohepta[a]naphthalenyl, tetradecahydro-1H-cycloocta[e]indenyl, tetradecahydro-1H-cyclohepta[e]azulenyl, hexadecahydrocycloocta[b]naphthalenyl, hexadecahydrocyclohepta[a]heptalenyl, tricyclo-pentadecanyl, tricyclo-octadecanyl, tricyclo-nonadecanyl, tricyclo-icosanyl, and the like.

As used herein, the term "—($C_4$-$C_{12}$)cycloalkenyl" refers to a cyclic hydrocarbon having from 4 to 12 carbon atoms, and including at least one carbon-carbon double bond. Representative —($C_4$-$C_{12}$)cycloalkenyls include cyclobutenyl, -cyclopentenyl, -cyclopentadienyl, -cyclohexenyl, -cyclohexadienyl, -cycloheptenyl, -cycloheptadienyl, -cycloheptatrienyl, -cyclooctenyl, -cyclooctadienyl, -cyclooctatrienyl, -cyclooctatetraenyl, -cyclononenyl, -cyclononadienyl, -cyclodecenyl, -cyclodecadienyl, -norbornenyl, and the like.

As used herein, "—($C_7$-$C_{14}$)bicycloalkenyl" means a bicyclic hydrocarbon ring system having at least one carbon-carbon double bond in at least one of the rings and from 7 to 14 carbon atoms. Representative —($C_7$-$C_{14}$)bicycloalkenyls include -bicyclo[3.2.0]hept-2-enyl, -indenyl, -pentalenyl, -naphthalenyl, -azulenyl, -heptalenyl, -1,2,7,8-tetrahydronaphthalenyl, and the like.

As used herein, "—($C_8$-$C_{20}$)tricycloalkenyl" means a tri-cyclic hydrocarbon ring system having at least one carbon-carbon double bond in one of the rings and from 8 to 20 carbon atoms. Representative —($C_8$-$C_{20}$)tricycloalkenyls include -anthracenyl, -phenanthrenyl, -phenalenyl, -acenaphthylenyl, as-indacenyl, s-indacenyl, 2,3,6,7,8,9,10,11-octahydro-1H-cycloocta[e]indenyl, 2,3,4,7,8,9,10,11-octahydro-1H-cyclohepta[a]naphthalenyl, 8,9,10,11-tetrahydro-7H-cyclohepta[a]naphthalenyl, 2,3,4,5,6,7,8,9,10,11,12,13-dodecahydro-1H-cyclohepta[a]heptalenyl, 1,2,3,4,5,6,7,8,9,10,11,12,13,14-tetradecahydro-dicyclohepta[a,c]cyclooctenyl, 2,3,4,5,6,7,8,9,10,11,12,13-dodecahydro-1H-dibenzo[a,d]cyclononenyl, and the like.

As used herein, "-(3- to 12-membered)heterocycle" or "-(3- to 12-membered)heterocyclo" means a 3- to 12-membered monocyclic heterocyclic ring which is either saturated, or partially saturated, or non-aromatic. A 3-membered heterocycle can contain up to 1 heteroatom; a 4-membered heterocycle can contain up to 2 heteroatoms; a 5-membered heterocycle can contain up to 4 heteroatoms; a 6-membered heterocycle can contain up to 4 heteroatoms; and a 7-membered heterocycle can contain up to 5 heteroatoms. Each heteroatom is independently selected from nitrogen (which can be quaternized), oxygen, and sulfur (including sulfoxide and sulfone). The -(3- to 12-membered)heterocycle can be attached via a nitrogen or carbon atom. Representative -(3- to 12-membered)heterocycles include aziridinyl, thiazolidinyl, morpholinyl, pyrrolidinonyl, pyrrolidinyl, piperidinyl, piperazinyl, 2,3-dihydrofuranyl, dihydropyranyl, hydantoinyl, valerolactamyl, oxiranyl, oxetanyl, tetrahydrofuranyl, tetrahydropyranyl, dihydropyridinyl, tetrahydropyridinyl, tetrahydropyrimidinyl, tetrahydrothiophenyl, tetrahydrothiopyranyl, oxepanyl, thiepinyl, 3,4,5,6-tetrahydro-2H-azepinyl, 1,4-thiazepinyl, azocinyl, thiocanyl, and the like.

As used herein, "-(5- to 12-membered)heterocycle" or "-(5- to 12-membered)heterocyclo" means a 5- to 12-membered monocyclic heterocyclic ring which is either saturated, or unsaturated, or non-aromatic. A 5-membered heterocycle can contain up to 4 heteroatoms; a 6-membered heterocycle can contain up to 4 heteroatoms; and a 7-membered heterocycle can contain up to 5 heteroatoms. Representative (5- to 12-membered)heterocycles include thiazolidinyl, morpholinyl, pyrrolidinonyl, pyrrolidinyl, piperidinyl, piperazinyl, 2,3-dihydrofuranyl, dihydropyranyl, hydantoinyl, valerolactamyl, tetrahydrofuranyl, tetrahydropyranyl, dihydropyridinyl, tetrahydropyridinyl, tetrahydropyrimidinyl, tetrahydrothiophenyl, tetrahydrothiopyranyl, oxepanyl, thiepinyl, 3,4,5,6-tetrahydro-2H-azepinyl, 1,4-thiazepinyl, azocinyl, thiocanyl, and the like.

As used herein, "-(4- to 8-membered)heterocycle" or "-(4- to 8-membered)heterocyclo" means a 4- to 8-membered monocyclic heterocyclic ring which is either saturated or unsaturated, or non-aromatic. A 4-membered heterocycle can contain up to 2 heteroatoms; a 5-membered heterocycle can contain up to 4 heteroatoms; a 6-membered heterocycle can contain up to 4 heteroatoms; and a 7-membered heterocycle can contain up to 5 heteroatoms. Each heteroatom is independently selected from nitrogen (which can be quaternized), oxygen, and sulfur (including sulfoxide and sulfone). The -(4- to 8-membered)heterocycle can be attached via a nitrogen or carbon atom. Representative -(4- to 8-membered)heterocycles include morpholinyl, piperidinyl, piperazinyl, 2,3-dihydrofuranyl, dihydropyranyl, hydantoinyl, valerolactamyl, oxiranyl, oxetanyl, tetrahydrofuranyl, tetrahydropyranyl, dihydropyridinyl, tetrahydropyridinyl, tetrahydropyrimidinyl, tetrahydrothiophenyl, tetrahydrothiopyranyl, and the like.

As used herein, "-(7- to 12-membered)bicycloheterocycle" or "-(7- to 12-membered)bicycloheterocyclo" means a 7- to 12-membered bicyclic, heterocyclic ring which is either saturated, unsaturated, or non-aromatic. At least one ring of the bicycloheterocycle contains at least one heteroatom. A -(7- to 12-membered)bicycloheterocycle contains from 1 to 4 heteroatoms independently selected from nitrogen (which can be quaternized), oxygen, and sulfur (including sulfoxide and sulfone). The -(7- to 12-membered)bicycloheterocycle can be attached via a nitrogen or carbon atom. Representative -(7- to 10-membered)bicycloheterocycles include -quinolinyl, -isoquinolinyl, -chromonyl, -coumarinyl, -indolyl, -indolizinyl, -benzo[b]furanyl, -benzo[b]thiophenyl, -benzo[d][1,3]dioxolyl, -indazolyl, -purinyl, -4H-quinolizinyl, -isoquinolyl, -quinolyl, -phthalazinyl, -naphthyridinyl, -carbazolyl, -β-carbolinyl, -indolinyl, isoindolinyl, -1,2,3,4-tetrahydroquinolinyl, -1,2,3,4-tetrahydroisoquinolinyl, pyrrolopyrrolyl and the like.

As used herein a "-(6- to 14-membered)aryl" means an aromatic carbocyclic ring containing 6 to 14 carbon atoms, including both mono- and bicyclic ring systems. Representative (5- to 14-membered)aryl groups include indenyl, -phenyl, -naphthyl, and the like.

As used herein a "-(7- to 12-membered)bicyclic aryl" means an bicyclic aromatic carbocyclic ring containing 7 to 12 carbon atoms. Representative (7- to 12-membered) bicyclic aryl groups include indenyl, -naphthyl, and the like.

As used herein a "-(6- to 14-membered)aryloxy" means an oxygen substituted by an aromatic carbocyclic ring containing 6 to 14 carbon atoms, including both mono- and bicyclic ring systems. Representative (6- to 14-membered) aryloxy groups include phenoxy and 4-fluorophenoxy, and the like.

As used herein a "hydroxy($C_1$-$C_6$)alkyl" means any of the above-mentioned $C_{1-6}$ alkyl groups substituted by one or more hydroxy groups. Representative hydroxy($C_1$-$C_6$)alkyl groups include hydroxymethyl, hydroxyethyl, hydroxypropyl and hydroxybutyl groups, and especially hydroxymethyl, 1-hydroxyethyl, 2-hydroxyethyl, 1,2-dihydroxyethyl, 2-hydroxypropyl, 3-hydroxypropyl, 3-hydroxybutyl, 4-hydroxybutyl, 2-hydroxy-1-methylpropyl, and 1,3-dihydroxyprop-2-yl.

As used herein a "dihydroxy($C_1$-$C_6$)alkyl" means any of the above-mentioned $C_{1-6}$ alkyl groups substituted by two hydroxy groups. Representative dihydroxy($C_1$-$C_6$)alkyl groups include dihydroxyethyl, dihydroxypropyl and dihydroxybutyl groups, and especially 1,2-dihydroxyethyl, 1,3-dihydroxypropyl, 2,3-dihydroxypropyl, 1,3-dihydroxybutyl, 1,4-dihydroxybutyl, and 1,3-dihydroxyprop-2-yl.

As used herein a "-(5- to 12-membered)carbocyclic ring" means a mono- or bicyclic hydrocarbon ring system having from 5 to 12 carbon atoms, which is either saturated, unsaturated, non-aromatic or aromatic. Representative (5- to 12-membered)carbocyclic rings include cyclopentyl, cyclohexyl, cycloheptyl, cyclooctyl, cyclononyl, cyclodecyl, cycloundecyl, cyclododecyl, -indanyl, -norbornyl, -1,2,3,4-tetrahydronaphthalenyl, -5,6,7,8-tetrahydronaphthalenyl, -perhydronaphthalenyl, adamantyl, cyclopentenyl, -cyclopentadienyl, -cyclohexenyl, -cyclohexadienyl, -cycloheptenyl, -cycloheptadienyl, -cycloheptatrienyl, -cyclooctenyl, -cyclooctadienyl, -cyclooctatrienyl, -cyclooctatetraenyl, -cyclononenyl, -cyclononadienyl, -cyclodecenyl, -cyclodecadienyl, -norbornenyl, heptalenyl, and the like.

As used herein a "-(7- to 12-membered)bicyclic ring system" means a 7- to 12-membered carbocyclic or heterocyclic ring, which may be either unsaturated, saturated, non-aromatic or aromatic. Representative (7- to 12-membered)bicyclic ring systems include azulenyl, -norbornyl, -1,2,3,4-tetrahydronaphthalenyl, -5,6,7,8-tetrahydronaphthalenyl, -perhydronaphthalenyl, bicyclo[3.2.0]hept-2-enyl, -indenyl, naphthyl, -pentalenyl, -naphthalenyl, -azulenyl, -heptalenyl, -1,2,7,8-tetrahydronaphthalenyl, -quinolinyl, -isoquinolinyl, -chromonyl, -coumarinyl, -indolyl, -indolizinyl, -benzo[b]furanyl, -benzo[b]thiophenyl, -benzo[d][1,3]dioxolyl, -indazolyl, -purinyl, -4H-quinolizinyl, -isoquinolyl, -quinolyl, -phthalazinyl, -naphthyridinyl, -carbazolyl, -β-carbolinyl, -indolinyl, isoindolinyl, -1,2,3,4-tetrahydroquinolinyl, -1,2,3,4-tetrahydroisoquinolinyl, pyrrolopyrrolyl, and the like.

As used herein, "-(5- to 12-membered)heteroaryl" means an aromatic heterocycle ring of 5 to 12 members, including both mono- and bicyclic ring systems, where at least one carbon atom (of one or both of the rings) is replaced with a heteroatom independently selected from nitrogen, oxygen, and sulfur, or at least two carbon atoms of one or both of the rings are replaced with a heteroatom independently selected from nitrogen, oxygen, and sulfur. In one embodiment, one of the bicyclic -(5- to 12-membered)heteroaryl rings contains at least one carbon atom. In another embodiment, both of the bicyclic -(5- to 12-membered)heteroaryl rings contain at least one carbon atom. Representative -(5- to 12-membered)heteroaryls include pyridyl, furyl, benzofuranyl, thiophenyl, benzothiophenyl, quinolinyl, isoquinolinyl, pyrrolyl, indolyl, oxazolyl, benzoxazolyl, imidazolyl, benzimidazolyl, thiazolyl, benzothiazolyl, isoxazolyl, oxadiazolinyl, pyrazolyl, isothiazolyl, pyridazinyl, pyrimidyl, pyrimidinyl, pyrazinyl, thiadiazolyl, triazinyl, thienyl, thiadiazolyl, cinnolinyl, phthalazinyl, quinazolinyl, and the like.

As used herein, the terms "halo" and "halogen" refer to fluoro, chloro, bromo or iodo.

As used herein, "—$CH_2$(halo)" means a methyl group where one of the hydrogens of the methyl group has been replaced with a halogen. Representative —$CH_2$(halo) groups include —$CH_2F$, —$CH_2Cl$, —$CH_2Br$, and —$CH_2I$.

As used herein, "—CH(halo)$_2$" means a methyl group where two of the hydrogens of the methyl group have been replaced with a halogen. Representative —CH(halo)$_2$ groups include —$CHF_2$, —$CHCl_2$, —$CHBr_2$, —CHBrCl, —CHClI, and —$CHI_2$.

As used herein, "—C(halo)$_3$" means a methyl group where each of the hydrogens of the methyl group has been replaced with a halogen. Representative —C(halo)$_3$ groups include —$CF_3$, —$CCl_3$, —$CBr_3$, and —$CI_3$.

As used herein, the term "optionally substituted" refers to a group that is either unsubstituted or substituted.

Optional substituents on optionally substituted groups, when not otherwise indicated, include 1, 2, or 3 groups each independently selected from the group consisting of —($C_1$-$C_6$)alkyl, OH, halo, —C(halo)$_3$, —CH(halo)$_2$, —$CH_2$(halo), $NH_2$, —NH($C_1$-$C_6$)alkyl, CN, SH, -(5- to 12-membered)carbocyclic ring, -(5- to 12-membered)heterocycle, phenyl, benzyl, (=O), halo($C_1$-$C_6$)alkyl-, —($C_2$-$C_6$)alkenyl, —($C_2$-$C_6$)alkynyl, hydroxy($C_1$-$C_6$)alkyl-, $OR^{4a}$ (such as —OC(halo)$_3$ and —O($C_1$-$C_6$)alkyl), —$CONR^{5b}R^{6b}$, and —$COOR^{7a}$; where $R^{4a}$ is selected from the group consisting of —($C_1$-$C_6$)alkyl, —($C_2$-$C_6$)alkenyl, —($C_2$-$C_6$)alkynyl, —C(halo)$_3$, hydroxy($C_1$-$C_6$)alkyl-, —($C_3$-$C_{12}$)cycloalkyl, —($C_6$-$C_{14}$)bicycloalkyl, —($C_8$-$C_{20}$)tricycloalkyl, —($C_4$-$C_{12}$)cycloalkenyl, —($C_7$-$C_{14}$)bicycloalkenyl, —($C_8$-$C_{20}$)tricycloalkenyl, -(5- to 12-membered)aryl, -(5- to 12-membered)heteroaryl, -(3- to 12-membered)heterocycle, and -(7- to 12-membered)bicycloheterocycle; $R^{5b}$ and $R^{6b}$ are each independently selected from the group consisting of —($C_1$-$C_6$)alkyl, —($C_3$-$C_8$)cycloalkyl, (($C_3$-$C_8$)cycloalkyl)-($C_1$-$C_6$)alkyl-, or together with the nitrogen atom to which they may both be attached form a (4- to 8-membered)heterocycle; and $R^{7a}$ is selected from the group consisting of hydrogen, —($C_1$-$C_6$)alkyl, —($C_2$-$C_6$)alkenyl, —($C_2$-$C_6$)alkynyl, —($C_3$-$C_{12}$)cycloalkyl, —($C_4$-$C_{12}$)cycloalkenyl, (($C_3$-$C_{12}$)cycloalkyl)-($C_1$-$C_6$)alkyl-, (($C_4$-$C_{12}$)cycloalkenyl)-($C_1$-$C_6$)alkyl-, —($C_1$-$C_6$)alkoxy-$COOR^7$, —NH—C(=O)—NH—($C_1$-$C_6$)alkyl, —NH—C(=O)-(5- to 12-membered)aryl, —NH—C(=O)—($C_1$-$C_6$)alkyl-(5- to 12-membered)aryl, —NH—($C_1$-$C_6$)alkyl-$COOR^7$, —NH—C(=O)—($C_1$-$C_6$)alkyl-$COOR^7$, —NH—C(=O)—CH($NH_2$)—($C_1$-$C_6$)alkyl-$COOR^7$, —($C_3$-$C_{12}$)cycloalkyl, -(5- to 12-membered)aryl, -(5- to 12-membered)aryloxy, —($C_1$-$C_6$)alkoxy-$CONR^5R^6$, —NH—($C_1$-$C_6$)alkyl-$CONR^5R^6$, —C(O)NH—($C_1$-$C_6$)alkyl-$COOR^7$, —($C_1$-$C_6$)alkyl-C(=O)—($C_1$-$C_6$)alkoxy, —($C_1$-$C_6$)alkoxy-C(=O)—($C_1$-$C_6$)alkyl, —($C_1$-$C_6$)alkyl-CN, —($C_1$-$C_6$)alkyl-$COOR^7$, —($C_1$-$C_6$)alkoxy-$COOR^7$, —($C_3$-$C_{12}$)cycloalkyl, (($C_3$-$C_{12}$)cycloalkyl)-($C_1$-$C_6$)alkyl-, (($C_3$-$C_{12}$)cycloalkyl)-($C_1$-$C_6$)alkoxy-, (($C_3$-$C_{12}$)cycloalkyl)-($C_1$-$C_6$)alkoxy-($C_1$-$C_6$)alkyl-, —($C_4$-$C_{12}$)cycloalkenyl, (($C_4$-$C_{12}$)cycloalkenyl)-($C_1$-$C_6$)alkyl-, (($C_4$-$C_{12}$)cycloalkenyl)-($C_1$-$C_6$)alkoxy-, (($C_4$-$C_{12}$)cycloalkenyl)-($C_1$-$C_6$)alkoxy-($C_1$-$C_6$)alkyl-, -(5- to 12-membered)aryl, ((5- to 12-membered)aryl)-($C_1$-$C_6$)alkyl-, ((5- to 12-membered)aryl)-($C_1$-$C_6$)alkoxy-, ((5- to 12-membered)aryl)-($C_1$-$C_6$)alkoxy-($C_1$-$C_6$)alkyl-, -(5- to 12-membered)heteroaryl, ((5- to 12-membered)heteroaryl)-($C_1$-$C_6$)alkyl-, ((5- to 12-membered)heteroaryl)-($C_1$-$C_6$)alkoxy-, ((5- to 12-membered)heteroaryl)-($C_1$-$C_6$)alkoxy-($C_1$-$C_6$)alkyl-, -(3- to 12-membered)heterocycle, ((3- to 12 membered)heterocycle)-($C_1$-$C_6$)alkyl-, ((3- to 12 membered)heterocycle)-($C_1$-$C_6$)alkoxy-, and ((3- to 12 membered)heterocycle)-($C_1$-$C_6$)alkoxy-($C_1$-$C_6$)alkyl-; wherein $R^5$, $R^6$, and $R^7$ are as defined above for Formula I.

As used herein, the term "Z is unsubstituted" means that Z is "—$(CH_2)_m$—" and m is selected from 1, 2, 3, 4, 5, or 6.

As used herein, the term "Z is substituted" means that Z is "—$(CH_2)_m$—" and m is selected from 1, 2, 3, 4, 5, or 6 and one or two of the hydrogen atoms has been independently replaced by a —($C_1$-$C_6$)alkyl group.

As used herein, compounds that bind to receptors and mimic the regulatory effects of endogenous ligands are defined as "agonists". Compounds that bind to receptors and are only partly effective as agonists are defined as "partial agonists". Compounds that bind to receptors but produce no regulatory effect, but rather block the binding of ligands to the receptors are defined as "antagonists". (Ross and Kenakin, "Ch. 2: Pharmacodynamics: Mechanisms of Drug Action and the Relationship Between Drug Concentration and Effect", pp. 31-32, in *Goodman & Gilman's the Pharmacological Basis of Therapeutics*, 10$^{th}$ Ed. (J. G. Hardman, L. E. Limbird and A. Goodman-Gilman eds., 2001).

Compounds of the Invention can be in the form of prodrugs of the compounds of Formula I", Formula IA", Formula IB", Formula IC", Formula ID"; Formula I', Formula IA', Formula IB', Formula IC', or Formula ID'; Formula I, Formula IA, Formula IB, Formula IC, or Formula ID. Prodrugs are covalently bonded carrier molecules that release an active compound of Formula I", Formula IA", Formula IB", Formula IC", Formula ID"; Formula I', Formula IA', Formula IB', Formula IC', or Formula ID'; Formula I, Formula IA, Formula IB, Formula IC, or Formula ID in vivo. Non-limiting examples of prodrugs will typically include esters of the Compounds of the Invention that can be metabolized to the active compound by the action of enzymes in the body. Such prodrugs may be prepared by reacting a compound of Formula I", Formula IA", Formula IB", Formula IC", Formula ID"; Formula I', Formula IA', Formula IB', Formula IC', or Formula ID'; Formula I, Formula IA, Formula IB, Formula IC, or Formula ID, with an anhydride such as succinic anhydride.

Compounds of the Invention can be isotopically-labeled (i.e., radio-labeled). Examples of isotopes that can be incorporated into the disclosed compounds include isotopes of hydrogen, carbon, nitrogen, oxygen, phosphorous, fluorine and chlorine, such as $^2$H, $^3$H, $^{11}$C, $^{13}$C, $^{14}$C, $^{15}$N, $^{18}$O, $^{17}$O, $^{31}$P, $^{32}$P, $^{35}$S, $^{18}$F and $^{36}$Cl, respectively, and preferably $^3$H, $^{11}$C, and $^{14}$C. Isotopically-labeled Compounds of the Invention can be prepared by methods known in the art in view of this disclosure. For example, tritiated Compounds of the Invention can be prepared by introducing tritium into the particular compound by catalytic dehalogenation with tritium. This method may include reacting a suitable halogen-substituted precursor of a Compound of the Invention with tritium gas in the presence of an appropriate catalyst such as Pd/C in the presence of a base. Other suitable methods for preparing tritiated compounds are generally described in Filer, Isotopes in the Physical and Biomedical Sciences, Vol. 1, Labeled Compounds (Part A), Chapter 6 (1987). $^{14}$C-labeled compounds can be prepared by employing starting materials having a $^{14}$C carbon.

Isotopically labeled Compounds of the Invention, as well as the pharmaceutically acceptable salts, prodrugs and solvates thereof, can be used as radioligands to test for the binding of compounds to an opioid or ORL-1 receptor. For example, a radio-labeled Compound of the Invention can be used to characterize specific binding of a test or candidate compound to the receptor. Binding assays utilizing such radio-labeled compounds can provide an alternative to animal testing for the evaluation of chemical structure-activity relationships. In a non-limiting embodiment, the present invention provides a method for screening a candidate compound for the ability to bind to an opioid or ORL-1 receptor, comprising the steps of: a) introducing a fixed concentration of the radio-labeled compound to the receptor under conditions that permit binding of the radio-labeled compound to the receptor to form a complex; b) titrating the complex with a candidate compound; and c) determining the binding of the candidate compound to said receptor.

Compounds of the Invention disclosed herein may contain one or more asymmetric centers, thus giving rise to enantiomers, diastereomers, and other stereoisomeric forms. The present invention encompasses all such possible forms, as well as their racemic and resolved forms and mixtures thereof, and the uses thereof. The individual enantiomers may be separated according to methods known to those of ordinary skill in the art in view of the present disclosure. When the compounds described herein contain olefinic double bonds or other centers of geometric asymmetry, and unless specified otherwise, they include both E and Z geometric isomers. All tautomers are intended to be encompassed by the present invention as well.

As used herein, the term "stereoisomer" is a general term for all isomers of individual molecules that differ only in the orientation of their atoms in space. It includes enantiomers and isomers of compounds with more than one chiral center that are not mirror images of one another (diastereoisomers).

The term "chiral center" refers to a carbon atom to which four different groups are attached.

The terms "enantiomer" and "enantiomeric" refer to a molecule that cannot be superimposed on its mirror image and hence is optically active such that the enantiomer rotates the plane of polarized light in one direction and its mirror image compound rotates the plane of polarized light in the opposite direction.

The term "racemic" refers to a mixture of equal parts of enantiomers and which mixture is optically inactive. Racemic compounds can be separated into their enantiomers by chiral chromatography.

The term "resolution" refers to the separation or concentration or depletion of one of the two enantiomeric forms of a molecule.

The terms "a" and "an" refer to one or more.

Compounds of the Invention encompass all salts of the disclosed compounds of Formula I", Formula IA", Formula IB", Formula IC", Formula ID"; Formula I', Formula IA', Formula IB', Formula IC', or Formula ID'; Formula I, Formula IA, Formula IB, Formula IC, or Formula ID. The present invention preferably includes any and all non-toxic, pharmaceutically acceptable salts of the disclosed compounds. Examples of pharmaceutically acceptable salts include inorganic and organic acid addition salts and basic salts. The pharmaceutically acceptable salts include, but are not limited to, metal salts such as sodium salt, potassium salt, cesium salt, and the like; alkaline earth metals such as calcium salt, magnesium salt and the like; organic amine salts such as triethylamine salt, pyridine salt, picoline salt, ethanolamine salt, triethanolamine salt, dicyclohexylamine salt, N,N'-dibenzylethylenediamine salt and the like; inorganic acid salts such as hydrochloride, hydrobromide, phosphate, sulphate and the like; organic acid salts such as citrate, lactate, tartrate, maleate, fumarate, mandelate, acetate, dichloroacetate, trifluoroacetate, oxalate, formate and the like; sulfonates such as methanesulfonate, benzenesulfonate, p-toluenesulfonate and the like; and amino acid salts such as arginate, glutamate and the like.

Acid addition salts can be formed by mixing a solution of the particular compound of the present invention with a solution of a pharmaceutically acceptable non-toxic acid such as hydrochloric acid, fumaric acid, maleic acid, succinic acid, acetic acid, citric acid, tartaric acid, carbonic acid, phosphoric acid, oxalic acid, dichloroacetic acid, and the like. Basic salts can be formed by mixing a solution of the particular compound of the present invention and a pharmaceutically acceptable non-toxic base such as sodium hydroxide, potassium hydroxide, choline hydroxide, sodium carbonate and the like.

Compounds of the Invention also encompass solvates of the disclosed compounds of Formula I", Formula IA", Formula IB", Formula IC", Formula ID"; Formula I', Formula IA', Formula IB', Formula IC', or Formula ID'; Formula I, Formula IA, Formula IB, Formula IC, or Formula ID. The term "solvate" as used herein is a combination, physical association and/or solvation of a compound of Formula I", Formula IA", Formula IB", Formula IC", Formula ID"; Formula I', Formula IA', Formula IB', Formula IC', or Formula ID'; Formula I, Formula IA, Formula IB, Formula IC, or Formula ID with a solvent molecule such as, e.g. a disolvate, monosolvate or hemisolvate, where the ratio of solvent molecule to compound of Formula I", Formula IA", Formula IB", Formula IC", Formula ID"; Formula I', Formula IA', Formula IB', Formula IC', or Formula ID'; Formula I, Formula IA, Formula IB, Formula IC, or Formula ID is 2:1, 1:1 or 1:2, respectively. This physical association involves varying degrees of ionic and covalent bonding, including hydrogen bonding. In certain instances, the solvate can be isolated, such as when one or more solvent molecules are incorporated into the crystal lattice of a crystalline solid. Thus, "solvate" encompasses both solution-phase and isolatable solvates. A compound of Formula I", Formula IA", Formula IB", Formula IC", Formula ID"; Formula I', Formula IA', Formula IB', Formula IC', or Formula ID'; Formula I, Formula IA, Formula IB, Formula IC, or Formula ID or may be present as a solvated form with a pharmaceutically acceptable solvent, such as water, methanol, ethanol, and the like, and it is intended that the invention include both solvated and unsolvated forms of Formula I", Formula IA", Formula IB", Formula IC", Formula ID"; Formula I', Formula IA', Formula IB', Formula IC', or Formula ID'; Formula I, Formula IA, Formula IB, Formula IC, or Formula ID compounds. One type of solvate is a hydrate. A "hydrate" relates to a particular subgroup of solvates where the solvent molecule is water. Solvates typically can function as pharmacological equivalents. Preparation of solvates is known in the art. See, for example, M. Caira et al, *J. Pharmaceut. Sci.*, 93(3):601-611 (2004), which describes the preparation of solvates of fluconazole with ethyl acetate and with water. Similar preparation of solvates, hemisolvates, hydrates, and the like are described by E. C. van Tonder et al., *AAPS Pharm. Sci. Tech.*, 5(1): Article 12 (2004), and A. L. Bing-ham et al., *Chem. Commun.*, 603-604 (2001). A typical, non-limiting, process of preparing a solvate would involve dissolving a compound of Formula I", Formula IA", Formula IB", Formula IC", Formula ID"; Formula I', Formula IA', Formula IB', Formula IC', or Formula ID'; Formula I, Formula IA, Formula IB, Formula IC, or Formula ID in a desired solvent (organic, water, or a mixture thereof) at temperatures above about 20° C. to about 25° C., then cooling the solution at a rate sufficient to form crystals, and isolating the crystals by known methods, e.g., filtration. Analytical techniques such as infrared spectroscopy can be used to confirm the presence of the solvent in a crystal of the solvate.

The present invention also provides the use of a Compound of the Invention in the manufacture of a medicament for treating or preventing a Condition. In one embodiment, the Condition is pain, such as acute or chronic pain. In one embodiment, a Compound of the Invention has agonist activity at the μ, δ and/or κ receptors. In another embodiment a Compound of the Invention has agonist activity at the μ receptor. In another embodiment, a Compound of the Invention has antagonist activity at the ORL-1 receptor. In another embodiment, certain Compounds of the invention can stimulate one receptor (e.g., a μ, δ and/or κ agonist) and inhibit a different receptor (e.g., an ORL-1 antagonist). In another embodiment, the Compound of the Invention is an agonist at the μ receptor, and an antagonist at the ORL-1 receptor. In another embodiment, the Compound of the Invention is an antagonist at the μ receptor, and an agonist at the κ receptor.

LIST OF ABBREVIATIONS

ACN acetonitrile
AcOH acetic acid
AIBN 2,2-azobisisobutyronitrile
Alloc allyloxycarbonyl
aq. aqueous
atm atmosphere(s)
Bn benzyl
Boc tert-butoxycarbonyl
Boc$_2$O di-tert-butyl dicarbonate
Bz benzoyl
° C. degrees Celcius
CAN ceric ammonium nitrate
Cbz benzyloxycarbonyl
CSA 10-camphorsulfonic acid
d day(s)
DABCO 1,4-diazabicyclo[2.2.2]octane
DBU 1,8-diazabicyclo[5.4.0]undec-7-ene
DCM dichloromethane
DDQ 2,3-dichloro-5,6-dicyano-1,4-benzoquinone
DEAD diethyl azodicarboxylate
DIAD diisopropyl azodicarboxylate
DIBAL diisobutylaluminum hydride
DIPEA diisopropylethylamine
DMAC dimethylacetamide
DMAP 4-dimethylaminopyridine
DME 1,2-dimethoxyethane
DMF dimethylformamide
DMPU N,N-dimethylpropyleneurea
DMSO dimethylsulfoxide
EDCI 1-ethyl-3-(3-dimethylaminopropyl)carbodiimide)
Et$_2$O diethyl ether
EtOAc ethyl acetate
EtOH ethanol
FMOC 9-fluorenylmethyloxycarbonyl h hour(s)
HATU 2-(7-aza-1H-benzotriazole-1-yl)-1,1,3,3-tetramethyluronium hexafluorophosphate
HPLC high pressure liquid chromatography
i-PrOH iso-propanol
LAH lithium aluminum hydride
LDA lithium diisopropylamide
mCPBA meta-chloroperoxybenzoic acid
MEM β-methoxyethoxymethyl
MeOH methanol
min minute(s)
MOM methoxymethyl
MPLC medium pressure liquid chromatography
Ms methanesulfonyl
MsCl methanesulfonyl chloride
NaHMDS sodium hexamethyldisilazide
NBS N-bromosuccinimide
NMO N-methylmorpholine N-oxide
NMP N-methyl-2-pyrrolidone
PCC pyridinium chlorochromate
Pd/C palladium on carbon
Pd(dppf)Cl$_2$ [1,1'-bis(diphenylphosphino)ferrocene]dichloropalladium(II)
Pd(Ph$_3$P)$_2$Cl$_2$ bis(triphenylphosphine)palladium(II)dichloride
(Ph)$_3$P triphenylphosphine
Piv pivaloyl
PMB p-methoxybenzyl
PTSA p-toluenesulfonic acid
PyBOP benzotriazol-1-yl-oxytripyrrolidinophosphonium hexafluorophosphate
RT room temperature
TBAF tetrabutylammonium fluoride
TBDMS tert-butyldimethylsilyl
t-BuOH tert-butyl alcohol
TEA triethylamine
Tf trifluoromethanesulfonyl
TFA trifluoroacetic acid
TFAA trifluoroacetic anhydride
THF tetrahydrofuran
THP 2-tetrahydropyranyl
TMS trimethylsilyl
TMEDA N,N,N',N'-tetramethylethylenediamine

Synthesis of Compounds

Compounds of Formula I", I' and I can be made using conventional organic synthesis in view of this disclosure, or by the illustrative methods shown in the schemes below.

Scheme A

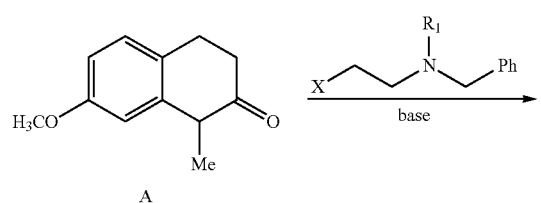

A

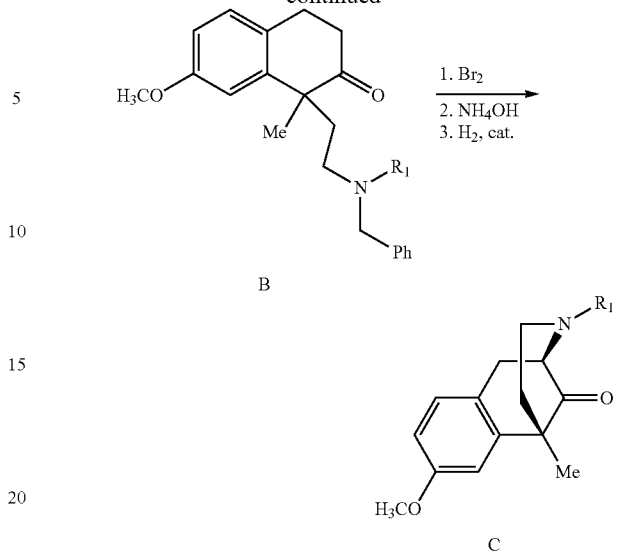

Ketone C is prepared as generally described in U.S. Pat. No. 3,956,336A. Compound A [*J. Amer. Chem. Soc.*, 1961, 83, 1492] is alkylated with a haloethyl amine in the presence of a base such as sodium hydride, in a solvent such as benzene to give compound B. Compound B is treated with bromine in a suitable solvent such as acetic acid to give the alpha-bromo ketone, which is cyclized to give the quaternary salt by treatment with a suitable base such as ammonium hydroxide. Hydrogenolysis of the quaternary salt in the presence of hydrogen and a suitable catalyst such as palladium on carbon in a suitable solvent such as acetic acid gives the amino ketone C.

Scheme B

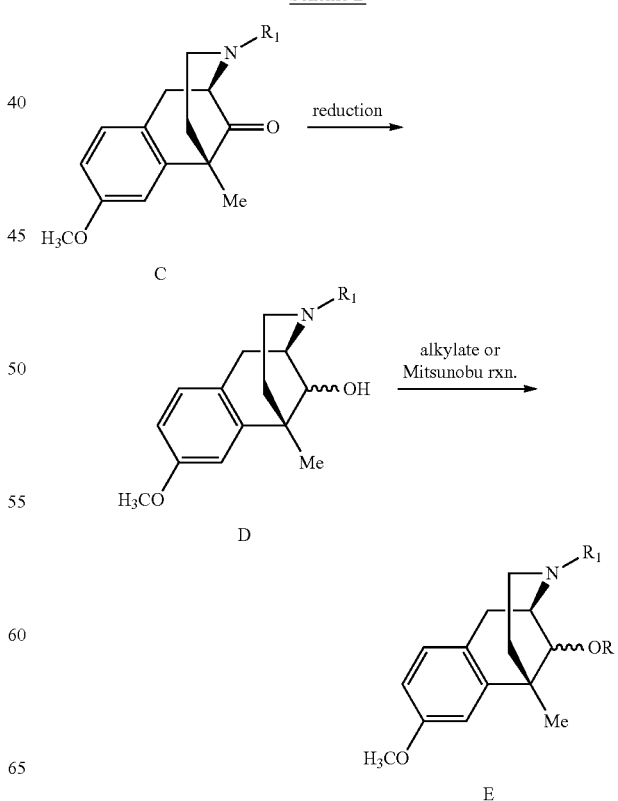

Ketone C is reduced with a suitable reducing agent such as sodium borohydride in a suitable solvent such as methanol (MeOH) to give alcohol D. Compound D can be converted into ether E by alkylation using a suitable base such as sodium hydride in a suitable solvent such as dimethylformamide (DMF). An alternate method of ether formation is via a Mitsunobu reaction (e.g. Hughes, D. L. *Org. Prep.* 1996, 28, 127) using the appropriate phenol and suitable reagents such as triphenylphosphine and diisopropyl azodicarboxylate (DIAD) in a suitable solvent such as tetrahydrofuran (THF).

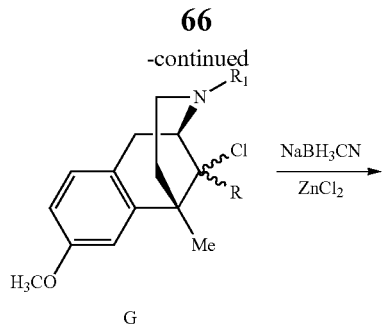

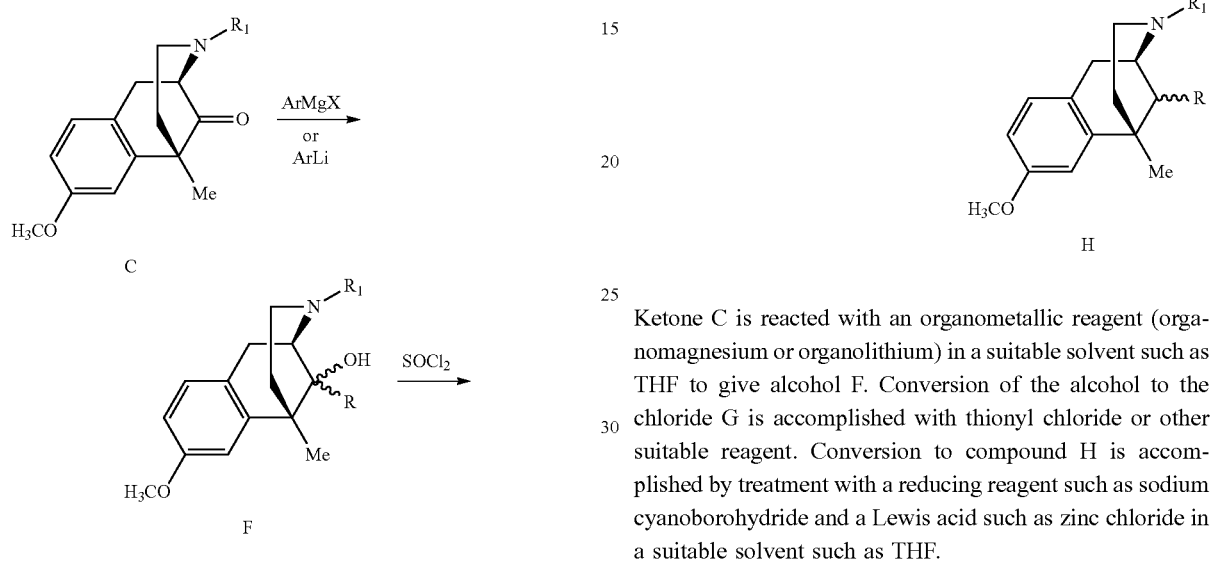

Ketone C is reacted with an organometallic reagent (organomagnesium or organolithium) in a suitable solvent such as THF to give alcohol F. Conversion of the alcohol to the chloride G is accomplished with thionyl chloride or other suitable reagent. Conversion to compound H is accomplished by treatment with a reducing reagent such as sodium cyanoborohydride and a Lewis acid such as zinc chloride in a suitable solvent such as THF.

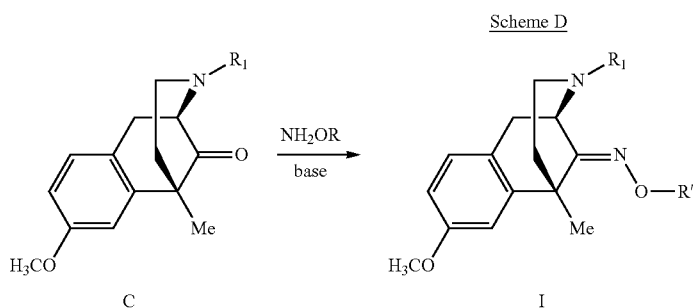

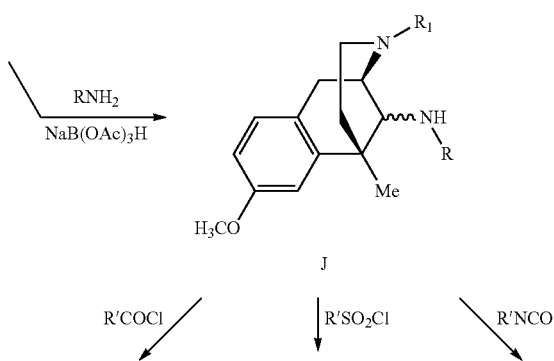

Ketone C is reacted with a hydroxylamine in a suitable solvent such as ethanol (EtOH) in the presence of a suitable base such as sodium acetate to form oxime I. Ketone C is reacted with an amine under reductive amination conditions with a suitable reducing agent such as sodium triacetoxyborohydride in a suitable solvent such as acetonitrile (AcCN) to give amine J, which can be functionalized with suitable reagents such as acid chlorides, sulfonyl chlorides and isocyanates in a suitable solvent such as dichloromethane (DCM) in the presence of a suitable base such as triethyl amine (TEA) to obtain compound K, L, or M.

Alcohol is converted to chloride N by treatment with methanesulfonyl chloride in the presence of a suitable base such as triethyl amine (TEA) in a suitable solvent such as DCM. Reaction of compound N with an amine in the presence of a suitable base such as TEA in a suitable solvent such as DCM gives compound O.

Ketone C is converted to aldehyde P by reaction with a suitable phosphonium salt in the presence of a suitable base such as potassium tert-butoxide (KOtBu) in a suitable solvent such as THF. Treatment of compound P with acid gives the aldehyde Q which can be converted to the alcohol R by treatment with a suitable reducing agent such as $NaBH_4$ in a suitable solvent such as EtOH.

Scheme G

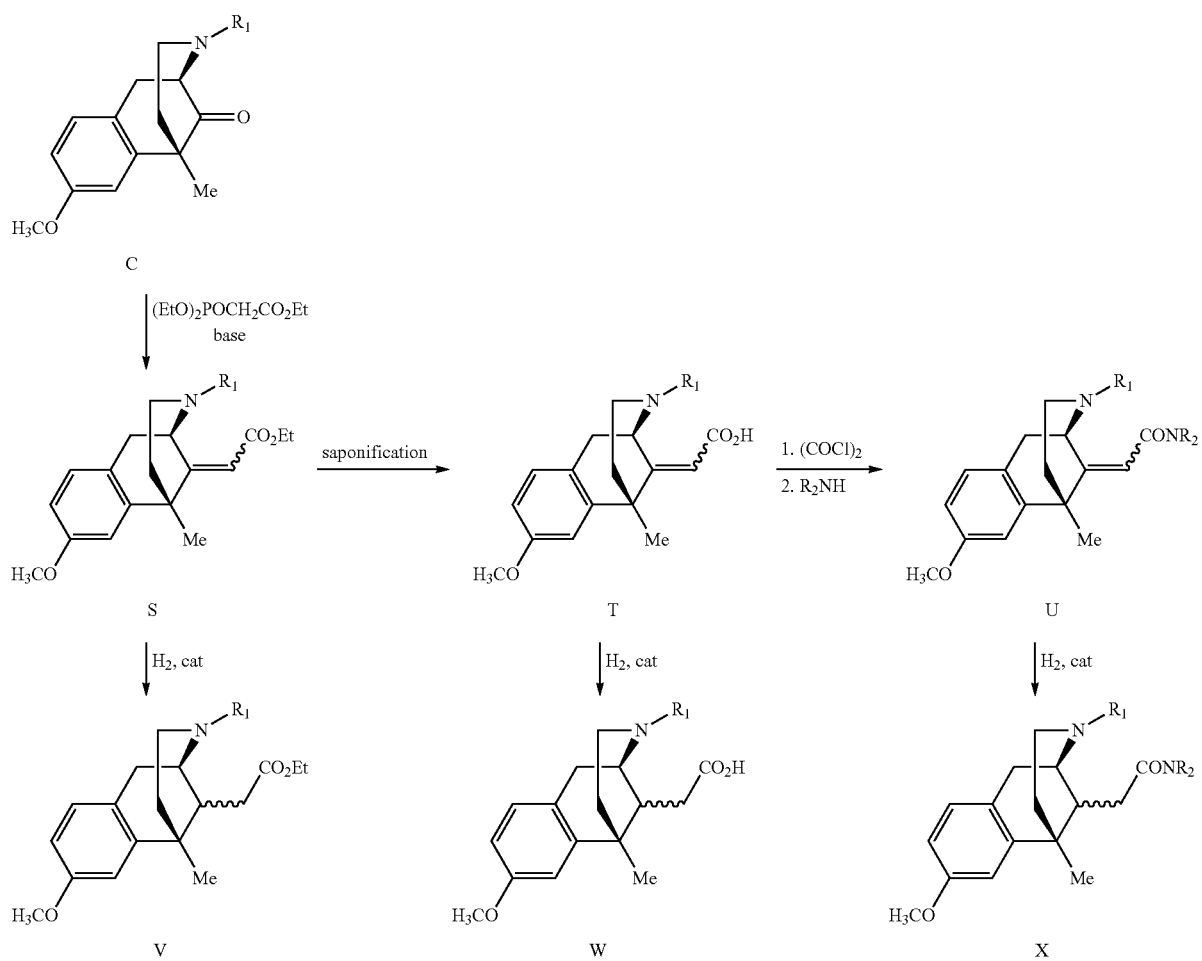

Ketone C is converted to ester S by reaction with an appropriate phosphonate ester in the presence of a suitable base such as sodium hexamethylsilazide (NaHMDS) in a suitable solvent such as THF. Ester S is saponified to acid T by reaction with a suitable base such as potassium hydroxide (KOH) in a suitable solvent such as MeOH/water. Acid T is converted to amide U by conversion to an acid chloride by treatment with a suitable chlorinating agent such as oxalyl chloride and subsequent reaction with an appropriate amine in the presence of a suitable base such as diisopropylethylamine (DIPEA) in a suitable solvent such as DCM. Each of the unsaturated compounds (S, T and U) can be converted to their saturated analogs by reduction with hydrogen in the presence of a suitable catalyst such as Pd/C in a suitable solvent such as MeOH.

Scheme H

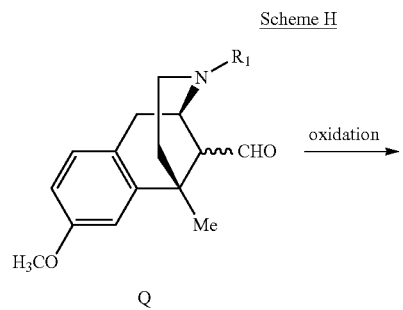

Aldehyde Q is oxidized to acid Y by reaction with a suitable oxidizing agent such as sodium chlorite and sodium bisulfate in suitable solvent such as a mixture of water and AcCN. Acid Y is converted to amide Z by conversion to an acid chloride by treatment with a suitable chlorinating agent such as oxalyl chloride and subsequent reaction with an appropriate amine in the presence of a suitable base such as DIPEA in a suitable solvent such as DCM.

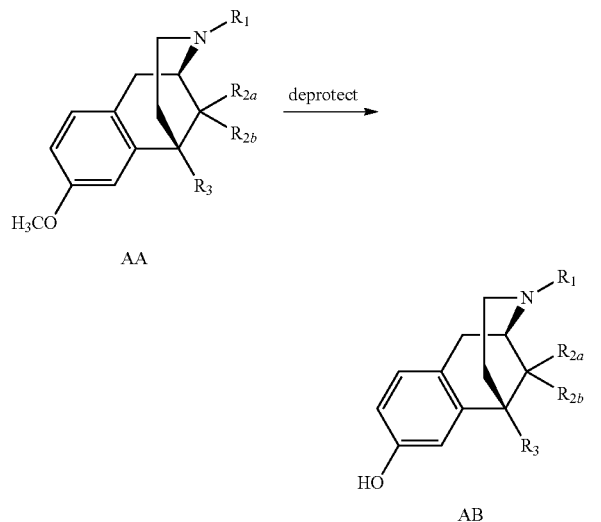

Aryl ether AA is cleaved to the phenol AB by treatment with a suitable reagent such as boron tribromide (BBr$_3$) in a suitable solvent such as DCM (e.g. Greene, T. W. "Protective Groups in Organic Synthesis", J. Wiley & Sons, NY, 1981).

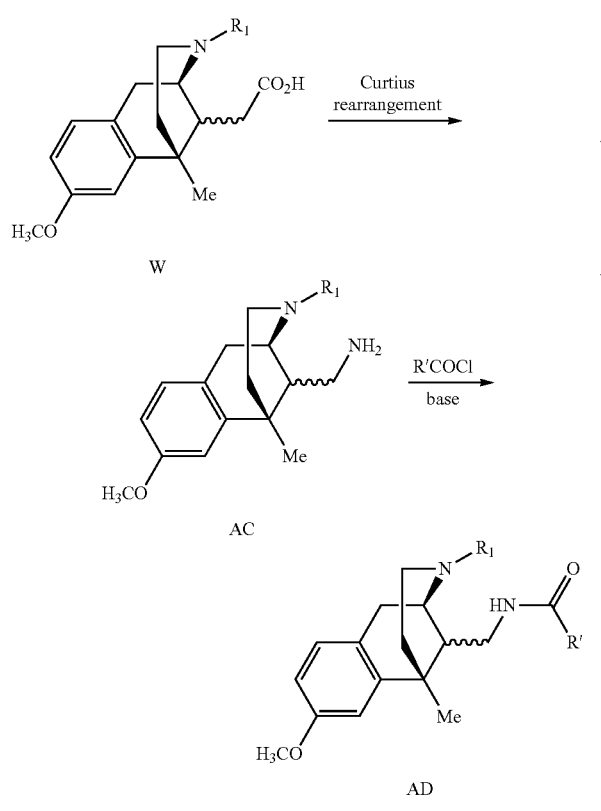

Acid W is converted to amine AC by Curtius rearrangement using a suitable reagent such as diphenylphosphoryl azide (DPPA) in the presence of a base such as TEA in a suitable solvent such as toluene, followed by an aqueous workup. Coupling with a suitable acid chloride in the presence of a suitable base such as TEA in a suitable solvent such as DCM gives the amide AD.

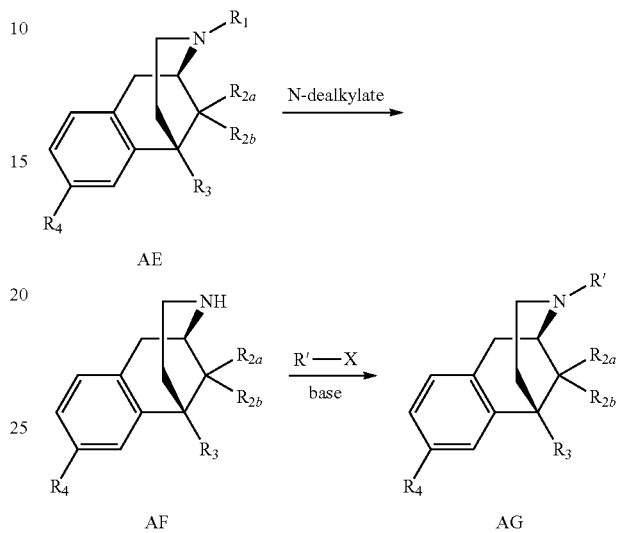

Amine AE is N-dealkylated to give the secondary amine AF by any number of different methods known to one skilled in the art such as treatment with m-chloroperoxybenzoic acid (MCPBA) in the presence of iron (II) chloride (FeCl$_2$) (Monkovic et al. Secondary Amines from the Iron(II) Ion-Catalyzed Reaction of Amine Oxides: A General Method for the Dealkylation of Tertiary Amines. *Synthesis*, 1985, 770). Amine AF is alkylated to give amine AG by treatment with an appropriate alkyl halide in the presence of a suitable base such as TEA in a suitable solvent such as DCM.

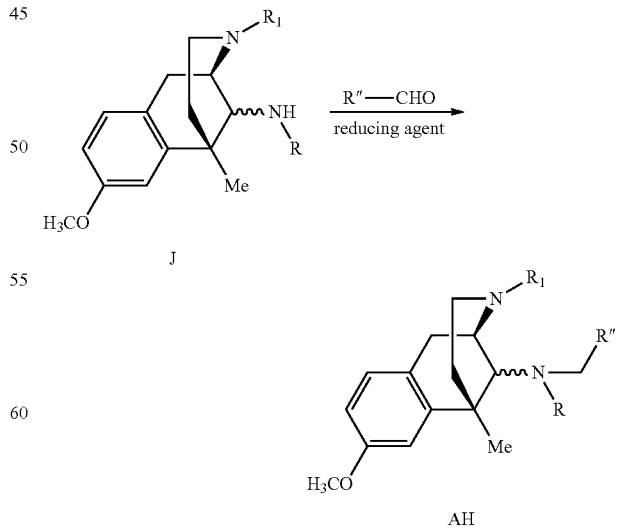

Compound J is reacted with an aldehyde under reductive amination conditions with a suitable reducing agent such as sodium triacetoxyborohydride in a suitable solvent such as ACN to give Compound AH.

Testing of Compounds

µ-Opioid Receptor Binding Assay Procedures:

Radioligand dose-displacement binding assays for µ-opioid receptors used 0.3 nM [$^3$H]-diprenorphine (Perkin Elmer, Shelton, Conn.), with 5 mg membrane protein/well in a final volume of 500 µl binding buffer (10 mM $MgCl_2$, 1 mM EDTA, 5% DMSO, 50 mM HEPES, pH 7.4). Reactions were carried out in the absence or presence of increasing concentrations of unlabeled naloxone. All reactions were conducted in 96-deep well polypropylene plates for 2 hr at room temperature. Binding reactions were terminated by rapid filtration onto 96-well Unifilter GF/C filter plates (Perkin Elmer, Shelton, Conn.), presoaked in 0.5% polyethylenimine using a 96-well tissue harvester (Perkin Elmer, Shelton, Conn.) followed by performing three filtration washes with 500 µl of ice-cold binding buffer. Filter plates were subsequently dried at 50° C. for 2-3 hours. BetaScint scintillation cocktail (Perkin Elmer, Shelton, Conn.) was added (50 µl/well), and plates were counted using a Packard Top-Count for 1 min/well. The data were analyzed using the one-site competition curve fitting functions in GraphPad PRISM™ v. 3.0 or higher (San Diego, Calif.), or an in-house function for one-site competition curve-fitting.

µ-Opioid Receptor Binding Data:

Generally, the lower the Ki value, the more effective the Compounds of the Invention will be at treating or preventing pain or another Condition. Typically, the Compounds of the Invention will have a Ki (nM) of about 1000 or less for binding to µ-opioid receptors. In one embodiment the Compounds of the Invention will have a Ki (nM) of about 300 or less for binding to µ-opioid receptors. In one embodiment, Compounds of the Invention will have a Ki (nM) of about 100 or less. In another embodiment, Compounds of the Invention will have a Ki (nM) of about 10 or less. In still another embodiment, Compounds of the Invention will have a Ki (nM) of about 1 or less. In still another embodiment, Compounds of the Invention will have a Ki (nM) of about 0.1 or less.

µ-Opioid Receptor Functional Assay Procedures:

[$^{35}$S]GTPγS functional assays were conducted using freshly thawed µ-receptor membranes prepared in-house from a cell line expressing recombinant µ opioid receptor in a HEK-293, CHO or U-2 OS cell background, or purchased from a commercial source (Perkin Elmer, Shelton, Conn.; or DiscovRx, Fremont, Calif.). Assay reactions were prepared by sequentially adding the following reagents to binding buffer (100 mM NaCl, 10 mM $MgCl_2$, 20 mM HEPES, pH 7.4) on ice (final concentrations indicated): membrane protein (0.026 mg/mL), saponin (10 mg/mL), GDP (3 mM) and [$^{35}$S]GTPγS (0.20 nM; Perkin Elmer, Shelton, Conn.). The prepared membrane solution (190 µl/well) was transferred to 96-shallow well polypropylene plates containing 10 µl of 20x concentrated stock solutions of the agonist [D-Ala$^2$, N-methyl-Phe$^4$ Gly-ol$^5$]-enkephalin (DAMGO) prepared in dimethyl sulfoxide (DMSO). Plates were incubated for 30 min at about 25° C. with shaking. Reactions were terminated by rapid filtration onto 96-well Unifilter GF/B filter plates (Perkin Elmer, Shelton, Conn.) using a 96-well tissue harvester (Perkin Elmer, Shelton, Conn.) followed by three filtration washes with 200 µl of ice-cold wash buffer (10 mM $NaH_2PO_4$, 10 mM $Na_2HPO_4$, pH 7.4). Filter plates were subsequently dried at 50° C. for 2-3 hr. BetaScint scintillation cocktail (Perkin Elmer, Shelton, Conn.) was added (50 µl/well) and plates were counted using a Packard Top-Count for 1 min/well. Data were analyzed using the sigmoidal dose-response curve fitting functions in GraphPad PRISM v. 3.0, or an in-house function for non-linear, sigmoidal dose-response curve-fitting.

µ-Opioid Receptor Functional Data:

µ GTP $EC_{50}$ is the concentration of a compound providing 50% of the maximal response for the compound at a µ-opioid receptor. Compounds of the Invention will typically have a µ GTP $EC_{50}$ (nM) of about 5000 or less. In certain embodiments, Compounds of the Invention will have a µ GTP $EC_{50}$ (nM) of about 2000 or less; or about 1000 or less; or about 100 or less; or about 10 or less; or about 1 or less; or about 0.1 or less.

µ GTP $E_{max}$ (%) is the maximal effect elicited by a compound relative to the effect elicited by DAMGO, a standard µ agonist. Generally, the µ GTP $E_{max}$ (%) value measures the efficacy of a compound to treat or prevent pain or other Conditions. Typically, Compounds of the Invention will have a µ GTP $E_{max}$ (%) of greater than about 10%; or greater than about 20%. In certain embodiments, Compounds of the Invention will have a µ GTP $E_{max}$ (%) of greater than about 50%; or greater than about 65%; or greater than about 75%; or greater than about 85%; or greater than about 100%.

κ-Opioid Receptor Binding Assay Procedures:

Membranes from recombinant HEK-293 cells, CHO or U-2 OS cells expressing the recombinant human κ opioid receptor (κ) were prepared by lysing cells in ice cold hypotonic buffer (2.5 mM $MgCl_2$, 50 mM HEPES, pH 7.4) (10 mL/10 cm dish) followed by homogenization with a tissue grinder/Teflon pestle. Membranes from a cell line naturally expressing kappa opioid receptors can also be used. Membranes were collected by centrifugation at 30,000xg for 15 min at 4° C. and pellets were resuspended in hypotonic buffer to a final concentration of 1-3 mg/mL. Protein concentrations were determined using the BioRad protein assay reagent with bovine serum albumen as standard. Aliquots of κ receptor membranes were stored at –80° C.

Radioligand dose displacement assays used 0.4 nM [$^3$H]-U69,593 (GE Healthcare, Piscataway, N.J.; 40 Ci/mmole) with 15 µg membrane protein (recombinant κ opioid receptor expressed in HEK 293 cells; in-house prep) in a final volume of 200 µl binding buffer (5% DMSO, 50 mM Trizma base, pH 7.4). Non-specific binding was determined in the presence of 10 µM unlabeled naloxone or U69,593. All reactions were performed in 96-well polypropylene plates for 1 hr at a temperature of about 25° C. Binding reactions were terminated by rapid filtration onto 96-well Unifilter GF/C filter plates (Perkin Elmer, Shelton, Conn.) presoaked in 0.5% polyethylenimine (Sigma). Harvesting was performed using a 96-well tissue harvester (Perkin Elmer, Shelton, Conn.) followed by five filtration washes with 200 µl ice-cold binding buffer. Filter plates were subsequently dried at 50° C. for 1-2 hours. Fifty µl/well scintillation cocktail (Perkin Elmer, Shelton, Conn.) was added and plates were counted in a Packard Top-Count for 1 min/well.

κ-Opioid Receptor Binding Data:

In certain embodiments, the Compounds of the Invention will have a Ki (nM) for κ receptors of about 10,000 or more (which, for purposes of this invention, is interpreted as having no binding to the κ receptors). Certain Compounds of the Invention will have a Ki (nM) of about 20,000 or less for κ receptors. In certain embodiments, Compounds of the Invention will have a Ki (nM) of about 10,000 or less; or about 5000 or less; or about 1000 or less; or about 500 or less; or about 450 or less; or about 350 or less; or about 200 or less; or about 100 or less; or about 50 or less; or about 10 or less; or about 1 or less; or about 0.1 or less.

κ-Opioid Receptor Functional Assay Procedures:

Functional [$^{35}$S]GTPγS binding assays were conducted as follows. κ opioid receptor membrane solution was prepared by sequentially adding final concentrations of 0.026 μg/μl κ membrane protein (in-house), 10 μg/mL saponin, 3 μM GDP and 0.20 nM [$^{35}$S]GTPγS to binding buffer (100 mM NaCl, 10 mM MgCl$_2$, 20 mM HEPES, pH 7.4) on ice. The prepared membrane solution (190 μl/well) was transferred to 96-shallow well polypropylene plates containing 10 μl of 20× concentrated stock solutions of agonist prepared in DMSO. Plates were incubated for 30 min at a temperature of about 25° C. with shaking. Reactions were terminated by rapid filtration onto 96-well Unifilter GF/B filter plates (Perkin Elmer, Shelton, Conn.) using a 96-well tissue harvester (Packard) and followed by three filtration washes with 200 μl ice-cold binding buffer (10 mM NaH$_2$PO$_4$, 10 mM Na$_2$HPO$_4$, pH 7.4). Filter plates were subsequently dried at 50° C. for 2-3 hours. Fifty μl/well scintillation cocktail (Perkin Elmer, Shelton, Conn.) was added and plates were counted in a Packard Top-Count for 1 min/well.

κ-Opioid Receptor Functional Data:

κ GTP EC$_{50}$ is the concentration of a compound providing 50% of the maximal response for the compound at a κ receptor. Certain Compounds of the Invention will have a κ GTP EC$_{50}$ (nM) of about 20,000 or less to stimulate κ opioid receptor function. In certain embodiments, Compounds of the Invention will have a κ GTP EC$_{50}$ (nM) of about 10,000 or less; or about 5000 or less; or about 2000 or less; or about 1500 or less; or about 1000 or less; or about 600 or less; or about 100 or less; or about 50 or less; or about 25 or less; or about 10 or less; or about 1 or less; or about 0.1 or less.

κ GTP E$_{max}$ (%) is the maximal effect elicited by a compound relative to the effect elicited by U69,593. Certain Compounds of the Invention will have a κ GTP E$_{max}$ (%) of greater than about 1%; or greater than about 5%; or greater than about 10%; or greater than about 20%. In certain embodiments, Compounds of the Invention will have a κ GTP E$_{max}$ (%) of greater than about 50%; or greater than about 75%; or greater than about 90%; or greater than about 100%.

δ-Opioid Receptor Binding Assay Procedures:

δ-opioid Receptor Binding Assay Procedures can be conducted as follows. Radioligand dose-displacement assays use 0.3 nM [$^3$H]-Naltrindole (Perkin Elmer, Shelton, Conn.; 33.0 Ci/mmole) with 5 μg membrane protein (Perkin Elmer, Shelton, Conn.) in a final volume of 500 μl binding buffer (5 mM MgCl$_2$, 5% DMSO, 50 mM Trizma base, pH 7.4). Non-specific binding is determined in the presence of 25 μM unlabeled naloxone. All reactions are performed in 96-deep well polypropylene plates for 1 hr at a temperature of about 25° C. Binding reactions are terminated by rapid filtration onto 96-well Unifilter GF/C filter plates (Perkin Elmer, Shelton, Conn.) presoaked in 0.5% polyethylenimine (Sigma). Harvesting is performed using a 96-well tissue harvester (Perkin Elmer, Shelton, Conn.) followed by five filtration washes with 500 μl ice-cold binding buffer. Filter plates are subsequently dried at 50° C. for 1-2 hours. Fifty μl/well scintillation cocktail (Perkin Elmer, Shelton, Conn.) is added and plates are counted in a Packard Top-Count for 1 min/well.

δ-Opioid Receptor Binding Data:

In certain embodiments, the Compounds of the Invention will have a Ki (nM) for δ receptors of about 10,000 or more (which, for the purposes of this invention, is interpreted as having no binding to the δ receptors). Certain Compounds of the Invention will have a Ki (nM) of about 20,000 or less for δ receptors. In one embodiment, the Compounds of the Invention will have a Ki (nM) of about 10,000 or less; or of about 9000 or less. In another embodiment, the Compounds of the Invention will have a Ki (nM) of about 7500 or less; or of about 6500 or less; or of about 5000 or less; or of about 3000 or less; or of about 2500 or less. In another embodiment, the Compounds of the Invention will have a Ki (nM) of about 1000 or less; or of about 500 or less; or of about 350 or less; or of about 250 or less; or of about 100 or less; or of about 10 or less.

δ-Opioid Receptor Functional Assay Procedures:

Functional [$^{35}$S]GTPγS binding assays can be conducted as follows. δ opioid receptor membrane solution is prepared by sequentially adding final concentrations of 0.026 μg/μl δ membrane protein (Perkin Elmer, Shelton, Conn.), 10 μg/mL saponin, 3 μM GDP and 0.20 nM [$^{35}$S]GTPγS to binding buffer (100 mM NaCl, 10 mM MgCl$_2$, 20 mM HEPES, pH 7.4) on ice. The prepared membrane solution (190 μl/well) is transferred to 96-shallow well polypropylene plates containing 10 μl of 20× concentrated stock solutions of agonist prepared in DMSO. Plates are incubated for 30 min at a temperature of about 25° C. with shaking. Reactions are terminated by rapid filtration onto 96-well Unifilter GF/B filter plates (Perkin Elmer, Shelton, Conn.) using a 96-well tissue harvester (Packard) and followed by three filtration washes with 200 μl ice-cold binding buffer (10 mM NaH$_2$PO$_4$, 10 mM Na$_2$HPO$_4$, pH 7.4). Filter plates are subsequently dried at 50° C. for 1-2 hours. Fifty μl/well scintillation cocktail (Perkin Elmer, Shelton, Conn.) is added and plates are counted in a Packard Top-count for 1 min/well.

δ-Opioid Receptor Functional Data:

δ GTP EC$_{50}$ is the concentration of a compound providing 50% of the maximal response for the compound at a δ receptor. Certain Compounds of the Invention will have a δ GTP EC$_{50}$ (nM) of about 20,000 or less; or about 10,000 or less. In certain embodiments, the Compounds of the Invention will have a δ GTP EC$_{50}$ (nM) of about 3500 or less; or of about 1000 or less; or of about 500 or less; or of about 100 or less; or of about 90 or less; or of about 50 or less; or of about 25 or less; or of about 10 or less.

δ GTP E$_{max}$ (%) is the maximal effect elicited by a compound relative to the effect elicited by met-enkephalin. Certain Compounds of the Invention of the invention will have a δ GTP E$_{max}$ (%) of greater than about 1%; or of greater than about 5%; or of greater than about 10%. In one embodiment, the Compounds of the Invention will have a δ GTP E$_{max}$ (%) of greater than about 30%. In other embodiments, the Compounds of the Invention will have a δ GTP E$_{max}$ (%) of greater than about 50%; or of greater than about 75%; or of greater than about 90%. In another embodiment, the Compounds of the Invention will have a δ GTP E$_{max}$ (%) of about 100% or greater.

ORL-1 Receptor Binding Assay Procedure:

Membranes from recombinant HEK-293 cells expressing the human opioid receptor-like receptor (ORL-1) (Perkin Elmer, Shelton, Conn.) are prepared by lysing cells in ice-cold hypotonic buffer (2.5 mM MgCl$_2$, 50 mM HEPES, pH 7.4) (10 ml/10 cm dish) followed by homogenization with a tissue grinder/Teflon pestle. Membranes are collected by centrifugation at 30,000×g for 15 min at 4° C. and pellets resuspended in hypotonic buffer to a final concentration of 1-3 mg/ml. Protein concentrations are determined using the BioRad protein assay reagent with bovine serum albumen as standard. Aliquots of the ORL-1 receptor membranes are stored at −80° C.

Radioligand binding assays (screening and dose-displacement) use 0.1 nM [$^3$H]-nociceptin (Perkin Elmer, Shelton, Conn.; 87.7 Ci/mmole) with 12 µg membrane protein in a final volume of 500 µl binding buffer (10 mM MgCl$_2$, 1 mM EDTA, 5% DMSO, 50 mM HEPES, pH 7.4). Non-specific binding is determined in the presence of 10 nM unlabeled nociceptin (American Peptide Company). All reactions are performed in 96-deep well polypropylene plates for 1 h at room temperature. Binding reactions are terminated by rapid filtration onto 96-well Unifilter GF/C filter plates (Perkin Elmer, Shelton, Conn.) presoaked in 0.5% polyethylenimine (Sigma). Harvesting is performed using a 96-well tissue harvester (Perkin Elmer, Shelton, Conn.) followed by three filtration washes with 500 µl ice-cold binding buffer. Filter plates are subsequently dried at 50° C. for 2-3 hours. Fifty µl/well scintillation cocktail (Perkin Elmer, Shelton, Conn.) is added and plates are counted in a Packard Top-Count for 1 min/well. The data from screening and dose-displacement experiments are analyzed using Microsoft Excel and the curve fitting functions in GraphPad PRISM™, v. 3.0 or higher, respectively, or an in-house function for one-site competition curve-fitting.

ORL-1 Receptor Binding Data:

Certain Compounds of the Invention will have a Ki (nM) of about 1000 or less. In one embodiment, the Compounds of the Invention will have a Ki (nM) of about 500 or less. In other embodiments, the Compounds of the Invention will have a Ki (nM) of about 300 or less; or of about 100 or less; or of about 50 or less; or of about 20 or less. In yet other embodiments, the Compounds of the Invention will have a Ki (nM) of about 10 or less; or of about 1 or less; or of about 0.1 or less.

ORL-1 Receptor Functional Assay Procedure:

Membranes from recombinant HEK-293 cells expressing the human opioid receptor-like (ORL-1) (Perkin Elmer, Shelton, Conn.) are prepared by lysing cells in ice-cold hypotonic buffer (2.5 mM Mg Cl$_2$, 50 mM HEPES, pH 7.4) (10 ml/10 cm dish) followed by homogenization with a tissue grinder/Teflon pestle. Membranes are collected by centrifugation at 30,000×g for 15 min at 4° C., and pellets resuspended in hypotonic buffer to a final concentration of 1-3 mg/ml. Protein concentrations are determined using the BioRad protein assay reagent with bovine serum albumen as standard. Aliquots of the ORL-1 receptor membranes are stored at −80° C.

Functional [$^{35}$S]GTPγS binding assays are conducted as follows. ORL-1 membrane solution is prepared by sequentially adding final concentrations of 0.026 µg/µl ORL-1 membrane protein, 10 µg/ml saponin, 3 µM GDP and 0.20 nM [$^{35}$S]GTPγS to binding buffer (100 mM NaCl, 10 mM MgCl$_2$, 20 mM HEPES, pH 7.4) on ice. The prepared membrane solution (190 µl/well) is transferred to 96-shallow well polypropylene plates containing 10 µl of 20× concentrated stock solutions of agonist/nociceptin prepared in DMSO. Plates are incubated for 30 min at room temperature with shaking. Reactions are terminated by rapid filtration onto 96-well Unifilter GF/B filter plates (Perkin Elmer, Shelton, Conn.) using a 96-well tissue harvester (Packard) and followed by three filtration washes with 200 µl ice-cold binding buffer (10 mM NaH$_2$PO$_4$, 10 mM Na$_2$HPO$_4$, pH 7.4). Filter plates are subsequently dried at 50° C. for 2-3 hours. Fifty µl/well scintillation cocktail (Perkin Elmer, Shelton, Conn.) is added and plates are counted in a Packard Top-Count for 1 min/well. Data are analyzed using the sigmoidal dose-response curve fitting functions in GraphPad PRISM v. 3.0 or higher, or an in-house function for non-linear, sigmoidal dose-response curve-fitting.

ORL-1 Receptor Functional Data:

ORL-1 GTP EC$_{50}$ is the concentration of a compound providing 50% of the maximal response for the compound at an ORL-1 receptor. In certain embodiments, the Compounds of the Invention that have a high binding affinity (i.e. low K, value) will have an ORL-1 GTP EC$_{50}$ (nM) of greater than about 10,000 (i.e. will not stimulate at therapeutic concentrations) In certain embodiments Compounds of the Invention will have an ORL-1 GTP EC$_{50}$ (nM) of about 20,000 or less. In one embodiment, the Compounds of the Invention will have an ORL-1 GTP EC$_{50}$ (nM) of about 10,000 or less; or of about 5000 or less; or of about 1000 or less. In still other embodiments, the Compounds of the Invention will have an ORL-1 GTP EC$_{50}$ (nM) of about 100 or less; or of about 10 or less; or of about 1 or less; or of about 0.1 or less.

ORL-1 GTP E$_{max}$% is the maximal effect elicited by a compound relative to the effect elicited by nociceptin, a standard ORL-1 agonist. In certain embodiments, Compounds of the Invention will have an ORL-1 GTP E$_{max}$ of less than 10% (which, for the purposes of this invention, is interpreted as having antagonist activity at ORL-1 receptors). Certain Compounds of the Invention will have an ORL-1 GTP E$_{max}$ (%) of greater than 1%; or of greater than 5%; or of greater than 10%. In other embodiments the Compounds of the Invention will have an ORL-1 GTP E$_{max}$ of greater than 20%; or of greater than 50%; or of greater than 75%; or of greater than 88%; or of greater than 100%.

In Vivo Assays for Prevention or Treatment of Pain

Test Animals:

Each experiment uses rats weighing between 200-260 g at the start of the experiment. The rats are group-housed and have free access to food and water at all times, except prior to oral administration of a Compound of the Invention when food is removed for about 16 hours before dosing. A control group acts as a comparison to rats treated with a Compound of the Invention. The control group is administered the carrier for the Compound of the Invention. The volume of carrier administered to the control group is the same as the volume of carrier and Compound of the Invention administered to the test group.

Acute Pain:

To assess the actions of a Compound of the Invention for the treatment or prevention of acute pain, the rat tail flick can be used. Rats are gently restrained by hand and the tail exposed to a focused beam of radiant heat at a point 5 cm from the tip using a tail flick unit (Model 7360, commercially available from Ugo Basile of Italy). Tail flick latencies are defined as the interval between the onset of the thermal stimulus and the flick of the tail. Animals not responding within 20 seconds are removed from the tail flick unit and assigned a withdrawal latency of 20 seconds. Tail flick latencies are measured immediately before (pre-treatment) and 1, 3, and 5 hours following administration of a Compound of the Invention. Data are expressed as tail flick latency(s) and the percentage of the maximal possible effect (% MPE), i.e., 20 seconds, is calculated as follows:

$$\%MPE = \frac{[(\text{post administration latency}) - (\text{pre-administration latency})]}{(20s - \text{pre-administration latency})} \times 100$$

The rat tail flick test is described in F. E. D'Amour et al., "A Method for Determining Loss of Pain Sensation," *J. Pharmacol. Exp. Ther.* 72:74-79 (1941).

To assess the actions of a Compound of the Invention for the treatment or prevention of acute pain, the rat hot plate test can also be used. Rats are tested using a hot plate apparatus consisting of a clear plexiglass cylinder with a heated metal floor maintained at a temperature of 48-52° C. (Model 7280, commercially available from Ugo Basile of Italy). Rats are placed into the cylinder on the hot plate apparatus for a maximum duration of 30 s, or until it exhibits a nocifensive behavior (behavioral endpoint), at which time it is removed from the hot plate, and the response latency recorded. Hot plate latencies are measured immediately before (pre-treatment) and 1, 3, and 5 hours following administration of a Compound of the Invention. The nocifensive behavioral endpoint is defined as any of the following: 1) paw withdrawal, either as a sustained lift or with shaking or licking; 2) alternating foot lifting; 3) escape or attempted escape from the testing device; or 4) vocalization. Data are expressed as response latency(s) and the percentage of the maximal possible effect is calculated as described above for the tail flick test. The hot plate test is described in G. Woolfe and A. D. Macdonald, *J. Pharmacol. Exp. Ther.* 80:300-307 (1944).

Inflammatory Pain:

To assess the actions of a Compound of the Invention for the treatment or prevention of inflammatory pain, the Freund's complete adjuvant ("FCA") model of inflammatory pain can be used. FCA-induced inflammation of the rat hind paw is associated with the development of persistent inflammatory mechanical hyperalgesia and provides reliable prediction of the anti-hyperalgesic action of clinically useful analgesic drugs (L. Bartho et al., "Involvement of Capsaicin-sensitive Neurones in Hyperalgesia and Enhanced Opioid Antinociception in Inflammation," *Naunyn-Schmiedeberg's Archives of Pharmacol.* 342:666-670 (1990)). The left hind paw of each animal is administered a 50 µL intraplantar injection of 50% FCA. Prior to injection of FCA (baseline) and 24 hour post injection, the animal is assessed for response to noxious mechanical stimuli by determining the PWT, as described below. Rats are then administered a single injection of 1, 3, or 10 mg/kg of either a Compound of the Invention; 30 mg/kg of a control drug selected from Celebrex, indomethacin or naproxen; or carrier. Responses to noxious mechanical stimuli are determined 1, 3, 5 and 24 hours post administration. Percentage reversal of hyperalgesia for each animal is defined as:

$$\%Reversal = \frac{[(\text{post administration} PWT) - (\text{pre-administration} PWT)]}{[(\text{baseline } PWT) - (\text{pre-administration } PWT)]} \times 100$$

Neuropathic Pain:

To assess the actions of a Compound of the Invention for the treatment or prevention of neuropathic pain, either the Seltzer model or the Chung model can be used.

In the Seltzer model, the partial sciatic nerve ligation model of neuropathic pain is used to produce neuropathic hyperalgesia in rats (Z. Seltzer et al., "A Novel Behavioral Model of Neuropathic Pain Disorders Produced in Rats by Partial Sciatic Nerve Injury," *Pain* 43:205-218 (1990)). Partial ligation of the left sciatic nerve is performed under isoflurane/$O_2$ inhalation anaesthesia. Following induction of anesthesia, the left thigh of the rat is shaved and the sciatic nerve exposed at high thigh level through a small incision and is carefully cleared of surrounding connective tissues at a site near the trocanther just distal to the point at which the posterior biceps semitendinosus nerve branches off of the common sciatic nerve. A 7-0 silk suture is inserted into the nerve with a ⅜ curved, reversed-cutting mini-needle and tightly ligated so that the dorsal ⅓ to ½ of the nerve thickness is held within the ligature. The wound is closed with a single muscle suture (4-0 nylon (Vicryl)) and vetbond tissue glue. Following surgery, the wound area is dusted with antibiotic powder. Sham-treated rats undergo an identical surgical procedure except that the sciatic nerve is not manipulated. Following surgery, animals are weighed and placed on a warm pad until they recover from anesthesia. Animals are then returned to their home cages until behavioral testing begins. The animal is assessed for response to noxious mechanical stimuli by determining PWT, as described below, prior to surgery (baseline), then immediately prior to and 1, 3, and 5 hours after drug administration. Percentage reversal of neuropathic hyperalgesia is defined as:

$$\%Reversal = \frac{[(\text{post administration} PWT) - (\text{pre-administration} PWT)]}{[(\text{baseline } PWT) - (\text{pre-administration } PWT)]} \times 100$$

In the Chung model, the spinal nerve ligation model of neuropathic pain is used to produce mechanical hyperalgesia, thermal hyperalgesia and tactile allodynia in rats. Surgery is performed under isoflurane/$O_2$ inhalation anaesthesia. Following induction of anaesthesia, a 3 cm incision is made and the left paraspinal muscles are separated from the spinous process at the $L_4$-$S_2$ levels. The $L_6$ transverse process is carefully removed with a pair of small rongeurs to identify visually the $L_4$-$L_6$ spinal nerves. The left $L_5$ (or $L_5$ and $L_6$) spinal nerve(s) is isolated and tightly ligated with silk thread. A complete hemostasis is confirmed and the wound is sutured using non-absorbable sutures, such as nylon sutures or stainless steel staples. Sham-treated rats undergo an identical surgical procedure except that the spinal nerve(s) is not manipulated. Following surgery animals are weighed, administered a subcutaneous (s.c.) injection of saline or ringers lactate, the wound area is dusted with antibiotic powder and they are kept on a warm pad until they recover from the anesthesia. Animals are then returned to their home cages until behavioral testing begins. The animals are assessed for response to noxious mechanical stimuli by determining PWT, as described below, prior to surgery (baseline), then immediately prior to and 1, 3, and 5 hours after being administered a Compound of the Invention. The animal can also be assessed for response to noxious thermal stimuli or for tactile allodynia, as described below. The Chung model for neuropathic pain is described in S. H. Kim, "An Experimental Model for Peripheral Neuropathy Produced by Segmental Spinal Nerve Ligation in the Rat," *Pain* 50(3):355-363 (1992).

Response to Mechanical Stimuli as an Assessment of Mechanical Hyperalgesia:

The paw pressure assay can be used to assess mechanical hyperalgesia. For this assay, hind paw withdrawal thresholds (PWT) to a noxious mechanical stimulus are determined using an analgesymeter (Model 7200, commercially available from Ugo Basile of Italy) as described in C. Stein, "Unilateral Inflammation of the Hindpaw in Rats as a Model of Prolonged Noxious Stimulation: Alterations in Behavior and Nociceptive Thresholds," *Pharmacol. Biochem. and*

*Behavior* 31:451-455 (1988). The maximum weight that is applied to the hind paw is set at 250 g and the end point is taken as complete withdrawal of the paw. PWT is determined once for each rat at each time point and either only the affected (ipsilateral; same side as the injury) rear paw is tested, or both the ipsilateral and contralateral (non-injured; opposite to the injury) rear paw are tested.

Response to Thermal Stimuli as an Assessment of Thermal Hyperalgesia:

The plantar test can be used to assess thermal hyperalgesia. For this test, hind paw withdrawal latencies to a noxious thermal stimulus are determined using a plantar test apparatus (commercially available from Ugo Basile of Italy) following the technique described by K. Hargreaves et al., "A New and Sensitive Method for Measuring Thermal Nociception in Cutaneous Hyperalgesia," *Pain* 32(1):77-88 (1988). The maximum exposure time is set at 32 seconds to avoid tissue damage and any directed paw withdrawal from the heat source is taken as the end point. Three latencies are determined at each time point and averaged. Either only the affected (ipsilateral) paw is tested, or both the ipsilateral and contralateral (non-injured) paw are tested.

Assessment of Tactile Allodynia:

To assess tactile allodynia, rats are placed in clear, plexiglass compartments with a wire mesh floor and allowed to habituate for a period of at least 15 minutes. After habituation, a series of von Frey monofilaments are presented to the plantar surface of the affected (ipsilateral) foot of each rat. The series of von Frey monofilaments consists of six monofilaments of increasing diameter, with the smallest diameter fiber presented first. Five trials are conducted with each filament with each trial separated by approximately 2 minutes. Each presentation lasts for a period of 4-8 seconds or until a nociceptive withdrawal behavior is observed. Flinching, paw withdrawal or licking of the paw are considered nociceptive behavioral responses.

Assessment of Respiratory Depression:

To assess respiratory depression, rats can be prepared by implanting a femoral artery cannula via which blood samples are taken. Blood samples are taken prior to drug administration, then 1, 3, 5 and 24 hours post-treatment. Blood samples are processed using an arterial blood gas analyzer (e.g., IDEXX VetStat with Respiratory/Blood Gas test cartridges). Comparable devices are a standard tool for blood gas analysis (e.g., D. Torbati et al., 2000 *Intensive Care Med.* (26) 585-591).

Assessment of Gastric Motility:

Animals are treated with vehicle, reference compound or test article by oral gavage at a volume of 10 mL/kg. At one hour post-dose, all animals are treated with charcoal meal solution (5% non-activated charcoal powder in a solution of 1% carboxymethylcellulose in water) at a volume of 10 mL/kg. At two hours post-dose (one hour post-charcoal), animals are sacrificed by carbon dioxide inhalation or isoflurane overdose and the transit of charcoal meal identified. The stomach and small intestine are removed carefully and each placed on a saline-soaked absorbent surface. The distance between the pylorus and the furthest progression of charcoal meal is measured and compared to the distance between the pylorus and the ileocecal junction. The charcoal meal transit is expressed as a percentage of small intestinal length traveled.

Pharmaceutical Compositions

Due to their activity, the Compounds of the Invention are advantageously useful in human and veterinary medicine.

As described above, the Compounds of the Invention are useful for treating or preventing a Condition in a subject in need thereof. The Compounds of the Invention can be administered to any animal requiring modulation of the opioid and/or ORL-1 receptors.

When administered to a subject, a Compound of the Invention can be administered as a component of a composition that comprises a pharmaceutically acceptable carrier or excipient. A Compound of the Invention can be administered by any appropriate route, as determined by the medical practitioner. Methods of administration may include intradermal, intramuscular, intraperitoneal, parenteral, intravenous, subcutaneous, intranasal, epidural, oral, sublingual, buccal, intracerebral, intravaginal, transdermal, transmucosal, rectal, by inhalation, or topical (particularly to the ears, nose, eyes, or skin). Delivery can be either local or systemic. In certain embodiments, administration will result in the release of a Compound of the Invention into the bloodstream.

Pharmaceutical compositions of the invention can take the form of solutions, suspensions, emulsions, tablets, pills, pellets, multi-particulates, capsules, capsules containing liquids, capsules containing powders, capsules containing multi-particulates, lozenges, sustained-release formulations, thin films, suppositories, aerosols, sprays, or any other form suitable for use. In one embodiment, the composition is in the form of a capsule (see, e.g., U.S. Pat. No. 5,698,155). Other examples of suitable pharmaceutical excipients are described in *Remington's Pharmaceutical Sciences* 1447-1676 (Alfonso R. Gennaro ed., 19th ed. 1995), incorporated herein by reference.

Pharmaceutical compositions of the invention preferably comprise a suitable amount of a pharmaceutically acceptable excipient so as to provide the form for proper administration to the subject. Such a pharmaceutical excipient can be a diluent, suspending agent, solubilizer, binder, disintegrant, preservative, coloring agent, lubricant, and the like. The pharmaceutical excipient can be a liquid, such as water or an oil, including those of petroleum, animal, vegetable, or synthetic origin, such as peanut oil, soybean oil, mineral oil, sesame oil, and the like. The pharmaceutical excipient can be saline, gum acacia, gelatin, starch paste, talc, keratin, colloidal silica, urea, and the like. In addition, auxiliary, stabilizing, thickening, lubricating, and coloring agents can be used. In one embodiment, the pharmaceutically acceptable excipient is sterile when administered to an animal. Water is a particularly useful excipient when a Compound of the Invention is administered intravenously. Saline solutions and aqueous dextrose and glycerol solutions can also be employed as liquid excipients, particularly for injectable solutions. Suitable pharmaceutical excipients also include starch, glucose, lactose, sucrose, gelatin, malt, rice, flour, chalk, silica gel, sodium stearate, glycerol monostearate, talc, sodium chloride, dried skim milk, glycerol, propylene glycol, water, ethanol, and the like. The invention compositions, if desired, can also contain minor amounts of wetting or emulsifying agents, or pH buffering agents. Specific examples of pharmaceutically acceptable carriers and excipients that can be used to formulate oral dosage forms are described in the *Handbook of Pharmaceutical Excipients*, American Pharmaceutical Association (1986).

In certain embodiments, the Compounds of the Invention are formulated for oral administration. A Compound of the Invention to be orally delivered can be in the form of tablets, capsules, gelcaps, caplets, lozenges, aqueous or oily solutions, suspensions, granules, powders, emulsions, syrups, or elixirs, for example. When a Compound of the Invention is incorporated into oral tablets, such tablets can be compressed, tablet triturates, enteric-coated, sugar-coated, film-coated, multiply compressed or multiply layered.

An orally administered Compound of the Invention can contain one or more additional agents such as, for example, sweetening agents such as fructose, aspartame or saccharin; flavoring agents such as peppermint, oil of wintergreen, or cherry; coloring agents; and preserving agents, and stabilizers, to provide stable, pharmaceutically palatable dosage forms. Techniques and compositions for making solid oral dosage forms are described in *Pharmaceutical Dosage Forms: Tablets* (Lieberman, Lachman and Schwartz, eds., 2nd ed.) published by Marcel Dekker, Inc. Techniques and compositions for making tablets (compressed and molded), capsules (hard and soft gelatin) and pills are also described in *Remington's Pharmaceutical Sciences* 1553-1593 (Arthur Osol, ed., 16$^{th}$ ed., Mack Publishing, Easton, Pa. 1980). Liquid oral dosage forms include aqueous and nonaqueous solutions, emulsions, suspensions, and solutions and/or suspensions reconstituted from non-effervescent granules, optionally containing one or more suitable solvents, preservatives, emulsifying agents, suspending agents, diluents, sweeteners, coloring agents, flavoring agents, and the like. Techniques and compositions for making liquid oral dosage forms are described in *Pharmaceutical Dosage Forms: Disperse Systems*, (Lieberman, Rieger and Banker, eds.) published by Marcel Dekker, Inc.

When a Compound of the Invention is formulated for parenteral administration by injection (e.g., continuous infusion or bolus injection), the formulation can be in the form of a suspension, solution, or emulsion in an oily or aqueous vehicle, and such formulations can further comprise pharmaceutically necessary additives such as one or more stabilizing agents, suspending agents, dispersing agents, and the like. When a Compound of the Invention is to be injected parenterally, it can be, e.g., in the form of an isotonic sterile solution. A Compound of the Invention can also be in the form of a powder for reconstitution as an injectable formulation.

In certain embodiments, a Compound of the Invention is formulated into a pharmaceutical composition for intravenous administration. Typically, such compositions comprise sterile isotonic aqueous buffer. Where necessary, the compositions can also include a solubilizing agent. A Compound of the Invention for intravenous administration can optionally include a local anesthetic such as benzocaine or prilocaine to lessen pain at the site of the injection. Generally, the ingredients are supplied either separately or mixed together in unit dosage form, for example, as a dry lyophilized powder or water free concentrate in a hermetically sealed container such as an ampule or sachette indicating the quantity of active agent. Where a Compound of the Invention is to be administered by infusion, it can be dispensed, for example, with an infusion bottle containing sterile pharmaceutical grade water or saline. Where a Compound of the Invention is administered by injection, an ampule of sterile water for injection or saline can be provided so that the ingredients can be mixed prior to administration.

When a Compound of the Invention is to be administered by inhalation, it can be formulated into a dry aerosol, or an aqueous or partially aqueous solution.

In another embodiment, a Compound of the Invention can be delivered in a vesicle, in particular a liposome (see Langer, *Science* 249:1527-1533 (1990); and Treat et al., *Liposomes in the Therapy of Infectious Disease and Cancer* 317-327 and 353-365 (1989)).

In certain embodiments, a Compound of the Invention is administered locally. This can be achieved, for example, by local infusion during surgery, topical application, e.g., in conjunction with a wound dressing after surgery, by injection, by means of a catheter, by means of a suppository or enema, or by means of an implant, said implant being of a porous, non-porous, or gelatinous material, including membranes, such as sialastic membranes, or fibers.

In certain embodiments, a Compound of the Invention can be delivered in an immediate release form. In other embodiments, a Compound of the Invention can be delivered in a controlled-release system or sustained-release system. Controlled- or sustained-release pharmaceutical compositions can have a common goal of improving drug therapy over the results achieved by their non-controlled or non-sustained-release counterparts. In one embodiment, a controlled- or sustained-release composition comprises a minimal amount of a Compound of the Invention to treat or prevent the Condition (or a symptom thereof) in a minimum amount of time. Advantages of controlled- or sustained-release compositions include extended activity of the drug, reduced dosage frequency, and increased compliance. In addition, controlled- or sustained-release compositions can favorably affect the time of onset of action or other characteristics, such as blood levels of the Compound of the Invention, and can thus reduce the occurrence of adverse side effects.

Controlled- or sustained-release compositions can initially release an amount of a Compound of the Invention that promptly produces the desired therapeutic or prophylactic effect, and gradually and continually release other amounts of the Compound of the Invention to maintain a level of therapeutic or prophylactic effect over an extended period of time. To maintain a constant level of the Compound of the Invention in the body, the Compound of the Invention can be released from the dosage form at a rate that will replace the amount of Compound of the Invention being metabolized and excreted from the body. Controlled- or sustained-release of an active ingredient can be stimulated by various conditions, including but not limited to, changes in pH, changes in temperature, concentration or availability of enzymes, concentration or availability of water, or other physiological conditions or compounds.

Controlled-release and sustained-release means for use according to the present invention may be selected from those known in the art. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; and 5,733,566, each of which is incorporated herein by reference. Such dosage forms can be used to provide controlled- or sustained-release of one or more active ingredients using, for example, hydropropylmethyl cellulose, other polymer matrices, gels, permeable membranes, osmotic systems, multilayer coatings, microparticles, multiparticulates, liposomes, microspheres, or a combination thereof to provide the desired release profile in varying proportions. Suitable controlled- or sustained-release formulations known in the art, including those described herein, can be readily selected for use with the active ingredients of the invention in view of this disclosure. See also Goodson, "Dental Applications" (pp. 115-138) in *Medical Applications of Controlled Release*, Vol. 2, *Applications and Evaluation*, R. S. Langer and D. L. Wise eds., CRC Press (1984). Other controlled- or sustained-release systems that are discussed in the review by Langer, *Science* 249:1527-1533 (1990) can be selected for use according to the present invention. In one embodiment, a pump can be used (Langer, *Science* 249:1527-1533 (1990);

Sefton, *CRC Crit. Ref Biomed. Eng.* 14:201 (1987); Buchwald et al., *Surgery* 88:507 (1980); and Saudek et al., *N. Engl. J. Med.* 321:574 (1989)). In another embodiment, polymeric materials can be used (see *Medical Applications of Controlled Release* (Langer and Wise eds., 1974); *Controlled Drug Bioavailability, Drug Product Design and Performance* (Smolen and Ball eds., 1984); Ranger and Peppas, *J. Macromol. Sci. Rev. Macromol. Chem.* 23:61 (1983); Levy et al., *Science* 228:190 (1985); During et al., *Ann. Neurol.* 25:351 (1989); and Howard et al., *J. Neurosurg.* 71:105 (1989)). In yet another embodiment, a controlled- or sustained-release system can be placed in proximity of a target of a Compound of the Invention, e.g., the spinal column, brain, or gastrointestinal tract, thus requiring only a fraction of the systemic dose.

When in tablet or pill form, a pharmaceutical composition of the invention can be coated to delay disintegration and absorption in the gastrointestinal tract thereby providing a sustained action over an extended period of time. Selectively permeable membranes surrounding an osmotically active driving compound are also suitable for orally administered compositions. In these latter platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time-delay material such as glycerol monostearate or glycerol stearate can also be used. Oral compositions can include standard excipients such as mannitol, lactose, starch, magnesium stearate, sodium saccharin, cellulose, and magnesium carbonate. In one embodiment, the excipients are of pharmaceutical grade.

Pharmaceutical compositions of the invention include single unit dosage forms suitable for oral administration such as, but not limited to, tablets, capsules, gelcaps, and caplets that are adapted for controlled- or sustained-release.

The amount of the Compound of the Invention that is effective for the treatment or prevention of a condition can be determined by standard clinical techniques. In addition, in vitro and/or in vivo assays can optionally be employed to help identify optimal dosage ranges. The precise dose to be employed will also depend on, e.g., the route of administration and the extent of the Condition to be treated, and can be decided according to the judgment of a practitioner and/or each animal's circumstances. Variations in dosing may occur depending upon typical factors such as the weight, age, gender and physical condition (e.g., hepatic and renal function) of the animal being treated, the affliction to be treated, the severity of the symptoms, the frequency of the dosage interval, the presence of any deleterious side-effects, and the particular compound utilized, among other things.

Suitable effective dosage amounts can range from about 0.01 mg/kg of body weight to about 3000 mg/kg of body weight of the animal per day, although they are typically from about 0.01 mg/kg of body weight to about 2500 mg/kg of body weight of the animal per day or from about 0.01 mg/kg of body weight to about 1000 mg/kg of body weight of the animal per day. In one embodiment, the effective dosage amount is about 100 mg/kg of body weight of the animal per day or less. In another embodiment, the effective dosage amount ranges from about 0.01 mg/kg of body weight to about 100 mg/kg of body weight of the animal per day of a Compound of the Invention, in another embodiment, about 0.02 mg/kg of body weight to about 50 mg/kg of body weight of the animal per day, and in another embodiment, about 0.025 mg/kg of body weight to about 20 mg/kg of body weight of the animal per day.

Administration can be as a single dose or as a divided dose. In one embodiment, an effective dosage amount is administered about every 24 h until the Condition is abated. In another embodiment, an effective dosage amount is administered about every 12 h until the Condition is abated. In another embodiment, an effective dosage amount is administered about every 8 h until the Condition is abated. In another embodiment, an effective dosage amount is administered about every 6 h until the Condition is abated. In another embodiment, an effective dosage amount is administered about every 4 h until the Condition is abated. The effective dosage amounts described herein refer to total amounts administered; that is, if more than one Compound of the Invention is administered, the effective dosage amounts correspond to the total amount administered.

Where a cell capable of expressing the ORL-1 receptor is contacted with a Compound of the Invention in vitro, the amount effective for inhibiting or activating the ORL-1 receptor function in a cell will typically range from about $10^{-12}$ mol/L to about $10^{-4}$ mol/L, or from about $10^{-12}$ mol/L to about $10^{-5}$ mol/L, or from about $10^{-12}$ mol/L to about $10^{-6}$ mol/L, or from about $10^{-12}$ mol/L to about $10^{-9}$ mol/L of a solution or suspension of the compound in a pharmaceutically acceptable carrier or excipient. In one embodiment, the volume of solution or suspension comprising the Compound of the Invention will be from about 0.01 µL to about 1 mL. In another embodiment, the volume of solution or suspension will be about 200 µL.

Where a cell capable of expressing the µ-opioid receptors is contacted with a Compound of the Invention in vitro, the amount effective for inhibiting or activating the µ-opioid receptors function in a cell will typically range from about $10^{-12}$ mol/L to about $10^{4}$ mol/L, or from about $10^{-12}$ mol/L to about $10^{-5}$ mol/L, or from about $10^{-12}$ mol/L to about $10^{-6}$ mol/L, or from about $10^{-12}$ mol/L to about $10^{-9}$ mol/L of a solution or suspension of the Compound of the Invention in a pharmaceutically acceptable carrier or excipient. In one embodiment, the volume of solution or suspension comprising the Compound of the Invention will be from about 0.01 µL to about 1 mL. In another embodiment, the volume of solution or suspension will be about 200 µL.

Where a cell capable of expressing the δ-opioid receptors is contacted with a Compound of the Invention in vitro, the amount effective for inhibiting or activating the δ-opioid receptors function in a cell will typically range from about $10^{-12}$ mol/L to about $10^{-4}$ mol/L, or from about $10^{-12}$ mol/L to about $10^{-5}$ mol/L, or from about $10^{-12}$ mol/L to about $10^{-6}$ mol/L, or from about $10^{-12}$ mol/L to about $10^{-9}$ mol/L of a solution or suspension of the Compound of the Invention in a pharmaceutically acceptable carrier or excipient. In one embodiment, the volume of solution or suspension comprising the Compound of the Invention will be from about 0.01 µL to about 1 mL. In another embodiment, the volume of solution or suspension will be about 200 µL.

Where a cell capable of expressing the κ-opioid receptors is contacted with a Compound of the Invention in vitro, the amount effective for inhibiting or activating the κ-opioid receptors function in a cell will typically range from about $10^{-12}$ mol/L to about $10^{4}$ mol/L, or from about $10^{-12}$ mol/L to about $10^{-5}$ mol/L, or from about $10^{-12}$ mol/L to about $10^{-6}$ mol/L, or from about $10^{-12}$ mol/L to about $10^{-9}$ mol/L of a solution or suspension of the Compound of the Invention in a pharmaceutically acceptable carrier or excipient. In one embodiment, the volume of solution or suspension comprising the Compound of the Invention will be from about 0.01 µL to about 1 mL. In another embodiment, the volume of solution or suspension will be about 200 µL.

The Compounds of the Invention can be assayed in vitro or in vivo for the desired therapeutic or prophylactic activity prior to use in humans. Animal model systems can be used to demonstrate safety and efficacy. Certain Compounds of the Invention will have an $ED_{50}$ for treating pain ranging from about 0.5 mg/kg to about 20 mg/kg. Certain Compounds of the Invention will produce significant analgesia and/or anti-hyperalgesia at doses that do not induce respiratory depression. In contrast, oxygen tension, oxygen saturation and pH are significantly decreased, while carbon dioxide is significantly increased, in blood samples from rats given effective doses of conventional opioids, such as morphine.

According to the invention, methods for treating or preventing a Condition in an animal in need thereof can further comprise co-administering to the animal an effective amount of a second therapeutic agent in addition to a Compound of the Invention (i.e., a first therapeutic agent). An effective amount of the second therapeutic agent will be known or determinable by a medical practitioner in view of this disclosure and published clinical studies. In one embodiment of the invention, where a second therapeutic agent is administered to an animal for treatment of a Condition (e.g., pain), the minimal effective amount of the Compound of the Invention (i.e., the first therapeutic agent) will be less than its minimal effective amount would be in circumstances where the second therapeutic agent is not administered. In this embodiment, the Compound of the Invention and the second therapeutic agent can act either additively or synergistically to treat or prevent a Condition. Alternatively, the second therapeutic agent may be used to treat or prevent a disorder that is different from the Condition for which the first therapeutic agent is being administered, and which disorder may or may not be a Condition as defined hereinabove. In one embodiment, a Compound of the Invention is administered concurrently with a second therapeutic agent as a single composition comprising an effective amount of a Compound of the Invention and an effective amount of the second therapeutic agent. Alternatively, a composition comprising an effective amount of a Compound of the Invention and a second composition comprising an effective amount of the second therapeutic agent are concurrently administered. In another embodiment, an effective amount of a Compound of the Invention is administered prior or subsequent to administration of an effective amount of the second therapeutic agent. In this embodiment, the Compound of the Invention is administered while the second therapeutic agent exerts its therapeutic effect, or the second therapeutic agent is administered while the Compound of the Invention exerts its therapeutic effect for treating or preventing a Condition.

The second therapeutic agent can be, but is not limited to, an opioid agonist, a non-opioid analgesic, a non-steroidal anti-inflammatory agent, an antimigraine agent, a Cox-II inhibitor, a 5-lipoxygenase inhibitor, an anti-emetic, a β-adrenergic blocker, an anticonvulsant, an antidepressant, a $Ca^{2+}$-channel blocker, an anti-cancer agent, an agent for treating or preventing UI, an agent for treating or preventing anxiety, an agent for treating or preventing a memory disorder, an agent for treating or preventing obesity, an agent for treating or preventing constipation, an agent for treating or preventing cough, an agent for treating or preventing diarrhea, an agent for treating or preventing high blood pressure, an agent for treating or preventing epilepsy, an agent for treating or preventing anorexia/cachexia, an agent for treating or preventing drug abuse, an agent for treating or preventing an ulcer, an agent for treating or preventing IBD, an agent for treating or preventing IBS, an agent for treating or preventing addictive disorder, an agent for treating or preventing Parkinson's disease and parkinsonism, an agent for treating or preventing a stroke, an agent for treating or preventing a seizure, an agent for treating or preventing a pruritic condition, an agent for treating or preventing psychosis, an agent for treating or preventing Huntington's chorea, an agent for treating or preventing ALS, an agent for treating or preventing a cognitive disorder, an agent for treating or preventing a migraine, an agent for treating, preventing or inhibiting vomiting, an agent for treating or preventing dyskinesia, an agent for treating or preventing depression, or any mixture thereof.

Examples of useful opioid agonists include, but are not limited to, alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, heroin, hydrocodone, hydromorphone, hydroxyl)ethidine, isomethadone, ketobemidone, levorphanol, levophenacylmorphan, lofentanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, oxymorphone, papaveretum, pentazocine, phenadoxone, phenomorphan, phenazocine, phenoperidine, piminodine, piritramide, proheptazine, promedol, properidine, propiram, propoxyphene, sufentanil, tilidine, tramadol, pharmaceutically acceptable derivatives thereof, or any mixture thereof.

In certain embodiments, the opioid agonist is selected from codeine, hydromorphone, hydrocodone, oxycodone, dihydrocodeine, dihydromorphine, morphine, tramadol, oxymorphone, pharmaceutically acceptable derivatives thereof, or any mixture thereof.

Examples of useful non-opioid analgesics include, but are not limited to, non-steroidal anti-inflammatory agents, such as aspirin, ibuprofen, diclofenac, naproxen, benoxaprofen, flurbiprofen, fenoprofen, flubufen, ketoprofen, indoprofen, piroprofen, carprofen, oxaprozin, pramoprofen, muroprofen, trioxaprofen, suprofen, aminoprofen, tiaprofenic acid, fluprofen, bucloxic acid, indomethacin, sulindac, tolmetin, zomepirac, tiopinac, zidometacin, acemetacin, fentiazac, clidanac, oxpinac, mefenamic acid, meclofenamic acid, flufenamic acid, niflumic acid, tolfenamic acid, diflurisal, flufenisal, piroxicam, sudoxicam, isoxicam, a pharmaceutically acceptable derivative thereof, or any mixture thereof. Other suitable non-opioid analgesics include the following, non-limiting, chemical classes of analgesic, antipyretic, non-steroidal anti-inflammatory drugs: salicylic acid derivatives, including aspirin, sodium salicylate, choline magnesium trisalicylate, salsalate, diflunisal, salicylsalicylic acid, sulfasalazine, and olsalazin; para-aminophenol derivatives including acetaminophen and phenacetin; indole and indene acetic acids, including indomethacin, sulindac, and etodolac; heteroaryl acetic acids, including tolmetin, diclofenac, and ketorolac; anthranilic acids (fenamates), including mefenamic acid and meclofenamic acid; enolic acids, including oxicams (piroxicam, tenoxicam), and pyrazolidinediones (phenylbutazone, oxyphenthartazone); alkanones, including nabumetone; a pharmaceutically acceptable derivative thereof; or any mixture thereof. For a more detailed description of the NSAIDs, see Paul A. Insel, *Analgesic-Antipyretic* and *Anti-inflammatory Agents and Drugs Employed in the Treatment of Gout*, in Goodman & Gilman's *The Pharmacological Basis of Therapeutics* 617-57 (Perry B. Molinhoff and Raymond W. Ruddon eds., 9th ed 1996); and Glen R. Hanson, *Analgesic, Antipyretic and Anti-Inflammatory Drugs in Remington: The Science and Practice of Pharmacy* Vol IA 1196-1221 (A. R. Gennaro ed. 19th ed. 1995), which are hereby incorporated by reference in their entireties.

Examples of useful Cox-II inhibitors and 5-lipoxygenase inhibitors, as well as combinations thereof, are described in U.S. Pat. No. 6,136,839, which is hereby incorporated by reference in its entirety. Examples of useful Cox-II inhibitors include, but are not limited to, celecoxib, DUP-697, flosulide, meloxicam, 6-MNA, L-745337, rofecoxib, nabumetone, nimesulide, NS-398, SC-5766, T-614, L-768277, GR-253035, JTE-522, RS-57067-000, SC-58125, SC-078, PD-138387, NS-398, flosulide, D-1367, SC-5766, PD-164387, etoricoxib, valdecoxib, parecoxib, a pharmaceutically acceptable derivative thereof, or any mixture thereof.

Examples of useful antimigraine agents include, but are not limited to, alpiropride, bromocriptine, dihydroergotamine, dolasetron, ergocornine, ergocorninine, ergocryptine, ergonovine, ergot, ergotamine, flumedroxone acetate, fonazine, ketanserin, lisuride, lomerizine, methylergonovine, methysergide, metoprolol, naratriptan, oxetorone, pizotyline, propranolol, risperidone, rizatriptan, sumatriptan, timolol, trazodone, zolmitriptan, a pharmaceutically acceptable derivative thereof, or any mixture thereof.

Examples of useful anticonvulsants include, but are not limited to, acetylpheneturide, albutoin, aloxidone, aminoglutethimide, 4-amino-3-hydroxybutyric acid, atrolactamide, beclamide, buramate, calcium bromide, carbamazepine, cinromide, clomethiazole, clonazepam, decimemide, diethadione, dimethadione, doxenitroin, eterobarb, ethadione, ethosuximide, ethotoin, felbamate, fluoresone, gabapentin, 5-hydroxytryptophan, lamotrigine, magnesium bromide, magnesium sulfate, mephenyloin, mephobarbital, metharbital, methetoin, methsuximide, 5-methyl-5-(3-phenanthryl)-hydantoin, 3-methyl-5-phenyl-hydantoin, narcobarbital, nimetazepam, nitrazepam, oxcarbazepine, paramethadione, phenacemide, phenetharbital, pheneturide, phenobarbital, phensuximide, phenylmethylbarbituric acid, phenyloin, phethenylate sodium, potassium bromide, pregabaline, primidone, progabide, sodium bromide, solanum, strontium bromide, suclofenide, sulthiame, tetrantoin, tiagabine, topiramate, trimethadione, valproic acid, valpromide, vigabatrin, zonisamide, a pharmaceutically acceptable derivative thereof, or any mixture thereof.

Examples of useful $Ca^{2+}$-channel blockers include, but are not limited to, bepridil, clentiazem, diltiazem, fendiline, gallopamil, mibefradil, prenylamine, semotiadil, terodiline, verapamil, amlodipine, aranidipine, barnidipine, benidipine, cilnidipine, efonidipine, elgodipine, felodipine, isradipine, lacidipine, lercanidipine, manidipine, nicardipine, nifedipine, nilvadipine, nimodipine, nisoldipine, nitrendipine, cinnarizine, flunarizine, lidoflazine, lomerizine, bencyclane, etafenone, fantofarone, perhexyline, a pharmaceutically acceptable derivative thereof, or any mixture thereof.

Examples of useful therapeutic agents for treating or preventing UI include, but are not limited to, propantheline, imipramine, hyoscyamine, oxybutynin, dicyclomine, a pharmaceutically acceptable derivative thereof, or any mixture thereof.

Examples of useful therapeutic agents for treating or preventing anxiety include, but are not limited to, benzodiazepines, such as alprazolam, brotizolam, chlordiazepoxide, clobazam, clonazepam, clorazepate, demoxepam, diazepam, estazolam, flumazenil, flurazepam, halazepam, lorazepam, midazolam, nitrazepam, nordazepam, oxazepam, prazepam, quazepam, temazepam, and triazolam; non-benzodiazepine agents, such as buspirone, gepirone, ipsapirone, tiospirone, zolpicone, zolpidem, and zaleplon; tranquilizers, such as barbituates, e.g., amobarbital, aprobarbital, butabarbital, butalbital, mephobarbital, methohexital, pentobarbital, phenobarbital, secobarbital, and thiopental; propanediol carbamates, such as meprobamate and tybamate; a pharmaceutically acceptable derivative thereof; or any mixture thereof.

Examples of useful therapeutic agents for treating or preventing diarrhea include, but are not limited to, diphenoxylate, loperamide, a pharmaceutically acceptable derivative thereof, or any mixture thereof.

Examples of useful therapeutic agents for treating or preventing epilepsy include, but are not limited to, carbamazepine, ethosuximide, gabapentin, lamotrigine, phenobarbital, phenyloin, primidone, valproic acid, trimethadione, benzodiazepines, γ vinyl GABA, acetazolamide, felbamate, a pharmaceutically acceptable derivative thereof, or any mixture thereof.

Examples of useful therapeutic agents for treating or preventing drug abuse include, but are not limited to, methadone, desipramine, amantadine, fluoxetine, buprenorphine, an opiate agonist, 3-phenoxypyridine, levomethadyl acetate hydrochloride, serotonin antagonists, a pharmaceutically acceptable derivative thereof, or any mixture thereof.

Examples of non-steroidal anti-inflammatory agents, 5-lipoxygenase inhibitors, anti-emetics, β adrenergic blockers, antidepressants, and anti-cancer agents are known in the art and can be selected by those skilled in the art. Examples of useful therapeutic agents for treating or preventing memory disorder, obesity, constipation, cough, high blood pressure, anorexia/cachexia, an ulcer, IBD, IBS, addictive disorder, Parkinson's disease and parkinsonism, a stroke, a seizure, a pruritic condition, psychosis, Huntington's chorea, ALS, a cognitive disorder, a migraine, dyskinesia, depression, and/or treating, preventing or inhibiting vomiting include those that are known in the art and can be selected by those skilled in the art. A composition of the invention is prepared by a method comprising admixing a Compound of the Invention (or a pharmaceutically acceptable salt, prodrug or solvate thereof) with a pharmaceutically acceptable carrier or excipient. Admixing can be accomplished using methods known for admixing a compound (or derivative) and a pharmaceutically acceptable carrier or excipient. In one embodiment, the Compound of the Invention (or pharmaceutically acceptable salt, prodrug or solvate thereof) is present in the composition in an effective amount.

EXAMPLES

Example 1

2-(((8-methoxy-3,6-dimethyl-1,2,3,4,5,6-hexahydro-2,6-methanobenzo[d]azocin-11-ylidene)amino)oxy) acetic Acid (Compound 1)

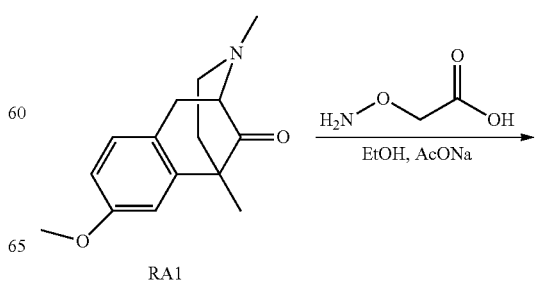

RA1

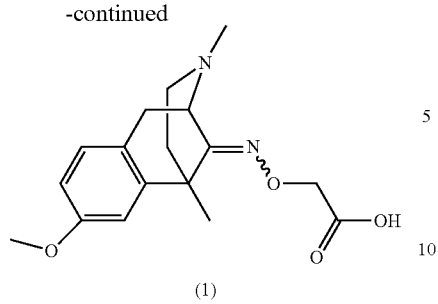

(1)

A mixture of RA1 (90 mg, 0.37 mmol), (aminooxy)acetic acid hemihydrochloride (0.56 mmol, Aldrich), NaOAc (1.2 mmol) and EtOH (2 mL) was shaken at 40° C. for 2 h. After cooling to RT, the reaction mixture was quenched with water (4 mL), and extracted with CHCl$_3$ (20 mL). The organic layer was concentrated and purified by reverse-phase prep HPLC (C18, 0-100% 0.1% TFA in water/0.1% TFA in ACN) to give Compound 1 (TFA-salt, 85 mg, 65%).

$^1$H NMR δ$_H$ (400 MHz, CD$_3$OD) 7.07 (d, J=8.3 Hz, 1H), 6.83 (d, J=2.6 Hz, 1H), 6.79 (dd, J=2.6 and 8.3 Hz, 1H), 5.22 (t, J=3.5 Hz, 1H), 4.65 (d, J=1.1 Hz, 2H), 3.69 (s, 3H), 3.35-3.40 (m, 2H), 2.95 (br., 4H), 2.1-2.2 (m, 1H), 1.78-1.82 (m, 2H), 1.53 (s, 3H); LC/MS, m/z=319.2 [M+H]$^+$ (Calc: 318.4).

Example 2

8-methoxy-3,6-dimethyl-1,2,3,4,5,6-hexahydro-2,6-methanobenzo[d]azocin-11-one Oxime (Compound 2)

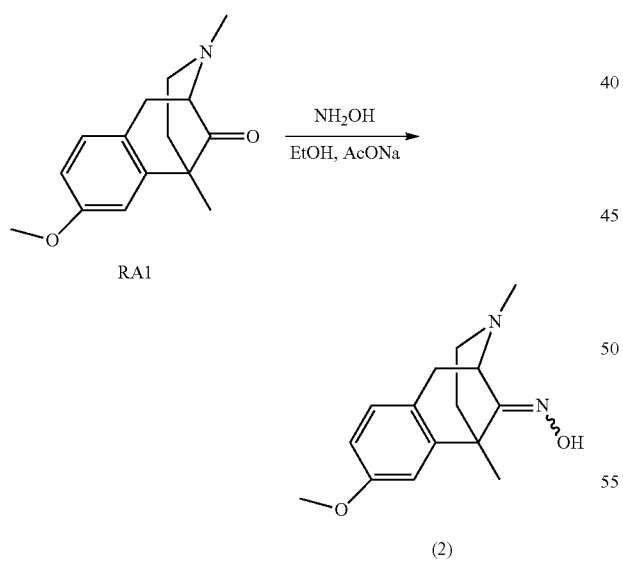

(2)

In a similar manner Compound 2 was prepared from RA1 (0.37 mmol) and hydroxylamine hydrochloride (0.56 mmol, Aldrich) following the procedure for Compound 1. Compound 2 was obtained as a white solid (70%).

$^1$H NMR δ$_H$ (400 MHz, CDCl$_3$) 7.43 (br., 1H), 7.03 (d, J=8.3 Hz, 1H), 6.81 (d, J=2.6 Hz, 1H), 6.73 (dd, J=2.6 and 8.3 Hz, 1H), 4.62 (d, J=6.1 Hz, 2H), 3.79 (s, 3H), 3.28 (d, J=18.0 Hz, 1H), 2.96 (dd, J=6.1 and 17.8 Hz, 1H), 2.48-2.56 (m, 2H), 2.46 (s, 3H), 2.08-2.15 (m, 1H), 1.55 (s, 3H), 1.5-1.54 (m, 1H); LC/MS, m/z=261.1 [M+H]$^+$ (Calc: 260.3).

Example 3

2-(((6R,11R)-8-methoxy-3,6-dimethyl-1,2,3,4,5,6-hexahydro-2,6-methanobenzo[d]azocin-11-yl)oxy)acetamide (Compound 3)

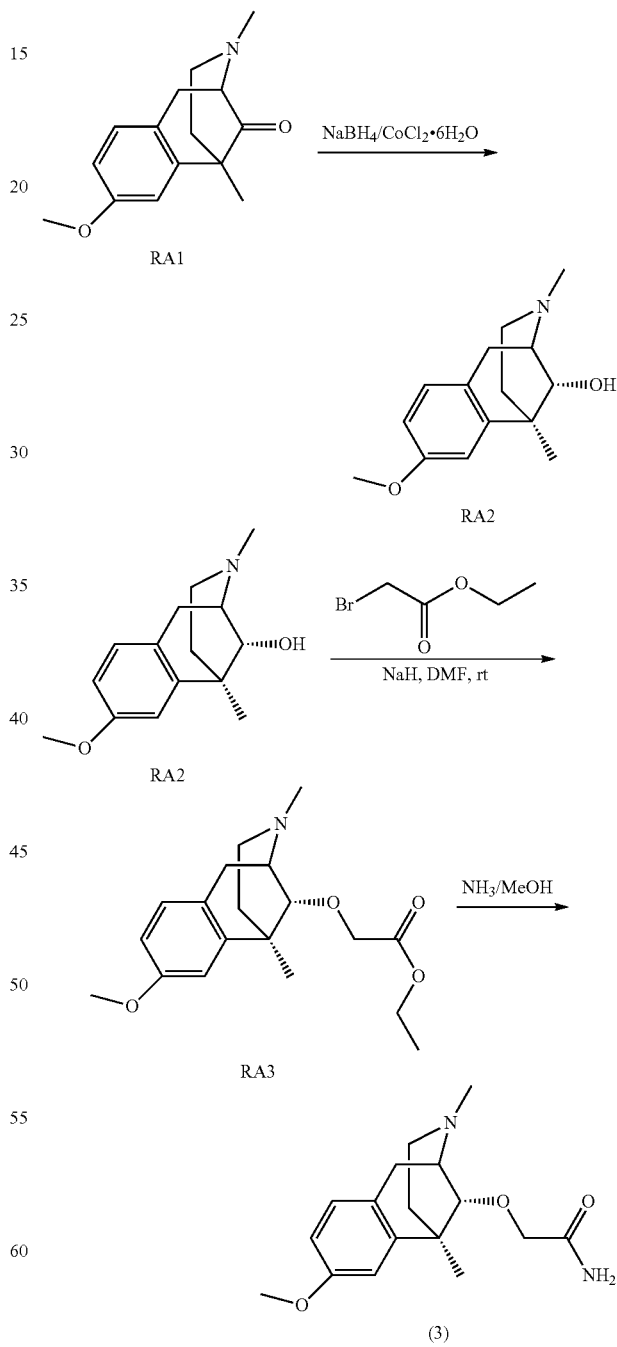

(3)

RA2 was prepared from RA1 following the literature procedure (0.5 g, 2.0 mmol) (T. A. Montzka, and J. D.

Matiskella U.S. Pat. No. 3,956,336, May 11, 1976), and purified by column chromatography (Silica gel).

RA2 (CHCl$_3$/MeOH 10/0.5, white solid, 0.35 g): $^1$H NMR δ$_H$ (400 MHz, CDCl$_3$) 7.05 (d, J=8.3 Hz, 1H), 6.81 (d, J=2.6 Hz, 1H), 6.73 (dd, J=2.6 and 8.3 Hz, 1H), 3.79 (s, 3H), 3.76-3.78 (m, 1H), 3.19 (t, J=5.5 Hz, 1H), 3.02 (d, J=18.8 Hz, 1H), 2.82 (dd, J=5.9 and 18.2 Hz, 1H), 2.43 (s, 3H), 2.32-2.37 (m, 1H), 2.04 (dt, J=3.1 and 12.2 Hz, 1H), 1.85 (dt, J=4.8 and 12.9 Hz, 1H), 1.74 (br., s, 1H), 1.51 (s, 3H), 1.41-1.46 (m, 1H); LC/MS, m/z=248.3 [M+H]$^+$ (Calc: 247.3).

NaH (1 mmol, 60% in mineral oil) was added to a solution of RA2 (0.28 mmol) in 2 mL DMF at 0° C. under nitrogen. The reaction mixture was stirred at 0° C. for 1 h, then a solution of ethyl 2-bromoacetate (60 mg, in 1 mL DMF) was added. The reaction mixture was warmed to RT for 24 h. After aqueous work-up, the crude product RA3, LC/MS, m/z=334.4 [M+H]$^+$ (Calc: 333.4) was treated with ammonia (~7N in MeOH, 4 mL) at 0° C. The reaction mixture was shaken at RT for 48 h, then concentrated and purified by reverse-phase prep HPLC (C18, 0-100% 0.1% TFA in water/0.1% TFA in ACN) to yield Compound 3 (TFA-salt, white solid, 30 mg, 36%). $^1$H NMR δ$_H$ (400 MHz, CD$_3$OD) 7.14-7.18 (m, 1H), 6.89-6.93 (m, 1H), 6.83-6.87 (m, 1H), 4.88-4.90 (m, 1H), 4.1-4.25 (m, 3H), 3.7-3.82 (m, 4H), 3.12-3.26 (m, 2H), 2.97-3.02 (m, 3H), 2.62-2.70 (m, 1H), 1.9-2.2 (m, 1H), 1.7-1.76 (m, 1H), 1.54-1.64 (m, 3H); LC/MS, m/z=305.2 [M+H]$^+$ (Calc: 304.4).

Example 4

2-((((6R,11S)-8-methoxy-3,6-dimethyl-1,2,3,4,5,6-hexahydro-2,6-methanobenzo[d]azocin-11-yl)oxy)acetamide (Compound 4)

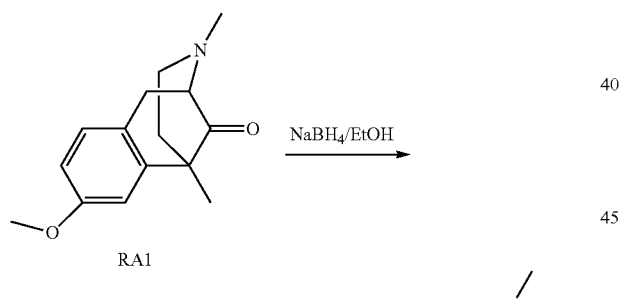

RA4 was prepared from RA1 following the literature procedure (0.5 g, 2.0 mmol) (T. A. Montzka, and J. D. Matiskella U.S. Pat. No. 3,956,336, May 11, 1976), and purified by column chromatography (Silica gel).

RA4: (CHCl$_3$/MeOH 10/0.3, white solid, 0.4 g): $^1$H NMR δ$_H$ (400 MHz, CDCl$_3$) 7.02 (d, J=8.6 Hz, 1H), 6.85 (d, J=2.6 Hz, 1H), 6.71 (dd, J=2.6 and 8.5 Hz, 1H), 3.79 (s, 3H), 3.57-3.59 (m, 1H), 3.4-3.5 (br, 1H), 3.19 (d, J=18.2 Hz, 1H), 3.11-3.14 (m, 1H), 2.77 (dd, J=6.4 and 18.4 Hz, 1H), 2.37 (s, 3H), 2.31-2.36 (m, 1H), 1.98-2.14 (m, 2H), 1.43 (s, 3H), 1.12-1.16 (m, 1H); LC/MS, m/z=248.6 [M+H]$^+$ (Calc: 247.3).

In a similar manner Compound 4 (TFA-salt, white solid, 25 mg, 30%) was prepared from RA4 following the procedure for Compound 3.

Compound 4: $^1$H NMR δ$_H$ (400 MHz, CD$_3$OD) 7.03 (d, J=8.5 Hz, 1H), 6.78-6.81 (m, 1H), 6.3 (dd, J=2.4 and 8.3 Hz, 1H), 4.74-4.75 (m, 1H), 4.06-4.44 (m, 4H), 3.67 (s, 1H), 3.34-3.46 (m, 4H), 2.97-3.02 (m, 3H), 3.02-3.12 (m, 1H), 2.74-2.84 (m, 1H), 2.08-2.22 (m, 1H), 1.44-1.54 (m, 4H); LC/MS, m/z=305.2 [M+H]$^+$ (Calc: 304.4).

Example 5

8-methoxy-3,6-dimethyl-1,2,3,4,5,6-hexahydro-2,6-methanobenzo[d]azocin-11-one O-(2-(diethylamino)ethyl)oxime (Compound 5)

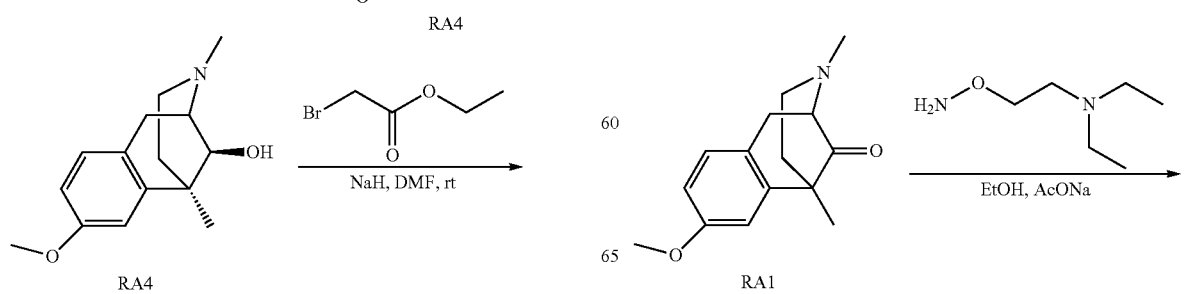

95

-continued

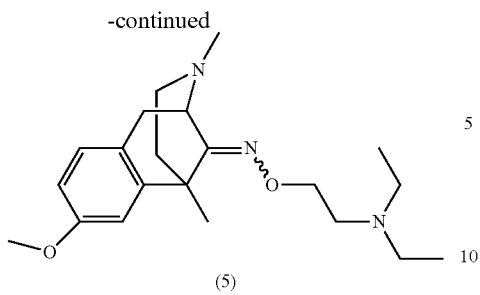

(5)

In a similar manner Compound 5 (TFA-salt, yellow oil, 57%) was prepared from RA1 and O-(2-diethylamino-ethyl) hydroxylamine (Hula Technology) following the procedure for Compound 3.

Compound 5: $^1$H NMR $\delta_H$ (400 MHz, CD$_3$OD) 7.07 (d, J=8.3 Hz, 1H), 6.83 (d, J=2.4 Hz, 1H), 6.79 (dd, J=2.4 and 8.6 Hz, 1H), 5.16 (d, J=6.6 Hz, 1H), 4.4 (t, J=5.1 Hz, 2H), 3.69 (s, 3H), 3.4-3.48 (m, 3H), 3.24-3.31 (m, 1H), 3.14-3.18 (m, 5H), 2.9-2.94 (m, 1H), 2.89 (s, 3H), 2.12-2.18 (m, 1H), 1.79-1.83 (m, 1H), 1.57 (s, 3H), 1.2 (t, J=7.1 Hz, 6H); LC/MS, m/z=360.3 [M+H]$^+$ (Calc: 359.5).

Example 6

8-methoxy-3,6-dimethyl-11-propylidene-1,2,3,4,5,6-hexahydro-2,6-methanobenzo[d]azocine (Compound 6)

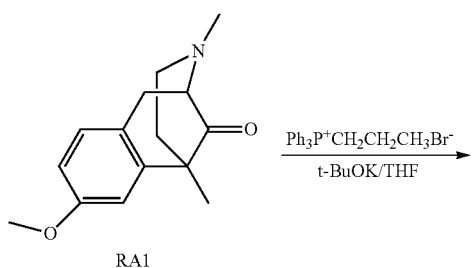

96

-continued

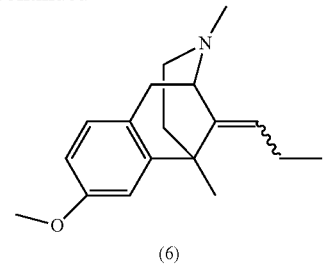

(6)

t-BuOK (1M in THF) was added to a mixture of RA1 (0.1 g, 0.4 mmol) and propyltriphenylphosphonium bromide (0.8 mmol) in 5 mL THF at rt. After stirring at RT for 12 h, the reaction was quenched with water (10 mL), extracted with EtOAc (40 mL), concentrated and purified by reverse-phase prep HPLC (C18, 0-100% 0.1% TFA in water/0.1% TFA in ACN) to yield Compound 6 as yellow oil (TFA-salt, 80 mg, 50%).

Compound 6: $^1$H NMR $\delta_H$ (400 MHz, CD$_3$OD) 7.02 (dd, J=8.5 and 8.6 Hz, 1H), 6.7-6.8 (m, 2H), 5.58 (dd, J=7.2 and 7.4 Hz, 1H), 3.86-3.96 (m, 1H), 3.68 (s, 3H), 3.3-3.36 (m, 1H), 3.06-3.14 (m, 2H), 2.7-2.84 (m, 4H), 1.98-2.4 (m, 3H), 1.74-1.78 (m, 3H), 1.36-1.56 (m, 1H); LC/MS, m/z=272.2 [M+H]$^+$ (Calc: 271.4).

Example 7

3-(cyclopropylmethyl)-8-methoxy-6-methyl-1,2,3,4,5,6-hexahydro-2,6-methanobenzo[d]azocin-11-one (RA11)

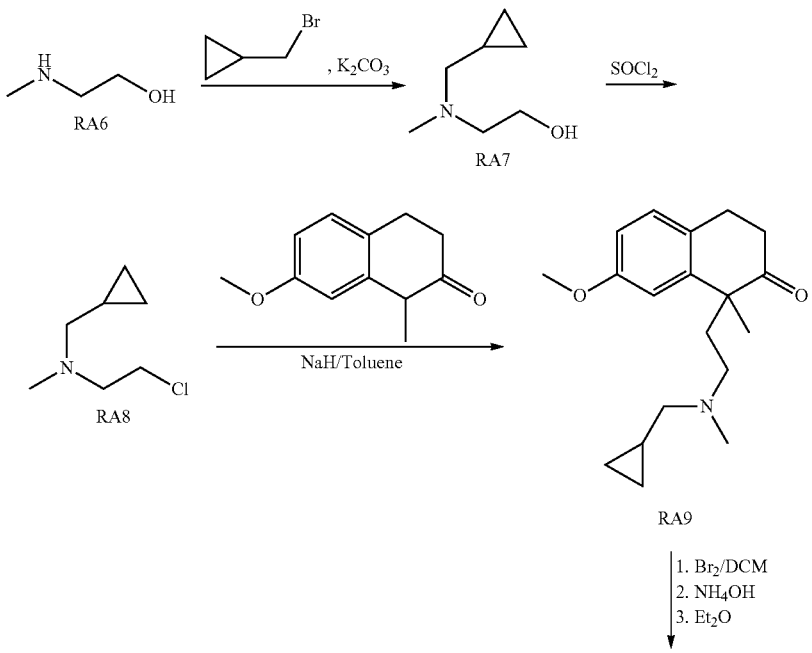

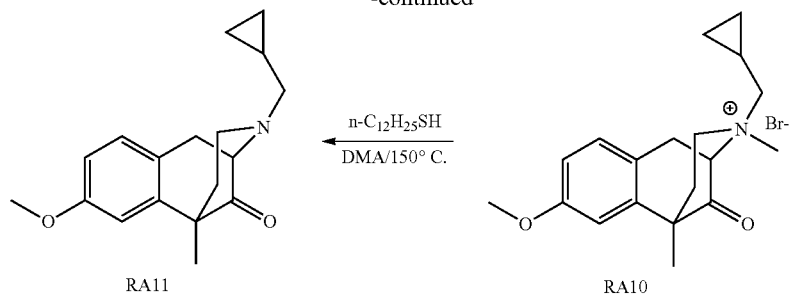

(Bromomethyl)cyclopropane (80 g, 0.59 mol, Combi_Blocks) was added dropwise to a suspension of compound RA6 (1.1 mol, Aldrich) and K$_2$CO$_3$ (0.58 mol) in CH$_3$CN/water (400 mL/1 mL) under nitrogen over 30 min at RT. The reaction mixture was heated at 50° C. for 24 h. After cooling to RT, the reaction mixture was concentrated under vacuum (<25° C.) to remove most of the solvent, then quenched with water (400 mL), and extracted with EtOAc (2×300 mL). The combined organic layer was washed with brine (100 mL), concentrated and purified by column chromatography (silica gel, EtOAc/MeOH/NH$_4$OH 10/1.5/0.1) to give RA7 as a colorless oil (60 g, 80%): $^1$H NMR δ$_H$ (400 MHz, CDCl$_3$) 3.45 (t, J=5.4 Hz, 2H), 3.19 (br., 1H), 2.44 (t, J=5.3 Hz, 2H), 2.22 (s, 3H), 2.2 (d, J=6.6 Hz, 2H), 0.73-0.81 (m, 1H), 0.38-0.43 (m, 2H), −0.08-0.1 (m, 2H).

Thionyl chloride (0.68 mol, 50 mL in 100 mL CHCl$_3$) was added to a solution of RA7 (0.47 mol, 60 g in 400 mL CHCl$_3$) at 0° C. over 2 h. The reaction mixture was warmed to RT, and stirred at RT for 16 h. The reaction mixture was concentrated under vacuum to give a yellow oil, which was washed with Et$_2$O (100 mL), and toluene (100 mL). The solid was collected under argon, washed with hexanes, and dried under vacuum to give RA8 (HCl-salt, yellow solid, 75 g): $^1$H NMR δ$_H$ (400 MHz, CD$_3$OD) 4.02 (dd, J=1.1 and 6.1 Hz, 2H), 3.75 (dt, J=6.3 and 13.8 Hz, 1H), 3.56 (dt, J=5.7 and 13.8 Hz), 3.22 (dd, J=7.4 and 13.5 Hz, 1H), 3.14 (dd, J=7.3 and 13.4 Hz, 1H), 3.01 (s, 3H), 1.15-1.22 (m, 1H), 0.78-0.82 (m, 2H), 0.46-0.52 (m, 2H). The HCl-salt (50 g) was suspended in 200 mL CHCl$_3$ under nitrogen, cooled with ice-water, and neutralized to pH ~9 with NH$_4$OH (14% aqueous). The CHCl$_3$ layer was separated, washed with brine and concentrated under vacuum (<15° C.) to give RA8 as a colorless oil (40 g, used immediately).

7-Methoxy-1-methyl-2-tetralone (0.16 mol in 100 mL toluene) was added to a suspension of NaH (60%, 8 g, 0.2 mol) in 300 mL toluene at 80° C. over 1 h. After 1 h at 80° C., this reaction mixture was treated with RA8 (0.18 mol, 26 g in 60 mL of toluene), and continued at 80° C. for 5 h. The reaction mixture was cooled to RT, and poured over to ice-water (300 g). The aqueous layer was extracted with toluene (2×200 mL). The combined toluene layer was washed with brine, concentrated under vacuum to about 300 mL, cooled to 0° C. with ice-water, and treated with 6N HCl (60 mL aqueous). The reaction mixture was stirred at RT for 30 min. The aqueous layer was separated, cooled with ice-water, and neutralized with NH$_4$OH (14% aqueous solution) to pH ~9. The toluene layer was separated, washed with brine, concentrated, and purified by column chromatography (silica gel, DCM/MeOH 10/0.8) to give RA9 as a colorless oil (30 g, 62%): $^1$H NMR δ$_H$ (400 MHz, CDCl$_3$) 7.10 (d, J=8.3 Hz, 1H), 6.84 (d, J=2.6 Hz, 1H), 6.76 (dd, J=2.6 and 8.3 Hz, 1H), 3.82 (s, 3H), 3.06 (dt, J=7.3 and 15.5 Hz, 1H), 2.96 (dt, J=6.1 and 15.6 Hz, 1H), 2.66 (dd, J=6.1 and 7.6 Hz, 2H), 2.5 (dt, J=8.3 and 13.8 Hz, 1H), 2.1-2.14 (m, 4H), 1.98-2.05 (m, 3H), 1.76-1.82 (m, 1H), 1.42 (s, 3H), 0.64-0.72 (m, 1H), 0.39-0.43 (m, 2H), −0.01-0.02 (m, 2H).

Bromine (0.11 mol, 17 g in 20 mL DCM and 8 mL AcOH) was added to a solution of RA9 (Yao-012d) (0.1 mol, 30 g in 200 mL DCM and 10 mL AcOH) over 30 min at 0° C. The reaction mixture was warmed to RT over 4 h, and stirred at RT for 24 h. The reaction mixture was poured over ice-water (40 g), and neutralized with NH$_4$OH (14% aqueous solution) to pH ~9. The organic layer was washed with brine, and concentrated under vacuum (<20° C.) to give a brown oil. Ether (100 mL) was added to the brown oil, and the mixture was stirred at RT under nitrogen for 4 h. The solid was collected under nitrogen, washed with Et$_2$O and dried under vacuum to give RA10 as a yellow solid (15 g, 40%): $^1$H NMR δ$_H$ (400 MHz, CD$_3$OD) 7.2-7.4 (m, 1H), 6.93-6.97 (m, 1H), 6.89-6.91 (m, 1H), 4.42 (dt, J=1.3 and 5.9 Hz, 0.3H), 4.27 (dt, J=1.3 and 5.9 Hz, 0.7H), 3.94-3.98 (m, 1H), 3.78-3.81 (m, 1H), 3.45-3.65 (3H), 3.35-3.42 (m, 1.7H), 3.27 (m, 2.3H), 2.53-2.63 (m, 1H), 2.02-2.14 (m, 1H), 1.62 (s, 2.2H), 1.59 (s, 0.8H), 1.2-1.26 (m, 1H), 0.82-0.94 (m, 2H), 0.51-0.64 (m, 2H).

1-Dodecanethiol (25 mmol, 6 mL, Aldrich) was added to a suspension of RA10 (32 mmol, 12 g in 30 mL DMA) at 150° C. under nitrogen over 2 min. After 30 min, the reaction mixture was cooled to RT, diluted with 200 mL EtOAc, and washed with water (150 mL, and 2N NaOH 25 mL). The organic layer was washed with brine (100 mL), concentrated and purified by column chromatography (EtOAc/hexane 2/11) to yield RA11 (yellow solid, 4.1 g, 40%). $^1$H NMR δ$_H$ (400 MHz, CDCl$_3$) 6.91 (d, J=8.3 Hz, 1H), 6.63 (dd, J=2.6 and 8.3 Hz, 1H), 6.61 (d, J=2.4 Hz, 1H), 3.66 (s, 3H), 3.53 (d, J=6.1 Hz, 1H), 3.32 (d, J=17.6 Hz, 1H), 2.98 (dd, J=6.4 and 17.8 Hz, 1H), 2.64 (ddd, J=1.5, 5.2 and 12.9 Hz, 1H), 2.35 (d, J=6.6 Hz, 2H), 2.03-2.11 (m, 1H), 1.56-1.61 (m, 1H), 1.34 (s, 3H), 0.68-0.74 (m, 1H), 0.38-0.42 (m, 2H), −0.04-0.05 (m, 2H); LC/MS, m/z=304.2 [M+H$_2$O+H]$^+$ (Calc: 285.4).

Example 8

4-(11,11-dihydroxy-8-methoxy-6-methyl-1,2,5,6-tetrahydro-2,6-methanobenzo[d]azocin-3(4H)-yl)-N,N-dimethyl-2,2-diphenylbutanamide (Compound 7); 4-((6R,11S)-11-hydroxy-8-methoxy-6-methyl-1,2,5,6-tetrahydro-2,6-methanobenzo[d]azocin-3(4H)-yl)-N,N-dimethyl-2,2-diphenylbutanamide (Compound 17); and 4-(11-(hydroxyimino)-8-methoxy-6-methyl-1,2,5,6-tetrahydro-2,6-methanobenzo[d]azocin-3(4H)-yl)-N,N-dimethyl-2,2-diphenylbutanamide (Compound 19)

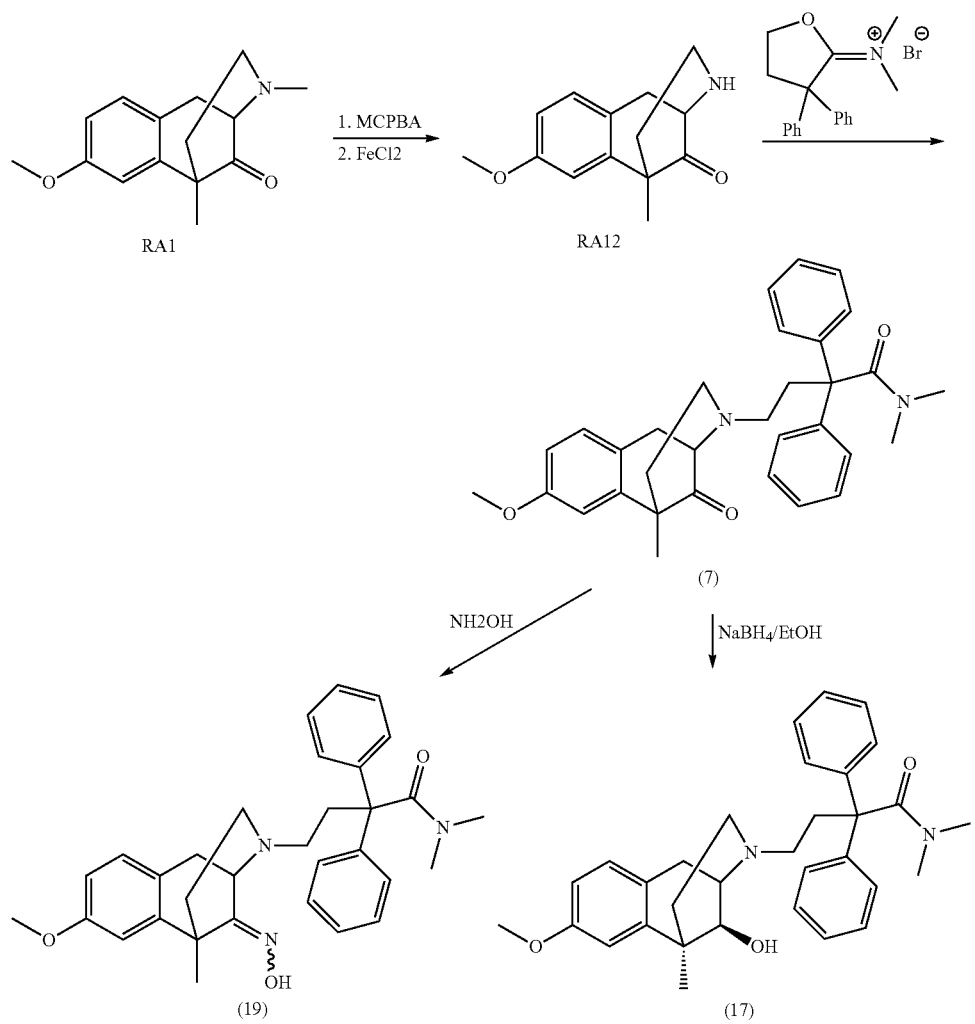

MCPBA (2 mmol, 85% pure, in 5 mL of DCM) was added to a solution of RA1 (0.25 g, 2 mmol) in 4 mL DCM at −5 to 0° C. After 30 min, a solution of FeCl$_2$ (1M aqueous, 0.2 mL) was added. The reaction mixture was stirred at 0° C. for 1 h, and 2 h at RT. The reaction was quenched with NaOH (2N aqueous, 2 mL). The organic layer was separated, and concentrated to yield crude RA12 as yellow oil {LC/MS, m/z=232.4 [M+H$_2$O+H]$^+$ (Calc: 231.3)}.

Dihydro-N,N-dimethyl-3,3-diphenyl-2(3H)-furanaminium bromide (0.2 g, 0.58 mmol) was added to a solution of RA12 (0.1 g, 0.43 mmol) and TEA (1 mmol) in CHCl$_3$ (2 mL) at 0° C. The reaction mixture was warmed to RT, and stirred at RT for 48 h. The reaction was quenched with NaOH (0.5N aqueous, 4 mL). The organic layer was separated, concentrated and purified by HPLC to give Compound 7 (TFA-salt, white solid, 20 mg, 8% in two steps). $^1$H NMR δ$_H$ (400 MHz, CD$_3$CN) 10.2 (br., 1H), 7.24-7.38 (m, 10H), 6.98 (d, J=8.5 Hz, 0.2H), 6.83 (d, J=8.5 Hz, 0.8H), 6.62-6.78 (m, 2H), 3.62 (s, 3H), 3.42 (d, J=6.0 Hz, 1H), 2.18-3.05 (m, 15H), 1.3-1.42 (m, 4H); LC/MS, m/z=515.2 [M+H$_2$O+H]$^+$ (Calc: 496.6).

NaBH$_4$ (0.1 g, 33 mmol) was added to a solution of Compound 7 (0.1 g, 0.2 mmol) in 4 mL of EtOH at 0° C. The reaction mixture was stirred at RT for 1 h, quenched with water, extracted with CHCl$_3$, and purified by HPLC to yield Compound 17 (TFA-salt, white solid, 40 mg). $^1$H NMR δ$_H$ (400 MHz, CD₃OD) 7.28-7.46 (m, 10H), 6.9-6.94 (m, 1H), 6.66-6.8 (m, 2H), 3.7-3.75 (m, 1H), 3.64-3.66 (m, 3H), 3.44-3.48 (m, 1H), 2.93-3.15 (m, 6H), 2.3-2.75 (m, 6H), 2.25 (s, 3H), 1.23-1.45 (m, 4H); LC/MS, m/z=499.2 [M+H]⁺ (Calc: 498.7).

In a similar manner Compound 19 was prepared from Compound 7 (0.2 mmol) and hydroxylamine hydrochloride (0.3 mmol, Aldrich) following the procedure for Compound 1. Compound 19 was purified by reverse-phase prep HPLC (C18, 0-100% 0.1% TFA in water/0.1% TFA in ACN) (white solid, TFA-salt, 40 mg). $^1$H NMR $\delta_H$ (400 MHz, CD₃OD) 7.22-7.42 (m, 10H), 7.02 (d, J=8.3 Hz, 0.6H), 6.88 (d, J=8.3 Hz, 0.4H), 6.67-6.8 (m, 2H), 5.02-5.07 (m, 1H), 3.64 (s, 3H), 3.22-3.25 (m, 1H), 3.0-3.05 (m, 2H), 2.87 (s, 3H), 2.4-2.8 (m, 5H), 2.22 (s, 3H), 1.56-1.96 (m, 2H), 1.52 (s, 1.2H), 1.42 (s, 1.8H); LC/MS, m/z=512.3 [M+H]⁺ (Calc: 511.7).

Example 9

(6R,11S)-8-methoxy-N,3,6-trimethyl-1,2,3,4,5,6-hexahydro-2,6-methanobenzo[d]azocin-11-amine (Compound 8); and (6R,11R)-8-methoxy-N,3,6-trimethyl-1,2,3,4,5,6-hexahydro-2,6-methanobenzo[d]azocin-11-amine (Compound 9)

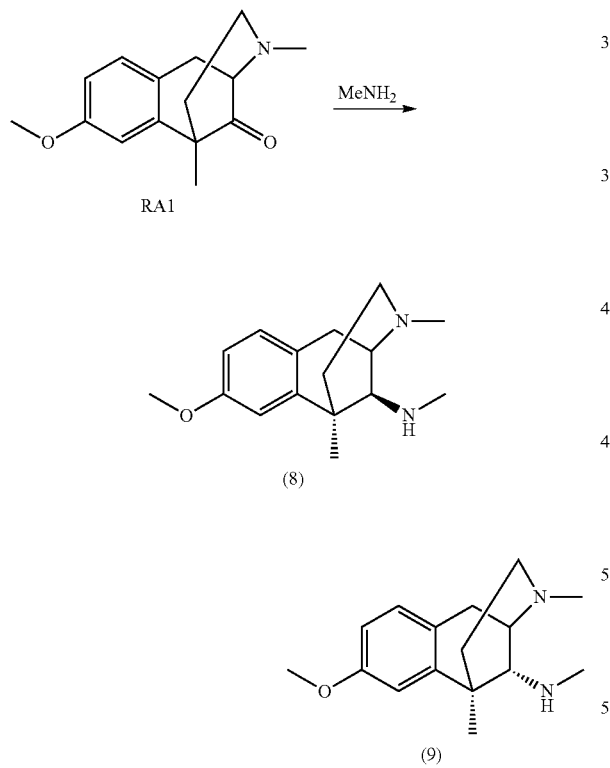

A mixture of RA1 (0.1 g, 0.4 mmol), MeNH₂ (2N in THF, 0.5 mL, 1 mmol), and 4 A Molecular Sieve in CH₃CN (1 mL) was shaken at RT. After 2 h, sodium triacetoxyborohydride (0.8 mmol) was added, and the reaction mixture was shaken at RT for 16 h. The reaction was quenched with NaOH (1N aqueous, 2 mL), extracted with EtOAc (10 mL), concentrated and purified by HPLC to yield Compound 8 and Compound 9.

Compound 8 (white solid, TFA-salt, 15%, RT 0.865 min): $^1$H NMR $\delta_H$ (400 MHz, CD₃OD) 7.55 (d, J=8.9 Hz, 1H), 6.95-6.99 (m, 2H), 4.38 (dd, J=3.7 and 5.9 Hz, 1H), 3.8-3.86 (m, 4H), 3.48 (d, J=20.1 Hz, 1H), 3.22-3.3 (m, 2H), 3.07 (s, 3H), 2.85 (s, 3H), 2.72-2.81 (m, 1H), 2.18-2.22 (m, 1H), 1.8-1.85 (m, 1H), 1.72 (m, 3H); LC/MS, m/z=261.3 [M+H]⁺ (Calc: 260.4).

Compound 9 (white solid, TFA-salt, 40%, RT 1.717 min): $^1$H NMR $\delta_H$ (400 MHz, CD₃OD) 7.05 (d, J=8.5 Hz, 1H), 6.86 (d, J=2.2 Hz, 1H), 6.76 (dd, J=2.6 and 8.3 Hz, 1H), 3.78-3.8 (m, 1H), 3.68 (s, 3H), 3.28-3.38 (m, 2H), 3.04 (dd, J=5.1 and 19.5 Hz, 1H), 2.74-2.8 (m, 1H), 2.72 (s, 3H), 2.63 (s, 3H), 2.32-2.4 (m, 1H), 2.02-2.1 (m, 1H), 1.48 (m, 3H), 1.4-1.43 (m, 1H); LC/MS, m/z=261.3 [M+H]⁺ (Calc: 260.4).

Example 10

3-(cyclopropylmethyl)-8-methoxy-6-methyl-1,2,3,4,5,6-hexahydro-2,6-methanobenzo[d]azocin-11-one O-methyl Oxime (Compound 10)

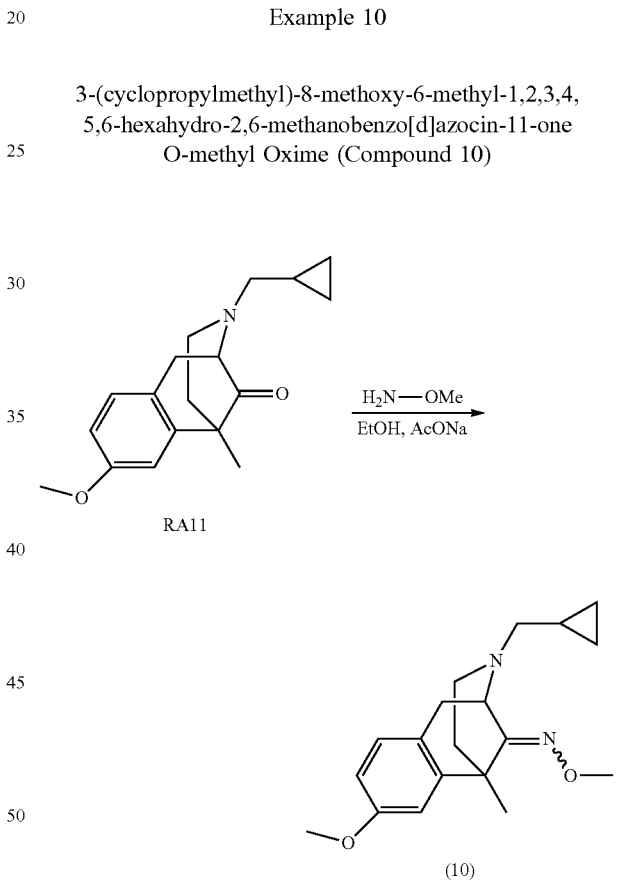

In a similar manner Compound 10 was prepared from RA11 (0.1 g, 0.35 mmol) and o-methylhydroxylamine hydrochloride (0.5 mmol, Aldrich) following the same procedure for Compound 1. Compound 10 was purified by reverse-phase prep HPLC (C18, 0-100% 0.1% TFA in water/0.1% TFA in ACN) (TFA-salt, white solid, 80%). $^1$H NMR $\delta_H$ (400 MHz, CD₃OD) 7.05 (d, J=8.5 Hz, 1H), 6.83 (d, J=2.6 Hz, 1H), 6.78 (dd, J=2.6 and 8.3 Hz, 1H), 5.33 (s, 1H), 3.86 (s, 3H), 3.68 (s, 3H), 3.0-3.38 (m, 5H), 2.6-2.8 (m, 1H), 2.0-2.18 (m, 1H), 1.7-1.82 (m, 1H), 1.56 (s, 3H), 1.0-1.04 (m, 1H), 0.66-0.71 (m, 2H), 0.36-0.41 (m, 2H); LC/MS, m/z=315.1 [M+H]⁺ (Calc: 314.4).

Example 11

((6S,11R)-8-methoxy-3,6-dimethyl-1,2,3,4,5,6-hexahydro-2,6-methanobenzo[d]azocin-11-yl)methanol (Compound 11)

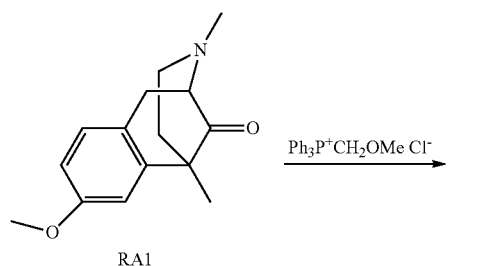

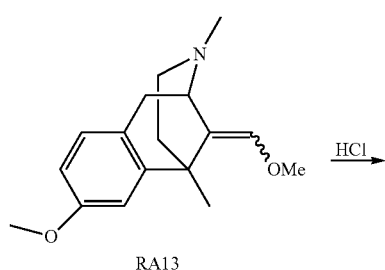

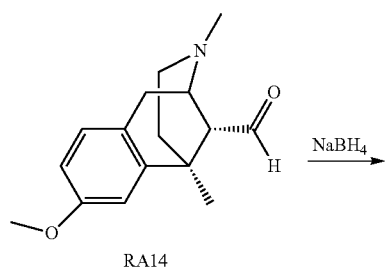

t-BuOk (1M in THF, 2.2 mL, 2.2 mmol) was added to a solution of RA1 (0.3 g, 1.2 mmol) and (methoxymethyl)triphenylphosphonium chloride (0.6 g, 1.7 mmol, Aldrich) in 10 mL of THF at RT. The reaction mixture was stirred at RT for 16 h. After aqueous work-up, the resulting mixture was extracted with EtOAc, and purified by column (silica gel, CHCl$_3$/MeOH 10/0.3) to yield RA13 [yellow oil, 0.25 g, LC/MS, m/z=274.2 [M+H]$^+$ (Calc: 273.4)].

A mixture of RA13 (0.12 g, 0.4 mmol) and p-toluenesulfonic acid monohydrate (0.15 g, 0.8 mmol) in 5 mL 1,4-dioxane was shaken at RT for 2 h, then 100° C. for 14 h. After cooling to 0° C., the reaction mixture was diluted with EtOAc (15 mL), and neutralized with saturated NaHCO$_3$. The organic layer was concentrated to yield the crude RA14 [LC/MS, m/z=260.4 [M+H]$^+$ (Calc: 259.3)], which was dissolved in 2 mL EtOH and treated with NaBH$_4$ (50 mg) at RT for 30 min. The reaction was quenched with water, and purified by reverse-phase prep HPLC (C18, 0-100% 0.1% TFA in water/0.1% TFA in ACN) to yield Compound 10 (TFA-salt, white solid, 60 mg, 42%). $^1$H NMR $\delta_H$ (400 MHz, CD$_3$OD) 6.92 (d, J=8.5 Hz, 1H), 6.65 (d, J=2.6 Hz, 1H), 6.62 (dd, J=2.6 and 8.5 Hz, 1H), 3.65 (dd, J=5.2 and 13.3 Hz, 1H), 3.62 (s, 3H), 3.2-3.4 (m, 1H), 3.35 (dd, J=10.5 and 11.8 Hz, 1H), 2.94 (d, J=18.3 Hz, 1H), 2.64 (dd, J=5.9 and 18.6 Hz, 1H), 2.34-2.39 (m, 1H), 2.32 (s, 3H), 2.0-2.07 (m, 1H), 1.89-1.95 (m, 1H), 1.72-1.78 (m, 1H), 1.29 (s, 3H), 1.19-1.24 (m, 1H); LC/MS, m/z=262.4 [M+H]$^+$ (Calc: 261.4).

Example 12

(Z)-ethyl 2-(8-methoxy-3,6-dimethyl-1,2,3,4,5,6-hexahydro-2,6-methanobenzo[d]azocin-11-ylidene)acetate (Compound 12); (Z)-2-(8-methoxy-3,6-dimethyl-1,2,3,4,5,6-hexahydro-2,6-methanobenzo[d]azocin-11-ylidene)acetic Acid (Compound 13); ethyl 2-((6S,11R)-8-methoxy-3,6-dimethyl-1,2,3,4,5,6-hexahydro-2,6-methanobenzo[d]azocin-11-yl)acetate (Compound 14); and 2-((6S,11R)-8-methoxy-3,6-dimethyl-1,2,3,4,5,6-hexahydro-2,6-methanobenzo[d]azocin-11-yl)acetic Acid (Compound 15)

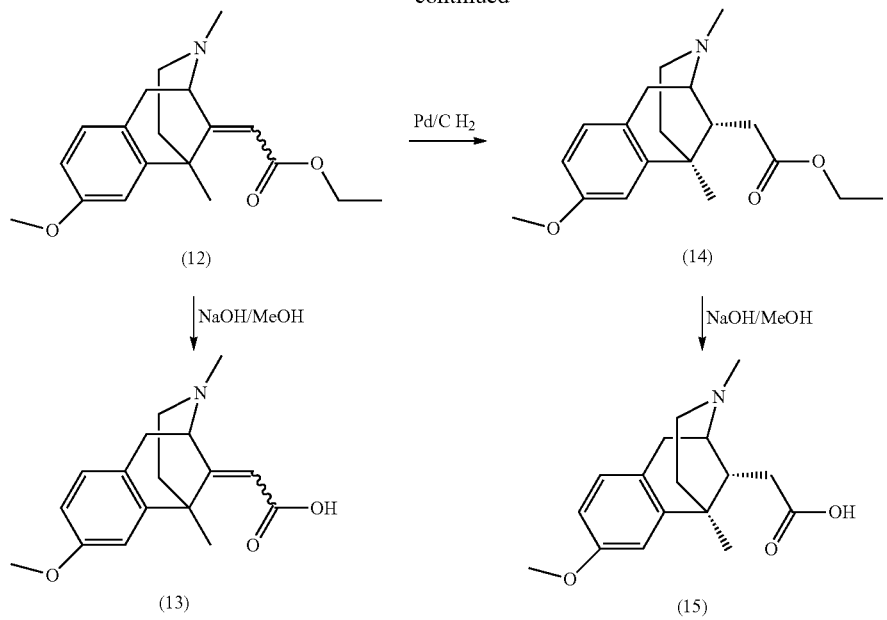

RA1 (0.8 mmol, 0.2 g, in 3 mL THF) was added to a mixture of triethyl phosphonoacetate (1.3 mmol, 0.3 g in 10 mL THF) and NaH (5 mmol, 0.2 g, 60% in mineral oil) at RT under argon. The reaction mixture was stirred at RT for 16 h. After it was cooled to 0° C., the reaction mixture was quenched with water (20 mL), extracted with EtOAc (2×50 mL). The combined organic layer was concentrated, and purified by reverse-phase prep HPLC (C18, 0-100% 0.1% TFA in water/0.1% TFA in ACN) to yield Compound 12 (TFA-salt, white solid, 0.2 g, 58%). $^1$H NMR 8H (400 MHz, CD$_3$OD) 7.12 (s, 1H), 6.93 (d, J=2.3 Hz, 1H), 6.88 (dd, J=2.6 and 8.5 Hz, 1H), 6.24 (d, J=42.2 Hz, 1H), 5.91 (d, J=4.8 Hz, 1H), 4.18-4.25 (m, 2H), 3.78 (s, 3H), 3.4-3.6 (m, 2H), 3.1-3.21 (m, 2H), 2.99 (s, 3H), 1.8-2.3 (m, 2H), 1.67 (s, 3H), 1.27-1.31 (m, 3H); LC/MS, m/z=316.2 [M+H]$^+$ (Calc: 315.4).

NaOH (1 mmol, 2N in water, 0.5 mL) was added to a solution of Compound 12 (0.05 mmol, 20 mg, TFA-salt) in 2 mL MeOH at 0° C. The reaction mixture was shaken at RT for 5 h. The solvent was evaporated under vacuum, the residue was dissolved in 4 mL CHCl$_3$, and neutralized to pH ~2 with 1N HCl. The organic layer was separated, concentrated, and purified by reverse-phase prep HPLC (C18, 0-100% 0.1% TFA in water/0.1% TFA in ACN) to give Compound 13 as TFA-salt (white solid, 15 mg, 80%). $^1$H NMR $\delta_H$ (400 MHz, CD$_3$OD) 7.04 (d, J=8.1 Hz, 1H), 6.84 (d, J=2.4 Hz, 1H), 6.78 (dd, J=2.2 and 8.5 Hz, 1H), 6.14 (d, J=35.3 Hz, 1H), 5.82 (d, J=6.3 Hz, 1H), 3.68 (s, 3H), 3.24-3.5 (m, 2H), 3.0-3.16 (m, 2H), 2.89 (s, 3H), 1.8-2.2 (m, 2H), 1.58 (s, 3H); LC/MS, m/z=288.1 [M+H]$^+$ (Calc: 287.4).

A mixture of Compound 12 (0.1 mmol, 50 mg, TFA-salt) and Pd/C (10%, 0.2 g) in EtOH/CHCl$_3$ (2 mL/6 mL) was shaken under hydrogen (10 PSI) for 12 h. The catalyst was filtered, and the product was purified by reverse-phase prep HPLC (C18, 0-100% 0.1% TFA in water/0.1% TFA in ACN) to give Compound 14 (white solid, TFA-salt, 30 mg).

$^1$H NMR $\delta_H$ (400 MHz, CD$_3$OD) 7.07 (d, J=9.2 Hz, 1H), 6.75-6.77 (m, 2H), 4.04-4.07 (m, 2H), 3.74-3.77 (m, 1H), 3.69 (s, 3H), 3.03-3.15 (m, 3H), 2.86 (s, 3H), 2.59-2.66 (m, 1H), 2.41-2.46 (m, 2H), 1.89-2.07 (m, 2H), 1.58-1.63 (m, 1H), 1.37 (s, 3H), 1.17 (t, J=7.2 Hz, 3H); LC/MS, m/z=318.1 [M+H]$^+$ (Calc: 317.4).

In a similar manner Compound 15 (TFA-salt, white solid) was prepared from Compound 14 (0.05 mmol) following the same procedure for Compound 13.

$^1$H NMR $\delta_H$ (400 MHz, CD$_3$OD) 7.07 (d, J=8.2 Hz, 1H), 6.74-6.78 (m, 2H), 3.77-3.8 (m, 1H), 3.69 (s, 3H), 3.03-3.15 (m, 3H), 2.85 (s, 3H), 2.58-2.64 (m, 1H), 2.39-2.45 (m, 2H), 1.88-2.02 (m, 2H), 1.56-1.63 (m, 1H), 1.38 (s, 3H); LC/MS, m/z=290.1 [M+H]$^+$ (Calc: 289.4).

Example 13

3,6-dimethyl-1,2,3,4,5,6-hexahydro-2,6-methanobenzo[d]azocine-8,11,11-triol (RA15); and 11,11-dihydroxy-3,6-dimethyl-1,2,3,4,5,6-hexahydro-2,6-methanobenzo[d]azocin-8-yl Isobutyrate (RA16)

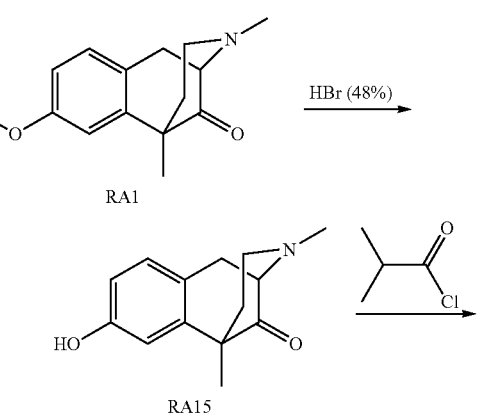

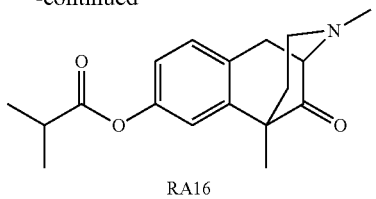

RA16

HBr (1.5 mL 48% aqueous) was added to RA1 (0.8 mmol, 0.2 g) at RT. The mixture was stirred under argon at 100° C. for 16 h. The reaction mixture was poured over ice-water, neutralized with NH$_4$OH (14% aqueous) to pH ~9, and extracted with CHCl$_3$. The organic layer was concentrated and purified by reverse-phase prep HPLC (C18, 0-100% 0.1% TFA in water/0.1% TFA in ACN) to yield RA15 (TFA-salt, 120 mg, white solid).

$^1$H NMR $\delta_H$ (400 MHz, CD$_3$OD) 7.01 (d, J=8.2 Hz, 0.6H), 6.92 (d, J=8.3 Hz, 0.4H), 6.54-6.68 (m, 2H), 3.28-3.8 (m, 3H), 2.58-3.18 (m, 5H), 2.16-2.24 (m, 1H), 1.28-1.96 (m, 4H); LC/MS, m/z=250.2 [M+H]$^+$ (Calc: 249.3).

Isobutyryl chloride (0.55 mmol, 60 mg) was added to a solution of crude RA15 (0.5 mmol, 120 mg) and triethylamine (1 mmol) in 3 mL DCM at 0° C. The reaction mixture was warmed to RT overnight. After aqueous work-up, the product was purified by flash column chromatography (silica gel, EtOAc/Hexanes 7/3) to yield 100 mg of RA16 as white solid (53%).

$^1$H NMR $\delta_H$ (400 MHz, CDCl$_3$) 7.15 (d, J=8.1 Hz, 1H), 6.93 (dd, J=2.3 and 8.3 Hz, 1H), 6.91 (d, J=2.2 Hz, 1H), 3.56 (d, J=18.2 Hz, 1H), 3.39 (d, J=6.2 Hz, 1H), 3.14 (dd, J=6.4 and 18.2 Hz, 1H), 2.72-2.83 (m, 2H), 2.52-2.57 (m, 1H), 2.47 (s, 3H), 2.2-2.28 (m, 1H), 1.71-1.76 (m, 1H), 1.47 (s, 3H), 1.33 (s, 3H), 1.30 (s, 3H); LC/MS, m/z=320.2 [M+H]$^+$ (Calc: 319.4).

Example 14

(E)-3-(furan-3-yl)-N-((6R,11R)-8-methoxy-3,6-dimethyl-1,2,3,4,5,6-hexahydro-2,6-methanobenzo[d]azocin-11-yl)-N-methylacrylamide (Compound 16); and (E)-3-(furan-3-yl)-N-((6R,11S)-8-methoxy-3,6-dimethyl-1,2,3,4,5,6-hexahydro-2,6-methanobenzo[d]azocin-11-yl)-N-methylacrylamide (Compound 20)

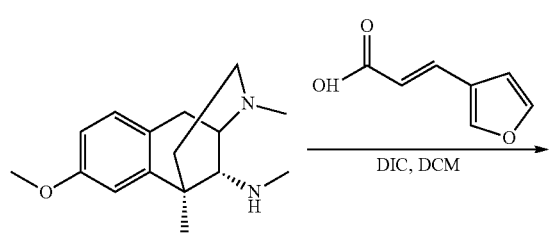

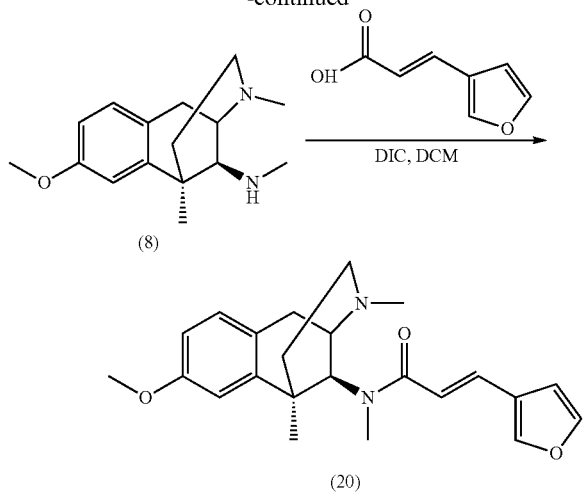

1,3-Diisopropylcarbodiimide (DIC, 0.12 mmol, Aldrich) was added to a solution of Compound 9 (0.1 mmol, 25 mg), 3-(3-furyl)acrylic acid (0.12 mmol) and 1-hydroxybenzotriazole (0.05 mmol) in 4 mL DCM at 0° C. The reaction mixture was shaken at RT for 48 h. The solid was filtered, the filtrate was washed with NaOH (1N 1 mL), and purified by reverse-phase prep HPLC (C18, 0-100% 0.1% TFA in water/0.1% TFA in ACN) to yield 15 mg of Compound 16 (TFA-salt, white solid). $^1$H NMR $\delta_H$ (400 MHz, CD$_3$OD) 7.75 (s, 1H), 7.48 (d, J=15.1 Hz, 1H), 7.44 (s, 1H), 7.11 (d, J=8.6 Hz, 1H), 6.86 (d, J=2.4 Hz, 1H), 6.8 (dd, J=2.4 and 8.3 Hz, 1H), 6.74 (s, 1H), 6.69-6.71 (m, 2H), 3.66-3.74 (m, 4H), 3.24-3.32 (m, 1H), 3.02-3.16 (m, 3H), 2.87 (s, 3H), 2.77 (s, 3H), 2.56-2.64 (m, 1H), 1.98-2.06 (m, 1H), 1.62-1.68 (m, 1H), 1.45 (s, 3H); LC/MS, m/z=381.5 [M+H]$^+$ (Calc: 380.5).

In a similar manner Compound 20 was prepared from Compound 8 (0.1 mmol) and 3-(3-furyl)acrylic acid (0.12 mmol). The product was purified by reverse-phase prep HPLC (C18, 0-100% 0.1% TFA in water/0.1% TFA in ACN) (TFA-salt, white solid, 10 mg). $^1$H NMR $\delta_H$ (400 MHz, CD$_3$OD) 7.8 (s, 1H), 7.62 (d, J=14.9 Hz, 1H), 7.44 (s, 1H), 7.05 (d, J=8.3 Hz, 1H), 6.76-6.84 (m, 4H), 4.01 (s, 1H), 3.89 (s, 1H), 3.69 (s, 3H), 3.36-3.39 (m, 2H), 3.28 (s, 3H), 3.15-3.19 (m, 1H), 2.84 (s, 3H), 2.64-2.72 (m, 1H), 2.08-2.36 (m, 1H), 1.48 (s, 3H), 1.4-1.46 (m, 1H); LC/MS, m/z=381.5 [M+H]$^+$ (Calc: 380.5).

Example 15

8-hydroxy-3,6-dimethyl-1,2,3,4,5,6-hexahydro-2,6-methanobenzo[d]azocin-11-one Oxime (Compound 18)

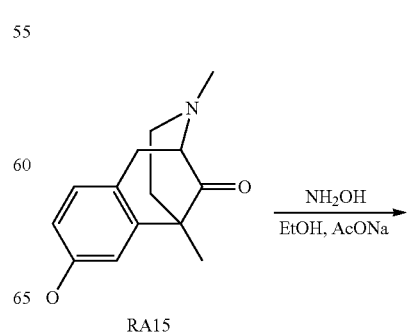

RA15

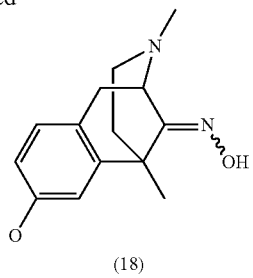

(18)

In a similar manner Compound 18 was prepared from RA15 (0.4 mmol) and hydroxylamine hydrochloride (0.6 mmol, Aldrich) following the procedure for Compound 1. Compound 18 was purified by reverse-phase prep HPLC (C18, 0-100% 0.1% TFA in water/0.1% TFA in ACN) to obtain a brown oil (TFA-salt, 40%). $^1$H NMR $\delta_H$ (400 MHz, CD$_3$OD) 7.96 (d, J=8.6 Hz, 1H), 6.72 (d, J=2.4 Hz, 1H), 6.63 (dd, J=2.4 and 8.3 Hz, 1H), 5.24 (d, J=5.9 Hz, 1H), 3.24-3.28 (m, 1H), 3.04-3.18 (m, 3H), 2.88 (s, 3H), 1.68-2.08 (m, 2H), 1.52 (s, 3H); LC/MS, m/z=247.2 [M+H]$^+$ (Calc: 246.3).

Example 16

4-((6R,11R)-8,11-dihydroxy-6-methyl-1,2,5,6-tetrahydro-2,6-methanobenzo[d]azocin-3(4H)-yl)-N,N-dimethyl-2,2-diphenylbutanamide (Compound 21); and 4-((6R,11S)-8,11-dihydroxy-6-methyl-1,2,5,6-tetrahydro-2,6-methanobenzo[d]azocin-3(4H)-yl)-N,N-dimethyl-2,2-diphenylbutanamide (Compound 22)

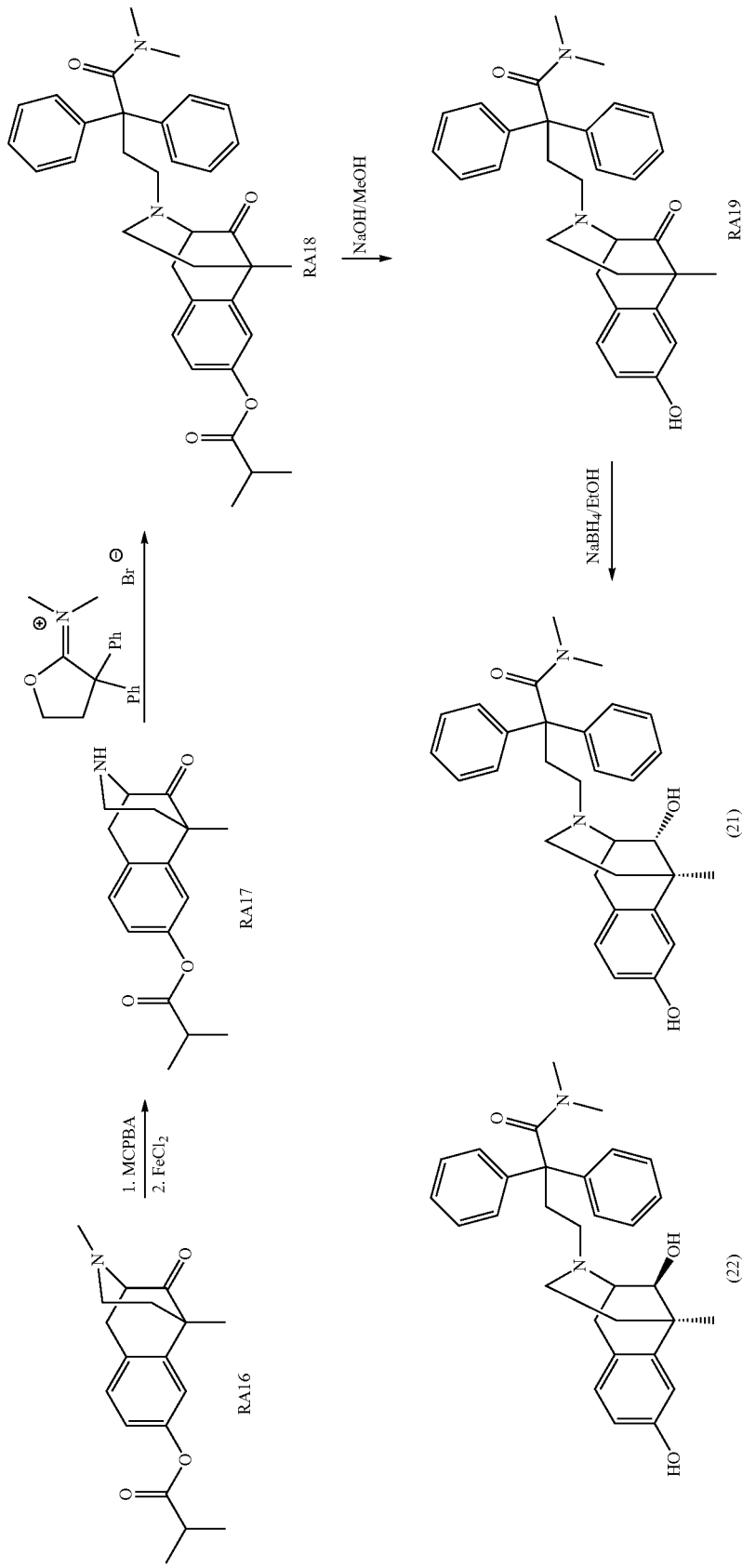

In a similar manner compound RA18 was prepared from RA16 following the procedure for Compound 7. The crude product RA18 {0.09 mmol, 50 mg, LC/MS m/z=571.3 [M+H$_2$O+H]$^+$ (Calc: 552.7)} was dissolved in MeOH/water (1 mL/1 mL), and treated with HBr (48% aqueous, 0.1 mL) at 65° C. for 4 h. After cooling to RT, the product was purified by reverse-phase prep HPLC (C18, 0-100% 0.1% TFA in water/0.1% TFA in ACN) to yield RA19 {TFA-salt, 30 mg, LC/MS m/z=501.5 [M+H$_2$O+H]$^+$ (Calc: 482.6)}.

NaBH$_4$ (40 mg, 1 mmol) was added to a solution of RA19 (0.05 mmol, 30 mg) in CHCl$_3$/EtOH (4 mL/2 mL) at 0° C. The reaction mixture was stirred for 2 h at 0° C.~RT. After aqueous work-up, the product was purified by reverse-phase prep HPLC (C18, 0-100% 0.1% TFA in water/0.1% TFA in ACN) to yield Compound 21 and Compound 22.

Compound 21 (white solid, 12 mg, RT 2.734 min): $^1$H NMR δ$_H$ (400 MHz, CD$_3$OD) 7.22-7.42 (m, 10H), 6.89 (d, J=8.3 Hz, 0.1H), 6.81 (d, J=8.3 Hz, 0.9H), 6.63-6.65 (m, 1H), 6.52 (dd, J=2.3 and 8.1 Hz, 1H), 3.7 (d, J=3.7 Hz, 1H), 3.48 (t, J=5.2 Hz, 1H), 3.0-3.08 (m, 2H), 2.95 (s, 3H), 2.62-2.72 (m, 3H), 2.32-2.48 (m, 2H), 2.24 (s, 3H), 1.8-1.9 (m, 2H), 1.48-1.54 (m, 1H), 1.4 (s, 2.7H), 1.33 (s, 0.3H); LC/MS, m/z=485.2 [M+H]$^+$ (Calc: 484.6).

Compound 22 (white solid, 8 mg, RT 2.901 min): $^1$H NMR δ$_H$ (400 MHz, CD$_3$OD) 7.23-7.42 (m, 10H), 6.8-6.84 (m, 1H), 6.53-6.62 (m, 2H), 3.69-3.74 (m, 1H), 3.41-3.48 (m, 1H), 2.88-3.08 (m, 6H), 2.52-2.72 (m, 3H), 2.3-2.42 (m, 2H), 2.24 (s, 3H), 1.5-1.9 (m, 2H), 1.3-1.4 (m, 3H), 1.18-1.25 (m, 1H); LC/MS, m/z=485.2 [M+H]$^+$ (Calc: 484.6).

Example 17

(E)-3-(furan-3-yl)-N-((2R,6R,11S)-8-methoxy-3,6-dimethyl-1,2,3,4,5,6-hexahydro-2,6-methanobenzo[d]azocin-11-yl)acrylamide (Compound 23); and (E)-N-ethyl-3-(furan-3-yl)-N-((2R,6R,11S)-8-methoxy-3,6-dimethyl-1,2,3,4,5,6-hexahydro-2,6-methanobenzo[d]azocin-11-yl)acrylamide (Compound 25)

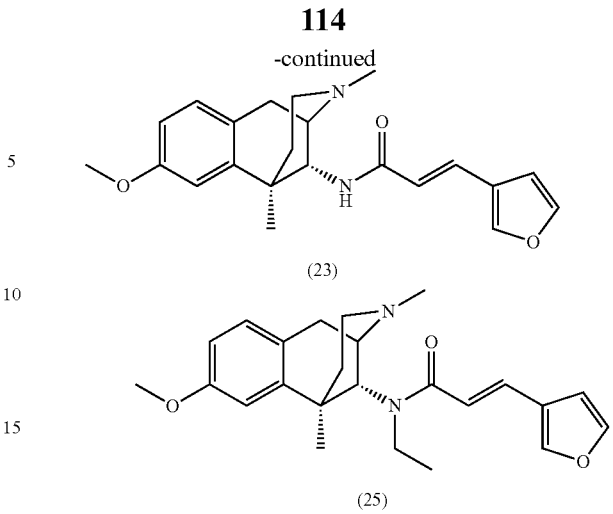

A mixture of Compound 2 (0.2 g, 0.7 mmol) and PtO$_2$ (25 mg, 0.1 mmol) in AcOH (10 mL) was shaken under H$_2$ (30 PSI) for 30 h. CHCl$_3$ (100 mL) was added, and the catalyst was filtered. The filtrate was neutralized to pH ~9 with NH$_4$OH (28% aqueous). The CHCl$_3$ layer was concentrated under vacuum to yield crude product RA20, LC/MS, m/z=247.5 [M+H]$^+$ (Calc: 246.4); and RA21, LC/MS, m/z=275.4 [M+H]$^+$ (Calc: 274.4)].

1,3-Diisopropylcarbodiimide (DIC, 0.12 mL, 0.8 mmol) was added to the above crude product, 3-(3-furyl)acrylic acid (0.11 g, 0.8 mmol) and 1-hydroxybenzotriazole (0.07 mmol) in 4 mL DCM at 0° C. The reaction mixture was shaken at RT for 14 h. The solid was filtered, the filtrate was washed with NaOH (1N 1 mL), and purified by reverse-phase prep HPLC (C18, 0-100% 0.1% TFA in water/0.1% TFA in ACN) to yield Compound 23 and Compound 25.

Compound 23 (TFA-salt, white solid, 20 mg): $^1$H NMR δ$_H$ (400 MHz, CD$_3$OD) 7.68 (s, 1H), 7.36-7.41 (m, 2H), 7.11 (d, J=8.3 Hz, 1H), 6.84 (d, J=2.4 Hz, 1H), 6.81 (dd, J=2.4 and 8.3 Hz, 1H), 6.48 (d, J=2.2 Hz, 1H), 6.33 (d, J=15.8 Hz, 1H), 4.26 (d, J=2.6 Hz, 1H), 3.82 (s, 1H), 3.65 (s, 3H), 3.04-3.18 (m, 3H), 2.84 (s, 3H), 2.56-2.62 (m, 1H), 1.96-2.03 (m, 1H), 1.64-1.71 (m, 1H), 1.42 (s, 3H); LC/MS, m/z=367.2 [M+H]$^+$ (Calc: 366.4).

Compound 25 (TFA-salt, white solid, 30 mg): $^1$H NMR δ$_H$ (400 MHz, CD$_3$OD) 7.76 (s, 1H), 7.52 (d, J=15.2 Hz, 1H), 7.45 (s, 1H), 7.13 (d, J=8.6 Hz, 1H), 6.8-6.91 (m, 2H), 6.68 (s, 1H), 6.63 (d, J=15.2 Hz, 1H), 4.82-4.85 (m, 1H), 3.82 (s, 1H), 3.72 (s, 3H), 3.24-3.36 (m, 2H), 2.94-3.16 (m, 3H), 2.88 (s, 3H), 2.6-2.68 (m, 1H), 1.96-2.04 (m, 1H), 1.62-1.68 (m, 1H), 1.44 (s, 3H), 0.92 (t, J=7.1 Hz, 3H); LC/MS, m/z=395.2 [M+H]$^+$ (Calc: 394.5).

Example 18

(E)-3-(furan-3-yl)-N-((2R,6R,11S)-8-hydroxy-3,6-dimethyl-1,2,3,4,5,6-hexahydro-2,6-methanobenzo[d]azocin-11-yl)-N-methylacrylamide (Compound 24)

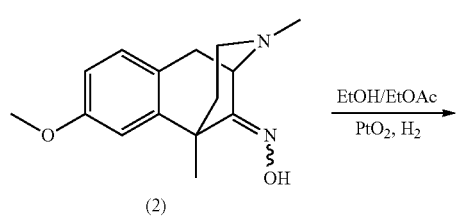

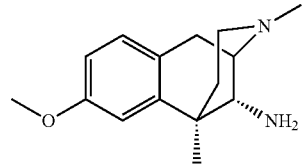

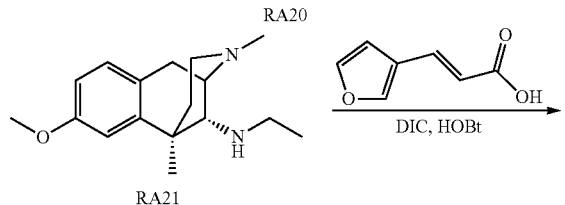

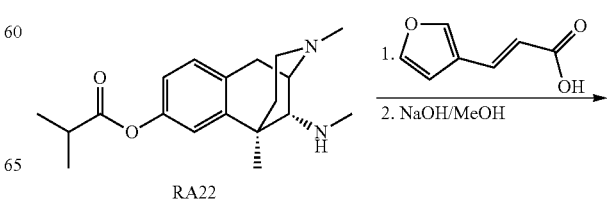

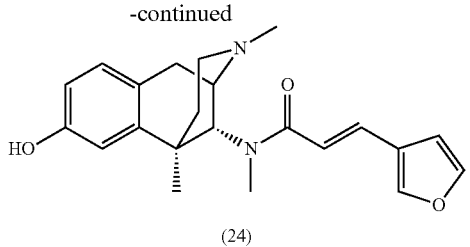

(24)

1,3-Diisopropylcarbodiimide (DIC, 0.1 g, 0.8 mmol) was added to a solution of RA22 (0.25 g, 0.8 mmol), 3-(3-furyl) acrylic acid (0.2 g, 1.4 mmol) and 1-hydroxybenzotriazole (0.14 mmol) in 4 mL DCM at 0° C. The reaction mixture was shaken at RT for 14 h. The solid was filtered, the filtrate was washed with NaOH (1N 1 mL), and concentrated under vacuum. The residue was dissolved in 4 mL MeOH, and treated with 0.5 mL NaOH (2N aqueous) at RT for 14 h. After being concentrated under vacuum, the residue was dissolved in CHCl₃ (10 mL), and neutralized to pH ~3 with 1N HCl. The organic layer was concentrated and purified by reverse-phase prep HPLC (C18, 0-100% 0.1% TFA in water/0.1% TFA in ACN) to yield Compound 24 (TFA-salt, white solid, 60 mg). $^1$H NMR $\delta_H$ (400 MHz, CD₃OD) 7.76 (s, 0.1H), 7.74 (s, 0.9H), 7.47 (d, J=15.1 Hz, 1H), 7.43 (s, 1H), 6.99 (d, J=8.5 Hz, 1H), 6.68-6.76 (m, 3H), 6.64 (dd, J=2.2 and 8.3 Hz, 1H), 4.76-4.8 (m, 1H), 3.68-3.72 (m, 1H), 2.98-3.16 (m, 3H), 2.86 (s, 3H), 2.78 (s, 3H), 2.58-2.64 (m, 1H), 1.98-2.05 (m, 1H), 1.58-1.64 (m, 1H), 1.41 (s, 3H); LC/MS, m/z=367.2 [M+H]⁺ (Calc: 366.4).

Example 19

4-fluoro-N'-((2S,6R)-8-methoxy-3,6-dimethyl-1,2,3, 4,5,6-hexahydro-2,6-methanobenzo[d]azocin-11-ylidene)benzohydrazide (Compound 26)

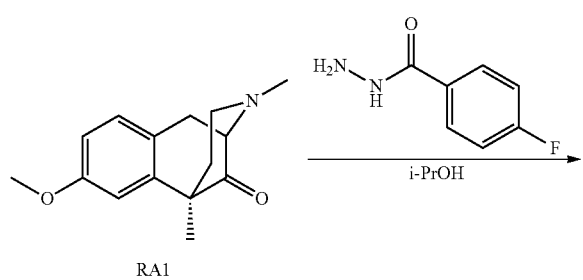

(26)

A mixture of RA1 (120 mg, 0.48 mmol) and 4-fluorobenzohydrazide (0.52 mmol, 80 mg, Oakwood) in i-PrOH/AcOH (2 mL/0.2 mL) was shaken at 60° C. for 3 h. The solvents were removed under vacuum, and the product was purified by reverse-phase prep HPLC (C18, 0-100% 0.1% TFA in water/0.1% TFA in ACN).

Compound 26 (TFA-salt, white solid, 30 mg): $^1$H NMR $\delta_H$ (400 MHz, CD₃OD) 7.8 (dd, J=5.2 and 8.5 Hz, 2H), 7.14 (t, J=7.2 Hz, 2H), 6.97 (d, J=8.3 Hz, 1H), 6.79 (d, J=1.9 Hz, 1H), 6.68 (dd, J=2.6 and 8.3 Hz, 1H), 4.2 (d, J=5.9 Hz, 1H), 3.68 (s, 3H), 3.24-3.3 (m, 1H), 2.98-3.04 (m, 1H), 2.44-2.48 (m, 2H), 2.36 (s, 3H), 2.0-2.08 (m, 1H), 1.58 (s, 3H), 1.2-1.54 (m, 1H); LC/MS, m/z=382.2 [M+H]⁺ (Calc: 381.4).

Example 20

N-((2R,6R,11S)-8-hydroxy-3,6-dimethyl-1,2,3,4,5,6-hexahydro-2,6-methanobenzo[d]azocin-11-yl)-N-methyl-2-(4-(methylsulfonyl)phenyl)acetamide (Compound 27)

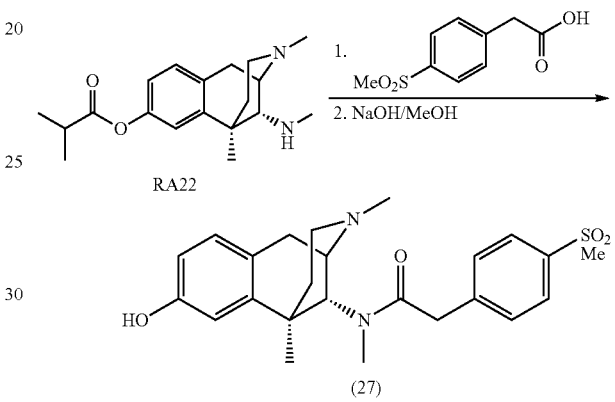

(27)

In a similar manner, Compound 27 was prepared following the procedure for Compound 24 using 4-(methylsulfonyl)phenylacetic acid (Aldrich) instead of 3-(3-furyl)acrylic acid. Compound 27 was purified by reverse-phase prep HPLC (C18, 0-100% 0.1% TFA in water/0.1% TFA in ACN) (TFA-salt, 30 mg, white solid). $^1$H NMR $\delta_H$ (400 MHz, CD₃OD) 7.8-7.86 (m, 2H), 7.5 (d, J=8.5 Hz, 0.5H), 7.41 (d, J=8.5 Hz, 1.5H), 6.96-7.01 (m, 1H), 6.68-6.74 (m, 1H), 6.6-6.65 (m, 1H), 4.6-4.9 (m, 1H), 3.64-3.96 (m, 3H), 3.24-3.32 (m, 1H), 3.0-3.1 (m, 6H), 2.6-2.86 (m, 6H), 1.94-2.2 (m, 1H), 1.58-1.62 (m, 1H), 1.38-1.44 (m, 3H); LC/MS, m/z=443.1 [M+H]⁺ (Calc: 442.6).

Example 21

4-(((2R,6R,11S)-8-hydroxy-3,6-dimethyl-1,2,3,4,5, 6-hexahydro-2,6-methanobenzo[d]azocin-11-yl) (methyl)amino)-4-oxobutanoic Acid (Compound 28)

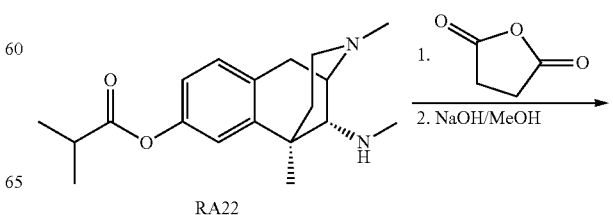

117
-continued

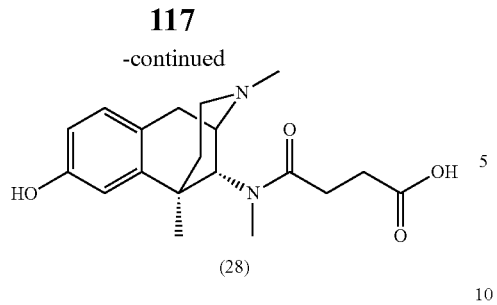

(28)

118
-continued (29)

Succinic anhydride (50 mg, 0.5 mmol) was added to a solution of RA22 (0.1 g, 0.3 mmol) in CHCl₃ (2 mL) at 0° C. The reaction mixture was shaken at RT for 24 h. After aqueous work-up, the crude product was dissolved in 4 mL of MeOH, and treated with 0.5 mL NaOH (2N aqueous) at RT for 14 h. The solvent was removed under vacuum. The residue was dissolved in CHCl₃ (10 mL), and neutralized to pH ~3 with 1N HCl. The organic layer was concentrated and purified by reverse-phase prep HPLC (C18, 0-100% 0.1% TFA in water/0.1% TFA in ACN) to yield Compound 28 as TFA-salt (white solid, 30 mg). ¹H NMR $\delta_H$ (400 MHz, CD₃OD) 6.98 (d, J=8.3 Hz, 1H), 6.73 (d, J=2.4 Hz, 1H), 6.63 (dd, J=2.4 and 8.3 Hz, 1H), 4.62-4.9 (m, 1H), 3.58-3.82 (m, 1H), 2.9-3.18 (m, 4H), 2.83 (s, 3H), 2.65 (s, 3H), 2.5-2.57 (m, 4H), 1.92-2.02 (m, 1H), 1.57-1.62 (m, 1H), 1.36-1.45 (m, 3H); LC/MS, m/z=347.1 [M+H]⁺ (Calc: 346.4).

Example 22

(2R,6R,11S)-3,6-dimethyl-11-(methyl(phenethyl)amino)-1,2,3,4,5,6-hexahydro-2,6-methanobenzo[d]azocin-8-ol (Compound 29)

A mixture of RA22 (0.15 g, 0.47 mmol), phenylacetaldehyde (0.1 g, 0.8 mmol), and 4 A MS (0.2 g) in 1 mL CH₃CN was shaken at RT for 2 h. Then, NaB(OAc)₃H (0.2 g, 0.9 mmol) was added. The reaction mixture was shaken at RT for 16 h. The solid was filtered, and washed with CHCl₃ (10 mL). The filtrate was washed with water, and concentrated. The residue was dissolved in MeOH (4 mL)/HBr (48% aqueous, 0.4 mL), and the mixture was heated at 60° C. for 14 h. The solvent was evaporated under vacuum and purified by reverse-phase prep HPLC (C18, 0-100% 0.1% TFA in water/0.1% TFA in ACN) to yield Compound 29 as TFA-salt (32 mg, white solid). ¹H NMR $\delta_H$ (400 MHz, CD₃OD) 7.12-7.17 (m, 2H), 7.04-7.09 (m, 1H), 6.99-7.02 (m, 2H), 6.92 (d, J=8.3 Hz, 1H), 6.68 (d, J=2.6 Hz, 1H), 6.6 (dd, J=2.6 and 8.3 Hz, 1H), 3.86 (s, 1H), 2.88-3.18 (m, 6H), 2.84 (s, 3H), 2.6-2.76 (m, 3H), 2.36 (s, 3H), 1.84-1.88 (m, 1H), 1.43-1.46 (m, 1H), 1.38 (s, 3H); LC/MS, m/z=351.1 [M+H]⁺ (Calc: 350.5).

Example 23 tert-butyl 4-((((2R,6S,11R)-8-hydroxy-3,6-dimethyl-1,2,3,4,5,6-hexahydro-2,6-methanobenzo[d]azocin-11-yl)amino)methyl)piperidine-1-carboxylate (Compound 30); and tert-butyl 4-((((2R,6S,11R)-8-hydroxy-3,6-dimethyl-1,2,3,4,5,6-hexahydro-2,6-methanobenzo[d]azocin-11-yl)(methyl)amino)methyl)piperidine-1-carboxylate (Compound 31)

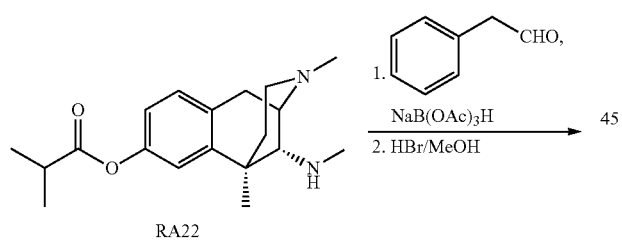

RA22

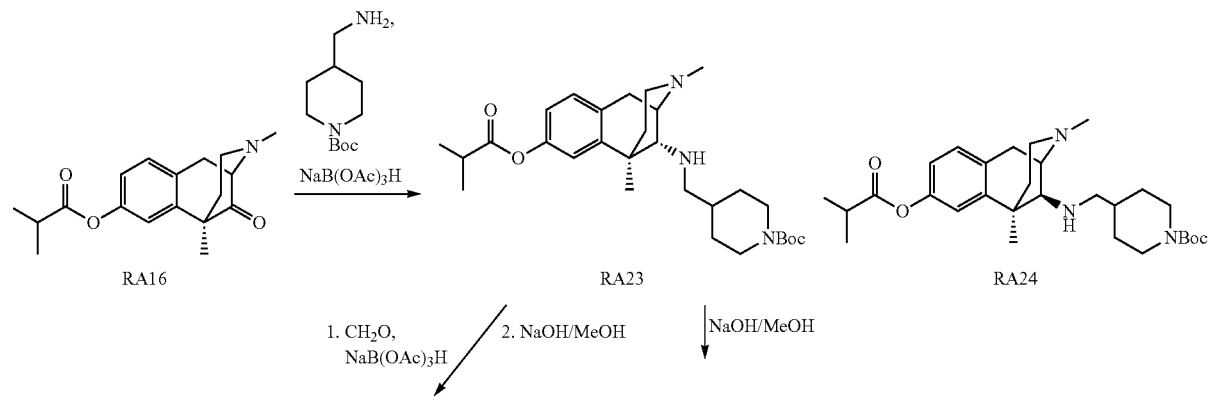

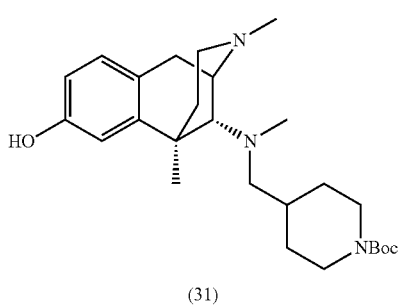

(31)

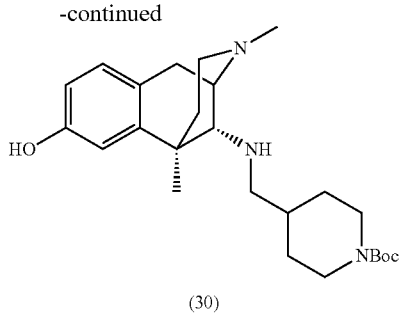

(30)

A mixture of RA16 (0.2 g, 0.6 mmol), 1-Boc-4-(aminomethyl)piperidine (200 mg, 0.9 mmol), and 4 A MS in 1 mL CH₃CN was shaken at RT for 2 h, then NaB(OAc)₃H (0.3 g, 1.4 mmol) was added. The reaction mixture was shaken at RT for 16 h. The solid was filtered, and washed with CHCl₃ (10 mL). The filtrate was washed with water, concentrated and purified by reverse-phase prep HPLC (C18, 0-100% 0.1% TFA in water/0.1% TFA in ACN) to give the desired product RA23 (100 mg, RT 0.907 min, and 90 mg of RA24, RT 1.201 min) as TFA-salt.

A mixture of RA23 (20 mg, 0.04 mmol in 1 mL of MeOH) and 2N NaOH aqueous (0.1 mL) was shaken at RT for 24 h. After the reaction was quenched with TFA (2N in CH₃CN 0.1 mL), the product was purified by reverse-phase prep HPLC (C18, 0-100% 0.1% TFA in water/0.1% TFA in ACN) to yield Compound 30 as TFA-salt (white solid, 10 mg). ¹H NMR δ$_H$ (400 MHz, CD₃OD) 7.03 (d, J=8.3 Hz, 1H), 6.73 (d, J=2.4 Hz, 1H), 6.69 (dd, J=2.4 and 8.3 Hz, 1H), 4.12 (s, 1H), 3.99 (d, J=13.4 Hz, 2H), 3.58 (s, 1H), 3.24-3.3 (m, 1H), 3.1-3.18 (m, 2H), 2.94 (s, 3H), 2.9 (d, J=5.3 Hz, 1H), 2.79 (dd, J=8.6 and 12.5 Hz, 1H), 2.62-2.72 (m, 3H), 2.06-2.13 (m, 1H), 1.82-1.88 (m, 1H), 1.62-1.68 (m, 3H), 1.56 (s, 3H), 1.34 (s, 9H), 0.99-1.09 (m, 2H); LC/MS, m/z=430.2 [M+H]⁺ (Calc: 429.6).

NaB(OAc)₃H (80 mg, 0.37 mmol) was added to a solution of RA23 (20 mg, 0.04 mmol) and formaldehyde (36% aqueous, 0.05 mL, 0.6 mmol) in 0.4 mL CH₃CN at RT. The reaction mixture was shaken at RT for 12 h. The reaction was quenched with MeOH (2 mL) and NaOH (2N aqueous, 0.4 mL). The resulting mixture was shaken at RT for 24 h. After the solvents were evaporated under vacuum, the residue was dissolved in CHCl₃ (6 mL), and neutralized to pH ~2 with TFA (2N in CH₃CN). The organic layer was concentrated and purified by reverse-phase prep HPLC (C18, 0-100% 0.1% TFA in water/0.1% TFA in ACN) to yield Compound 31 as TFA-salt (white solid, 6 mg). ¹H NMR δ$_H$ (400 MHz, CD₃OD) 6.92 (d, J=8.6 Hz, 1H), 6.69 (d, J=2.4 Hz, 1H), 6.54 (dd, J=2.4 and 8.3 Hz, 1H), 3.92 (d, J=12.9 Hz, 2H), 3.82 (s, 1H), 3.02-3.18 (m, 4H), 2.86 (s, 3H), 2.56-2.68 (m, 3H), 2.36-2.42 (m, 2H), 2.05 (s, 3H), 1.82-1.86 (m, 1H), 1.56-1.65 (m, 3H), 1.46-1.52 (m, 1H), 1.44 (s, 3H), 1.34 (s, 9H), 0.76-0.88 (m, 2H); LC/MS, m/z=444.3 [M+H]⁺ (Calc: 443.6).

Example 24

4-(2-((6S,11R)-8-hydroxy-3,6-dimethyl-1,2,3,4,5,6-hexahydro-2,6-methanobenzo[d]azocin-11-yl)acetamido)benzoic Acid (Compound 32); and 2-(2-((6S,11R)-8-hydroxy-3,6-dimethyl-1,2,3,4,5,6-hexahydro-2,6-methanobenzo[d]azocin-11-yl) acetamido)benzoic Acid (Compound 35)

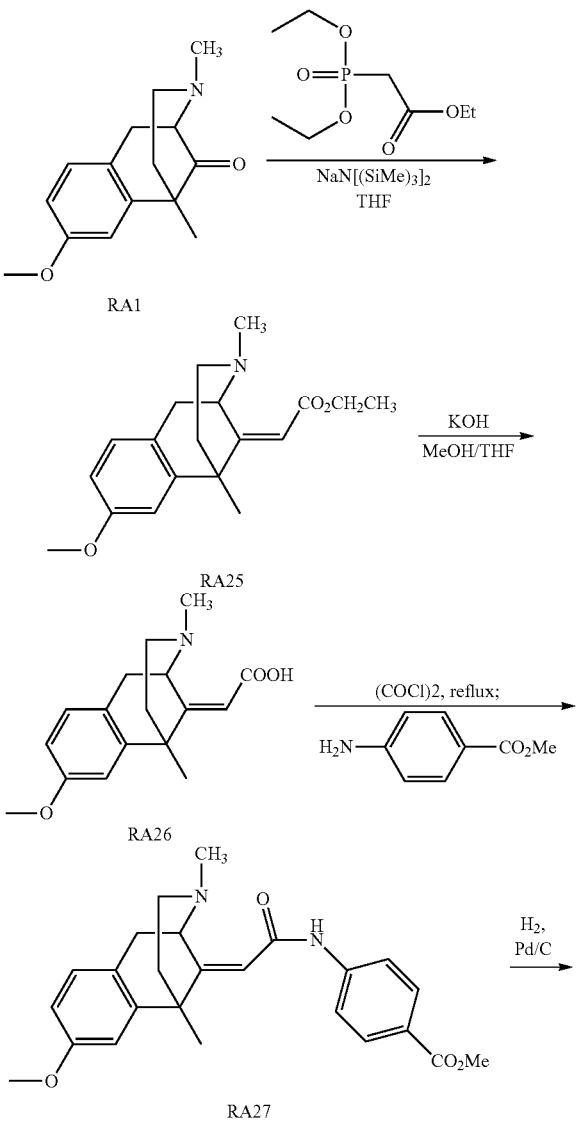

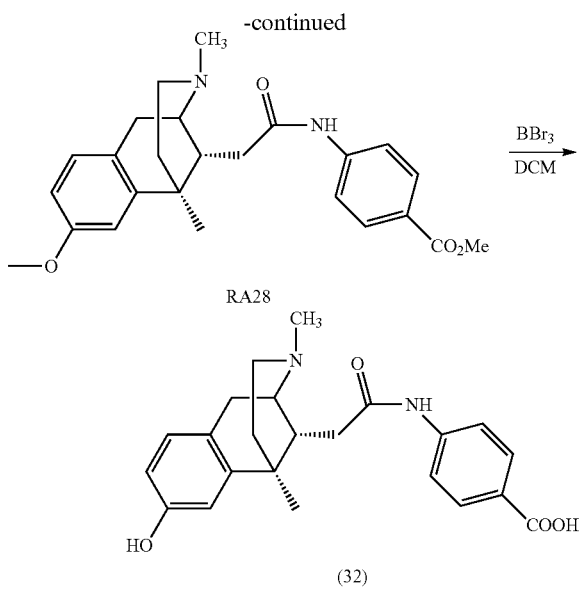

To an ice-cooled solution of triethyl phosphonoacetate (112 mg, 1.2 eq, 0.54 mmol) in anhydrous THF (2 mL), sodium bis(trimethylsilyl)amide (1.0 M in THF, 0.68 mL, 1.5 eq, 0.68 mmol) was added dropwise. After stirring for 15 min, compound RA1 (104 mg, 0.42 mmol) in THF (1 mL) was slowly added. The resulting mixture was stirred at RT overnight, quenched with water (2 mL) and extracted with EtOAc (50 mL×2). The combined organic extracts were dried over $Na_2SO_4$, filtered and concentrated. The crude material was purified by flash column chromatography (silica gel, 0-50% EtOAc/hexanes) to give 89 mg of RA25 as an oil.

$^1$H NMR $\delta_H$ (400 MHz, $CDCl_3$) 7.05 (d, J=8.55 Hz, 1H), 6.85 (d, J=2.85 Hz, 1H), 6.77 (dd, J=2.85 and 8.55 Hz, 1H), 5.93 (s, 1H), 5.23 (d, J=5.92 Hz, 1H), 4.18 (m, 3H), 3.78 (s, 3H), 3.38 (m, 1H), 2.94 (dd, J=6.36 and 18.20 Hz, 1H), 2.51 (m, 2H), 2.45 (s, 3H), 2.00 (m, 1H), 1.57 (m, 1H), 1.29 (t, J=7.02 Hz, 3H).

LC/MS, m/z=316 [M+H]$^+$ (Calc: 315).

To a solution of compound RA25 (320 mg, 1 mmol) in MeOH/THF (2 mL, 1:1) was added KOH (2 mL, 2N in water). The resulting mixture was stirred at RT for 3 h and the MeOH evaporated. After cooling to 0° C., the solution was neutralized to pH=4 by using 1N HCl. The precipitate was filtered, washed with $Et_2O$, and dried to give 244 mg of RA26 as a white solid.

$^1$H NMR $\delta_H$ (400 MHz, DMSO-$d_6$) 12.90 (br s, 1H), 7.11 (d, J=8.55 Hz, 1H), 6.90 (d, J=2.63 Hz, 1H), 6.86 (dd, J=8.55 Hz, 1H), 6.07 (br s, 1H), 5.59 (d, J=6.36 Hz, 1H), 3.75 (s, 3H), 3.60 (m, 1H), 3.20-3.40 (m, 3H), 2.15 (m, 1H), 1.71 (m, 1H), 1.58 (s, 3H).

LC/MS, m/z=288 [M+H]$^+$ (Calc: 287).

To a round-bottomed flask were added RA26 (200 mg, 0.70 mmol), oxalyl chloride (2 mL) and 1-2 drops of DMF. The resulting mixture was heated to reflux for 30 min, then the oxalyl chloride was removed in vacuo. The residue was dissolved in anhydrous DCM (4 mL) and methyl 4-aminobenzoate (88 mg, 1.2 eq, 0.84 mmol) and diisopropylethylamine (DIEA, 1 mL) were added. The mixture was stirred at RT overnight and then concentrated. The crude material was purified by flash column chromatography (silica gel, 0-5% MeOH/DCM) to give 222 mg of RA27 as a brown foam.

LC/MS, m/z=421 [M+H]$^+$ (Calc: 420).

To a solution of RA27 (200 mg, 0.48 mmol) in MeOH (5 mL) was added 10% Pd in charcoal (50 mg). The reaction bottle was sealed, de-gassed, and then subjected to a $H_2$ balloon. After stirring at RT overnight, the solution was filtered and concentrated to give RA28. The crude material was used directly in the next step without further purification.

$^1$H NMR $\delta_H$ (400 MHz, DMSO-$d_6$) 10.41 (br s, 1H), 7.91 (d, J=8.77 Hz, 2H), 7.27 (d, J=8.77 Hz, 2H), 7.16 (d, J=8.11 Hz, 1H), 6.88 (m, 2H), 3.82 (s, 3H), 3.75 (s, 3H), 3.70 (m, 1H), 2.93-3.25 (m, 4H), 2.81 (s, 3H), 2.71 (m, 1H), 2.39-2.57 (m, 2H), 2.13 (m, 1H), 1.99 (m, 1H), 1.56 (d, J=14.25 Hz, 1H), 1.40 (s, 3H).

LC/MS, m/z=423 [M+H]$^+$ (Calc: 422).

To a dry ice-cooled solution (−78° C.) of RA28 (200 mg, 0.47 mmol) in DCM (4 mL) was added $BBr_3$ (0.5 mL in DCM). The reaction mixture was slowly warmed to room temperature over 3 h, and then quenched with sat. $NH_4Cl$ (1 mL). After evaporation of the DCM, the residue was dissolved in MeOH (2 mL) and purified by reverse phase column chromatography (C18, ACN/water with 0.1% TFA, 0-95%) to give 79 mg of Compound 32 TFA salt as a white powder.

$^1$H NMR $\delta_H$ (400 MHz, MeOD) 10.02 (s, 1H), 7.87 (m, 2H), 7.57 (m, 2H), 7.00 (d, J=8.33 Hz, 1H), 6.71 (d, J=2.41 Hz, 1H), 6.63 (dd, J=2.41 and 8.33 Hz, 1H), 3.78 (m, 1H), 3.03-3.16 (m, 3H), 2.86 (s, 3H), 2.16 (m, 1H), 1.95 (dt, J=4.82 and 14.25 Hz, 1H), 1.61 (m, 1H), 1.40 (s, 3H).

LC/MS, m/z=395 [M+H]$^+$ (Calc: 394).

In a similar manner 2-(2-(((6S,11R)-8-hydroxy-3,6-dimethyl-1,2,3,4,5,6-hexahydro-2,6-methanobenzo[d]azocin-11-yl)acetamido)benzoic acid (Compound 35) was prepared from RA26 using methyl 2-aminobenzoate rather than methyl 4-aminobenzoate. Purification by reverse phase column chromatography (C18, ACN/water with 0.1% TFA, 0-95%) gave Compound 35 TFA salt as a white powder.

$^1$H NMR $\delta_H$ (400 MHz, MeOD) 8.37 (d, J=8.33 Hz, 1H), 7.96 (dd, J=1.53 and 8.11 Hz, 1H), 7.46 (dt, J=1.53 and 7.23 Hz, 1H), 7.07 (dt, J=1.10 and 7.23 Hz, 1H), 6.99 (d, J=8.11 Hz, 1H), 6.69 (d, J=2.63 Hz, 1H), 6.63 (dd, J=2.63 and 8.33 Hz, 1H), 3.78 (m, 1H), 3.06-3.18 (m, 3H), 2.84 (s, 3H), 2.49-2.70 (m, 3H), 2.12 (m, 1H), 1.93 (m, 1H), 1.59 (d, J=13.81 Hz, 1H), 1.40 (s, 3H).

LC/MS, m/z=395 [M+H]$^+$ (Calc: 394).

Example 25

5-(((2R,6S,11S)-8-hydroxy-3,6-dimethyl-1,2,3,4,5,6-hexahydro-2,6-methanobenzo[d]azocin-11-yl)methoxy)nicotinic Acid (Compound 33); 3-(((2R,6S,11S)-8-hydroxy-3,6-dimethyl-1,2,3,4,5,6-hexahydro-2,6-methanobenzo[d]azocin-11-yl)methoxy)benzoic Acid (Compound 41)

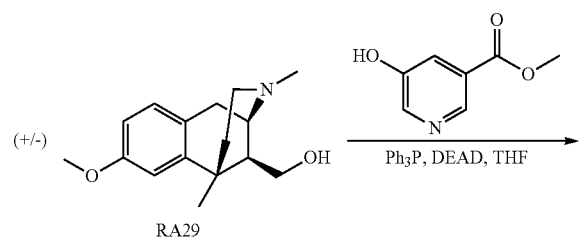

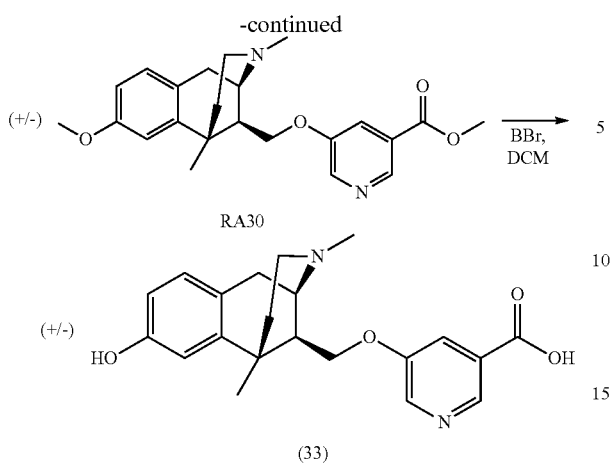

To a mixture of Ph₃P (0.262 g, 1.00 mmol, 1.5 eq) in THF (5 mL) was added diethyl azodicarboxylate (DEAD) (40% in toluene, 0.45 mL, 0.99 mmol, 1.5 eq). This was stirred for 2 min then methyl 5-hydroxynicotinate (0.106 g, 0.692 mmol, 1.05 eq) was added. After 2 more min a solution of compound RA29 (0.172 g, 0.658 mmol, 1 eq) in THF (5 mL) was added. After stirring overnight the reaction mixture was chromatographed over silica gel with 0-25% EtOAc in hexanes. The product fractions were evaporated in vacuo to give the product RA30 as a tan solid (0.141 g). LC/MS, m/z=397 [M+H]⁺ (Calc: 396).

Compound RA30 (0.141 g, 0.356 mmol) was suspended in DCM (5 mL) and cooled on an ice-salt bath. BBr₃ (0.32 mL, 3.3 mmol, 9 eq) was added. The ice-salt bath was removed after 10 min and the reaction stirred for 3 days. The reaction mixture was diluted with an additional 10 mL DCM and quenched with 5 mL 5N NaOH. The layers were separated and the aqueous portion washed once more with 10 mL DCM. The combined organics were back extracted once with 5 mL water and the second aqueous portion combined with the first aqueous portion. The aqueous portion was adjusted to pH ~7 with 5N HCl then evaporated in vacuo. The residue was triturated with 15 mL ACN, filtered and washed successively with 10 mL ACN then twice with 10 mL MeOH. The filtrates were evaporated in vacuo to a residue, acidified with TFA and purified via reverse-phase chromatography (C18, ACN/water with 0.1% TFA, 0-50%). The product fractions were frozen and lyophilized to give the product Compound 33 TFA salt as a cream-colored powder (0.046 g).

¹H NMR $\delta_H$ (400 MHz, DMSO-d₆) 13.57 (br s, 1H), 9.32 (br s, 1H), 9.17 (br s, 1H), 8.72 (d, J=1.5 Hz, 1H), 8.61 (d, J=2.9 Hz, 1H), 7.95 (dd, J=2.9, 1.8 Hz, 1H), 7.02 (d, J=8.3 Hz, 1H), 6.80 (d, J=2.4 Hz, 1H), 6.68 (dd, J=8.3, 2.4 Hz, 1H), 4.52-4.43 (m, 2H), 4.14 (br d, J=5.0 Hz, 1H), 3.37-3.29 (m, 1H), 3.22-3.14 (m, 1H), 3.14-3.06 (m, 1H), 2.86 (d, J=4.4 Hz, 3H), 2.57-2.43 (m, 2H), 2.11 (dt, J=14.0, 3.9 Hz, 1H), 1.46-1.38 (m, 4H).

LC/MS, m/z=369 [M+H]⁺ (Calc: 368).

In a similar manner 3-(((2R,6S,11S)-8-hydroxy-3,6-dimethyl-1,2,3,4,5,6-hexahydro-2,6-methanobenzo[d]azocin-11-yl)methoxy)benzoic acid (Compound 41) was prepared from RA29 using methyl 3-hydroxybenzoate rather than methyl 5-hydroxynicotinate. Purification by reverse-phase chromatography (C18, ACN/water with 0.1% TFA, 0-60%) gave Compound 41 TFA salt as a white powder.

¹H NMR $\delta_H$ (400 MHz, DMSO-d₆) 13.08 (br s, 1H), 9.31 (s, 1H), 9.10 (br s, 1H), 7.62-7.60 (m, 1H), 7.60-7.57 (m, 1H), 7.46 (t, 1H), 7.33-7.29 (m, 1H), 7.02 (d, J=8.3 Hz, 1H), 6.80 (d, J=2.4 Hz, 1H), 6.67 (dd, J=8.1, 2.4 Hz, 1H), 4.43-4.34 (m, 2H), 4.13 (br d, J=4.6 Hz, 1H), 3.36-3.28 (m, 1H), 3.23-3.14 (m, 1H), 3.12-3.05 (m, 1H), 2.87 (d, J=4.6 Hz, 3H), 2.53-2.43 (m, 2H), 2.09 (dt, J=13.8, 4.6 Hz, 1H), 1.46-1.37 (m, 4H).

LC/MS, m/z=368 [M+H]⁺ (Calc: 367).

Example 26

5-(((6S,11R)-8-hydroxy-3,6-dimethyl-1,2,3,4,5,6-hexahydro-2,6-methanobenzo[d]azocin-11-yl)methoxy)nicotinic Acid (Compound 34)

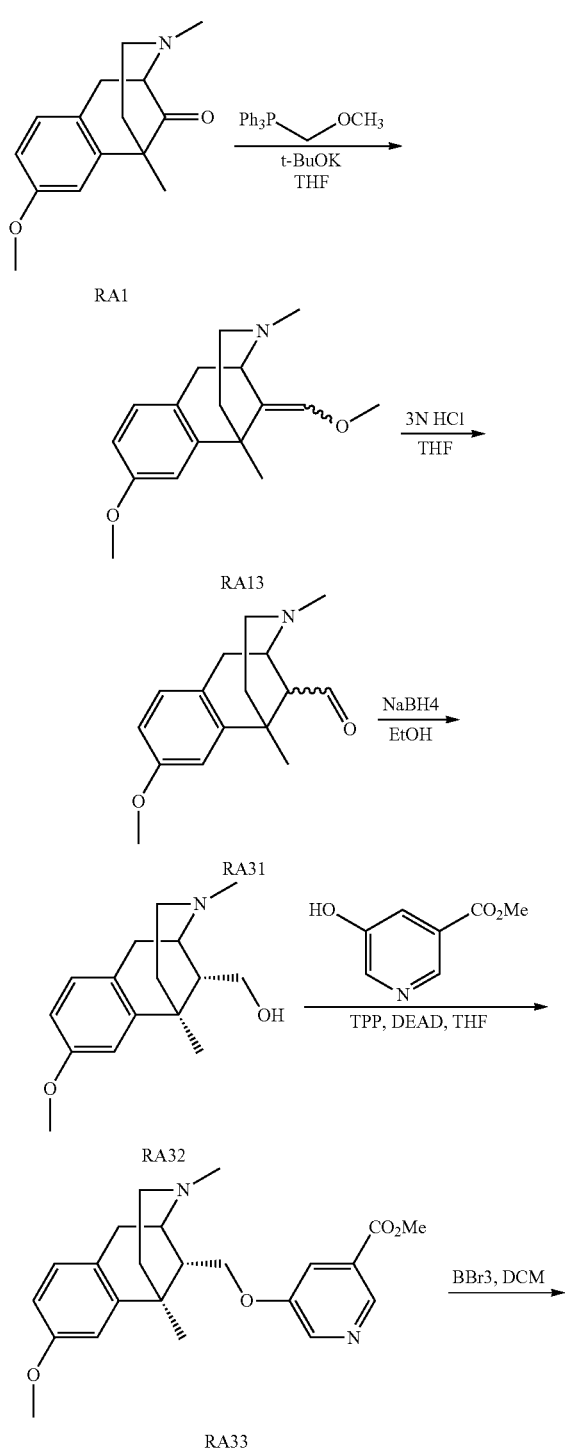

-continued

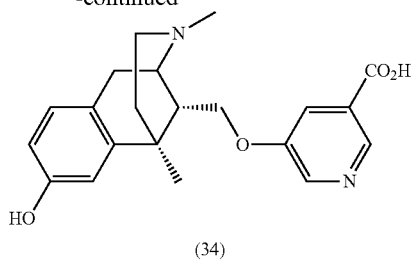

(34)

To a solution of compound RA1, (5.00 g, 20.41 mmol, 1 eq) and (methoxymethyl)triphenylphosphonium chloride (9.79 g, 28.57 mmol, 1.4 eq) in THF (148 mL) cooled in an ice bath was added potassium t-butoxide (36.7 mL of a 1M solution in THF, 36.7 mmol). The ice bath was removed and the mixture was stirred at room temperature for 5 h. The reaction mixture was poured onto cold $H_2O$ and extracted twice with EtOAc, washed with brine, concentrated and purified by flash chromatography (silica gel, 50-100% EtOAc in hexane followed by 10-30% MeOH in DCM) to afford 4.08 g of RA13 as a syrup.

LC/MS, m/z=274 $[M+H]^+$ (Calc: 273).

To a solution of RA13 (2.78 g, 10.18 mmol, 1.0 eq) in THF (25 ml) was added 3N HCl (34 mL, 101.8 mmol, 10.0 eq). The mixture was stirred for 6 h at 50° C. and then it was poured onto cold $H_2O$ (50 mL) and 2M NaOH (50 mL) was added to adjust the pH to 8. The mixture was extracted twice with DCM, dried over $Na_2SO_4$ and concentrated to afford 2.1 g of RA14 as a mixture of isomers. LC/MS, m/z=260 $[M+H]^+$ (Calc: 259).

To a solution of RA14 (3.34 g, 12.85 mmol, 1.0 eq) in EtOH (36 mL) at 0° C. was added $NaBH_4$ (0.53 g, 14.13 mmol, 1.1 eq). The mixture was stirred for 10 min, $H_2O$ (10 mL) was added, the EtOH was removed under reduced pressure and the organic portion was extracted with DCM, dried over $Na_2SO_4$ and concentrated to 2.6 g of a light yellow solid as a mixture of diastereomers which was purified by flash column chromatography (silica gel, 5-25% MeOH (1N $NH_3$)/DCM) to afford 1.48 gm of RA32 as the more polar isomer.

$^1$H NMR $\delta_H$ (300 MHz, DMSO-d6) 7.00 (d, J=7.9 Hz, 1H), 6.69-6.65 (m, 2H), 4.39 (t, J=4.82 Hz, 1H), 3.69 (s, 3H), 3.56-3.50 (m, 1H), 3.10 (m, 1H), 2.98-2.92 (m, 1H), 2.88 (d, J=19.1 Hz, 1H), 2.55-2.48 (m, 1H), 2.30 (m, 1H), 2.27 (s, 3H), 1.94-1.81 (m, 2H), 1.70 (td, J=4.4, 12.3 Hz, 1H), 1.30 (s, 3H), 1.18 (d, J=13.4 Hz, 1H), LC/MS, m/z=262 $[M+H]^+$ (Calc: 261).

To a mixture of RA32 (0.319 g, 1.22 mmol, 1.0 eq), methyl-5-hydroxy-3-pyridine carboxylate (0.46 g, 3.63 mmol, 3.0 eq), and triphenylphosphine (0.80 g, 3.63 mmol, 3.0 eq) in THF (6.4 mL) at 0° C. was added DEAD (1.58 g, 3.63 mmol, 3.0 eq). The ice bath was removed and the mixture was stirred for 16 h. $H_2O$ was added and the organic portion was extracted twice with EtOAc, dried over $Na_2SO_4$ and concentrated to 2.2 g of a crude mixture which was purified by flash column chromatography (silica gel, 5-25% MeOH (1N $NH_3$) in DCM) to afford 0.090 g of RA33. LC/MS, m/z=397 $[M+H]^+$ (Calc: 396).

A solution of RA33 (0.042 g, 0.106 mmol, 1.0 eq), in DCM (0.4 mL) at 0° C. was added a solution of boron tribromide (0.041 mL) in DCM (0.15 mL). After 5 h additional boron tribromide (0.020 mL) was diluted with DCM (0.10 mL) and added to the reaction. It was stirred for 16 h at room temperature, cooled in an ice bath and slowly neutralized with saturated $NaHCO_3$. The organic portion was separated, concentrated and purified on silica gel with 5-25% MeOH (1N $NH_3$) in DCM to afford 8.0 mg of Compound 34.

$^1$H NMR $\delta_H$ (300 MHz, CD3OD) 8.66 (s, 1H), 8.23 (d, J=2.8 Hz, 1H), 7.82 (m, 1H), 7.03 (d, J=8.3 Hz, 1H), 6.79 (d, J=2.4 Hz, 1H), 6.68 (dd, J=2.6 and 8.3 Hz, 1H), 4.93 (s, 2H), 4.36-4.32 (m, 1H), 3.92-3.88 (m, 1H), 3.82 (t, J=10.1 Hz, 1H), 3.20 (d, J=19.3 Hz, 1H), 3.05-2.95 (m, 2H), 2.83 (s, 3H), 2.65-2.54 (m, 2H), 2.10-2.00 (td, J=4.6 and 15.6 Hz, 1H), 1.59-1.56 (m, 1H), 1.56 (s, 3H), LC/MS, m/z=369 $[M+H]^+$ (Calc: 368).

Example 27

3-(((6R,11S)-11-hydroxy-8-methoxy-3,6-dimethyl-1,2,3,4,5,6-hexahydro-2,6-methanobenzo[d]azocin-11-yl)benzonitrile (Compound 37); 3-(((6R,11R)-11-hydroxy-8-methoxy-3,6-dimethyl-1,2,3,4,5,6-hexahydro-2,6-methanobenzo[d]azocin-11-yl)benzonitrile (Compound 60); 3-(((6S,11R)-8-methoxy-3,6-dimethyl-1,2,3,4,5,6-hexahydro-2,6-methanobenzo[d]azocin-11-yl)benzonitrile (Compound 36); and (6S,11R)-11-(3-(benzyloxy)phenyl)-8-methoxy-3,6-dimethyl-1,2,3,4,5,6-hexahydro-2,6-methanobenzo[d]azocine (Compound 61)

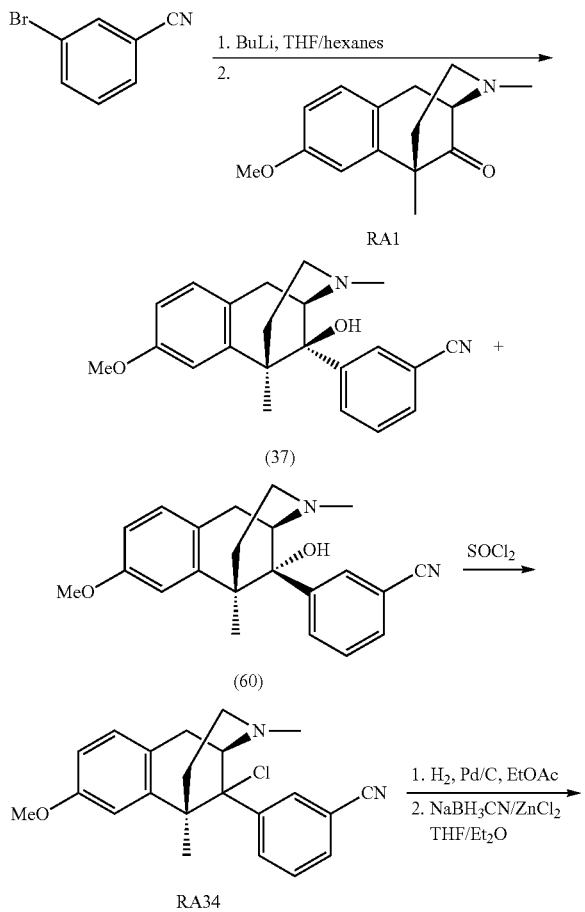

-continued

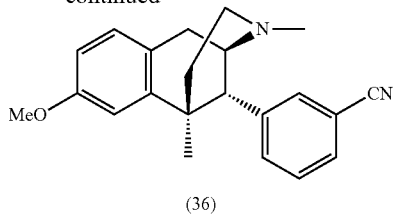

(36)

n-BuLi (2.5 Min hexanes, 4.2 mL, 10.5 mmol, 1.05 eq) was added slowly to 3-bromobenzonitrile (1.82 g, 10 mmol, 1 eq) in 24 mL THF at −78° C. and the solution stirred at −78° C. for 10 min. A solution of RA1 (1.23 g, 5 mmol, 0.5 eq) in 5 mL THF was added and the solution was allowed to warm from −78° C. to RT. After 90 min, EtOAc was added and the solution washed with sat. NaHCO3, dried with Na2SO4, and concentrated. The resulting material was purified by Medium Pressure Liquid Chromatography (MPLC) (0-50% EtOAc/hexanes, 40 g) to give Compound 60, 550 mg and Compound 37, 1.18 g as yellow oils.

Compound 60: $^1$H NMR $\delta_H$ (400 MHz, DMSO-d6) 8.77 (s, 1H), 8.64 (d, J=8.1 Hz, 1H), 8.26 (bs, 2H), 8.22 (s, 1H), 7.89 (d, J=7.0 Hz, 1H), 7.74 (d, J=7.0 Hz, 1H), 7.66 (t, J=7.2 Hz, 1H), 7.55 (t, J=7.2 Hz, 1H), 7.11 (d, J=7.4 Hz, 1H), 7.02 (d, J=7.4 Hz, 1H), 6.91 (s, 1H), 6.86-6.75 (m, 2H), 6.69 (d, J=7.4 Hz, 1H), 6.21 (s, 1H), 5.32 (bs, 1H), 4.0 (s, 1H), 3.75 (s, 3H), 3.71 (s, 3H), 3.34 (ABq, J=65.8, 18.4 Hz, 2H), 3.18-2.87 (m, 4H), 2.83 (s, 3H), 2.63-2.53 (m, 1H), 2.40 (s, 3H), 2.08 (t, J=10.8 Hz, 1H), 1.61 (s, 3H), 1.09 (s, 3H).

LC/MS, m/z=349 [M+H]$^+$ (Calc: 348).

Compound 37: $^1$H NMR $\delta_H$ (400 MHz, DMSO-d6) 9.36 (bs, 1H), 7.80-7.74 (m, 2H), 7.45-7.34 (m, 2H), 7.05 (d, J=8.6 Hz, 1H), 7.02 (d, J=2.5 Hz, 1H), 6.96 (s, 1H), 6.88 (dd, J=8.6, 2.5 Hz, 1H), 3.88 (d, J=5.5 Hz, 1H), 3.80 (s, 3H), 3.26 (d, J=19.7 Hz, 1H), 3.03 (d, J=11.0 Hz, 1H), 2.84 (d, J=4.6 Hz, 3H), 2.46-2.27 (m, 3H), 1.49 (s, 3H), 1.33 (d, J=12.0 Hz, 1H). LC/MS, m/z=349 [M+H]$^+$ (Calc: 348).

Thionyl chloride (35 mL, excess) was added to a mixture of Compound 37 and Compound 60 (2.24 g, 1 eq) and the solution heated at 70° C. for 90 min. The solution was concentrated and EtOAc was added. The solution was washed with sat. NaHCO$_3$, dried with Na$_2$SO$_4$, concentrated, and purified by MPLC (0-50% EtOAc/hexanes, 40 g) to give RA34 as a yellow oil, 1.0 g. EtOAc (50 mL) was added and the solution run with the Pd/C cartridge on the H-Cube [ThalesNano, model HC-2.SS] at 10 bar in a recirculating fashion at 1 mL/min. After 45 min. the pressure was increased to 30 bar and after 3.5 h the pressure increased to 60 bar and the flow rate dropped to 0.5 mL/min. The reaction was stopped after 6 h with very little conversion to product seen. The recovered RA34 (700 mg, 1 eq) was dissolved in 8 mL THF and a pre-mixed solution of NaBH$_3$CN (1 M in THF, 1 eq) and ZnCl2 (1 Min Et2O, 0.5 eq) was added. The solution was stirred at RT, and after 3 days 8 mL Et$_2$O was added, followed by a pre-mixed solution of NaBH$_3$CN (1 M in THF, 1 eq) and ZnCl2 (1 Min Et2O, 0.5 eq). After 8 days EtOAc was added and the solution washed with sat. NaHCO$_3$, dried with Na$_2$SO$_4$, and concentrated. The resulting material is purified by MPLC (0-40% EtOAc/hexanes, 12 g) to yield Compound 36 as a pale yellow solid, 235 mg.

$^1$H NMR $\delta_H$ (400 MHz, DMSO-d6) 9.39 (bs, 1H), 8.56 (bs, 1H), 7.99 (s, 1H), 7.92 (d, J=8.3 Hz, 1H), 7.84 (d, J=7.7 Hz, 1H), 7.74 (s, 1H), 7.72-7.68 (m, 1H), 7.65 (t, J=7.7 Hz, 1H), 7.48-7.39 (m, 2H), 7.36 (d, J=8.3 Hz, 1H), 7.25 (d, J=8.3 Hz, 1H), 6.93 (d, J=2.0 Hz, 1H), 6.83 (td, J=7.0, 2.4 Hz, 3H), 6.61 (d, J=2.4 Hz, 1H), 4.00 (t, J=10.3 Hz, 1H), 3.77 (s, 3H), 3.70 (s, 3H), 3.63 (d, J=17.3 Hz, 2H), 3.49-3.30 (m, 6H), 3.29-3.09 (m, 4H), 2.93 (d, J=4.4 Hz, 3H), 2.83-2.67 (m, 3H), 2.66 (d, J=4.4 Hz, 6H), 2.62-2.38 (m, 2H), 1.91 (d, J=16.6 Hz, 1H), 1.83-1.68 (m, 1H), 1.06 (s, 3H), 0.97 (s, 3H).

LC/MS, m/z=333 [M+H]$^+$ (Calc: 332).

In a similar manner Compound 61 was synthesized from RA1 using 3-benzyloxybromobenzene rather than 3-bromobenzonitrile. The material was purified by preparative HPLC [0-60% MeCN/H$_2$O (0.01% TFA)] to yield Compound 61 TFA salt.

$^1$H NMR $\delta_H$ (400 MHz, DMSO-d6) 9.21 (bs, 1H), 8.38 (bs, 1H), 7.48 (d, J=7.4 Hz, 2H), 7.42 (t, J=7.4 Hz, 3H), 7.39-7.33 (m, 6H), 7.31 (d, J=7.9 Hz, 2H), 7.24 (d, J=7.9 Hz, 1H), 7.16 (d, J=7.2 Hz, 1H), 7.13-7.08 (m, 2H), 7.03 (dd, J=8.1, 2.0 Hz, 1H), 6.91-6.76 (m, 5H), 6.74 (d, J=8.3 Hz, 1H), 6.60 (d, J=2.2 Hz, 1H), 5.17 (s, 2H), 4.95 (s, 2H), 3.93 (dd, J=13.8, 10.5 Hz, 2H), 3.73 (d, J=23.9 Hz, 6H), 3.59 (d, J=16.0 Hz, 3H), 3.45-3.19 (m, 6H), 3.08 (d, J=16.2 Hz, 2H), 2.93 (d, J=4.6 Hz, 3H), 2.81-2.67 (m, 2H), 2.65 (d, J=4.6 Hz, 5H), 1.8 (d, J=14.8 Hz, 2H), 1.76-1.65 (m, 2H), 0.99 (d, J=55.4 Hz, 6H).

LC/MS, m/z=414 [M+H]$^+$ (Calc: 413).

Example 28

3-(((6S,11R)-8-methoxy-3,6-dimethyl-1,2,3,4,5,6-hexahydro-2,6-methanobenzo[d]azocin-11-yl)benzamide (Compound 54); 3-((6R,11S)-11-hydroxy-8-methoxy-3,6-dimethyl-1,2,3,4,5,6-hexahydro-2,6-methanobenzo[d]azocin-11-yl)benzamide (Compound 63); and 3-((6R,11R)-11-hydroxy-8-methoxy-3,6-dimethyl-1,2,3,4,5,6-hexahydro-2,6-methanobenzo[d]azocin-11-yl)benzamide (Compound 67)

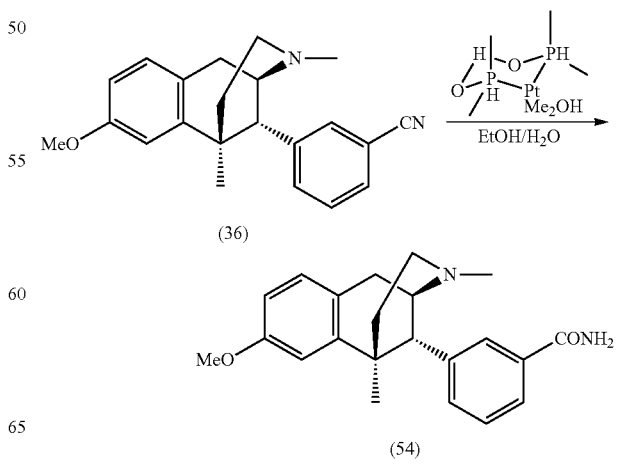

129
-continued

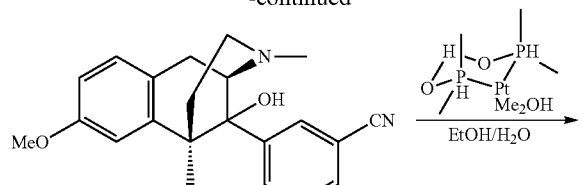

11S: (37)
11R: (60)

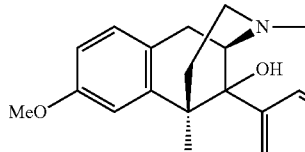

11S: (63)
11R: (67)

A 4:1 mixture of EtOH:H₂O was added to Compound 36 (100 mg, 0.3 mmol, 1 eq) and hydrido(dimethylphosphinous acid-kP)[hydrogen bis(dimethylphosphinito -kP)]platinum (II) [Strem] (13 mg, 0.03 mmol, 10 mol %). The solution was heated at 80° C. for 16 h, then concentrated. Purification by MPLC (0-100% EtOAc/hexanes) yielded Compound 54 as a white foam. A small portion was further purified by preparative HPLC [0-60% MeCN/H₂O (0.01% TFA)] to yield Compound 54 TFA salt.

¹H NMR δ$_H$ (400 MHz, DMSO-d6) 9.26 (bs, 1H), 8.49 (bs, 1H), 8.07 (s, 1H), 7.98 (s, 1H), 7.90 (s, 1H), 7.87-7.79 (m, 2H), 7.74 (d, J=8.3 Hz, 1H), 7.67 (t, J=4.0 Hz, 1H), 7.52 (t, J=7.9 Hz, 1H), 7.49 (s, 1H), 7.41 (s, 1H), 7.34 (d, J=7.9 Hz, 1H), 7.30-7.22 (m, 3H), 6.94 (d, J=2.4 Hz, 1H), 6.81 (ddd, J=15.4, 8.3, 2.4 Hz, 2H), 6.59 (d, J=2.4 Hz, 1H), 4.00 (t, J=13.4 Hz, 2H), 3.73 (d, J=29.8 Hz, 6H), 3.67-3.57 (m, 2H), 3.48-3.26 (m, 6H), 3.16 (dd, J=16.7, 5.0 Hz, 2H), 2.96 (d, J=4.6 Hz, 3H), 2.84-2.66 (m, 3H), 2.65-2.57 (m, 6H), 1.89 (d, J=15.1 Hz, 1H), 1.03 (d, J=32.2 Hz, 6H).

LC/MS, m/z=351 [M+H]⁺ (Calc: 350).

In a similar manner Compound 63 and Compound 67 were prepared from Compound 37 and Compound 60, respectively.

Compound 63: ¹H NMR δ$_H$ (400 MHz, DMSO-d6) 9.32 (bs, 1H), 8.11 (s, 1H), 7.92 (s, 1H), 7.72 (d, J=8.1 Hz, 1H), 7.39 (s, 1H), 7.20 (t, J=7.7 Hz, 1H), 7.09 (d, J=8.1 Hz, 1H), 7.03 (d, J=5.9 Hz, 1H), 7.01 (s, 1H), 6.85 (dd, J=8.1, 2.6 Hz, 1H), 6.83 (s, 1H), 3.83-3.77 (m, 2H), 3.80 (s, 3H), 3.24 (d, J=18.9 Hz, 2H), 3.03 (d, J=8.8 Hz, 1H), 2.85 (d, J=5.3 Hz, 3H), 2.48-2.43 (m, 6H), 1.75 (s, 1H), 1.51 (s, 3H), 1.31 (d, J=11.4 Hz, 1H).

LC/MS, m/z=367 [M+H]⁺ (Calc: 366).

Compound 67: ¹H NMR δ$_H$ (400 MHz, DMSO-d6) 8.64-8.58 (m, 1H), 8.28 (s, 1H), 8.13 (bs, 1H), 8.02 (s, 1H), 7.94 (d, J=7.5 Hz, 1H), 7.84 (d, J=7.5 Hz, 1H), 7.49 (d, J=7.7 Hz, 1H), 7.45 (d, J=3.9 Hz, 1H), 7.36-7.14 (m, 1H), 7.05 (d, J=8.1 Hz, 1H), 6.86 (d, J=2.2 Hz, 1H), 6.75 (dd, J=8.1, 2.2 Hz, 1H), 6.67-6.59 (m, 1H), 6.00 (s, 1H), 3.97 (d, J=4.4 Hz, 1H), 2.67 (s, 3H), 3.64 (s, 1H), 3.39 (dd, J=19.3, 5.3 Hz, 1H), 3.20 (d, J=18.9 Hz, 1H), 3.10-2.95 (m, 1H), 2.74 (d, J=4.6 Hz, 3H), 2.66-2.46 (m, 1H), 1.69 (s, 2H), 1.61 (s, 3H).

LC/MS, m/z=367 [M+H]⁺ (Calc: 366).

130
Example 29

3-(((6S,11R)-8-methoxy-3,6-dimethyl-1,2,3,4,5,6-hexahydro-2,6-methanobenzo[d]azocin-11-yl)benzoic Acid (Compound 38); and 3-((6R,11S)-11-hydroxy-8-methoxy-3,6-dimethyl-1,2,3,4,5,6-hexahydro-2,6-methanobenzo[d]azocin-11-yl) benzoic Acid (Compound 71)

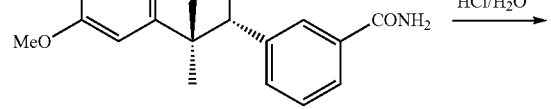

(54)

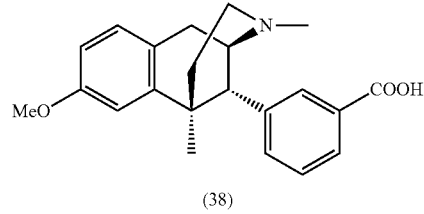

(38)

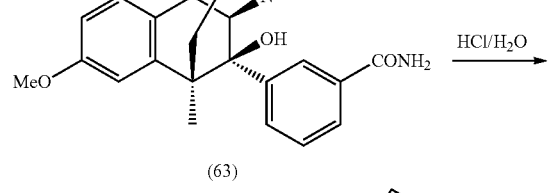

(63)

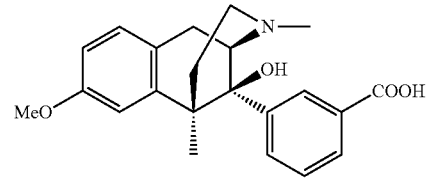

(71)

Compound 54 (50 mg, 0.14 mmol) was heated at 70° C. in 1.5 mL 6 M HCl for 21 h. Concentration followed by preparative HPLC purification [0-60% MeCN/H₂O (0.01% TFA)] gave Compound 38 TFA salt.

¹H NMR δ$_H$ (400 MHz, DMSO-d6) 13.13 (bs, 1H), 13.03 (bs, 1H), 9.30 (bs, 1H), 8.55 (bs, 1H), 8.11 (s, 1H), 7.92 (d, J=7.8 Hz, 1H), 7.89 (s, 1H), 7.84 (d, J=8.5 Hz, 1H), 7.76 (d, J=7.8 Hz, 1H), 7.57 (t, J=7.8 Hz, 1H), 7.43-7.29 (m, 3H), 7.27 (d, J=8.5 Hz, 1H), 6.94 (d, J=2.2 Hz, 1H), 6.82 (dd, J=11.8, 2.2 Hz, 2H), 6.60 (d, J=2.4 Hz, 1H), 4.02 (t, J=11.6 Hz, 1H), 3.73 (d, J=28.9 Hz, 6H), 3.67 (dd, J=15.0, 12.2 Hz, 2H), 3.44-3.27 (m, 6H), 3.25-3.08 (m, 2H), 2.96 (d, J=4.4 Hz, 3H), 2.84-2.63 (m, 4H), 1.89 (d, J=15.0 Hz, 1H), 1.80-1.67 (m, 1H), 1.0 (d, J=28.7 Hz, 6H).

LC/MS, m/z=352 [M+H]⁺ (Calc: 351).

In a similar manner Compound 71 was prepared from Compound 63. Purification by MPLC (0-20% (10% NH4OH/MeOH)/DCM, 12 g) gave Compound 71 as its ammonium carboxylate salt as a clear oil.

¹H NMR δ$_H$ (400 MHz, DMSO-d6) 8.11 (s, 1H), 7.74 (d, J=7.5 Hz, 1H), 7.38-7.08 (m, 5H), 7.00 (d, J=8.7 Hz, 1H), 6.93 (d, J=2.2 Hz, 1H), 6.79 (dd, J=8.3, 2.2 Hz, 1H), 3.77 (s,

3H), 3.34 (s, 2H), 3.10 (d, J=17.3 Hz, 1H), 2.39-2.08 (m, 4H), 1.38 (s, 3H), 1.23-1.07 (m, 1H).

LC/MS, m/z=368 [M+H]⁺ (Calc: 367).

Example 30

N-((2R,6R,11R)-8-hydroxy-3,6-dimethyl-1,2,3,4,5, 6-hexahydro-2,6-methanobenzo[d]azocin-11-yl)-N-methylbenzamide (Compound 39); 3-(((2R,6R, 11S)-8-hydroxy-3,6-dimethyl-1,2,3,4,5,6-hexahydro-2,6-methanobenzo[d]azocin-11-yl)(methyl) carbamoyl)benzoic Acid (Compound 47); 3-(((2R, 6R,11R)-8-hydroxy-3,6-dimethyl-1,2,3,4,5,6-hexahydro-2,6-methanobenzo[d]azocin-11-yl) (methyl)carbamoyl)benzoic Acid (Compound 48); and 4-(((2R,6R,11R)-8-hydroxy-3,6-dimethyl-1,2,3, 4,5,6-hexahydro-2,6-methanobenzo[d]azocin-11-yl) (methyl)carbamoyl)benzoic Acid (Compound 59)

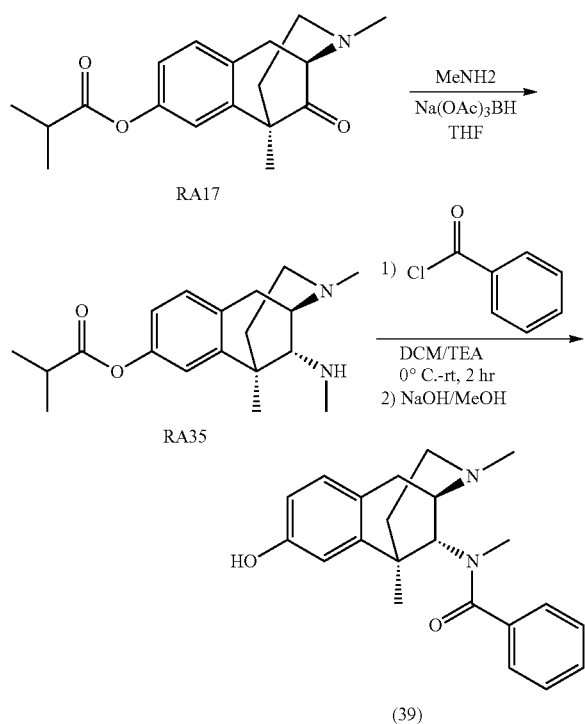

A mixture of RA17 (500 mg, 1.66 mmol), MeNH₂ (2M in THF, 1 mL, 2 mmol) and 0.1 g 4 Å molecular sieves in anhydrous ACN (5 mL) was stirred at RT for 2 h. Na(OAc)₃BH [704 mg, 2.32 mmol] was added and the resulting mixture stirred at RT overnight. The reaction mixture was basified using sat. NaHCO₃ and extracted with EtOAc. The EtOAc solution was dried over MgSO₃ and the solvent evaporated under reduced pressure. The crude compound RA35 was used in the next step without further purification.

Crude RA35 (36 mg, 0.11 mmol) was dissolved in DCM (5 mL) and TEA (0.2 mL, 1.43 mmol) was added. The mixture was cooled to 0° C. with an ice bath and then benzoyl chloride (0.038 mL, 0.12 mmol) was added dropwise via a syringe. After the addition was complete the reaction mixture was slowly warmed to RT over 2 h. The reaction mixture was loaded onto a silica gel column using hexanes/acetone (5:1) as eluent to give the ester intermediate, which was stirred in a mixture of 2N NaOH/MeOH (2 mL/2 mL) at 50° C. for 1 h. The resulting mixture was cooled with an ice bath and the pH adjusted to 7 using 1N HCl, and then extracted with EtOAc. The EtOAc solution was dried over MgSO₄ and the solvent evaporated under reduced pressure. The crude material was subjected to flash column using DCM/MeOH (95:5) as eluent to give 20 mg of Compound 39 as a white solid.

¹H NMR δ_H (400 MHz, CD₃OD) 7.30-7.60 (m, 5H), 7.10 (m, 1H), 6.80 (s, 1H), 6.70 (m, 1H), 5.05 (s, 1H), 4.05 (s, 1H), 2.50-3.50 (m, 10H), 1.70-2.10 (m, 2H), 1.55 (s, 3H).

LC/MS, m/z=351 [M+H]⁺ (Calc: 350).

In a similar manner Compound 47 was prepared from RA35 using methyl 3-(chlorocarbonyl)benzoate rather than benzoyl chloride. Purification by reverse phase column chromatography (C18, ACN/water with 0.1% TFA, 0-95%) gave Compound 47 TFA salt as a white solid.

¹H NMR δ_H (400 MHz, CD₃OD) 8.10 (m, 2H), 7.70 (m, 1H), 7.50 (m, 1H), 7.05 (m, 1H), 6.80 (s, 1H), 6.65 (m, 1H), 4.15 (s, 1H), 3.95 (s, 1H), 3.40 (s, 2H), 2.30-3.30 (m, 8H), 1.60 (s, 3H), 1.40 (m, 1H).

LC/MS, m/z=395 [M+H]⁺ (Calc: 394).

In a similar manner Compound 48 was prepared from RA35 using methyl 3-(chlorocarbonyl)benzoate rather than benzoyl chloride. Purification by reverse phase column chromatography (C18, ACN/water with 0.1% TFA, 0-95%) gave Compound 48 TFA salt as a white solid.

¹H NMR δ_H (400 MHz, CD₃OD) 7.90-8.00 (m, 2H), 7.40-7.60 (m, 2H), 6.90 (m, 1H), 6.70 (m, 1H), 6.50 (m, 1H), 4.90 (s, 1H), 3.95 (s, 1H), 2.30-3.30 (m, 9H), 2.10 (m, 1H), 1.65 (m, 1H), 1.50 (s, 3H).

LC/MS, m/z=395 [M+H]⁺ (Calc: 394).

In a similar manner Compound 59 was prepared from RA35 using methyl 4-(chlorocarbonyl)benzoate rather than benzoyl chloride. Purification by reverse phase column chromatography (C18, ACN/water with 0.1% TFA, 0-95%) gave Compound 59 TFA salt as a white solid.

¹H NMR δ_H (400 MHz, CD₃OD) 7.95 (m, 2H), 7.40 (m, 2H), 6.90 (m, 1H), 6.65 (m, 1H), 6.50 (m, 1H), 4.90 (s, 1H), 3.95 (s, 1H), 2.30-3.30 (m, 9H), 2.10 (m, 1H), 1.65 (m, 1H), 1.50 (s, 3H).

LC/MS, m/z=395 [M+H]⁺ (Calc: 394).

Example 31

3-(((6S,11R)-8-hydroxy-3,6-dimethyl-1,2,3,4,5,6-hexahydro-2,6-methanobenzo[d]azocin-11-yl) methoxy)benzoic Acid (Compound 40)

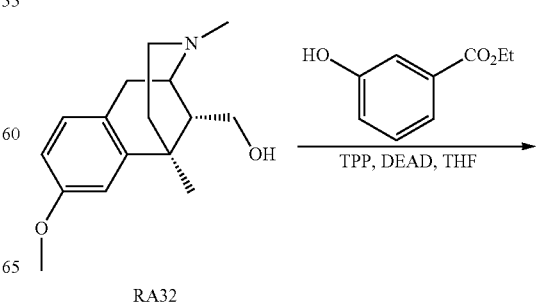

-continued

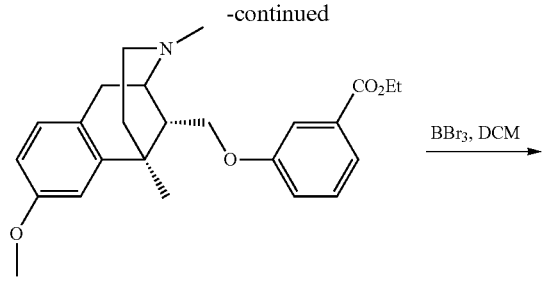

RA36

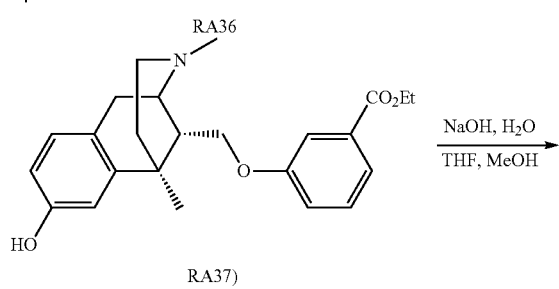

RA37)

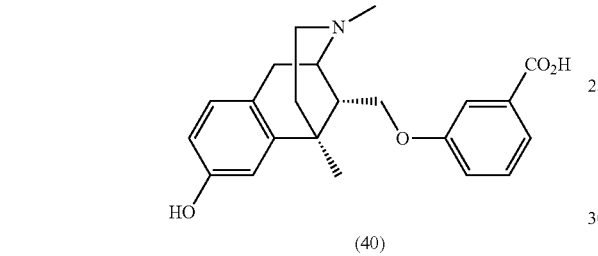

(40)

To a mixture of RA32 (0.316 g, 1.21 mmol, 1.0 eq), ethyl-3-hydroxybenzoate (0.50 g, 3.02 mmol, 2.5 eq), and triphenylphosphine (0.79 g, 3.02 mmol, 2.5 eq) in THF (5.1 mL) at 0° C. was added DEAD (1.40 mL, 3.02 mmol, 2.5 eq). The ice bath was removed and the mixture was stirred for 16 h. H$_2$O was added and the organic portion was extracted twice with EtOAc, dried over Na$_2$SO$_4$ and concentrated. The crude product was purified by flash column chromatography (silica gel, 0-90% EtOAc in hexanes and 0-15% MeOH in DCM) to afford 46 mg of RA36. LC/MS, m/z=410 [M+H]$^+$ (Calc: 409).

To a solution of RA36 (0.046 g, 0.112 mmol, 1.0 eq), in DCM (0.5 mL) at 0° C. was added a solution of boron tribromide (0.043 mL) in DCM (0.10 mL). The ice bath was removed and the mixture was stirred for 16 h at room temperature. It was cooled in an ice bath, slowly neutralized with saturated NaHCO$_3$, concentrated to dryness to afford crude RA37 which was reacted "as is" in the next step. LC/MS, m/z=396 [M+H]$^+$ (Calc: 395).

To a mixture of crude RA37 from the previous step in THF (0.5 mL) was added a solution of NaOH (0.18 g, 0.448 mmol, 4.0 eq) in H$_2$O (0.5 mL). MeOH (0.5 mL) was added and the mixture was stirred for 16 h at room temperature. Additional NaOH (0.18 g, 0.448 mmol, 4.0 eq) was added and the mixture was stirred for 6 h at room temperature. It was neutralized with dilute hydrochloric acid and concentrated to dryness on silica gel and purified by flash chromatography with 0-20% MeOH (1N NH$_3$) in DCM to afford a solid which was triturated with MeOH and dried to afford 14.7 mg of Compound 40 ammonium salt as a white solid.

$^1$H NMR δ$_H$ (300 MHz, D2O) 7.32-7.30 (d, J=7.7 Hz, 1H), 7.23-7.17 (m, 2H), 6.94 (d, J=8.3 Hz, 1H), 6.84 (d, J=8.3 Hz, 1H), 6.72 (s, 1H), 6.64 (d, 8.3 Hz, 1H), 4.20-4.15 (m, 1H), 3.95-3.91 (m, 1H), 3.59-3.52 (t, 10.1 Hz, 1H), 3.04-2.95 (m, 3H), 2.78 (s, 3H), 2.68-2.58 (m, 1H), 2.46-2.39 (m, 1H), 1.91 (t, J=16.9 Hz, 1H), 1.50 (d, J=15.6 Hz, 1H), 1.37 (s, 3H), LC/MS, m/z=368 [M+H]$^+$ (Calc: 367).

Example 32

(6S,11R)-11-(3-(1H-tetrazol-5-yl)phenyl)-8-methoxy-3,6-dimethyl-1,2,3,4,5,6-hexahydro-2,6-methanobenzo[d]azocine (Compound 42); (6R, 11R)-11-(3-(1H-tetrazol-5-yl)phenyl)-8-methoxy-3,6-dimethyl-1,2,3,4,5,6-hexahydro-2,6-methanobenzo[d]azocin-11-ol (Compound 65); and (6R,11S)-11-(3-(1H-tetrazol-5-yl)phenyl)-8-methoxy-3,6-dimethyl-1,2,3,4,5,6-hexahydro-2,6-methanobenzo[d]azocin-11-ol (Compound 66)

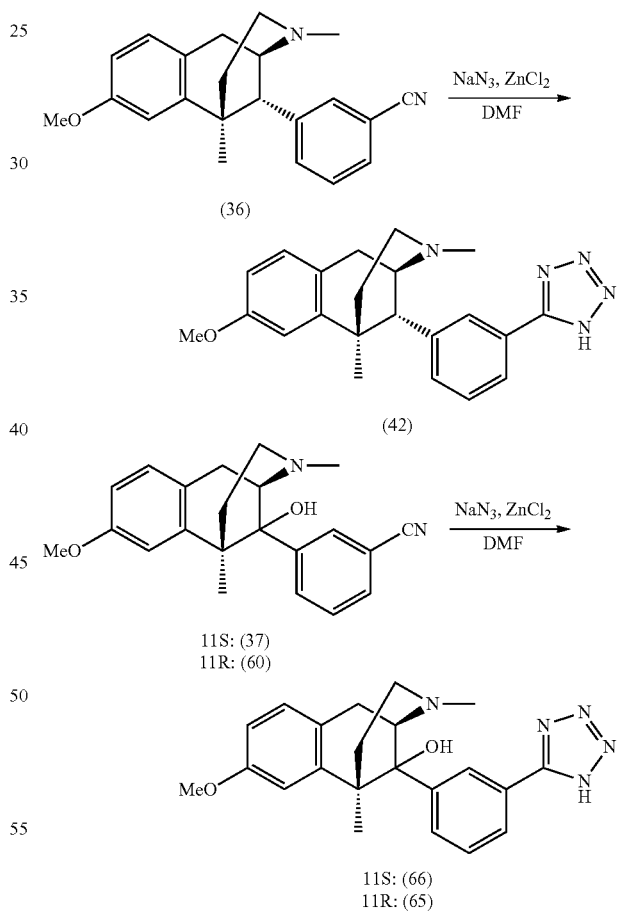

A solution of Compound 36 (33 mg, 0.1 mmol, 1 eq), NaN$_3$ (10 mg, 0.15 mmol, 1.5 eq), and ZnCl$_2$ (20 mg, 0.15 mmol, 1.5 eq) in 0.4 mL DMF was heated at 140° C. for 18 h. The solution was cooled to RT and 2 mL of water was added. The resulting solid was filtered, washed with hexanes and dried under vacuum to yield Compound 42 as a white solid.

$^1$H NMR δ$_H$ (400 MHz, ACN-d3) 8.20 (s, 1H), 8.11 (d, J=7.5 Hz, 1H), 7.73 (d, J=8.1 Hz, 1H), 7.66 (t, J=7.9 Hz, 1H), 7.28 (d, J=8.1 Hz, 1H), 6.86 (d, J=8.1 Hz, 1H), 6.82 (s, 1H), 3.80 (s, 3H), 3.79-3.71 (m, 1H), 3.67 (d, J=15.6 Hz, 1H), 3.41 (d, J=14.7 Hz, 1H), 3.06 (d, J=15.3 Hz, 1H), 2.89 (d, J=13.4 Hz, 1H), 2.82-2.73 (m, 1H), 2.71 (s, 3H), 2.62 (td, J=14.5, 3.8 Hz, 1H), 2.57-2.49 (m, 1H), 0.99 (s, 3H).

LC/MS, m/z=376 [M+H]$^+$ (Calc: 375).

In a similar manner Compound 66 and Compound 65 were prepared from Compound 37 and Compound 60, respectively.

Compound 66

$^1$H NMR δ$_H$ (400 MHz, ACN-d3) 8.45 (s, 1H), 7.98-7.67 (m, 2H), 7.28 (t, J=8.1 Hz, 1H), 7.17 (d, J=8.1 Hz, 1H), 7.08-6.99 (m, 2H), 6.88 (dd, J=8.6, 2.6 Hz, 1H), 3.90-3.83 (m, 1H), 3.85 (s, 3H), 3.19 (d, J=19.5 Hz, 1H), 3.12 (d, J=11.0 Hz, 1H), 2.87 (s, 3H), 2.79-2.49 (m, 3H), 1.55 (s, 3H), 1.40 (d, J=11.0 Hz, 1H).

LC/MS, m/z=392 [M+H]$^+$ (Calc: 391).

Compound 65

$^1$H NMR δ$_H$ (400 MHz, ACN-d3) 8.53 (s, 1H), 8.12 (d, J=8.3 Hz, 1H), 7.67 (t, J=2.9 Hz, 1H), 7.16 (d, J=8.3 Hz, 1H), 6.97 (d, J=2.6 Hz, 1H), 6.85 (dd, J=8.3, 2.6 Hz, 1H), 3.95 (bs, 1H), 3.79 (s, 3H), 3.80-3.77 (m, 1H), 3.58 (dd, J=21.0, 6.8 Hz, 1H), 3.25 (d, J=18.9 Hz, 2H), 2.81 (s, 3H), 2.78-2.67 (m, 2H), 1.80-1.69 (m, 2H), 1.68 (s, 3H).

LC/MS, m/z=392 [M+H]$^+$ (Calc: 391).

Example 33

(1S)-1-(5-chloro-6-((((6S,11R)-8-hydroxy-3,6-dimethyl-1,2,3,4,5,6-hexahydro-2,6-methanobenzo[d]azocin-11-yl)methoxy)pyridin-3-yl)ethane-1,2-diol (Compound 43)

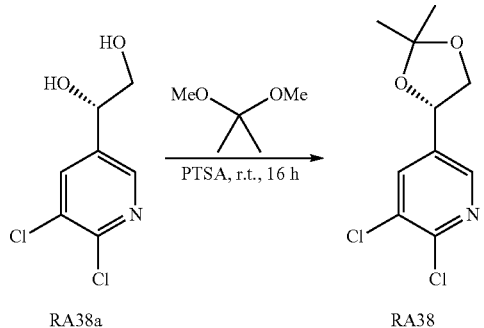

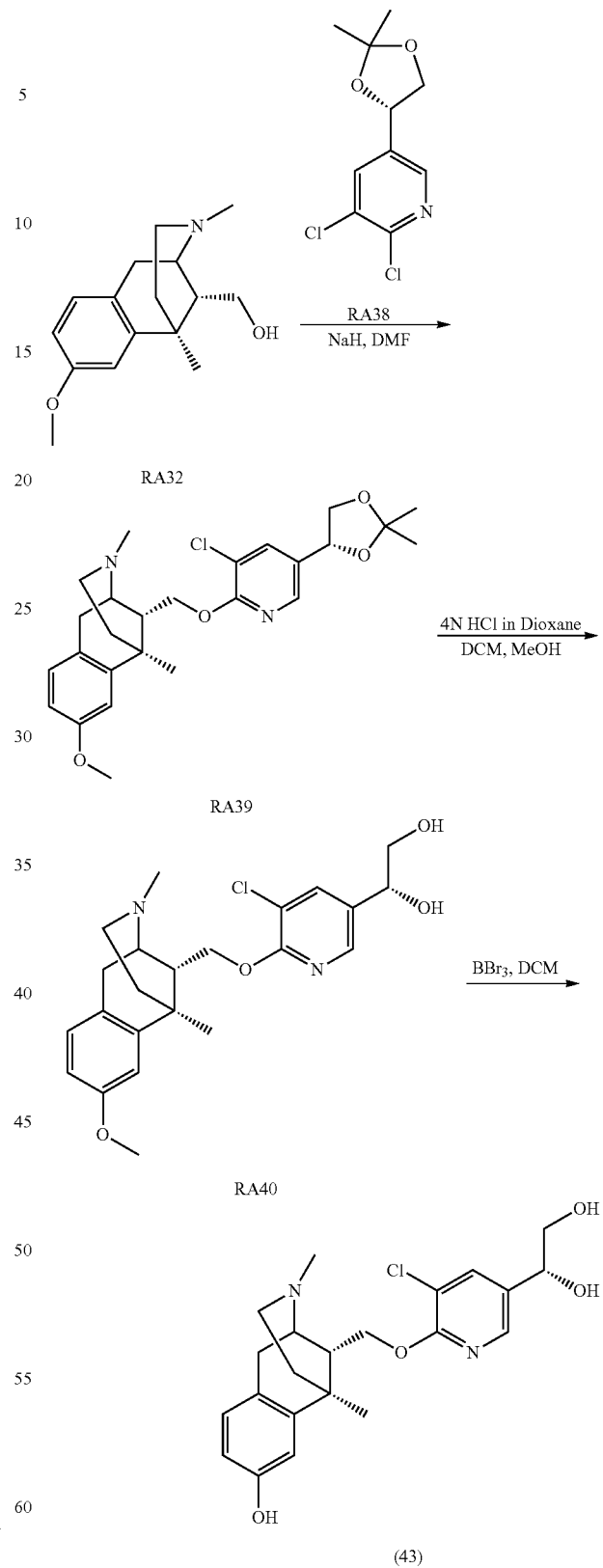

Into a flask containing a mixture of RA38a ((1.00 gm, 4.81 mmol) in 2,2-dimethoxypropane (9.8 ml) at room temperature was added paratoluenesulfonic acid mono hydrate (0.09 gm, 0.481 mmol). The solution was stirred for 16 hours at room temperature then cooled down with an ice bath and quenched with saturated aqueous sodium bicarbonate and extracted with ethyl acetate. The organic layer was separated, washed with brine, dried over sodium sulfate and concentrated to afford RA38) (99% yield, 1.18 gm) as an oil.

To a solution of RA32 (0.05 g, 0.192 mmol, 1.0 eq), in DMF (0.4 mL) at room temperature was added 60% sodium hydride in mineral oil (0.011 g, 0.287 mmol, 1.5 eq). The mixture was stirred for 45 min at room temperature and then it was cooled with an ice bath and a solution of RA38 (0.095 g, 0.384 mmol, 2.0 eq) in DMF (0.5 mL) was added and the mixture stirred for 16 h at room temperature. H$_2$O was added and the organic portion was extracted twice with EtOAc, dried over Na$_2$SO$_4$ and concentrated. The crude product was purified by flash chromatography (silica gel, 0-7% MeOH in DCM) to afford 70 mg of RA39. LC/MS, m/z=473 [M+H]$^+$ (Calc: 472).

To a solution of RA39 (0.025 g, 0.0529 mmol, 1.0 eq) in DCM (0.12 mL) and MeOH (0.02 mL) was added 4N HCl in dioxane (0.07 mL, 0.265 mmol, 5.0 eq). The solution was stirred for 16 h at room temperature and then concentrated to dryness to afford RA40 which was used "as is" in the next step. LC/MS, m/z=433 [M+H]$^+$ (Calc: 432).

A solution of RA40 (0.023 gm, 0.045 mmol, 1.0 eq) was dissolved in DCM (0.2 mL), cooled with an ice bath and treated with boron tribromide (0.018 mL, 0.182 mmol, 4.0 eq). The ice bath was removed and the mixture was stirred for 16 h at room temperature. It was quenched with H$_2$O and neutralized with solid NaHCO$_3$, concentrated to dryness and purified by flash chromatography (silica gel, 0-10% MeOH (1N NH$_3$) in DCM) to afford 4.3 mg of Compound 43: $^1$H NMR $\delta_H$ (300 MHz, CD$_3$OD) 7.88 (s, 1H), 7.68 (s, 1H), 6.85 (d, J=8.3 Hz, 1H), 6.62 (s, 1H), 6.50 (dd, J=2.6, 8.3 Hz, 1H), 4.52 (t, J=5.9 Hz, 1H), 4.49-4.44 (m, 1H), 3.92 (t, J=10.7 Hz, 1H), 3.55-3.46 (m, 2H), 3.30-3.27 (m, 1H), 3.25 (s, 1H), 2.97 (d, J=18.6 Hz, 1H), 2.59 (dd, J=5.9, 18.4 Hz, 1H), 2.39 (dd, J=5.3, 12.1 Hz, 1H), 2.33 (s, 3H), 2.31 (m, 1H), 2.09 (td, J=3.1, 12.5 Hz, 1H), 1.80 (td, J=4.6, 12.7 Hz, 1H), 1.38 (s, 3H), 1.27 (d, 14.2 Hz, 1H) LC/MS, m/z=419 [M+H]$^+$ (Calc: 418).

Example 34

4-(((6S,11S)-8-hydroxy-3,6-dimethyl-1,2,3,4,5,6-hexahydro-2,6-methanobenzo[d]azocin-11-yl)methoxy)benzamide (Compound 44)

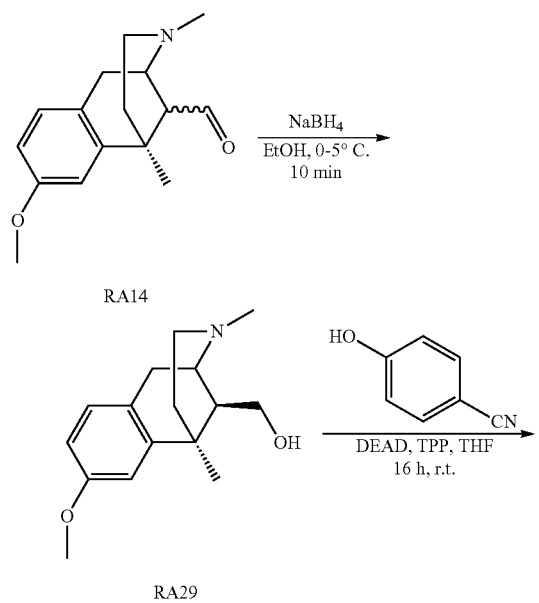

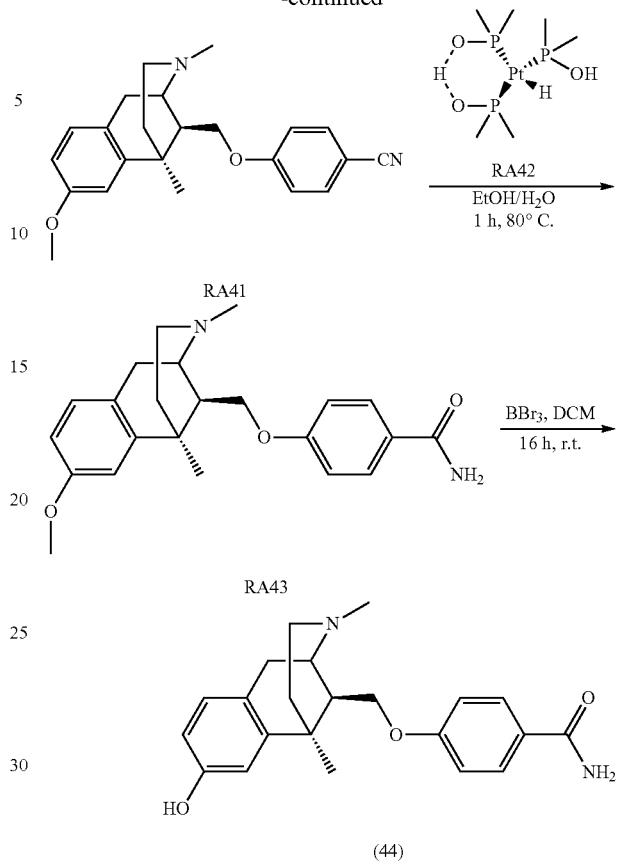

To a solution of RA14 (3.34 g, 12.85 mmol, 1.0 eq) in EtOH (36 mL) at 0° C. was added NaBH$_4$ (0.53 g, 14.13 mmol, 1.1 eq). The mixture was stirred for 10 min, H$_2$O (10 mL) was added, the EtOH was removed under reduced pressure and the organic portion was extracted with DCM, dried over Na$_2$SO$_4$ and concentrated to 2.6 g of a light yellow solid as a mixture of diastereomers which was purified by flash column chromatography (silica gel, 5-25% MeOH (1N NH$_3$)/DCM) to afford 0.8 g of RA29 as the less polar isomer.

$^1$H NMR $\delta_H$ (300 MHz, (CD$_3$)$_2$SO) 7.02 (d, J=8.3 Hz, 1H), 6.82 (d, J=2.6 Hz, 1H), 6.70 (dd, J=2.6, 8.3 Hz, 1H), 4.63 (brs, 1H), 3.87-3.82 (m, 1H), 3.74 (d, J=4.6 Hz, 1H), 3.70 (s, 3H), 3.22-3.16 (m, 1H), 3.09 (d, J=18.0 Hz, 1H), 2.57-2.49 (m, 1H), 2.32-2.26 (m, 1H), 2.25 (s, 3H), 1.92-1.77 (m, 1H), 1.62-1.56 (m, 1H), 1.33 (s, 3H), 1.08 (d, J=11.2 Hz, 1H), LC/MS, m/z=262 [M+H]$^+$ (Calc: 261).

To a mixture of RA29 (0.100 g, 0.383 mmol, 1.0 eq), 4-cyanophenol (0.114 g, 0.958 mmol, 2.5 eq), and triphenylphosphine (0.251 g, 0.958 mmol, 2.5 eq) in THF (1.3 mL) at 0° C. was added DEAD (0.17 g, 0.958 mmol, 2.5 eq). The ice bath was removed and the mixture was stirred for 16 h. H$_2$O was added and the organic portion was extracted twice with EtOAc, dried over Na$_2$SO$_4$ and concentrated to 0.72 g of a crude mixture which was purified by flash column chromatography (silica gel, 5-60% EtOAc in hexanes) to afford 0.038 g of RA41.

LC/MS, m/z=363 [M+H]$^+$ (Calc: 362).

To a suspension of RA41 (0.015 g, 0.0414 mmol, 1.0 eq) in ethanol (0.4 mL) was added RA42 0.002 g, 0.0041 mmol, 0.10 eq) and H$_2$O (0.1 mL). The mixture was stirred for 1 h at 80° C. and concentrated to dryness to afford RA43. LC/MS, m/z=381 [M+H]+ (Calc: 380).

A solution of RA43 (0.015 g, 0.039 mmol, 1.0 eq) in DCM (0.16 mL), cooled with an ice bath was treated with boron tribromide (0.015 mL, 0.156 mmol, 4.0 eq). The ice bath was removed and the mixture was stirred for 16 h at room temperature. It was quenched with $H_2O$, neutralized with solid $NaHCO_3$, concentrated to dryness and purified by flash chromatography (silica gel, 0-10% MeOH (1N NH3) in DCM) to afford 4.0 mg of Compound 44. $^1$H NMR $\delta_H$ (300 MHz, CD3OD) 7.76 (d, J=9.0 Hz, 2H), 6.95 (d, J=9.0 Hz, 2H), 6.86 (d, J=8.3 Hz, 1H), 6.71 (d, J=2.6 Hz, 1H), 6.51 (dd, J=2.6, 8.3 Hz, 1H), 4.38-4.28 (m, 2H), 3.38 (m, 1H), 3.14 (d, J=17.8 Hz, 1H), 2.68 (dd, J=6.1, 18.8 Hz, 1H), 2.40 (m, 1H), 2.32 (s, 3H), 2.15 (m, 1H), 2.18 (m, 1H), 1.91 (td, J=4.6, 13.2 Hz, 1H), 1.33 (s, 3H), 1.18 (d, J=12.1 Hz, 1H), LC/MS, m/z=367 [M+H]+ (Calc: 366).

Example 35

4-(3-(((2R,6R,11S)-8-hydroxy-3,6-dimethyl-1,2,3,4,5,6-hexahydro-2,6-methanobenzo[d]azocin-11-yl)-3-methylureido)benzoic Acid (Compound 45); 4-(3-42R,6R,11R)-8-hydroxy-3,6-dimethyl-1,2,3,4,5,6-hexahydro-2,6-methanobenzo[d]azocin-11-yl)-3-methylureido)benzoic Acid (Compound 46); and 3-(3-((2R,6R,11S)-8-hydroxy-3,6-dimethyl-1,2,3,4,5,6-hexahydro-2,6-methanobenzo[d]azocin-11-yl)-3-methylureido)propanoic Acid (Compound 68)

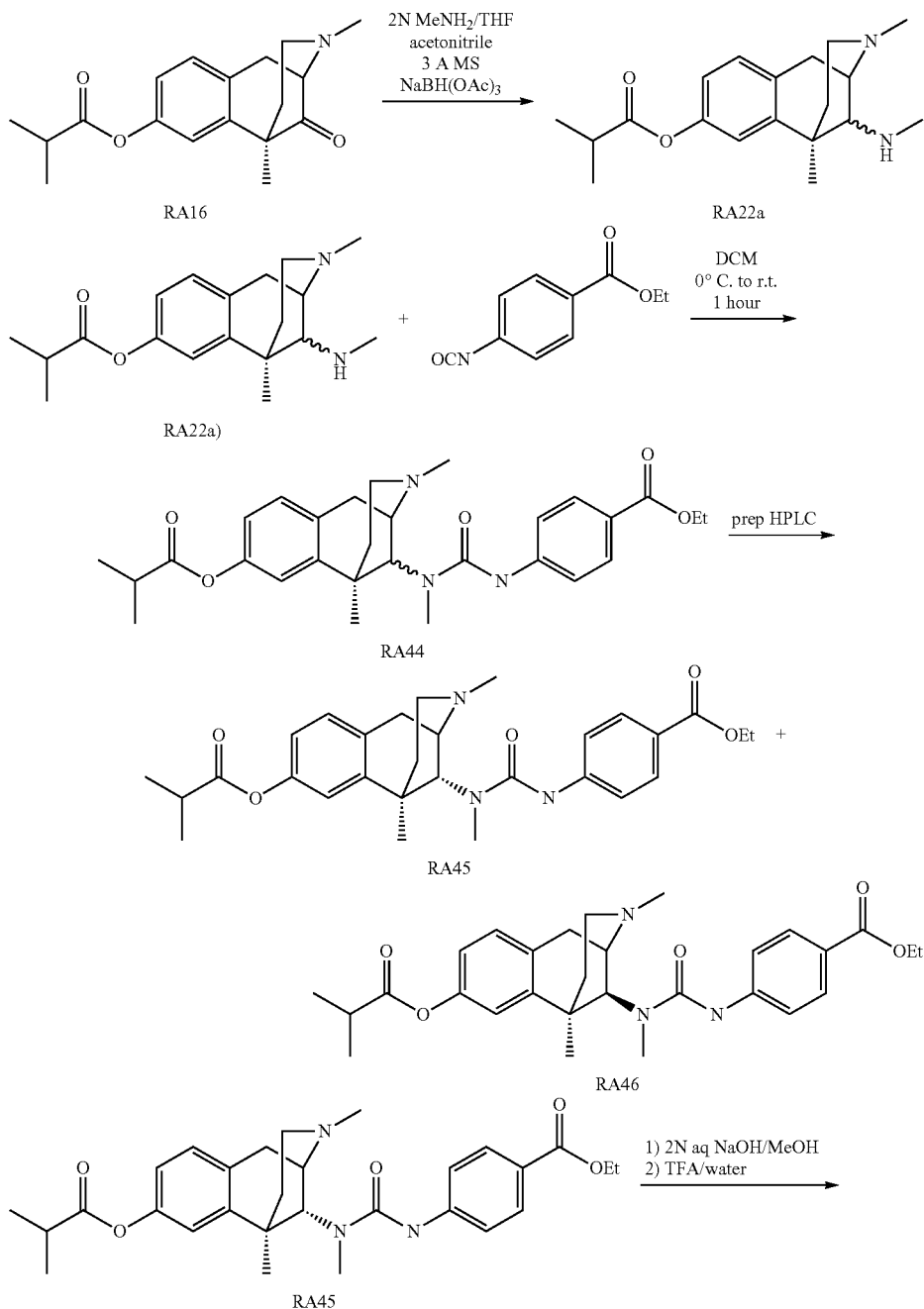

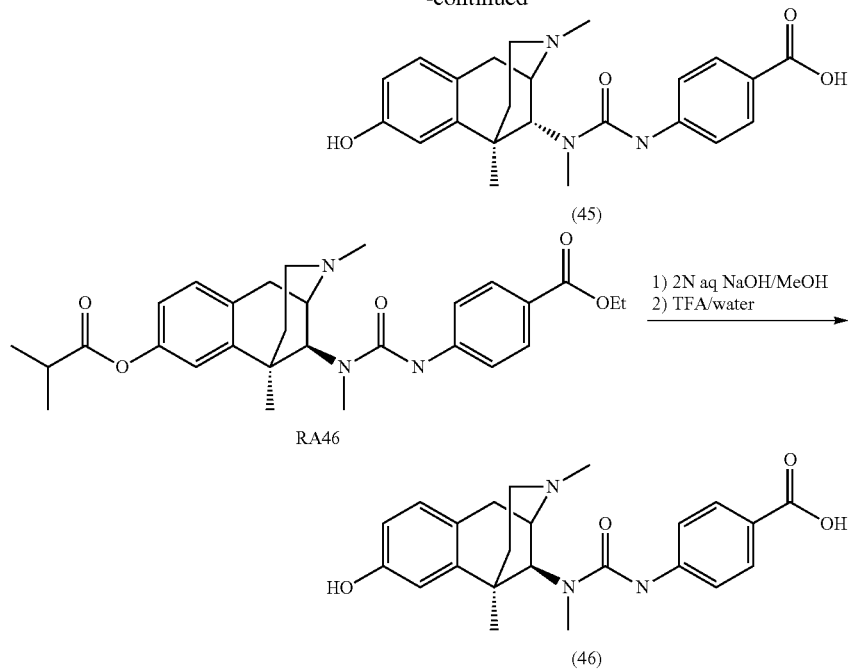

(45)

RA46

1) 2N aq NaOH/MeOH
2) TFA/water (46)

11,11-dihydroxy-3,6-dimethyl-1,2,3,4,5,6-hexahydro-2,6-methanobenzo[d]azocin-8-yl isobutyrate (RA16) (0.300 g, 0.940 mmol, 1 eq) was dissolved in dry ACN (3 mL) and 2N methylamine in THF (1.41 mL, 2.82 mmol, 3 eq) was added dropwise to the solution at room temperature. The mixture was shaken with 3 Å molecular sieves for 2 h at room temperature. Then, solid sodium triacetoxyborohydride (0.837 g, 3.95 mmol) was added in one portion. The mixture was shaken for 16 h at room temperature. The reaction mixture was quenched with 1 mL water and extracted with 2×6 mL DCM. The organic layers were combined, dried over $Na_2SO_4$, and concentrated under reduced pressure to provide 270 mg of crude RA22a as a dark gum.

LC/MS, m/z=317 $[M+H]^+$ (Calc: 316).

RA22a (50 mg, 0.157 mmol) was dissolved in DCM (3 mL) and cooled in a brine/ice bath. Ethyl 4-isocyanatobenzoate (30 mg, 0.157 mmol) was dissolved in DCM (1 mL) and added dropwise to the cooled solution. The bath was removed and the reaction mixture stirred for 1 h. The mixture was quenched with water (1 mL) and extracted with DCM (3 mL). The organic layer was dried over $Na_2SO_4$ and concentrated to give 52 mg of RA44. The crude residue was chromatographed by prep HPLC to give RA45 and R46. RA45 and RA46 were each dissolved in MeOH (3 mL) and hydrolyzed by adding 2N aq NaOH (0.5 mL) to the solutions and stirring for 16 h at room temperature. The reaction mixtures were concentrated to dryness and redissolved in 2 mL water. The solutions were cooled in an ice bath and acidified with TFA (2 mL) added dropwise. The acid solutions were chromatographed by prep HPLC to give Compound 45 TFA salt and Compound 46 TFA salt as brown oils.

Compound 45 TFA Salt $^1$H NMR $\delta_H$ (400 MHz, $CD_3OD$) 7.98-7.90 (m, 2H), 7.61-7.52 (m, 2H), 7.14-7.07 (m, 1H), 6.89-6.81 (m, 1H), 6.78-6.70 (m, 1H), 4.69-4.61 (m, 1H), 3.88-3.80 (m, 1H), 3.39-3.34 (m, 1H), 3.27-3.15 (m, 1H), 2.97 (s, 3H), 2.79 (s, 3H), 2.77-2.66 (m, 1H), 2.18-2.00 (m, 1H), 1.77-1.68 (m, 1H), 1.56 (s, 3H).

LC/MS, m/z=410 $[M+H]^+$ (Calc: 409);

Compound 46 TFA Salt $^1$H NMR $\delta_H$ (400 MHz, $CD_3OD$) 8.01-7.93 (m, 2H), 7.64-7.55 (m, 2H), 7.12-7.04 (m, 1H), 6.84-6.78 (m, 1H), 6.74-6.69 (m, 1H), 4.15-4.11 (m, 1H), 3.95-3.90 (m, 1H), 3.50-3.40 (m, 2H), 3.38-3.20 (m, 4H), 2.95 (s, 3H), 2.83-2.73 (m, 1H), 2.51-2.39 (m, 1H), 1.57 (s, 3H), 1.55-1.46 (m, 1H).

LC/MS, m/z=410 $[M+H]^+$ (Calc: 409).

3-(3-(((2R,6R,11S)-8-hydroxy-3,6-dimethyl-1,2,3,4,5,6-hexahydro-2,6-methanobenzo[d]azocin-11-yl)-3-methylureido)propanoic Acid (Compound 68)

(68)

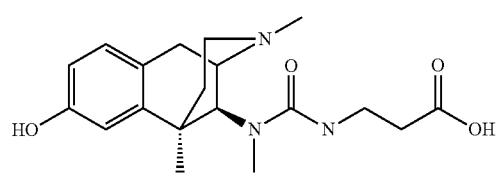

In a similar manner, 3-(3-((2R,6R,11S)-8-hydroxy-3,6-dimethyl-1,2,3,4,5,6-hexahydro-2,6-methanobenzo[d]azocin-11-yl)-3-methylureido)propanoic acid (Compound 68) was prepared from RA22a (86 mg, 0.272 mmol) using ethyl 3-isocyanatopropionate (39 mg, 0.272 mmol) rather than ethyl 4-isocyanatobenzoate. Purification by preparatory HPLC gave Compound 68 TFA salt as a brown oil.

$^1$H NMR $\delta_H$ (400 MHz, $CD_3OD$) 7.12-7.03 (m, 1H), 6.84-6.78 (m, 1H), 6.76-6.68 (m, 1H), 4.61-4.52 (m, 1H), 3.76-3.65 (m, 1H), 3.52-3.37 (m, 2H), 3.29-2.99 (m, 4H), 2.98-2.89 (m, 2H), 2.75-2.61 (m, 1H), 2.59-2.48 (m, 5H), 2.13-1.99 (m, 1H), 1.73-1.60 (m, 1H), 1.46 (s, 3H)
LC/MS, m/z=362 [M+H]⁺ (Calc: 361).

2-(3-(((2R,6S,11S)-8-hydroxy-3,6-dimethyl-1,2,3,4,5,6-hexahydro-2,6-methanobenzo[d]azocin-11-yl)-3-methylureido)-4-methylpentanoic Acid (Compound 76)

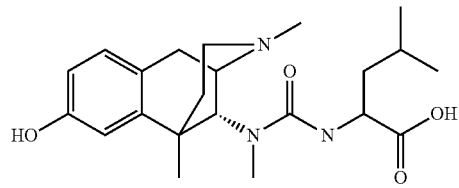
(76)

In a similar manner, Compound 76 was prepared from RA22a (396 mgs, 1.25 mmol) using ethyl 2-isocyanato-4-methylvalerate (278 mgs, 1.5 mmol) rather than ethyl 4-isocyanatobenzoate. Purification by preparatory HPLC gave Compound 76 TFA salt as a brown oil.
¹H NMR δ_H (400 MHz, CD3OD) 7.04-6.95 (m, 1H), 6.76-6.69 (m, 1H), 6.67-6.60 (m, 1H), 4.53-4.44 (m, 1H), 4.32-4.23 (m, 1H), 3.64-3.57 (m, 1H), 3.23-3.19 (m, 2H), 3.11-2.98 (m, 3H), 2.86-2.81 (m, 3H), 2.59-2.49 (m, 4H), 1.71-1.50 (m, 1H), 1.43-1.34 (m, 3H), 0.92-0.81 (m, 6H).
LC/MS, m/z=404 [M+H]⁺ (Calc: 403).

Example 36

2-(((2R,6R,11S)-8-hydroxy-3,6-dimethyl-1,2,3,4,5,6-hexahydro-2,6-methanobenzo[d]azocin-11-yl)(methyl)carbamoyl)benzoic Acid (Compound 49)

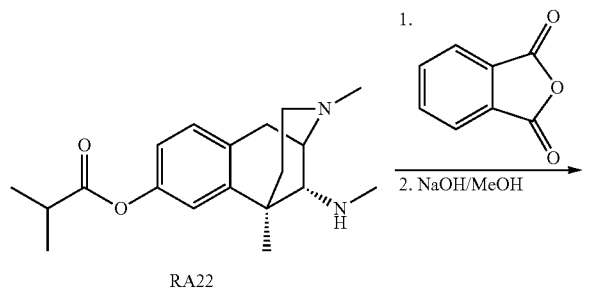

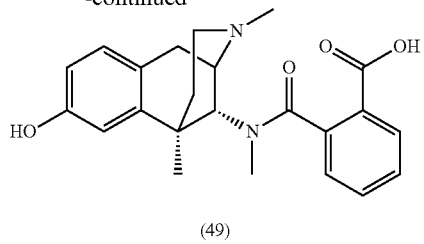
(49)

In a similar manner, Compound 49 was prepared following the procedure for Compound 24 using phthalic anhydride (Aldrich) instead of succinic anhydride. Compound 49 was purified by reverse-phase prep HPLC (C18, 0-100% 0.1% TFA in water/0.1% TFA in ACN) as TFA-salt (20 mg, white solid). ¹H NMR δ_H (400 MHz, CD₃OD) 7.99 (d, J=7.9 Hz, 1H), 7.59 (dt, J=1.3 and 7.9 Hz, 1H), 7.45 (dt, J=1.3 and 7.9 Hz, 1H), 7.22 (d, J=7.7 Hz, 1H), 6.97 (d, J=8.1 Hz, 1H), 6.73 (d, J=2.4 Hz, 1H), 6.61 (dd, J=2.4 and 8.3 Hz, 1H), 3.96-4.01 (m, 1H), 3.23-3.31 (m, 1H), 2.98-3.18 (m, 3H), 2.91 (s, 3H), 2.64-2.72 (m, 1H), 2.36 (s, 3H), 2.02-2.08 (m, 1H), 1.64-1.68 (m, 1H), 1.52 (s, 3H); LC/MS, m/z=395.2 [M+H]⁺ (Calc: 394.5).

Example 37

2-(4-(((2R,6R,11S)-8-hydroxy-3,6-dimethyl-1,2,3,4,5,6-hexahydro-2,6-methanobenzo[d]azocin-11-yl)amino)phenyl)ethanesulfonamide (Compound 58); 2-(4-(((2R,6R,11S)-8-hydroxy-3,6-dimethyl-1,2,3,4,5,6-hexahydro-2,6-methanobenzo[d]azocin-11-yl)amino)phenyl)ethanesulfonamide (Compound 50); and 2-(4-(((2R,6R,11S)-8-hydroxy-3,6-dimethyl-1,2,3,4,5,6-hexahydro-2,6-methanobenzo[d]azocin-11-yl)(methyl)amino)phenyl)ethanesulfonamide (Compound 51)

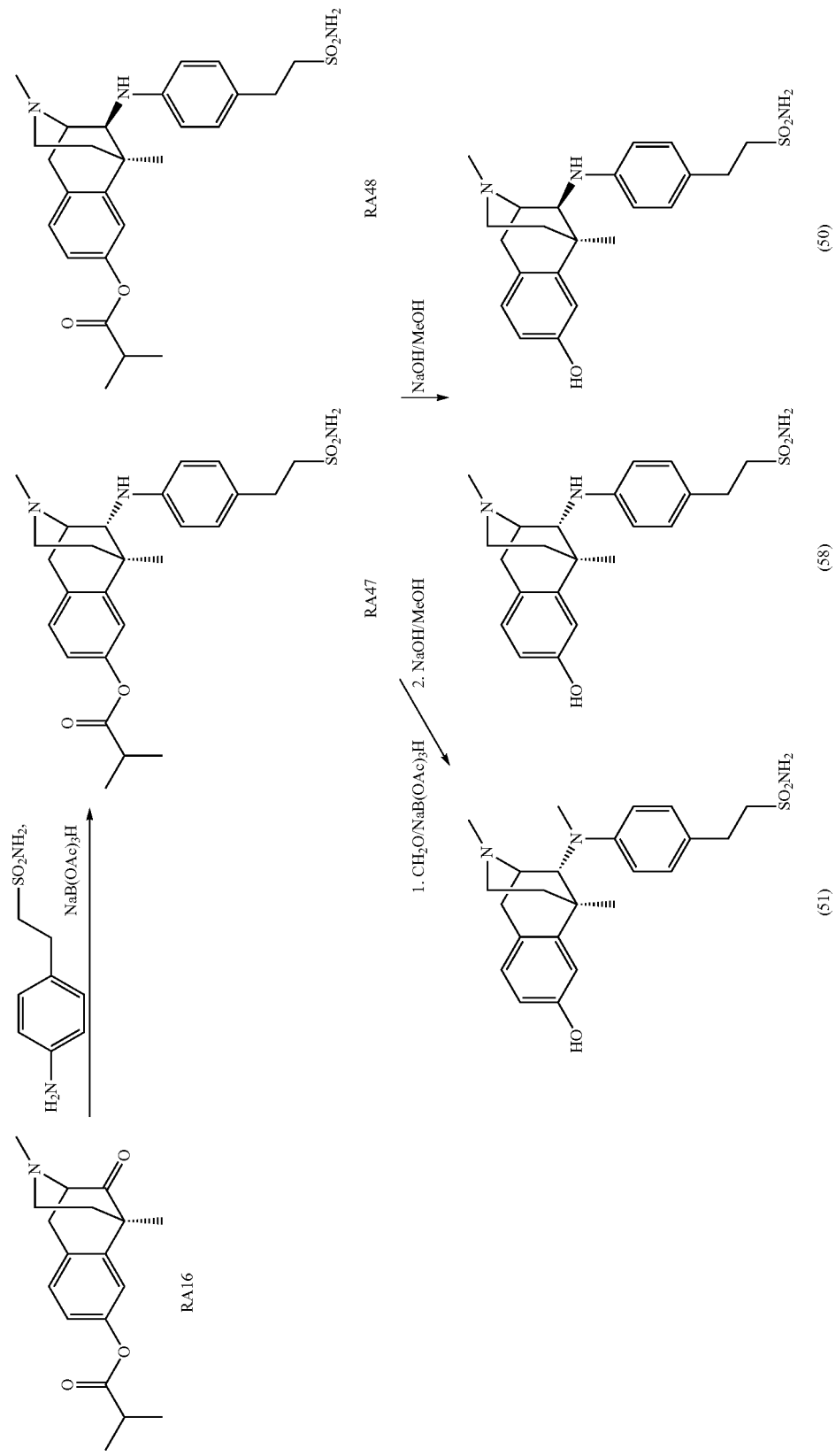

In a similar manner Compound 58 and Compound 50 were prepared following the procedure for Compound 30 sing 4-(2-aminoethyl)benzenesulfonamide (0.9 mmol, Aldrich) instead of 1-Boc-4-(aminomethyl)piperidine.

Compound 58 (white solid, 15 mg, RT 0.845 min): $^1$H NMR $\delta_H$ (400 MHz, CD$_3$OD) 7.76 (d, J=8.3 Hz, 2H), 7.35 (d, J=8.3 Hz, 2H), 7.02 (d, J=8.6 Hz, 1H), 6.74 (d, J=2.4 Hz, 1H), 6.7 (dd, J=2.4 and 8.3 Hz, 1H), 4.16 (s, 1H), 3.64 (s, 1H), 3.22-3.28 (m, 3H), 3.0-3.16 (m, 3H), 2.92 (s, 3H), 2.64-2.72 (m, 1H), 2.02-2.08 (m, 1H), 1.65 (d, J=12.5 Hz, 1H), 1.56 (s, 3H); LC/MS, m/z=416.2 [M+H]$^+$ (Calc: 415.6).

Compound 50 (white solid, 12 mg, RT 2.081 min): $^1$H NMR $\delta_H$ (400 MHz, CD$_3$OD) 7.77 (d, J=8.6 Hz, 2H), 7.38 (d, J=8.3 Hz, 2H), 6.94 (d, J=8.6 Hz, 1H), 6.73 (d, J=2.4 Hz, 1H), 6.58 (dd, J=2.4 and 8.3 Hz, 1H), 3.68 (s, 1H), 3.24-3.28 (m, 1H), 2.88-3.16 (m, 7H), 2.69 (s, 3H), 2.52-2.56 (m, 1H), 2.08-2.36 (m, 1H), 1.34 (s, 3H), 1.29 (d, J=13.5 Hz, 1H); LC/MS, m/z=416.2 [M+H]$^+$ (Calc: 415.6).

In a similar manner Compound 51 was prepared following the procedure for Compound 31. Compound 51 was purified by reverse-phase prep HPLC (C18, 0-100% 0.1% TFA in water/0.1% TFA in ACN), and obtained as a TFA-salt, white solid, 10 mg.

Compound 51: $^1$H NMR $\delta_H$ (400 MHz, CD$_3$OD) 7.68 (d, J=8.5 Hz, 2H), 7.16 (d, J=8.3 Hz, 2H), 6.89 (d, J=8.6 Hz, 1H), 6.65 (d, J=2.4 Hz, 1H), 6.58 (dd, J=2.4 and 8.3 Hz, 1H), 3.68 (s, 1H), 3.24-3.28 (m, 1H), 2.88-3.16 (m, 7H), 2.69 (s, 3H), 2.52-2.56 (m, 1H), 2.08-2.36 (m, 1H), 1.34 (s, 3H), 1.29 (d, J=13.5 Hz, 1H); LC/MS, m/z=430.2 [M+H]$^+$ (Calc: 429.6).

Example 38

4-(((6S,11R)-8-hydroxy-3,6-dimethyl-1,2,3,4,5,6-hexahydro-2,6-methanobenzo[d]azocine-11-carboxamido)benzoic Acid (Compound 52)

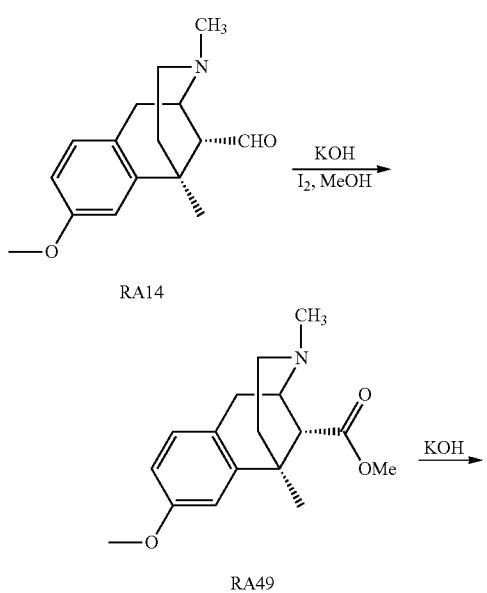

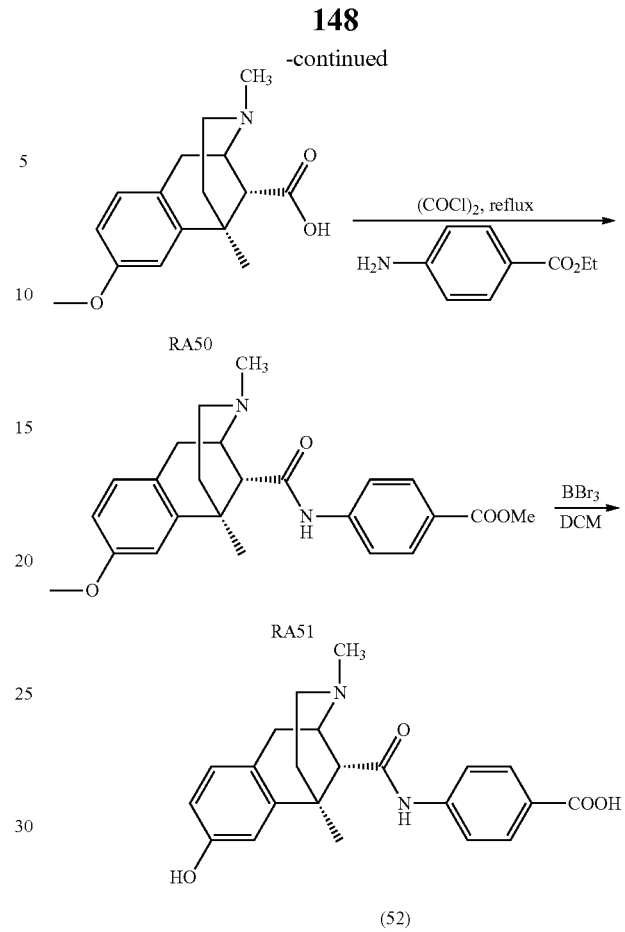

Compound RA14 ((600 mg, 2.32 mmol) was dissolved in MeOH (10 mL) and a solution of KOH (2.6 eq, 336 mg, 6.0 mmol) and iodine (1.3 eq, 766 mg, 3.0 mmol) in MeOH (each 2 mL) was successively added at RT. After 2 h, the solution was neutralized to pH=7 using AcOH. The mixture was diluted with DCM (50 mL), washed with 10% Na$_2$S$_2$O$_3$ (20 mL) and brine, dried over Na$_2$SO$_4$, and concentrated. The reside was purified by flash column chromatography (silica gel, 0-50% EtOAc/hexanes) to give 536 mg of RA49 as an oil.

$^1$H NMR $\delta_H$ (400 MHz, MeOD) 7.04 (d, J=8.33 Hz, 1H), 6.84 (d, J=2.63 Hz, 1H), 6.76 (dd, J=2.63 and 8.33 Hz, 1H), 3.78 (s, 3H), 3.73 (m, 1H), 3.62 (s, 3H), 3.13 (m, 1H), 3.01 (m, 1H), 2.79 (dd, J=3.73 and 12.28 Hz, 1H), 2.44 (dt, J=3.51 and 12.93 Hz, 1H), 1.88-1.98 (m, 2H), 1.57 (s, 3H), 1.47 (m, 1H).

LC/MS, m/z=290 [M+H]$^+$ (Calc: 289).

Compound RA49 (200 mg, 0.69 mmol) was dissolved in MeOH (4 mL) and then aq. KOH (2 N, 2 mL) was added. The resulting mixture was stirred at RT for 2 h, neutralized with aq HCl (1N) to pH=3, and diluted with DCM (50 mL). The organic layer was washed with brine, dried over Na$_2$SO$_4$, and concentrated to give RA50. The residue was used directly in the next step.

LC/MS, m/z=276 [M+H]$^+$ (Calc: 275).

In a similar manner to Compound 32, Compound 52 was prepared using RA50 rather than RA26. Purification by reverse phase column chromatography (C18, ACN/water with 0.1% TFA, 0-95%) gave Compound 52 TFA salt as a white powder.

¹H NMR δ_H (400 MHz, MeOD) 7.85 (m, 2H), 7.51 (m, 2H), 6.93 (m, 2H), 6.69 (d, J=2.41 Hz, 1H), 6.58 (dd, J=2.41 and 8.55 Hz, 2H), 4.02 (m, 1H), 2.91-3.17 (m, 4H), 2.89 (s, 3H), 2.72 (m, 1H), 1.92 (m, 1H), 1.57 (d, J=14.25 Hz, 1H), 1.48 (s, 3H).

LC/MS, m/z=381 [M+H]⁺ (Calc: 380).

Example 39

2-((((6S,11R)-8-hydroxy-3,6-dimethyl-1,2,3,4,5,6-hexahydro-2,6-methanobenzo[d]azocin-11-yl)methoxy)isonicotinamide (Compound 53)

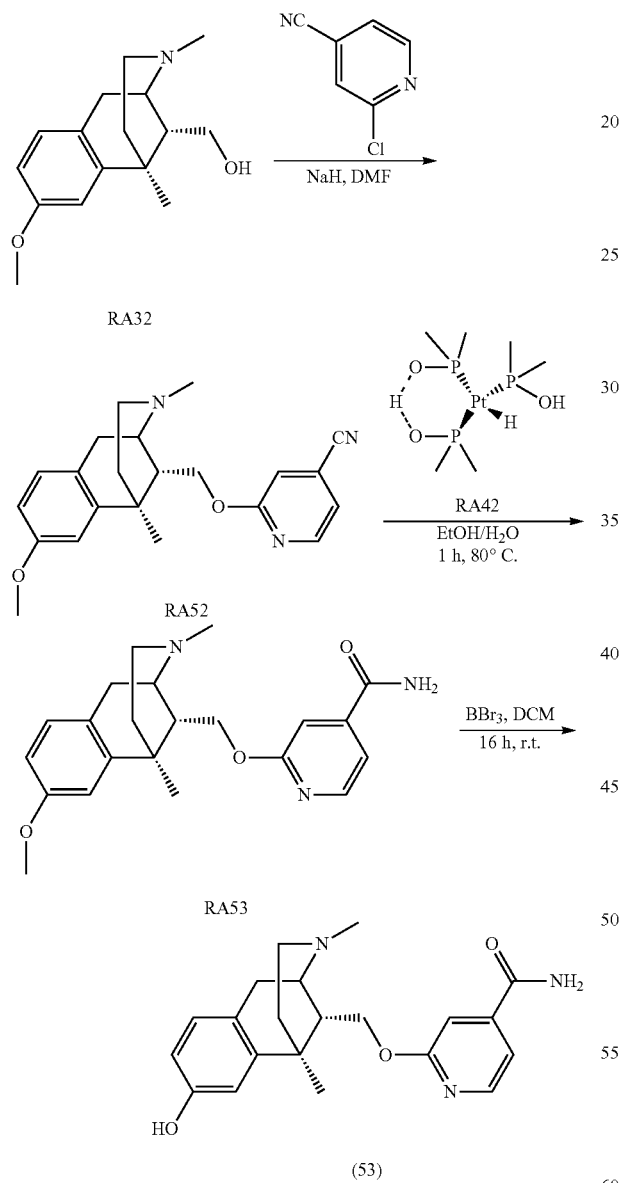

To a solution of RA32 (0.05 g, 0.192 mmol, 1.0 eq), in DMF (0.4 mL) at room temperature was added 60% sodium hydride in mineral oil (0.011 g, 0.287 mmol, 1.5 eq). The mixture was stirred for 45 min at room temperature and then it was cooled with an ice bath and a solution of 2-chloroisonicotinonitrile (0.053 g, 0.384 mmol, 2.0 eq) in DMF (0.4 mL) was added and the mixture was stirred for 1 h at room temperature. H₂O was added and the organic portion was extracted twice with EtOAc, dried over Na₂SO₄ and concentrated. The crude product was purified by flash chromatography (silica gel, 0-10% MeOH in DCM) to afford 58 mg of RA52. LC/MS, m/z=364 [M+H]⁺ (Calc: 363).

To a suspension of RA52 (0.042 g, 0.116 mmol, 1.0 eq) in ethanol (1.1 mL) was added RA42 (0.005 g, 0.012 mmol, 0.10 eq) and H₂O (0.3 mL). The mixture was stirred for 1.5 h at 80° C. and concentrated to dryness to afford RA53. LC/MS, m/z=382 [M+H]⁺ (Calc: 381).

A solution of RA53 (0.044 g, 0.115 mmol, 1.0 eq) in DCM (0.80 mL), cooled with an ice bath was treated with boron tribromide (0.045 mL, 0.461 mmol, 4.0 eq). The ice bath was removed and the mixture stirred for 16 h at room temperature. It was quenched with H₂O, neutralized with solid NaHCO₃, concentrated to dryness and purified by flash chromatography (silica gel, 0-10% MeOH (1N NH₃) in DCM) to afford 15 mg of Compound 53. ¹H NMR δ_H (300 MHz, CD₃OD) 8.08 (d, J=5.3 Hz, 1H), 7.19 (dd, J=1.3, 5.3 Hz, 1H), 7.08 (s, 1H), 6.84 (d, J=8.3 Hz, 1H), 6.62 (d, J=2.6 Hz, 1H), 6.50 (dd, J=2.6, 1.5 Hz 1H), 4.45-4.40 (m, 1H), 3.89 (t, J=10.1 Hz, 1H), 3.26 (m, 1H), 2.96 (d, J=18.6 Hz, 1H), 2.59 (dd, J=5.9, 18.6 Hz, 1H), 2.39 (dd, J=3.3, 12.3 Hz, 1H), 2.33 (s, 3H), 2.32-2.27 (m, 1H), 2.09 (td, J=3.1, 12.5 Hz, 1H), 1.79 (td, J=5.9, 14.0 Hz, 1H), 1.38 (s, 3H), 1.27 (d, J=11.8 Hz, 1H), LC/MS, m/z=368 [M+H]⁺ (Calc: 367).

Example 40

(2S)-1-(2-(((6S,11R)-8-hydroxy-3,6-dimethyl-1,2,3,4,5,6-hexahydro-2,6-methanobenzo[d]azocin-11-yl)acetyl)pyrrolidine-2-carboxylic Acid (Compound 55); and 1-(2-((6S,11R)-8-hydroxy-3,6-dimethyl-1,2,3,4,5,6-hexahydro-2,6-methanobenzo[d]azocin-11-yl)acetyl)piperidine-4-carboxylic Acid (Compound 72)

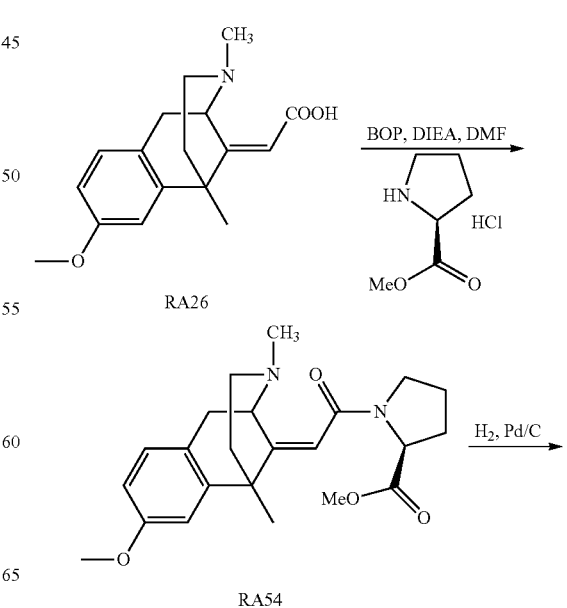

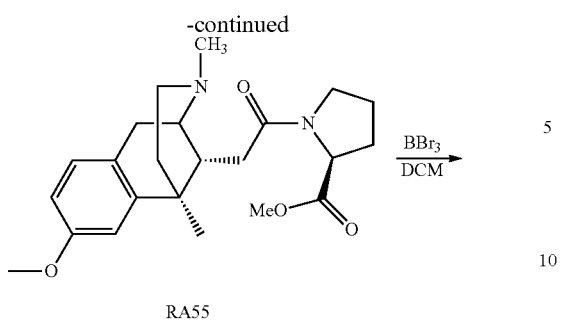

RA55

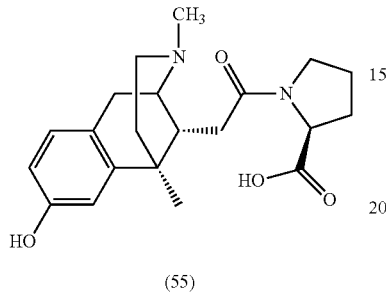

(55)

To a solution of RA26 (200 mg, 0.70 mmol) in DMF (4 mL) were added benzotriazol-1-yloxy-tri(dimethylamino)phosphonium hexafluorophosphate (BOP, 354 mg, 1.2 eq, 0.84 mmol), DIEA (1 mL) and (S)-methylpyrrolidine-2-carboxylate hydrochloride (116 mg, 0.7 mmol). The resulting mixture was stirred at room temperature overnight and then diluted with EtOAc (50 mL). The organic layer was washed with water (20 mL×2), brine (20 mL), dried over $Na_2SO_4$, and concentrated. The crude material was purified by flash column chromatography (silica gel, 0-5% MeOH/DCM) to give 167 mg of RA54 as a pale yellow foam which was used directly in the next step.

LC/MS, m/z=399 [M+H]$^+$ (Calc: 398).

To a solution of RA54 (150 mg, 0.38 mmol) in MeOH (5 mL) was added 10% Pd in charcoal (50 mg). The reaction bottle was sealed, de-gassed, and then subjected to a $H_2$ balloon. After stirring at RT overnight, the solution was filtered and concentrated to give RA55. The crude material RA55 was used directly in the next step without further purification.

To an dry ice-cooled solution (−78° C.) of RA55 (150 mg, 0.37 mmol) in DCM (4 mL) was added $BBr_3$ (0.5 mL in DCM). The reaction mixture was slowly warmed to room temperature over 3 h, and then quenched with sat. $NH_4Cl$ (1 mL). After evaporation of the DCM, the residue was dissolved in MeOH (2 mL) and purified by reverse phase column chromatography (C18, ACN/water with 0.1% TFA, 0-95%) to give 21 mg of Compound 55 TFA salt as a white powder.

$^1$H NMR $\delta_H$ (400 MHz, MeOD) 6.97 (t, J=8.55 Hz, 1H), 6.67 (d, J=2.19 Hz, 1H), 6.61 (m, 1H), 4.33 (m, 1H), 3.76 (m, 1H), 3.29-3.44 (m, 2H), 2.98-3.12 (m, 3H), 2.82 (s, 3H), 2.40-2.71 (m, 3H), 1.77-2.21 (m, 6H), 1.57 (m, 1H), 1.35 (d, J=8.77 Hz, 3H).

LC/MS, m/z=373 [M+H]$^+$ (Calc: 372).

In a similar manner, 1-(2-((6S,11R)-8-hydroxy-3,6-dimethyl-1,2,3,4,5,6-hexahydro-2,6-methanobenzo[d]azocin-11-yl)acetyl)piperidine-4-carboxylic acid (Compound 72) was prepared from RA26 using ethyl piperidine-4-carboxylate rather than (S)-methylpyrrolidine-2-carboxylate hydrochloride. Purification by reverse phase column chromatography (C18, ACN/water with 0.1% TFA, 0-95%) gave Compound 72 TFA salt as a white powder.

$^1$H NMR $\delta_H$ (400 MHz, MeOD) 6.97 (dd, J=3.51 and 8.33 Hz, 1H), 6.67 (t, J=2.41 Hz, 1H), 6.60 (dd, J=2.41 and 8.33 Hz, 1H), 4.26 (m, 1H), 3.73 (m, 1H), 3.62 (m, 1H), 2.91-3.11 (m, 2H), 2.83 (s, 3H), 2.41-2.78 (m, 5H), 1.75-2.08 (m, 4H), 1.38-1.60 (m, 3H), 1.35 (d, J=9.43 Hz, 1H).

LC/MS, m/z=387 [M+H]$^+$ (Calc: 386).

Example 41

(2R,6R,11S)-3-(cyclopropylmethyl)-8-methoxy-N,6-dimethyl-1,2,3,4,5,6-hexahydro-2,6-methanobenzo[d]azocin-11-amine (Compound 56)

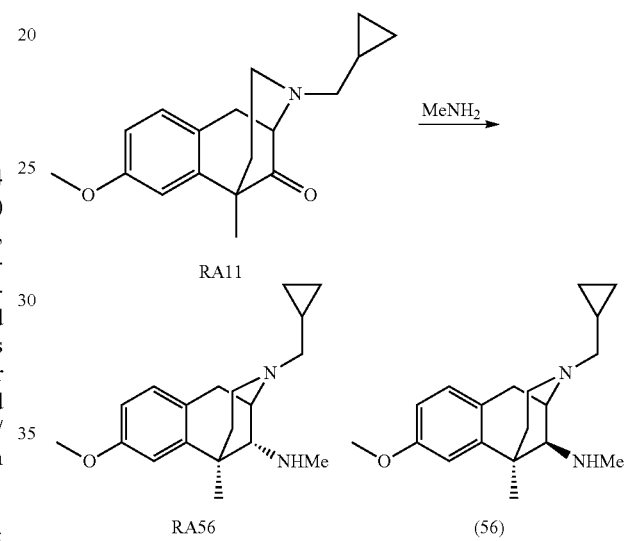

A mixture of RA11 (0.1 g, 0.4 mmol), $MeNH_2$ (2N in THF, 2 mL, 4 mmol) and 4 A MS was shaken at RT for 24 h. The solvent was evaporated under vacuum, then $CH_3CN$ (1 mL) and $NaB(OAc)_3H$ (0.2 g, 0.9 mmol) were added. The reaction mixture was shaken at RT for 24 h. The solid was filtered and washed with $CHCl_3$ (6 mL). The filtrate was washed with 0.2 N of NaOH aqueous (1 mL), concentrated and purified by reverse-phase prep HPLC (C18, 0-100% 0.1% TFA in water/0.1% TFA in ACN) to yield RA56 and Compound 56.

RA56 (TFA-salt, 20 mg, 10%, RT 1.101 min): $^1$H NMR $\delta_H$ (400 MHz, DMSO-$d_6$) 10.5 (br., 1H), 9.0 (br., 1H), 8.6 (br., 1H), 6.96-7.0 (m, 1H), 6.88-6.96 (m, 2H), 4.42 (s, 1H), 3.77 (s, 3H), 3.72-3.75 (m, 1H), 3.2-3.2 (m, 5H), 2.7 (s, 3H), 2.38-2.46 (m, 1H), 1.98-2.08 (m, 1H), 1.7 (d, J=13.8 Hz, 1H), 1.62 (s, 3H), 1.06-1.12 (m, 1H), 0.632-0.68 (m, 2H), 0.36-0.42 (m, 2H); LC/MS, m/z=301.4 [M+H]$^+$ (Calc: 300.4).

Compound 56 (TFA-salt, 70 mg, 40%, 1.363 min): $^1$H NMR $\delta_H$ (400 MHz, $CD_3CN$,) 7.05 (d, J=8.5 Hz, 1H), 6.85 (d, J=2.6 Hz, 1H), 6.78 (dd, J=2.6 and 8.5 Hz, 1H), 4.2 (s, 1H), 3.69 (s, 3H), 3.42 (s, 1H), 3.0-3.22 (m, 4H), 2.69-2.72 (m, 1H), 2.67 (s, 3H), 2.36-2.43 (m, 1H), 2.16-2.24 (m, 1H), 1.48 (s, 3H), 1.44 (d, J=14.2 Hz, 1H), 0.98-1.03 (m, 1H), 0.54-0.66 (m, 2H), 0.28-0.34 (m, 2H); LC/MS, m/z=301.4 [M+H]$^+$ (Calc: 300.4).

Example 42

(E)-N-((2R,6R,11S)-3-(cyclopropylmethyl)-8-methoxy-6-methyl-1,2,3,4,5,6-hexahydro-2,6-methanobenzo[d]azocin-11-yl)-3-(furan-3-yl)-N-methylacrylamide (Compound 57)

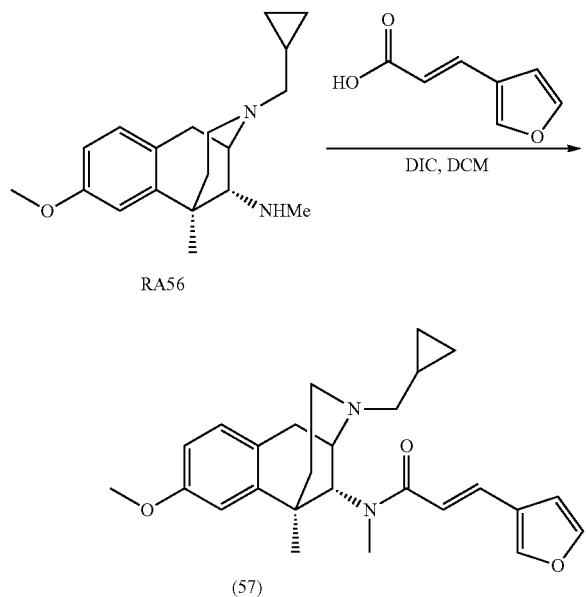

In a similar manner Compound 57 was prepared following the procedure for Compound 16. The product was purified by reverse-phase prep HPLC (C18, 0-100% 0.1% TFA in water/0.1% TFA in ACN), to obtain Compound 57 as a TFA-salt, white solid. $^1$H NMR $\delta_H$ (400 MHz, CD$_3$OD) 7.74 (s, 1H), 7.48 (d, J=14.1 Hz, 1H), 7.44 (s, 1H), 7.09 (d, J=8.6 Hz, 1H), 6.86 (d, J=2.4 Hz, 1H), 6.8 (dd, J=2.4 and 8.3 Hz, 1H), 6.74 (s, 1H), 6.68-6.74 (m, 2H), 4.96 (s, 0.2H), 4.84 (s, 0.8H), 3.96 (s, 1H), 7.72 (s, 3H), 3.2-3.34 (m, 3H), 2.94-3.12 (m, 2H), 2.77 (s, 3H), 2.52-2.6 (m, 1H), 2.02-2.12 (m, 1H), 1.64-1.68 (m, 1H), 1.45 (s, 3H), 1.0-1.08 (m, 1H), 0.67-0.72 (m, 2H), 0.36-0.4 (m, 2H); LC/MS, m/z=421.2 [M+H]$^+$ (Calc: 420.5).

In a similar manner, (E)-N-((2R,6R,11S)-3-(cyclopropylmethyl)-8-methoxy-6-methyl-1,2,3,4,5,6-hexahydro-2,6-methanobenzo[d]azocin-11-yl)-3-(furan-3-yl)-N-methylacrylamide (Compound 85) was prepared.

$^1$H NMR $\delta_H$ (400 MHz, CD$_3$OD) 7.87 (s, 1H), 7.64 (d, J=16.8 Hz, 1H), 7.49 (s, 1H), 7.08 (d, J=8.4 Hz, 1H), 6.75-6.84 (m, 4H), 4.21 (s, 1H), 3.88 (s, 1H), 3.69 (s, 3H), 3.32-3.66 (m, 3H), 3.25 (s, 3H), 2.98-3.12 (m, 2H), 2.61-2.68 (m, 1H), 2.28-2.37 (m, 1H), 1.49 (s, 3H), 1.45 (d, J=15.2 Hz, 1H), 1.01-1.13 (m, 1H), 0.62-0.73 (m, 2H), 0.35-0.45 (m, 2H).

LC/MS, m/z=421.2 [M+H]$^+$ (Calc: 420.5).

Example 43 methyl 3-((6R,11S)-11-hydroxy-8-methoxy-3,6-dimethyl-1,2,3,4,5,6-hexahydro-2,6-methanobenzo[d]azocin-11-yl)benzoate (Compound 64); and methyl 3-((6R,11R)-11-hydroxy-8-methoxy-3,6-dimethyl-1,2,3,4,5,6-hexahydro-2,6-methanobenzo[d]azocin-11-yl)benzoate (Compound 62)

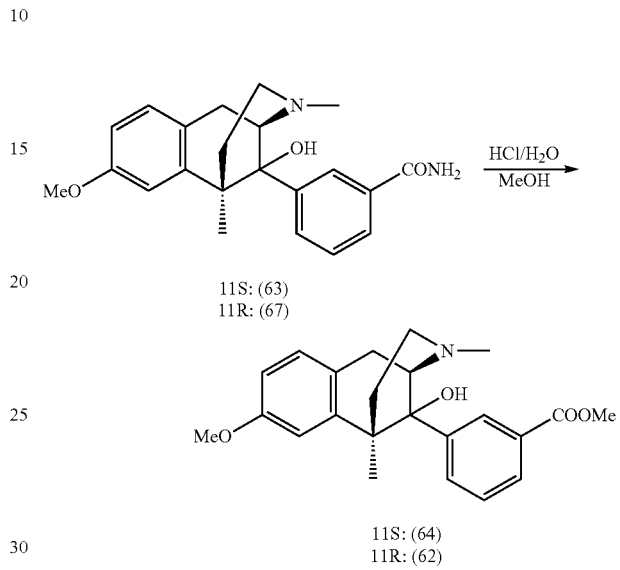

To Compound 63 (70 mg, 0.19 mmol) was added 1 mL of 6 M HCl and the resulting suspension stirred at 80° C. After 90 min, a few drops of MeOH were added to help solubilize Compound 63. After 3 h, 1 mL H$_2$O was added. After 6 h the solution was cooled to RT and concentrated. To the resulting residue was added 0.5 mL MeOH and 0.5 mL 1 M NaOH (0.5 mmol, 2.5 equiv.). The solution was stirred at RT for 16 h and at reflux for 3 h. Excess HCl/Et$_2$O was added and the solution concentrated. The resulting material was purified by preparative HPLC [0-60% MeCN/H$_2$O (0.01% TFA)] to yield Compound 64 TFA salt.

$^1$H NMR $\delta_H$ (400 MHz, ACN-d3) 8.38 (bs, 1H), 8.04 (s, 1H), 7.82 (d, J=6.6 Hz, 1H), 7.46 (d, J=8.1 Hz, 1H), 7.30 (t, J=8.1 Hz, 1H), 7.05 (t, J=2.6 Hz, 1H), 7.02 (s, 1H), 6.87 (dd, J=8.1, 2.6 Hz, 1H), 3.84 (s, 3H), 3.80 (s, 3H), 3.76 (d, J=5.3 Hz, 1H), 3.22-3.09 (m, 2H), 2.85 (s, 3H), 2.72-2.47 (m, 4H), 1.84 (s, 1H), 1.51 (s, 3H), 1.40 (dd, J=15.1, 3.0 Hz, 1H).

LC/MS, m/z=382 [M+H]$^+$ (Calc: 381).

In a similar manner Compound 62 TFA salt was synthesized analogously from Compound 67. $^1$H NMR $\delta_H$ (400 MHz, DMSO-d6) 8.91 (s, 1H), 8.74 (d, J=8.1 Hz, 1H), 8.45 (s, 1H), 8.23-8.12 (m, 2H), 8.00 (d, J=8.3 Hz, 1H), 7.85 (d, J=8.1 Hz, 1H), 7.63 (t, J=8.1 Hz, 1H), 7.45 (t, J=7.6 Hz, 1H), 7.12 (d, J=8.6 Hz, 1H), 7.01 (d, J=8.6 Hz, 1H), 6.92 (s, 1H), 6.79 (d, J=2.2 Hz, 1H), 6.68 (d, J=8.1 Hz, 1H), 6.15 (s, 1H), 3.99 (d, J=6.6 Hz, 1H), 3.90 (s, 1.5; H), 3.85 (s, 1.5H), 3.75 (s, 1.5H), 3.70 (s, 1.5H), 3.45 (dd, J=20.2, 6.6 Hz, 2H), 3.26 (d, J=19.3 Hz, 2H), 3.14 (d, J=5.9 Hz, 1H), 3.10 (d, J=9.9 Hz, 1H), 3.04-2.89 (m, 2H), 2.81 (d, J=4.2 Hz, 3H), 2.10 (td, J=12.4, 3.9 Hz, 2H), 1.71 (d, J=13.2 Hz, 2H), 1.66 (s, 3H), 1.09 (s, 3H), 1.08-1.01 (m, 1H).

LC/MS, m/z=382 [M+H]$^+$ (Calc: 381).

Example 44

(6R)-8-methoxy-3,6-dimethyl-11-(pyrrolidin-1-yl)-1,2,3,4,5,6-hexahydro-2,6-methanobenzo[d]azocine (Compound 69)

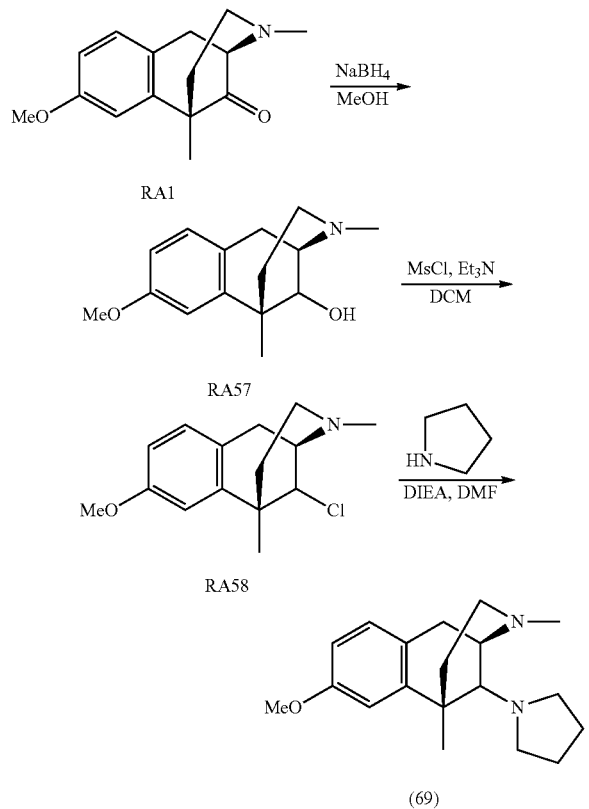

NaBH$_4$ (83 mg, 2.2 mmol, 1.2 eq) was added to RA1 (450 mg, 1.8 mmol, 1 eq) in 10 mL of MeOH and the solution stirred at RT for 90 min. EtOAc was added, the solution washed with sat. NaHCO$_3$, dried with Na$_2$SO$_4$, and concentrated to yield RA57 as a clear oil.

To RA57 (630 mg, 2.6 mmol, 1 eq) and Et$_3$N (1.1 mL, 7.9 mmol, 3 eq) in 12 mL DCM was added MsCl (0.24 mL, 3.1 mmol, 1.2 eq) and the solution stirred at RT. After 90 min. additional MsCl (0.24 mL, 3.1 mmol, 1.2 eq) was added. After 3 h additional MsCl (0.24 mL, 3.1 mmol, 1.2 eq) was added. After 19 h DCM was added and the solution washed with sat. NaHCO$_3$, dried with Na$_2$SO$_4$, and concentrated. The resulting residue was purified by MPLC (0-20% MeOH/DCM, 12 g) to yield RA58 as a yellow oil, 260 mg.

Pyrrolidine (13 uL, 0.16 mmol, 1.2 eq) was added to RA58 (35 mg, 0.13 mmol, 1 eq) and DIEA (69 uL, 0.39 mmol, 3 eq) in 0.5 mL DMF and the solution heated at 60° C. for 2 h. The temperature was increased to 120° C. for 1 h, then lowered again to 60° C. After 46 h the reaction was concentrated and purified by MPLC (0-20% MeOH/DCM, 12 g) and further purified by preparative HPLC [0-60% MeCN/H$_2$O (0.01% TFA)] to yield Compound 69 TFA salt.

$^1$H NMR δ$_H$ (400 MHz, MeOH-d4) 7.13 (d, J=8.6 Hz, 1H), 6.92 (d, J=2.4 Hz, 1H), 6.78 (dd, J=8.6, 2.4 Hz, 1H), 3.88-3.77 (m, 1H), 3.71 (s, 3H), 3.66-3.61 (m, 1H). 3.60-3.52 (m, 1H), 3.35-3.23 (m, 5H), 3.11-3.05 (m, 2H), 3.01 (s, 3H), 2.32-2.24 (m, 1H), 2.17-2.06 (m, 1H), 2.01-1.90 (m, 4H), 1.57 (s, 3H).

LC/MS, m/z=301 [M+H]$^+$ (Calc: 300).

Example 45

1-((6R)-8-methoxy-3,6-dimethyl-1,2,3,4,5,6-hexahydro-2,6-methanobenzo[d]azocin-11-yl)piperidin-4-amine (Compound 70)

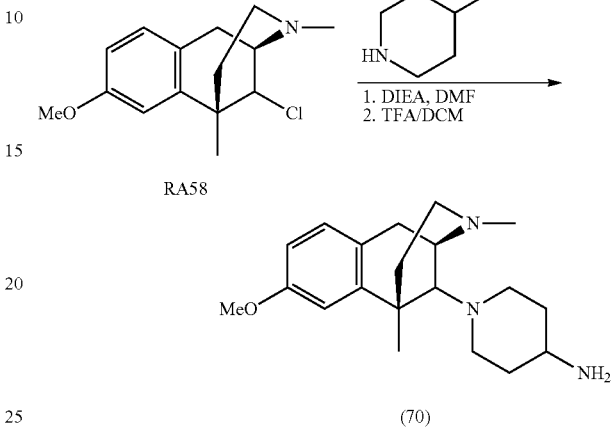

4-Boc-aminopiperidine (45 mg, 0.18 mmol, 1.2 eq) was added to RA58 (40 mg, 0.15 mmol, 1 eq) and DIEA (79 uL, 0.45 mmol, 3 eq) in 0.5 mL DMF and the solution heated at 60° C. for 40 h. The reaction was concentrated and purified by MPLC (0-20% MeOH/DCM, 12 g). To the purified residue was added 0.5 mL of 1:1 TFA:DCM. The reaction was stirred at RT for 1 h and concentrated. The resulting material was purified by preparative HPLC [0-60% MeCN/H$_2$O (0.01% TFA)] to yield Compound 70 TFA salt.

$^1$H NMR δ$_H$ (400 MHz, MeOH-d4) 6.96 (d, J=8.3 Hz, 1H), 6.70 (d, J=2.4 Hz, 1H), 6.66 (dd, J=8.3, 2.4 Hz, 1H), 3.73-3.67 (m, 1H), 3.67 (s, 3H), 3.46 (d, J=11.4 Hz, 1H), 3.33 (td, J=13.5, 5.7 Hz, 1H), 3.13-3.02 (m, 5H), 2.82-2.67 (m, 4H), 2.56-2.42 (m, 2H), 2.27 (t, J=10.8 Hz, 1H), 2.09 (td, J=13.6, 7.0 Hz, 1H), 2.04-1.90 (m, 2H), 1.65 (qd, J=11.6, 4.8 Hz, 1H), 1.49 (qd, J=12.0, 4.0 Hz, 1H), 1.42 (s, 3H).

LC/MS, m/z=330 [M+H]$^+$ (Calc: 329).

Example 46

2-(((2R,6R,11S)-3-(cyclopropylmethyl)-8-methoxy-6-methyl-1,2,3,4,5,6-hexahydro-2,6-methanobenzo[d]azocin-11-yl)(methyl)amino)acetic Acid (Compound 73)

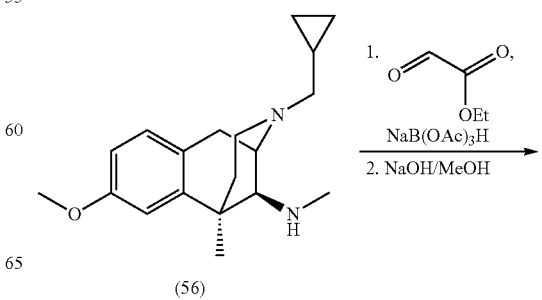

-continued

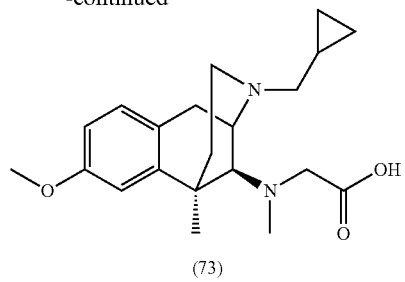

(73)

A mixture of Compound 56 (TFA-Salt, 50 mg, 0.12 mmol), glyoxylic acid ethyl ester (0.1 g, 1 mmol), TEA (0.05 mL, 0.4 mmol) and 4 A MS in $CH_3CN$ (0.5 mL) was shaken for 2 h, then $NaB(OAc)_3H$ (0.3 g, 1.4 mmol) was added. The reaction mixture was shaken at RT for 16 h. The solid was filtered, and washed with $CHCl_3$ (10 mL). The filtrate was washed with water, and concentrated. The residue was dissolved in 1 mL MeOH and treated with 0.2 mL NaOH (2N aqueous) at RT for 24 h. After aqueous work-up, the product was purified by reverse-phase prep HPLC (C18, 0-100% 0.1% TFA in water/0.1% TFA in ACN) to yield Compound 73 as TFA-salt (15 mg, white solid).

$^1$H NMR $\delta_H$ (400 MHz, $CD_3OD$) 7.15 (d, J=8.5 Hz, 1H), 6.95 (d, J=2.6 Hz, 1H), 6.85 (dd, J=2.6 and 8.3 Hz, 1H), 4.53 (d, J=5.3 Hz, 1H), 3.94 (d, J=18.9 Hz, 1H), 3.79 (s, 3H), 3.72 (d, J=18.2 Hz, 1H), 3.32-3.45 (m, 4H), 3.19-3.24 (m, 1H), 2.97 (dd, J=7.8 and 13.4 Hz, 1H), 2.83 (s, 3H), 2.66 (dt, J=3.5 and 13.2 Hz, 1H), 2.4 (dt, J=4.6 and 14.5 Hz, 1H), 1.64 (s, 3H), 1.54 (d, J=14.7 Hz), 1.16-1.23 (m, 1H), 0.75-0.84 (m, 2H), 0.49-0.53 (m, 2H); LC/MS, m/z=359.2 $[M+H]^+$ (Calc: 358.5).

Example 47

1-((6R)-8-methoxy-3,6-dimethyl-1,2,3,4,5,6-hexahydro-2,6-methanobenzo[d]azocin-11-yl)piperidine-3-carboxylic Acid (Compound 74)

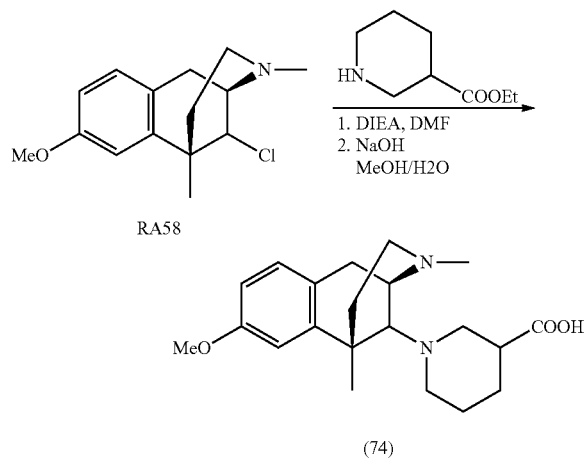

(74)

Ethyl nipecolate (35 uL, 0.18 mmol, 1.2 eq) was added to RA58 (40 mg, 0.15 mmol, 1 eq) and DIEA (79 uL, 0.45 mmol, 3 eq) in 0.5 mL DMF and the solution heated at 60° C. for 40 h. The reaction was concentrated and purified by MPLC (0-20% MeOH/DCM, 12 g). To the purified residue was added 0.4 mL MeOH and 0.2 mL 10% NaOH. The reaction was stirred at 80° C. for 1 h and concentrated. The resulting material was purified by preparative HPLC [0-60% $MeCN/H_2O$ (0.01% TFA)] to yield Compound 74 TFA salt.

$^1$H NMR $\delta_H$ (400 MHz, MeOH-d4) 6.97 (d, J=8.3 Hz, 1H), 6.70 (d, J=2.4 Hz, 1H), 6.66 (dd, J=8.3, 2.4 Hz, 1H), 3.70-3.63 (m, 1H), 3.67 (s, 3H), 3.47 (d, J=11.4 Hz, 1H), 3.37-3.27 (m, 1H), 3.09 (s, 3H), 3.01 (dt, J=11.6, 3.2 Hz, 1H), 2.79 (dd, J=14.5, 2.9 Hz, 1H), 2.70 (dd, J=11.1, 3.0, 2H), 2.66-2.59 (m, 1H), 2.53 (d, J=13.8 Hz, 1H), 2.46 (dd, J=13.4, 5.5 Hz, 1H), 2.35-2.18 (m, 2H), 2.07 (td, J=13.6, 7.0 Hz, 1H), 1.97-01.82 (m, 2H), 1.77-1.65 (m, 1H), 1.56 (q, J=11.0 Hz, 1H), 1.42 (s, 3H).

LC/MS, m/z=359 $[M+H]^+$ (Calc: 358).

Example 48

2-(3,4-dichlorophenyl)-N-(((6S,11S)-8-methoxy-3,6-dimethyl-1,2,3,4,5,6-hexahydro-2,6-methanobenzo[d]azocin-11-yl)methyl)acetamide (Compound 75)

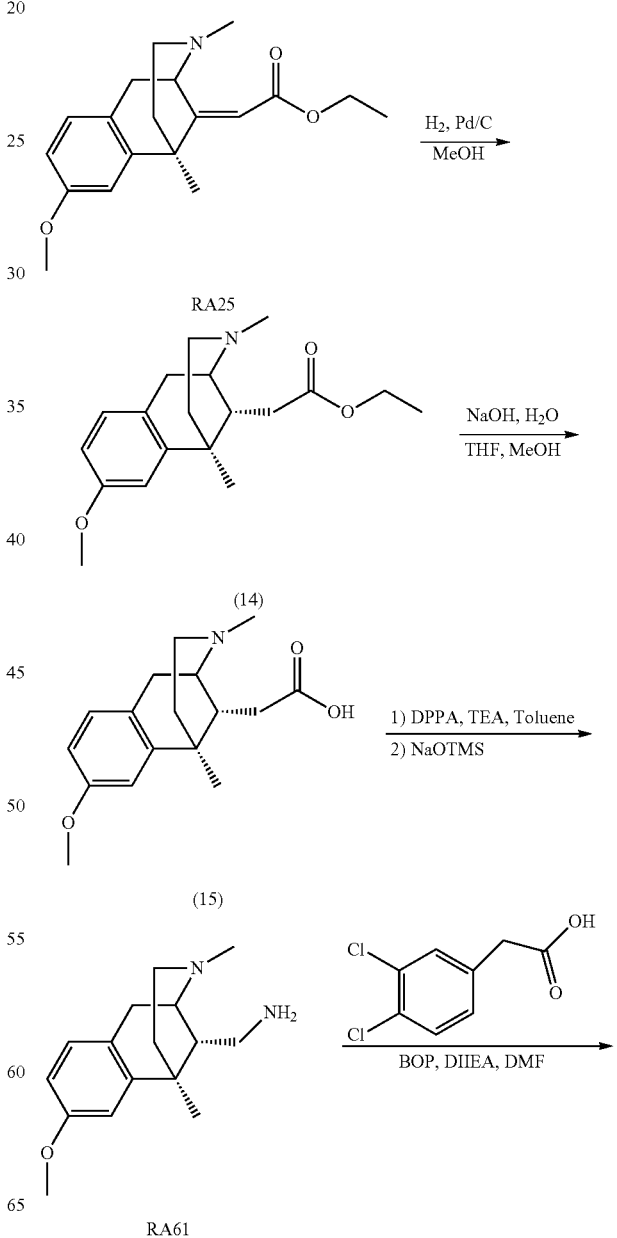

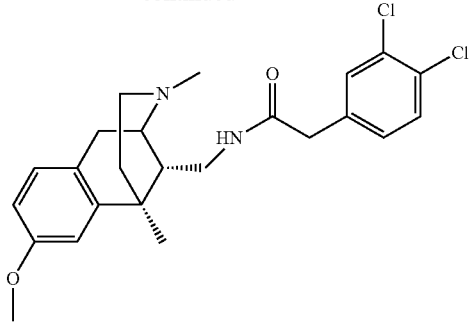

(75)

To a solution of RA25 (3.0 g, 9.51 mmol, 1.0 eq), in MeOH (30 mL) was added wet 10% palladium on carbon (0.50 g). The mixture was stirred for 16 h at room temperature under a balloon of hydrogen, filtered through Celite and concentrated to dryness to afford Compound 14. LC/MS, m/z=318 [M+H]$^+$ (Calc: 317).

To a solution of Compound 14 in THF (30 mL) at room temperature was added a solution of sodium hydroxide (1.06 g, 26.5 mmol, 3.0 eq) in H$_2$O (20 mL) followed by MeOH (13 mL). The solution was stirred for 2 h, the THF and MeOH were removed under reduced pressure, the pH was adjusted to 7.0 and the aqueous solution was concentrated to dryness. The solid residue was stirred with MeOH and the solid was removed by filtration and discarded. The filtrate was concentrated to afford Compound 15. LC/MS, m/z=290 [M+H]$^+$ (Calc: 289).

To a solution of Compound 15 (0.25 g, 0.865 mmol, 1.0 eq) in toluene (10 mL) was added triethylamine (0.12 mL, 0.865 mmol, 1.0 eq) and diphenylphosphoryl azide (0.186 mL, 0.865 mmol, 1.0 eq). The mixture was heated to reflux for 2 h, cooled with an ice bath and 1.0 M sodium trimethylsilanolate in THF (1.75 mL, 1.73 mmol, 2.0 eq) was added. The mixture was stirred at room temperature for 30 min, cooled with an ice bath, quenched with 10% citric acid, neutralized with NaHCO$_3$ and extracted with EtOAc and DCM. The combined organic layers were dried over sodium sulfate and concentrated to dryness and purified by flash chromatography (silica gel, EtOAc then 0-25% MeOH (1N NH$_3$) in DCM) to afford 0.042 g of RA61. $^1$H NMR δ$_H$ (300 MHz, CDCl$_3$) 6.94 (d, J=8.3 Hz 1H), 6.68 (d, J=2.6 Hz, 1H), 6.62 (dd, J=2.6, 8.3 Hz, 1H), 3.71 (s, 3H), 3.23 (m, 1H), 2.95 (d, J=18.4 Hz, 1H), 2.88 (dd, J=4.4, 12.9 Hz, 1H), 2.55 (dd, J=5.9, 18.2 Hz, 1H), 2.40 (m, 1H), 2.37 (s, 3H), 2.25-2.17 (t, J=12.7, 1H), 2.06-1.98 (td, J=3.3, 12.5 Hz, 1H), 1.84-1.76 (td, J=4.8, 12.7 Hz, 1H), 1.76-1.70 (m, 1H), 1.33 (s, 3H), 1.28 (m, 1H), 1.24 (m, 1H), LC/MS, m/z=261 [M+H]$^+$ (Calc: 260).

To a solution of RA61 (0.42 g, 0.162 mmol, 1.0 eq) in DMF (0.9 mL) was added diisopropylethylamine (0.063 g, 0.485 mmol, 3.0 eq), 3,4-dichlorophenylacetic acid (0.040 g, 0.194 mmol, 1.2 eq), and benzotriazole-1-yl-oxy-tris-(dimethylamino)-phosphonium hexafluorophosphate (0.086 g, 0.194 mmol, 1.2 eq). The mixture was stirred for 16 h at room temperature, brine was added and the mixture extracted with DCM. The organic layers were concentrated and purified by flash chromatography (silica gel, 0-25% MeOH in DCM) to afford 0.018 g of Compound 75. $^1$H NMR δ$_H$ (300 MHz, CD$_3$OD) 7.40-7.36 (m, 2H), 7.13 (dd, J=2.0, 8.1 Hz, 1H), 7.02 (d, J=8.5 Hz, 1H), 6.75-6.71 (m, 2H), 3.67 (s, 3H), 3.41 (m, 3H), 3.29 (dd, J=4.8, 14.0 Hz, 1H), 3.19-3.10 (m, 1H), 3.07-3.00 (m, 1H), 2.95-2.88 (m, 1H), 2.85-2.78 (dd, J=10.1, 14.0 Hz, 1H), 2.73 (s, 2H), 2.54 (d, J=9.4, 3H), 2.09 (m, 1H), 1.89-1.79 (td, J=5.0, 13.8 Hz, 1H), 1.46 (d, J=13.6 Hz, 1H), 1.41 (s, 3H), LC/MS, m/z=447 [M+H]$^+$ (Calc: 446).

Example 49

(E)-N-((2R,6R,11S)-3-(cyclopropylmethyl)-8-hydroxy-6-methyl-1,2,3,4,5,6-hexahydro-2,6-methanobenzo[d]azocin-11-yl)-3-(furan-3-yl)-N-methylacrylamide (Compound 77)

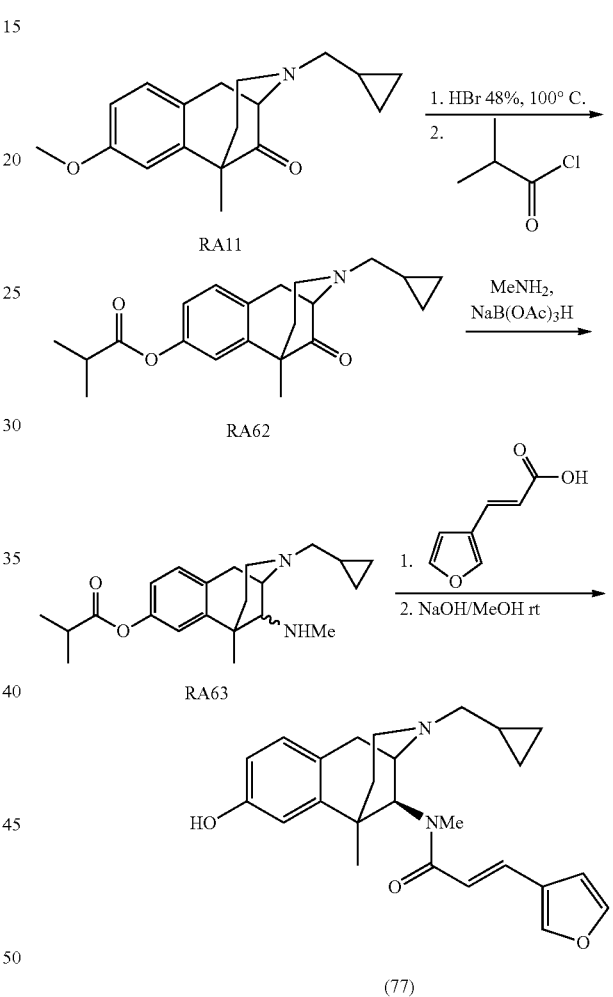

In a similar manner compound RA62 was prepared following the procedure for RA16. The product was purified by column (silica gel, EtOAc/Hexane 2/1); to yield RA62 as a colorless oil, 150 mg, 40%: $^1$H NMR δ$_H$ (400 MHz, CDCl$_3$) 7.0 (d, J=8.5 Hz, 1H), 6.8 (d, J=2.4 Hz, 1H), 6.77 (dd, J=2.6 and 5.4 Hz, 1H), 3.56 (d, J=6.1 Hz, 1H), 3.37 (d, J=18.4 Hz, 1H), 3.04 (dd, J=7.0 and 18.8 Hz), 2.58-2.68 (m, 3H), 2.36 (d, J=6.4 Hz, 2H), 2.04-2.12 (m, 1H), 1.56-1.62 (m, 1H), 1.33 (s, 3H), 1.18 (d, J=6.9 Hz, 6H), 0.68-0.73 (m, 1H), 0.39-0.42 (m, 2H), −0.08-0.02 (m, 2H).

A mixture of RA62 (0.15 g, 0.44 mmol), methylamine (2N in THF, 2 mL, 4 mmol) and 4 A MS in CH$_3$CN was shaken for 12 h, then NaB(OAc)$_3$H (0.4 g, 1.8 mmol) was added. The reaction mixture was shaken at RT for 24 h. The solid was filtered, and washed with CHCl₃ (10 mL). The filtrate was washed with 2N NaOH (2 mL aqueous). The organic layer was concentrated to yield 0.2 g of crude RA63 {(LC/MS, m/z=357.5 [M+H]⁺ (Calc: 356.5)}.

O-(7-Azabenzotriazol-1-yl)-N,N,N',N'-tetramethyluronium hexafluorophosphate (HATU, Applied Bio, 0.22 g, 0.6 mmol) was added to a solution of RA63 (0.2 g, 0.56 mmol), 3-(3-furyl)acrylic acid (100 mg, 0.7 mmol) and TEA (0.1 mL, 0.8 mmol) in DMF (1 mL) at RT. The reaction mixture was shaken at RT for 24 h. After aqueous work-up, the product was dissolved in 1 mL MeOH and treated with 0.2 mL NaOH (2N aqueous) at RT for 24 h. After aqueous work-up, the product was purified by reverse-phase prep HPLC (C18, 0-100% 0.1% TFA in water/0.1% TFA in ACN) to yield Compound 77 (the major isomer) as TFA-salt (30 mg, yellow solid): ¹H NMR δ$_H$ (400 MHz, CD₃OD) 7.8 (s, 1H), 7.62 (d, J=15.1 Hz, 1H), 7.48 (s, 1H), 6.98 (d, J=8.3 Hz, 1H), 6.84 (s, 1H), 6.79 (d, J=2.8 Hz, 1H), 6.71 (d, J=2.4 Hz, 1H), 6.62 (dd, J=2.6 and 8.3 Hz, 1H), 4.2 (d, J=3.9 Hz, 1H), 3.87 (s, 1H), 3.3-3.36 (m, 3H), 3.28 (s, 3H), 2.98-3.08 (m, 2H), 2.62-2.7 (m, 1H), 2.28-2.36 (m, 1H), 1.46 (s, 3H), 1.41-1.43 (m, 1H), 1.04-1.12 (m, 1H), 0.65-0.7 (m, 2H), 0.38-0.42 (m, 2H); LC/MS, m/z=407.3 [M+H]⁺ (Calc: 406.5).

In a similar manner, (E)-N-((6R,11R)-3-(cyclopropylmethyl)-8-hydroxy-6-methyl-1,2,3,4,5,6-hexahydro-2,6-methanobenzo[d]azocin-11-yl)-3-(furan-3-yl)-N-methylacrylamide (Compound 83) was prepared.

¹H NMR δ$_H$ (400 MHz, CD₃OD) 7.74 (s, 1H) 7.48 (d, J=15.2 Hz, 1H), 7.44 (s, 1H), 6.98 (d, J=8.8 Hz, 1H), 6.62-6.74 (m, 4H), 4.82-4.93 (m, 1H), 3.85-3.97 (m, 1H), 3.16-3.23 (m, 1H), 2.91-3.12 (m, 3H), 2.79 (s, 3H), 2.53-2.63 (m, 1H), 2.02-2.31 (m, 1H), 1.64 (d, J=14.8 Hz, 1H), 1.44 (s, 3H), 0.96-1.13 (m, 1H), 0.68 (d, J=7.6 Hz, 2H), 0.38-0.51 (m, 2H).

LC/MS, m/z=406.5 [M+H]⁺ (Calc: 407.3).

Example 50

3-(4-cyanophenyl)-1-((2R,6R,11S)-8-hydroxy-3,6-dimethyl-1,2,3,4,5,6-hexahydro-2,6-methanobenzo[d]azocin-11-yl)-1-methylurea (Compound 78); and 3-(4-cyanophenyl)-1-((2R,6R,11S)-8-hydroxy-3,6-dimethyl-1,2,3,4,5,6-hexahydro-2,6-methanobenzo[d]azocin-11-yl)-1-methylurea (Compound 79)

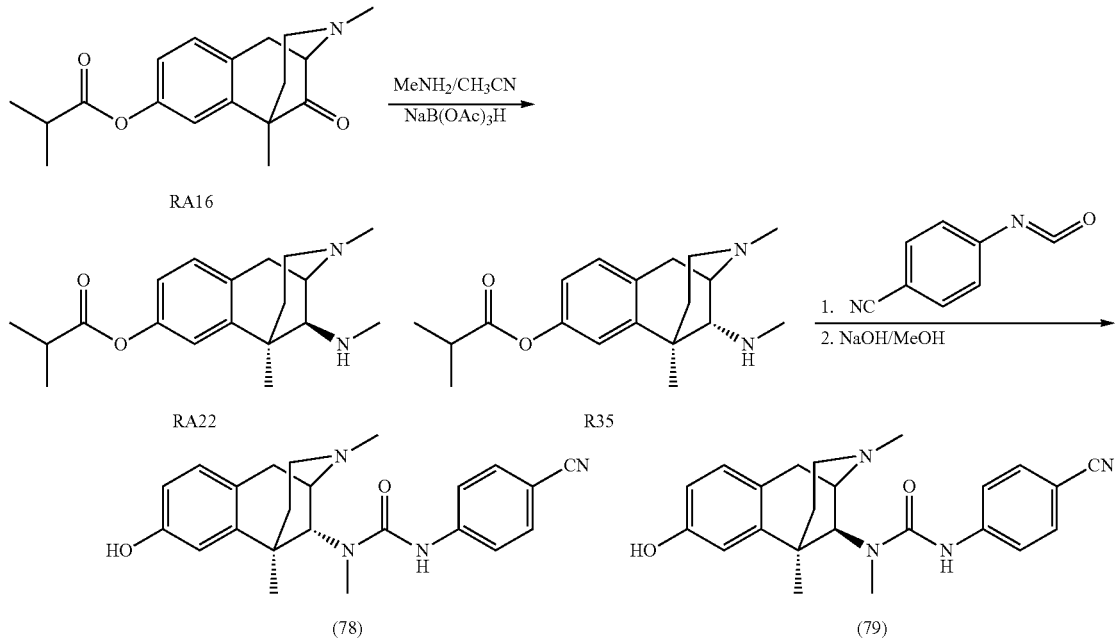

A mixture of RA16 (0.85 g, 2.7 mmol), MeNH₂ (33% in EtOH, 1 mL, Aldrich, 10 mmol) and 4 A MS (0.4 g) in 1 mL CH₃CN was shaken at RT for 4 h. The solvent was removed under vacuum. The residue was treated with CH₃CN (3 mL) and NaB(OAc)₃H (3.4 mmol). The reaction mixture was stirred at RT for 14 h. The solid was filtered. The filtrate was quenched with water (2 mL and 2N NaOH 2 mL), extracted with EtOAc and concentrated to yield 0.5 g of crude RA22/RA35 {m/z=317.4 [M+H]⁺ (Calc: 316.4)}.

4-Isocyanatobenzonitrile (1.4 mmol, 0.2 g, Aldrich) was added to a solution of RA22/RA35 (0.5 g, 1.6 mmol) in 4 mL CHCl₃ at 0° C. The reaction mixture was warmed to RT over 4 h, and shaken at RT for two days. The reaction mixture was quenched with water (1 mL), and the solvent was evaporated under vacuum. The residue was dissolved in MeOH (6 mL), and treated with NaOH (2N in water, 0.5 mL). The reaction mixture was shaken at RT for 14 h. After being concentrated under vacuum, the residue was dissolved in CHCl₃ (10 mL), and neutralized to pH ~3 with 1N HCl. The organic layer was concentrated and purified by column (CHCl₃/MeOH 10/1) to yield compounds Compound 78 and Compound 79.

Compound 78 (white solid, 110 mg, 22%, RT 1.650 min): ¹H NMR δ$_H$ (400 MHz, CDCl₃) 7.68 (d, J=8.7 Hz, 2H), 7.58 (d, J=8.8 Hz, 2H), 6.97 (d, J=8.3 Hz, 1H), 6.77 (d, J=2.6 Hz, 1H), 6.68 (dd, J=2.4 and 8.1 Hz, 1H), 3.8-4.1 (m, 1H), 3.08-3.17 (m, 2H), 2.64-2.72 (m, 4H), 2.5-2.56 (m, 1H), 2.46 (s, 3H), 2.04-2.22 (m, 1H), 1.94-2.02 (m, 1H), 1.48-1.52 (m, 1H), 1.47 (s, 3H); LC/MS, m/z=391.2 [M+H]⁺ (Calc: 390.5).

Compound 79 (white solid, 80 mg, 16%, RT 1.805 min): ¹H NMR δ$_H$ (400 MHz, CDCl₃) 7.57 (dd, J=1.9 and 8.7 Hz, 2H), 7.51 (d, J=8.7 Hz, 2H), 7.0 (d, J=7.9 Hz, 1H), 6.76 (d, J=2.6 Hz, 1H), 6.69 (dd, J=2.4 and 8.1 Hz, 1H), 3.64-3.69 (m, 1H), 3.52-3.56 (m, 1H), 3.24-3.26 (m, 1H), 3.14 (s, 3H), 2.96-3.04 (m, 1H), 2.6-2.66 (m, 1H), 2.55 (s, 3H), 2.36-2.44 (m, 1H), 2.16-2.22 (m, 1H), 1.47 (s, 3H), 1.24-1.32 (m, 1H); LC/MS, m/z=391.2 [M+H]$^+$ (Calc: 390.5).

In a similar manner the following compounds were prepared.

3-(4-cyanophenyl)-1-((6R,11S)-3-(cyclopropylmethyl)-8-hydroxy-6-methyl-1,2,3,4,5,6-hexahydro-2,6-methanobenzo[d]azocin-11-yl)-1-methylurea
(Compound 81)

$^1$H NMR $\delta_H$ (400 MHz, CD$_3$OD) 7.58 (s, 4H) 6.98 (d, J=8.8 Hz, 1H), 6.71 (d, J=2.8 Hz, 1H), 6.62 (dd, J=2.8 and 7.6 Hz, 1H), 4.24 (d, J=5.6 Hz, 1H), 3.27-3.40 (m, 1H), 3.23 (s, 3H), 3.00-3.11 (m, 1H), 2.62-2.70 (m, 1H), 2.28-2.37 (m, 1H), 1.47 (s, 3H), 1.44 (d, J=14.8 Hz, 1H), 1.04-1.13 (m, 1H), 0.66-0.71 (m, 2H), 0.38-0.44 (m, 2H).
LC/MS, m/z=431.3 [M+H]$^+$ (Calc: 430.5).

3-(4-cyanophenyl)-1-((6R,11R)-3-(cyclopropylmethyl)-8-hydroxy-6-methyl-1,2,3,4,5,6-hexahydro-2,6-methanobenzo[d]azocin-11-yl)-1-methylurea
(Compound 80)

$^1$H NMR $\delta_H$ (400 MHz, CD$_3$OD) 7.52-7.59 (m, 4H), 6.99 (d, J=8.8 Hz, 1H), 6.75 (s, 1H), 6.63-6.67 (m, 1H), 6.42 (s, 1H), 3.91-3.98 (m, 1H), 2.94-3.13 (m, 3H), 2.69 (s, 3H), 2.52-2.66 (m, 1H), 2.02-2.29 (m, 1H), 1.62 (d, J=14.0 Hz), 1.45 (s, 3H), 0.97-1.23 (m, 1H), 0.68 (d, J=15.6 Hz, 2H), 0.37-0.44 (m, 2H).
LC/MS, m/z=431.3 [M+H]$^+$ (Calc: 430.5).

Example 51

The following Tables provide the compound structures, and the results on the efficacy of binding and activity response of exemplified Compounds of the Invention at the ORL1, μ-, and κ-opioid receptors.

In TABLE 1, binding affinity of certain Compounds of the Invention to the ORL-1, μ-, and κ-opioid receptors was determined as described above in HEK-293 or CHO cells.

In TABLE 2, activity response of certain Compounds of the Invention to the μ- and κ-opioid receptors was determined as described above for functional assays using HEK-293 or CHO cells.

In TABLE 2A, activity response of certain Compounds of the Invention to the μ- and κ-opioid receptors was determined as described above for functional assays using U-2 OS cells.

In TABLE 3, the structure of the exemplified compounds is shown.

TABLE 1

Binding Affinity of Benzomorphan Analog Compounds

| | Ki (nM) | | |
|---|---|---|---|
| | | Opioid Receptor | |
| Ref. No. | ORL-1 | μ | κ |
| 1 | | >20 μM | 12098.38 |
| 2 | | >20 μM | 2581.00 ± 121.72 |
| 3 | | >20 μM | >20 μM |

TABLE 1-continued

Binding Affinity of Benzomorphan Analog Compounds

| | Ki (nM) | | |
|---|---|---|---|
| | | Opioid Receptor | |
| Ref. No. | ORL-1 | μ | κ |
| 4 | | >20 μM | >20 μM |
| 5 | | >20 μM | 10692.95± |
| 6 | | >20 μM | 3163.34 ± 1240.16 |
| 7 | | | 278.94 ± 39.80 |
| 8 | | | >20 μM |
| 9 | | | 18852.90 ± 3125.86 |
| 10 | | | 2140.72 ± 150.62 |
| 11 | | | >20 μM |
| 12 | | | >20 μM |
| 13 | | | >20 μM |
| 14 | | | 14295.63 |
| 15 | | | >20 μM |
| 16 | | | 186.49 ± 33.99 |
| 17 | | | 89.91 ± 14.68 |
| 18 | | | 5576.32 ± 1014.93 |
| 19 | | | 8516.26 ± 604.62 |
| 20 | | | 1946.74 ± 537.74 |
| 21 | | | 1220.02 ± 331.89 |
| 22 | | | 25.71 ± 8.74 |
| 23 | | | 13246.68 |
| 24 | | | 1.17 ± 0.09 |
| 25 | | | 147.19 ± 18.37 |
| 26 | | | >20 μM |
| 27 | | | 35.22 ± 9.38 |
| 28 | | | 18223.59 |
| 29 | | | 30.07 ± 11.75 |
| 30 | | | 7.66 ± 1.96 |
| 31 | | | 0.34 ± 0.09 |
| 32 | | | 12741.18 ± 2092.19 |
| 33 | | | 2835.01 ± 341.97 |
| 34 | | | 5985.04 ± 603.94 |
| 35 | | | >20 μM |
| 36 | | | 4187.46 ± 1054.00 |
| 37 | | | >20 μM |
| 38 | | | 17400.63 ± 5983.60 |
| 39 | | | 81.98 ± 10.36 |
| 40 | | | 3121.28 ± 482.94 |
| 41 | | | 1884.11 ± 279.98 |
| 42 | | | >20 μM |
| 43 | | | 515.84 ± 126.06 |
| 44 | | | 166.02 ± 62.34 |
| 45 | | | >20 μM |
| 46 | | | >20 μM |
| 47 | | | 19990.58 |
| 48 | | | >20 μM |
| 49 | | | >20 μM |
| 50 | | | 58.34 ± 10.09 |
| 51 | | | 7.83 ± 0.95 |
| 52 | | | >20 μM |
| 53 | | | 700.52 ± 57.96 |
| 54 | | | 258.53 ± 33.55 |
| 55 | | | >20 μM |
| 56 | | | 169.98 ± 51.94 |
| 57 | | 235.73 ± 70.22 | 4.61 ± 1.43 |
| 58 | | | 336.27 ± 87.49 |
| 59 | | | >20 μM |
| 60 | | | >20 μM |
| 61 | | | 2774.49 ± 850.38 |
| 62 | | | >20 μM |
| 63 | | | 340.14 ± 90.93 |
| 64 | | | 12412.96 |
| 65 | | | >20 μM |
| 66 | | | >20 μM |
| 67 | | | >20 μM |
| 68 | | | 799.12 ± 98.16 |
| 69 | | | 19844.43 |
| 70 | | | 4716.93 ± 29.55 |
| 71 | | | >20 μM |
| 72 | | | 14756.49 |
| 73 | | | >20 μM |
| 74 | | 229.98 ± 43.79 | 24.14 ± 5.93 |
| 75 | | | 184.78 ± 51.34 |

TABLE 1-continued

Binding Affinity of Benzomorphan Analog Compounds

| | | Ki (nM) | |
|---|---|---|---|
| | | Opioid Receptor | |
| Ref. No. | ORL-1 | μ | κ |
| 76 | | | 106.69 ± 1.33 |
| 77 | | | 4.30 ± 0.91 |
| 78 | | | 17.88 ± 4.33 |
| 79 | | | 3138.90 ± 804.72 |
| 80 | | | 1.19 ± 0.32 |
| 81 | | | 36.57 ± 4.94 |
| 82 | | | 10157.61 |
| 83 | | 1.78 ± 0.38 | 0.15 ± 0.02 |
| 84 | | | 269.27 ± 27.74 |
| 85 | | | 701.28 ± 94.11 |
| 86 | | | 978.95 ± 146.23 |
| 87 | | | 1.21 ± 0.24 |
| 88 | | | 4.74 ± 1.55 |
| 89 | | | 9.20 ± 0.90 |
| 90 | | | 1.74 ± 0.45 |
| 91 | | | 174.45 ± 25.67 |
| 92 | >20 μM | 54.50 ± 17.3 | 163.50 ± 3.83 |
| 93 | >20 μM | 3702.00 ± 91.40 | 5353.00 ± 540.70 |
| 94 | >20 μM | 36.80 ± 12.10 | 16.80 ± 2.51 |
| 95 | >20 μM | 1759.00 ± 324.20 | 4602.00 ± 764.20 |

TABLE 2

Activity Response of Benzomorphan Analog Compounds in HEK-293 or CHO Cells

| | GTPγS (EC$_{50}$: nM, E$_{max}$: %) | | | |
|---|---|---|---|---|
| | μ | | κ | |
| Ref. No. | EC$_{50}$ | E$_{max}$ | EC$_{50}$ | E$_{max}$ |
| 7 | | | >20 μM | −0.33 ± 0.67 |
| 16 | | | 1052.05 ± 262.24 | 15.00 ± 1.53 |
| 17 | | | >20 μM | |
| 22 | | | >20 μM | |
| 24 | | | 178.37 ± 25.08 | 30.67 ± 2.60 |
| 25 | | | >20 μM | −1.00 ± 0.00 |
| 27 | | | >20 μM | |
| 29 | | | 233.45 ± 74.94 | 28.25 ± 4.66 |
| 30 | 270.32 ± 33.89 | 49.67 ± 3.67 | >20 μM | 0.33 ± 0.67 |
| 31 | 12.33 ± 0.95 | 61.00 ± 3.00 | >20 μM | 1.00 ± 0.00 |
| 32 | 335.55 ± 92.84 | 23.00 ± 1.53 | | |
| 33 | 2451.89 ± 166.69 | 49.00 ± 3.67 | | |
| 34 | 3640.47 ± 372.93 | 16.00 ± 3.46 | | |
| 35 | 2568.62 ± 783.31 | 23.00 ± 0.58 | | |
| 36 | >20 μM | | | |
| 37 | >20 μM | | | |
| 38 | >20 μM | | | |
| 39 | 321.13 ± 22.21 | 89.75 ± 5.39 | >20 μM | −1.00 ± 0.00 |
| 40 | 3068.01 ± 468.81 | 25.67 ± 3.76 | | |
| 41 | 1224.96 ± 234.71 | 46.00 ± 3.79 | | |
| 42 | >20 μM | | | |
| 43 | 3389.03 ± 63.44 | 24.67 ± 3.28 | >20 μM | |
| 44 | 718.03 ± 249.07 | 65.00 ± 2.52 | 393.84 ± 88.38 | 17.67 ± 1.20 |
| 45 | 3845.14 ± 838.61 | 17.00 ± 3.06 | | |
| 46 | 13356.09 ± 2991.11 | 36.67 ± 3.18 | | |
| 47 | 8893.34 ± 654.64 | 58.67 ± 5.24 | | |
| 48 | 5187.29 ± 549.08 | 26.00 ± 4.16 | | |
| 49 | >20 μM | 31.33 ± 5.36 | | |
| 50 | 189.38 ± 13.68 | 93.75 ± 2.17 | >20 μM | |
| 51 | 1.44 ± 0.44 | 100.40 ± 7.22 | >20 μM | |
| 52 | 1029.16 ± 73.07 | 72.33 ± 3.48 | | |
| 53 | 1109.86 ± 209.60 | 82.67 ± 1.20 | | |
| 54 | >20 μM | | >20 μM | |
| 55 | 5911.18 ± 422.16 | 71.00 ± 8.08 | | |
| 56 | 3811.28 ± 725.51 | 36.67 ± 7.22 | 2583.28 ± 721.00 | 25.67 ± 1.67 |
| 57 | 314.67 ± 47.88 | 111.67 ± 7.22 | 351.43 ± 115.38 | 85.67 ± 3.93 |
| 58 | 750.70 ± 43.35 | 110.00 ± 7.55 | | |
| 59 | 3443.33 ± 183.49 | 76.33 ± 10.17 | | |
| 60 | 6093.08 ± 528.96 | 38.33 ± 0.88 | | |
| 61 | 5758.65 ± 1554.16 | 26.67 ± 0.88 | | |
| 62 | 7450.91 ± 470.09 | 24.00 ± 2.97 | | |
| 63 | >20 μM | | >20 μM | |
| 64 | >20 μM | | | |
| 65 | 5062.97 ± 1146.61 | 21.67 ± 2.85 | | |
| 66 | 6605.36 ± 198.95 | 20.67 ± 1.33 | | |
| 67 | >20 μM | | | |
| 68 | 549.95 ± 31.63 | 98.00 ± 1.73 | | |

TABLE 2-continued

Activity Response of Benzomorphan Analog Compounds in HEK-293 or CHO Cells

GTPγS (EC$_{50}$: nM, E$_{max}$: %)

| | μ | | κ | |
|---|---|---|---|---|
| Ref. No. | EC$_{50}$ | E$_{max}$ | EC$_{50}$ | E$_{max}$ |
| 69 | >20 μM | 24.33 ± 2.96 | | |
| 70 | 9380.74 ± 500.59 | 24.67 ± 0.88 | | |
| 71 | 13019.30 ± 1144.67 | 23.00 ± 4.58 | | |
| 72 | 4893.25 ± 508.01 | 70.33 ± 8.33 | | |
| 73 | 18050.23 ± 2716.99 | 25.00 ± 2.52 | | |
| 74 | 639.16 ± 147.03 | 31.67 ± 0.67 | 636.58 ± 65.05 | 53.00 ± 2.31 |
| 75 | 62.33 ± 13.71 | 111.50 ± 2.40 | >20 μM | 0.33 ± 0.67 |
| 76 | 810.87 ± 52.98 | 79.33 ± 3.48 | >20 μM | −0.33 ± 0.67 |
| 77 | 144.40 ± 11.00 | 56.50 ± 2.02 | >20 μM | −1.00 ± 0.00 |
| 78 | | | >20 μM | |
| 80 | 216.09 ± 38.74 | 92.40 ± 3.23 | >20 μM | |
| 81 | 1225.90 ± 172.97 | 31.20 ± 2.87 | >20 μM | |
| 82 | | | | |
| 83 | 10.55 ± 1.18 | 92.67 ± 5.21 | 2.67 ± 0.84 | 77.67 ± 1.76 |
| 87 | 5.29 ± 1.10 | 96.33 ± 2.96 | 24.02 ± 1.94 | 10.75 ± 1.49 |
| 88 | 7.58 ± 1.06 | 74.67 ± 1.86 | 24.67 ± 5.35 | 18.50 ± 2.84 |
| 89 | >20 μM | | >20 μM | |
| 90 | 5.92 ± 1.82 | 32.67 ± 5.78 | >20 μM | 1.00 ± 0.00 |
| 91 | 408.78 ± 19.46 | 89.67 ± 5.90 | 2811.03 ± 128.63 | 34.67 ± 5.93 |
| 92 | 68.90 ± 16.00 | 100.50 ± 3.12 | >20 μM | 3.50 ± 1.71 |
| 93 | 3137.00 ± 790.20 | 92.00 ± 4.30 | | |
| 94 | 40.80 ± 2.76 | 85.30 ± 4.98 | >20 μM | 4.60 ± 0.40 |
| 95 | 2120.00 ± 204.30 | 78.00 ± 3.06 | | |
| 128 | 7.67 ± 0.79 | 53.50 ± 3.52 | 0.35 ± 0.15 | 40.30 ± 2.19 |

TABLE 2A

Activity Response of Benzomorphan Analog Compounds in U-2 OS Cells

GTPγS (EC$_{50}$: nM, E$_{max}$: %)

| | μ | | κ | |
|---|---|---|---|---|
| Ref. No. | EC$_{50}$ | E$_{max}$ | EC$_{50}$ | E$_{max}$ |
| 22 | 299.80 ± 45.80 | 71.00 ± 3.46 | | |
| 25 | 49.80 ± 12.10 | 101.70 ± 1.67 | | |
| 26 | 1194.00 ± 93.90 | 91.00 ± 7.09 | | |
| 27 | 1.51 ± 0.24 | 102.70 ± 2.33 | | |
| 28 | 1562.00 ± 106.10 | 74.70 ± 4.63 | | |
| 29 | 0.044 ± 0.00 | 100.30 ± 1.45 | | |
| 30 | 33.60 ± 8.17 | 91.70 ± 4.33 | | |
| 31 | 0.41 ± 0.38 | 94.30 ± 3.18 | | |
| 32 | 232.90 ± 58.20 | 39.80 ± 2.46 | | |
| 39 | 18.30 ± 1.22 | 100.70 ± 3.76 | | |
| 50 | 42.00 ± 10.90 | 86.50 ± 4.14 | >20 μM | 9.78 ± 2.97 |
| 51 | 0.21 ± 0.021 | 113.00 ± 2.65 | | |
| 75 | 12.70 ± 1.52 | 103.70 ± 2.67 | | |
| 77 | 29.00 ± 0.86 | 77.70 ± 0.88 | | |
| 78 | 6.09 ± 0.45 | 109.30 ± 3.28 | | |
| 79 | 2198.00 ± 668.50 | 49.00 ± 3.46 | | |
| 80 | 0.20 ± 0.013 | 112.70 ± 3.53 | | |
| 82 | >20 μM | 31.70 ± 5.36 | | |
| 84 | 83.90 ± 13.30 | 90.70 ± 1.86 | | |
| 85 | 3238.00 ± 770.50 | 19.30 ± 2.33 | | |
| 86 | 2152.00 ± 210.50 | 14.70 ± 0.88 | | |
| 87 | 2.08 ± 0.12 | 99.30 ± 2.03 | | |
| 88 | 1.67 ± 0.16 | 85.70 ± 2.33 | | |
| 89 | >20 μM | 1.17 ± 1.01 | | |
| 90 | 7.02 ± 1.89 | 14.00 ± 1.00 | | |
| 91 | 377.80 ± 61.90 | 71.30 ± 3.53 | | |
| 92 | 149.30 ± 25.50 | 97.30 ± 3.53 | >20 μM | 1.00 ± 0.00 |
| 93 | 4559.00 ± 743.20 | 80.70 ± 4.48 | >20 μM | 2.00 ± 0.00 |
| 94 | 27.40 ± 4.20 | 85.30 ± 5.93 | >20 μM | 0.00 |

TABLE 2A-continued

Activity Response of Benzomorphan Analog Compounds in U-2 OS Cells

| | GTPγS (EC$_{50}$: nM, E$_{max}$: %) | | | |
| --- | --- | --- | --- | --- |
| | μ | | κ | |
| Ref. No. | EC$_{50}$ | E$_{max}$ | EC$_{50}$ | E$_{max}$ |
| 95 | 1437.00 ± 44.70 | 79.70 ± 8.41 | >20 μM | −1.00 |
| 96 | 6.01 ± 0.51 | 32.30 ± 0.88 | 6.41 ± 1.67 | |
| 97 | >20 μM | 2.50 ± 0.00 | >20 μM | 0.00 |
| 98 | 0.30 ± 0.027 | 103.70 ± 3.76 | 28.60 ± 3.21 | 95.30 ± 3.84 |
| 99 | 0.13 ± 0.01 | 71.00 ± 2.00 | 1.44 ± 0.053 | 72.30 ± 4.67 |
| 100 | 40.00 ± 3.25 | 102.30 ± 1.45 | 1757.00 ± 364.50 | 45.00 ± 2.08 |
| 101 | 3.73 ± 0.21 | 104.00 ± 2.08 | 1083.00 ± 112.90 | 66.70 ± 1.20 |
| 102 | >20 μM | 2.50 ± 0.00 | >20 μM | −1.00 |
| 103 | 116.80 ± 2.82 | 77.50 ± 1.26 | 287.10 ± 62.00 | 83.00 ± 8.02 |
| 104 | 51.30 ± 5.26 | 105.30 ± 0.88 | 1260.00 ± 229.00 | 79.70 ± 5.90 |
| 105 | 0.22 ± 0.052 | 32.70 ± 1.76 | >20 μM | 1.00 |
| 106 | >20 μM | 2.50 | >20μ | 1.00 |
| 107 | 46.20 ± 0.35 | 58.30 ± 0.33 | >20 μM | 1.00 |
| 108 | 0.39 ± 0.11 | 80.80 ± 2.50 | 3.27 ± 0.69 | 18.80 ± 1.25 |
| 109 | 29.00 ± 1.36 | 100.30 ± 3.18 | 191.50 ± 41.60 | 36.70 ± 0.67 |
| 110 | 11.60 ± 1.55 | 92.30 ± 2.03 | 25.40 ± 3.38 | 37.70 ± 2.03 |
| 111 | 2.23 ± 0.12 | 64.00 ± 4.00 | 42.60 ± 7.64 | 22.70 ± 2.33 |
| 112 | 7.56 ± 0.45 | 83.70 ± 1.45 | 23.40 ± 7.81 | 26.30 ± 0.88 |
| 113 | 0.45 ± 0.036 | 68.70 ± 3.71 | 0.052 ± 0.013 | 99.20 ± 1.65 |
| 114 | 152.10 ± 16.80 | 20.70 ± 0.67 | 18.90 ± 2.01 | 107.00 ± 4.36 |
| 115 | 159.30 ± 15.40 | 37.70 ± 1.67 | 53.40 ± 7.28 | 76.00 ± 6.66 |
| 116 | 3.12 ± 0.15 | 104.30 ± 2.96 | 69.40 ± 5.37 | 56.30 ± 3.93 |
| 117 | 822.40 ± 93.90 | 93.70 ± 5.36 | 3394 ± 439.20 | 79.70 ± 5.46 |
| 118 | 1.32 ± 0.04 | 101.00 ± 2.52 | 90.80 ± 7.63 | 75.20 ± 4.33 |
| 119 | 32.20 ± 3.26 | 100.30 ± 2.73 | 382.80 ± 21.90 | 96.70 ± 5.36 |
| 120 | 2938.00 ± 481.00 | 76.30 ± 3.48 | 2865.00 ± 231.10 | 62.30 ± 4.91 |
| 121 | 126.00 ± 15.40 | 91.70 ± 4.18 | 604.50 ± 68.10 | 18.30 ± 0.88 |
| 122 | 0.36 ± 0.01 | 101.70 ± 1.20 | 15.20 ± 2.63 | 94.50 ± 0.65 |
| 123 | 1.85.00 ± 0.16 | 104.00 ± 3.06 | 112.50 ± 5.80 | 74.00 ± 3.06 |
| 124 | 14.10 ± 0.48 | 98.00 ± 3.06 | 679.70 ± 67.70 | 77.30 ± 4.63 |
| 125 | 2620.00 ± 396.50 | 70.70 ± 2.33 | 443.40 ± 73.20 | 102.00 ± 5.69 |
| 126 | 146.90 ± 9.47 | 103.30 ± 2.40 | 1465.00 ± 91.30 | 63.70 ± 3.93 |
| 127 | >20μ | 3.67 ± 1.20 | 947.10 ± 68.00 | 93.00 ± 3.51 |
| 128 | 0.18 ± 0.069 | 47.80 ± 1.25 | 0.74 ± 0.13 | 90.70 ± 1.45 |
| 129 | 9.14 ± 1.19 | 20.00 ± 1.15 | 0.78 ± 0.070 | 97.30 ± 1.86 |
| 130 | 373.00 ± 104.60 | 29.00 ± 2.00 | 22.80 ± 3.38 | 71.00 ± 3.11 |
| 131 | 290.00 ± 5.32 | 69.00 ± 1.00 | >20 μM | 0.00 |
| 132 | 3.03 ± 0.17 | 95.30 ± 2.60 | 11.40 ± 1.58 | 89.00 ± 5.69 |
| 133 | 3.90 ± 0.74 | 22.30 ± 1.20 | 21.70 ± 3.16 | 42.00 ± 4.02 |
| 134 | 1.47 ± 0.58 | 16.00 ± 0.71 | >20 μM | 90.00 |
| 135 | 1700.00 ± 112.20 | 92.00 ± 2.65 | 2810.00 ± 397.20 | 22.00 ± 2.52 |
| 136 | 2332.00 ± 236.30 | 62.30 ± 3.84 | 3835.00 ± 540.80 | 22.30 ± 3.71 |
| 137 | 1322.00 ± 177.50 | 50.30 ± 1.76 | 3373.00 ± 753.00 | 30.00 ± 2.31 |
| 138 | >20 μM | 45.30 ± 2.33 | >20 μM | 35.50 ± 2.06 |
| 139 | 12.50 ± 2.18 | 87.00 ± 3.08 | 91.80 ± 4.88 | 48.00 ± 5.13 |
| 140 | 0.10 ± 0.01 | 82.00 ± 0.91 | 4.68 ± 0.40 | 107.20 ± 4.40 |

TABLE 3

Structure of Exemplified Compounds

| Ref. No. | Compound |
|---|---|
| 1 | *(structure)* |
| 2 | *(structure)* |
| 3 | *(structure)* |
| 4 | *(structure)* |
| 5 | *(structure)* |
| 6 | *(structure)* |

TABLE 3-continued

Structure of Exemplified Compounds

| Ref. No. | Compound |
|---|---|
| 7 | *(structure)* |
| 8 | *(structure)* |
| 9 | *(structure)* |
| 10 | *(structure)* |
| 11 | *(structure)* |
| 12 | *(structure)* |
| 13 | *(structure)* |

TABLE 3-continued
Structure of Exemplified Compounds
| Ref. No. | Compound |
|---|---|
| 14 | 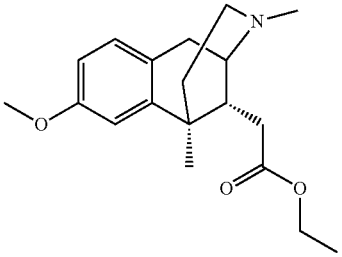 [SMILES: CCOC(=O)C[C@H]1C2Cc3ccc(OC)cc3[C@@]1(C)CCN2C] |
| 15 | 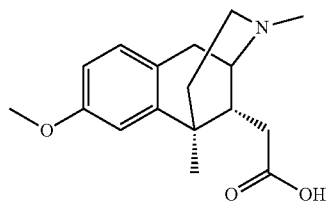 [SMILES: COc1ccc2c(c1)[C@@]1(C)CCN(C)C(C2)[C@@H]1CC(=O)O] |
| 16 | 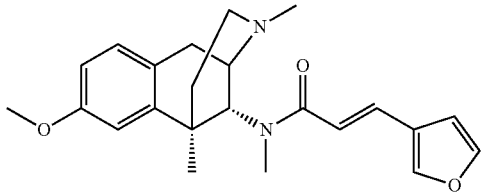 [SMILES: COc1ccc2c(c1)[C@@]1(C)CCN(C)C(C2)[C@@H]1N(C)C(=O)/C=C/c1ccoc1] |
| 17 | 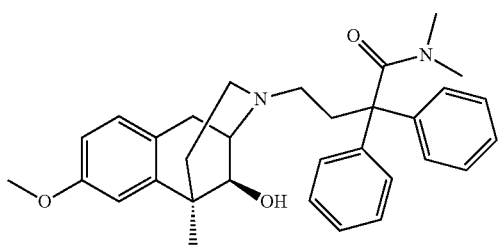 [SMILES: COc1ccc2c(c1)[C@@]1(C)CCN(CCC(C(=O)N(C)C)(c3ccccc3)c3ccccc3)C(C2)[C@H]1O] |
| 18 | 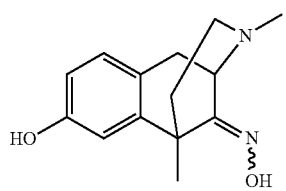 [SMILES: CN1CCC2(C)C(=NO)C1Cc1ccc(O)cc12] |
| 19 | 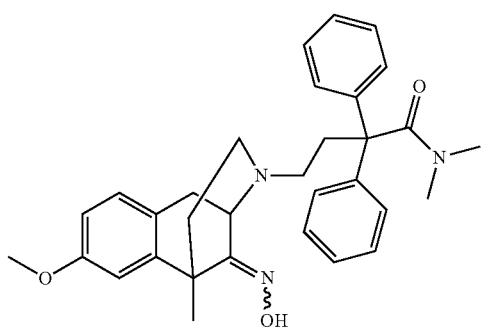 |
| 20 | 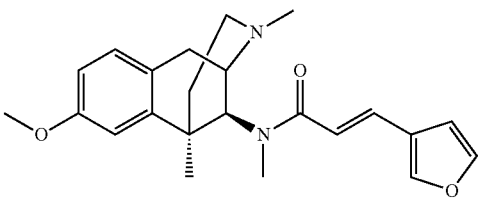 [SMILES: COc1ccc2c(c1)[C@@]1(C)CCN(C)C(C2)[C@H]1N(C)C(=O)/C=C/c1ccoc1] |
| 21 | 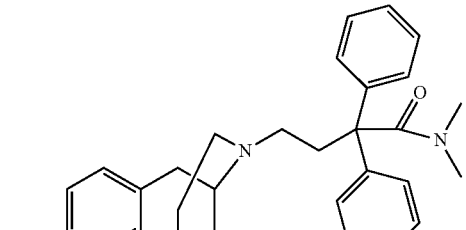 |
| 22 |  |
| 23 |  |
| 24 |  |
| 25 |  |

TABLE 3-continued

Structure of Exemplified Compounds

| Ref. No. | Compound |
|---|---|
| 26 | |
| 27 | |
| 28 | |
| 29 | |
| 30 | |
| 31 | |
| 32 | |
| 33 | |
| 34 | |
| 35 | |
| 36 | |
| 37 | |
| 38 | |

US 10,138,207 B2
177
TABLE 3-continued
Structure of Exemplified Compounds
| Ref. No. | Compound |
|---|---|
| 39 | 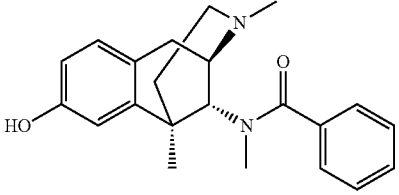 [SMILES: CN1CC[C@]2(C)c3cc(O)ccc3C[C@@H]1[C@@H]2N(C)C(=O)c1ccccc1] |
| 40 | 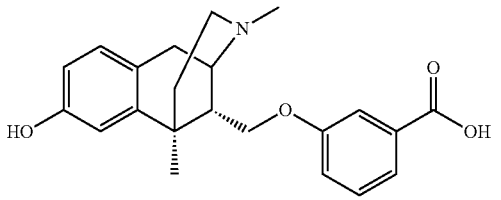 [SMILES: CN1CC[C@]2(C)c3cc(O)ccc3CC1[C@@H]2COc1cccc(C(=O)O)c1] |
| 41 | 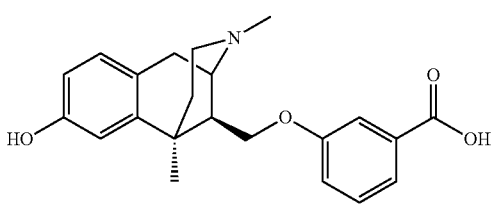 [SMILES: CN1CC[C@]2(C)c3cc(O)ccc3CC1[C@H]2COc1cccc(C(=O)O)c1] |
| 42 | 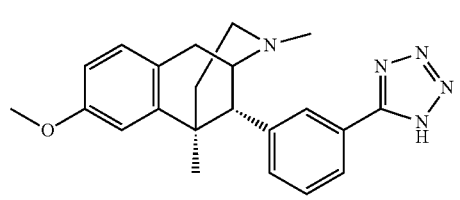 [SMILES: COc1ccc2c(c1)[C@@]1(C)CCN(C)C(C2)[C@@H]1c1cccc(-c2nnn[nH]2)c1] |
| 43 | 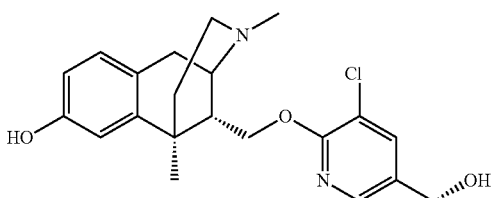 |
| 44 | 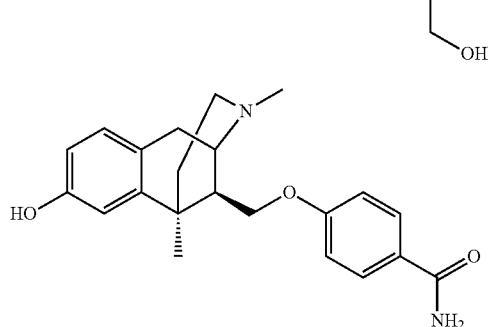 |
| 45 | 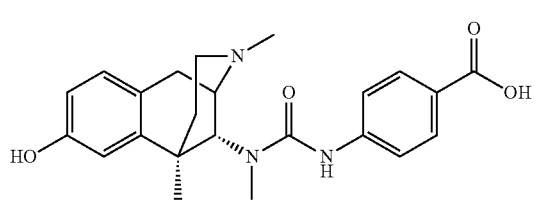 [SMILES: CN1CC[C@]2(C)c3cc(O)ccc3CC1[C@@H]2N(C)C(=O)Nc1ccc(C(=O)O)cc1] |
178
TABLE 3-continued
Structure of Exemplified Compounds
| Ref. No. | Compound |
|---|---|
| 46 | 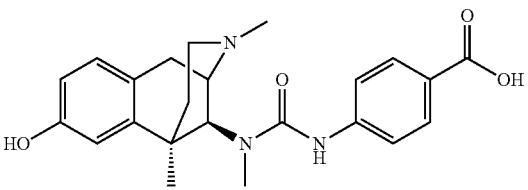 [SMILES: CN1CC[C@]2(C)c3cc(O)ccc3CC1[C@H]2N(C)C(=O)Nc1ccc(C(=O)O)cc1] |
| 47 | 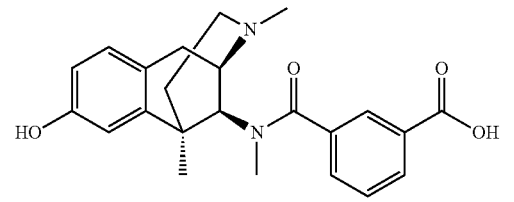 [SMILES: CN1CC[C@]2(C)c3cc(O)ccc3C[C@@H]1[C@H]2N(C)C(=O)c1cccc(C(=O)O)c1] |
| 48 | 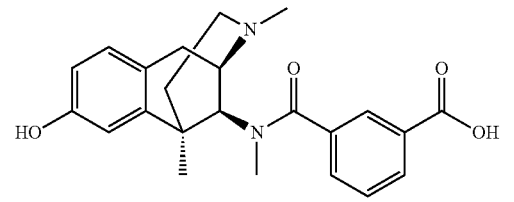 [SMILES: CN1CC[C@]2(C)c3cc(O)ccc3C[C@@H]1[C@H]2N(C)C(=O)c1cccc(C(=O)O)c1] |
| 49 | 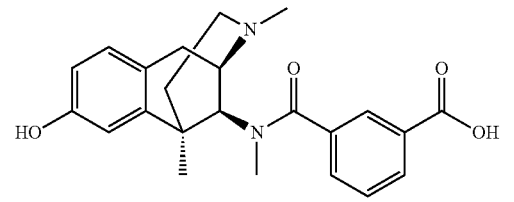 [SMILES: CN1CC[C@]2(C)c3cc(O)ccc3C[C@@H]1[C@H]2N(C)C(=O)c1cccc(C(=O)O)c1] |
| 50 | 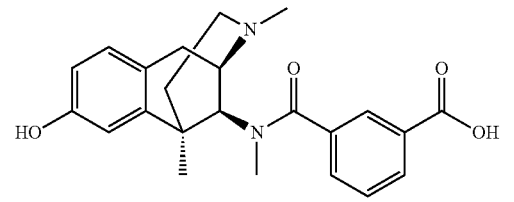 [SMILES: CN1CC[C@]2(C)c3cc(O)ccc3C[C@@H]1[C@H]2N(C)C(=O)c1cccc(C(=O)O)c1] |
| 51 | 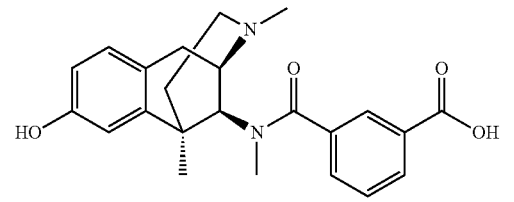 [SMILES: CN1CC[C@]2(C)c3cc(O)ccc3C[C@@H]1[C@H]2N(C)C(=O)c1cccc(C(=O)O)c1] |
| 52 | 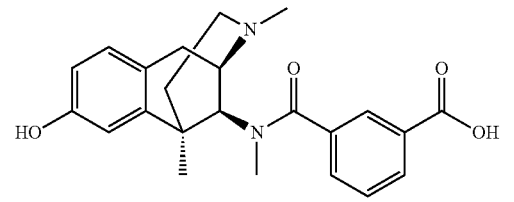 [SMILES: CN1CC[C@]2(C)c3cc(O)ccc3C[C@@H]1[C@H]2N(C)C(=O)c1cccc(C(=O)O)c1] |

TABLE 3-continued

Structure of Exemplified Compounds

| Ref. No. | Compound |
|---|---|
| 53 | [structure] |
| 54 | [structure] |
| 55 | [structure] |
| 56 | [structure] |
| 57 | [structure] |
| 58 | [structure] |
| 59 | [structure] |
| 60 | [structure] |
| 61 | [structure] |
| 62 | [structure] |
| 63 | [structure] |
| 64 | [structure] |
| 65 | [structure] |

TABLE 3-continued
Structure of Exemplified Compounds
| Ref. No. | Compound |
|---|---|
| 66 | 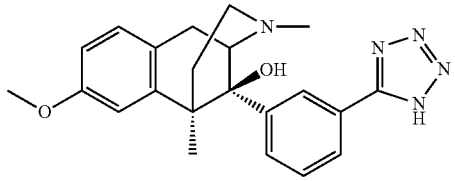 [SMILES: COc1ccc2c(c1)[C@@]1(C)CCN(C)C(C2)[C@]1(O)c1cccc(-c2nnn[nH]2)c1] |
| 67 | 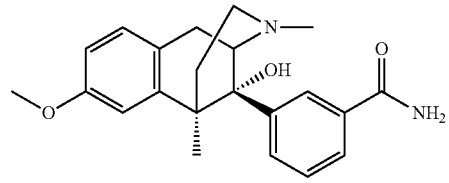 [SMILES: COc1ccc2c(c1)[C@@]1(C)CCN(C)C(C2)[C@@]1(O)c1cccc(C(N)=O)c1] |
| 68 | 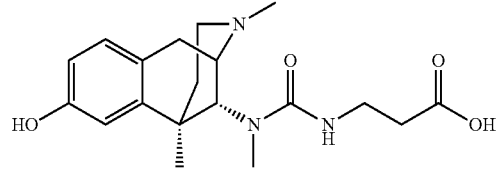 [SMILES: CN1CC[C@]2(C)c3cc(O)ccc3CC1[C@@H]2N(C)C(=O)NCCC(=O)O] |
| 69 | 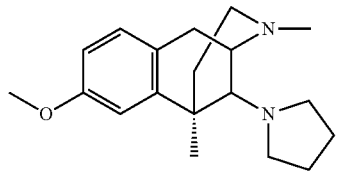 [SMILES: COc1ccc2c(c1)[C@@]1(C)CCN(C)C(C2)C1N1CCCC1] |
| 70 | 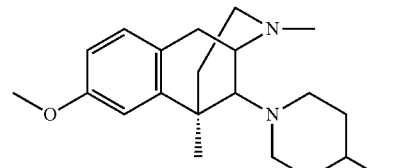 |
| 71 | 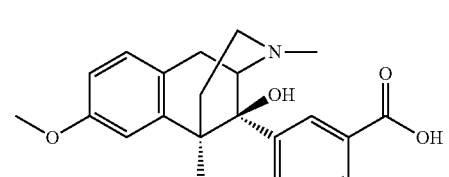 |
| 72 | 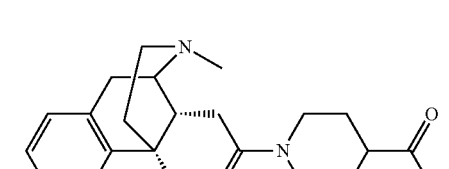 |
| 73 | 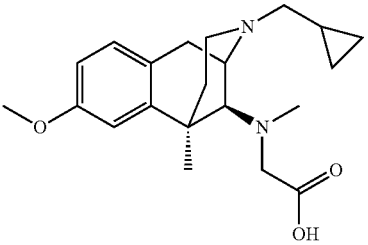 [SMILES: COc1ccc2c(c1)[C@@]1(C)CCN(CC3CC3)C(C2)[C@H]1N(C)CC(=O)O] |
| 74 | 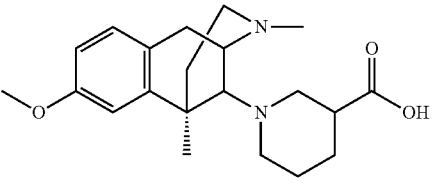 [SMILES: COc1ccc2c(c1)[C@@]1(C)CCN(C)C(C2)C1N1CCCC(C(=O)O)C1] |
| 75 | 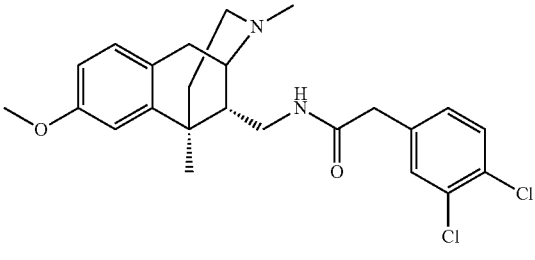 [SMILES: COc1ccc2c(c1)[C@@]1(C)CCN(C)C(C2)[C@@H]1CNC(=O)Cc1ccc(Cl)c(Cl)c1] |
| 76 | 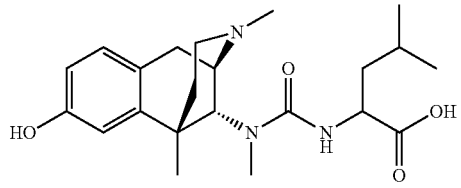 [SMILES: CC(C)CC(NC(=O)N(C)[C@H]1[C@H]2Cc3ccc(O)cc3[C@]1(C)CCN2C)C(=O)O] |
| 77 | 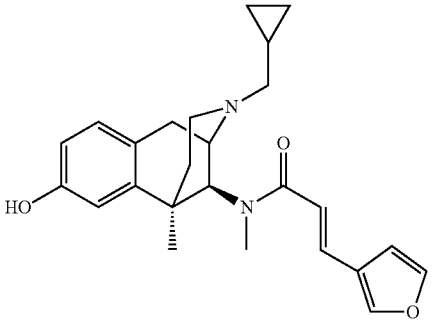 [SMILES: CN(C(=O)/C=C/c1ccoc1)[C@@H]1C2Cc3ccc(O)cc3[C@@]1(C)CCN2CC1CC1] |
| 78 | |

TABLE 3-continued

Structure of Exemplified Compounds

| Ref. No. | Compound |
|---|---|
| 79 | |
| 80 | |
| 81 | |
| 82 | |
| 83 | |
| 84 | |
| 85 | |

TABLE 3-continued
Structure of Exemplified Compounds
| Ref. No. | Compound |
|---|---|
| 86 | 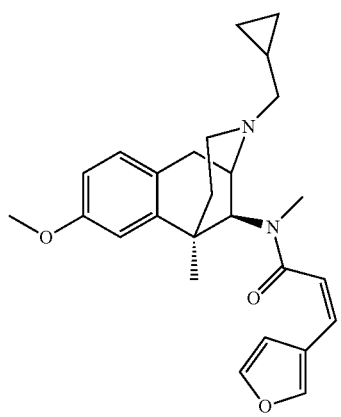 [SMILES: COc1ccc2c(c1)[C@@]1(C)CCN(CC3CC3)C(C2)[C@H]1N(C)C(=O)/C=C\c1ccoc1] |
| 87 | 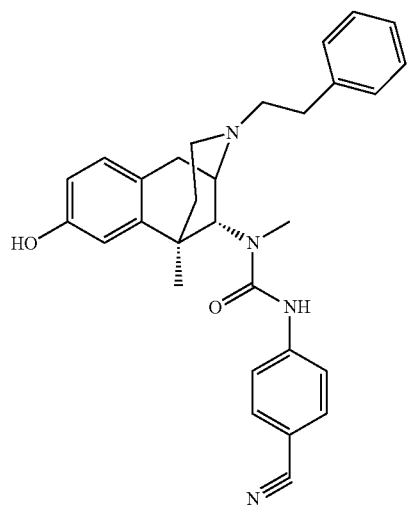 [SMILES: CN(C(=O)Nc1ccc(C#N)cc1)[C@H]1C2Cc3ccc(O)cc3[C@@]1(C)CCN2CCc1ccccc1] |
| 88 | 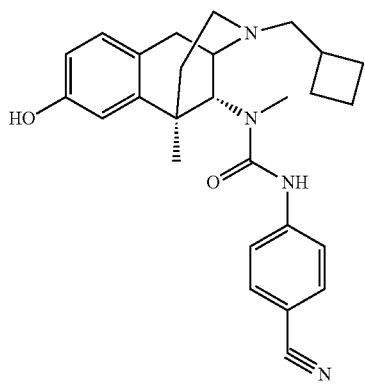 [SMILES: CN(C(=O)Nc1ccc(C#N)cc1)[C@H]1C2Cc3ccc(O)cc3[C@@]1(C)CCN2CC1CCC1] |
TABLE 3-continued
Structure of Exemplified Compounds
| Ref. No. | Compound |
|---|---|
| 89 | 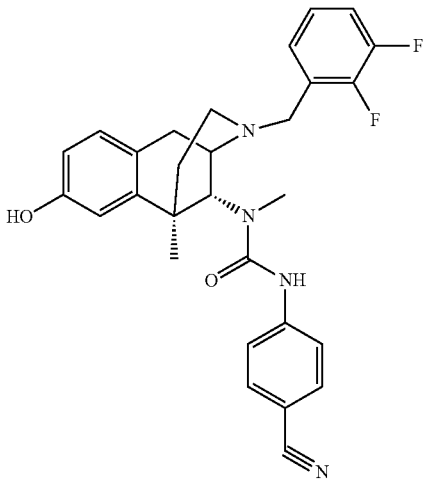 [SMILES: CN(C(=O)Nc1ccc(C#N)cc1)[C@H]1C2Cc3ccc(O)cc3[C@@]1(C)CCN2Cc1cccc(F)c1F] |
| 90 | 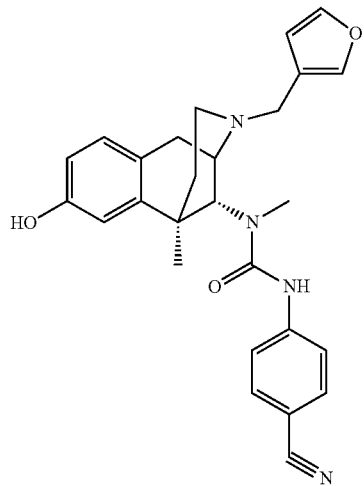 [SMILES: CN(C(=O)Nc1ccc(C#N)cc1)[C@H]1C2Cc3ccc(O)cc3[C@@]1(C)CCN2Cc1ccoc1] |
| 91 | 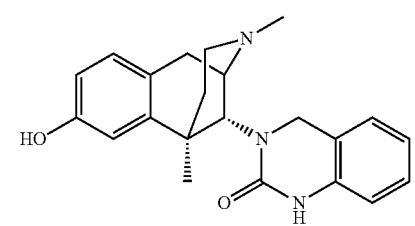 [SMILES: CN1CC[C@]2(C)c3cc(O)ccc3CC1[C@@H]2N1Cc2ccccc2NC1=O] |

TABLE 3-continued
Structure of Exemplified Compounds
| Ref. No. | Compound |
|---|---|
| 92 | 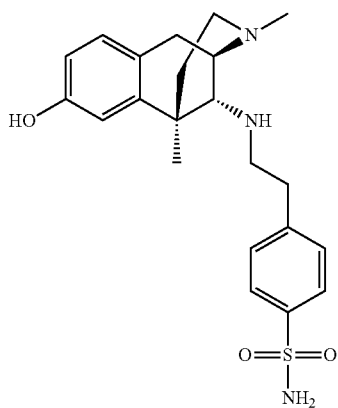 |
| 93 | 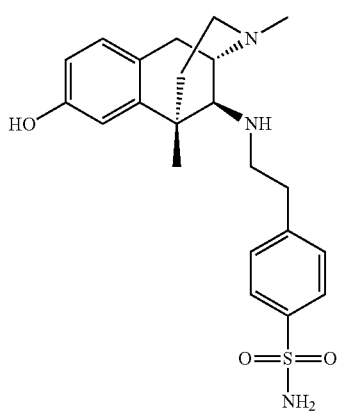 |
| 94 | 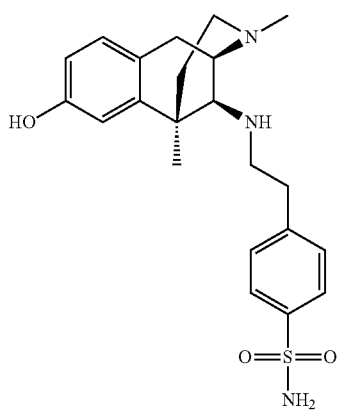 |
| 95 | 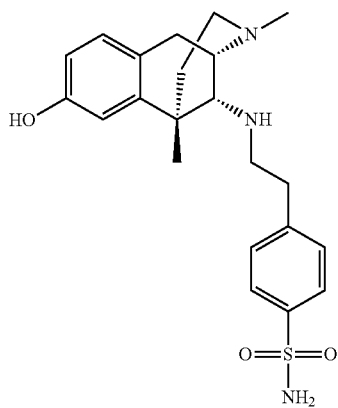 |
| 96 | 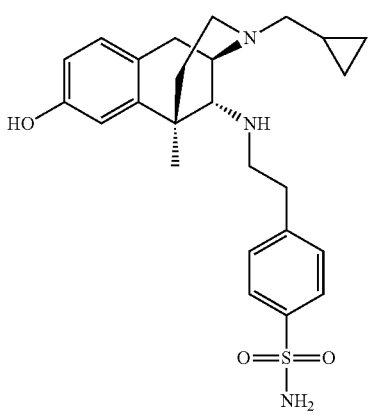 |
| 97 | 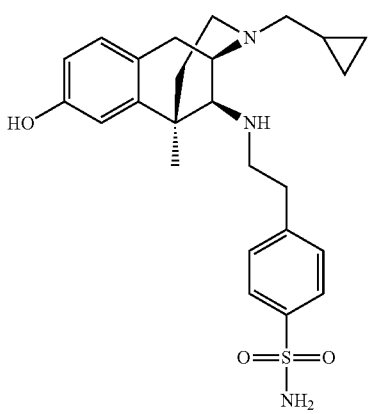 |

TABLE 3-continued

Structure of Exemplified Compounds

| Ref. No. | Compound |
|---|---|
| 98 | (structure: hydroxy-methyl-morphinan core with NH-CH2CH2-(3,4-dichlorophenyl) substituent) |
| 99 | (structure: hydroxy-methyl-morphinan core with NH-CH2CH2-(3,4-dichlorophenyl) substituent, different stereochemistry) |
| 100 | (structure: hydroxy-methyl-morphinan core with NH-CH2CH2-(4-methoxyphenyl) substituent) |
| 101 | (structure: hydroxy-methyl-morphinan core with NH-CH2CH2-(4-fluorophenyl) substituent) |
| 102 | (structure: hydroxy-morphinan core with N-CH2-cyclopropyl and NH-CH2-(piperidin-4-yl) substituent) |
| 103 | (structure: hydroxy-methyl-morphinan core with NH-CH2CH2-(pyridin-4-yl) substituent) |
| 104 | (structure: hydroxy-methyl-morphinan core with NH-CH2CH2-(thiophen-2-yl) substituent) |
| 105 | (structure: hydroxy-methyl-morphinan core with NH-CH2CH2-(4-tert-butylphenyl) substituent) |

TABLE 3-continued
Structure of Exemplified Compounds
| Ref. No. | Compound |
|---|---|
| 106 | 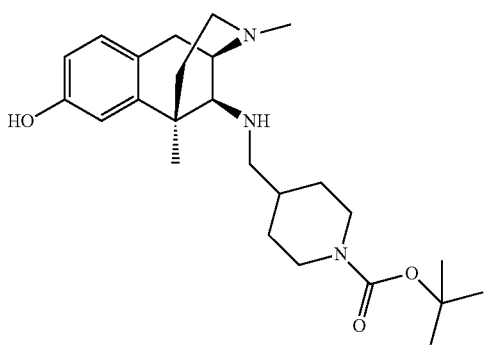 |
| 107 | 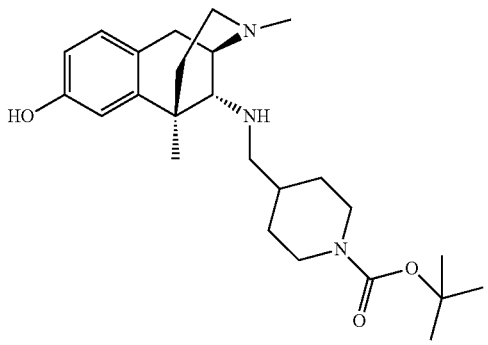 |
| 108 | 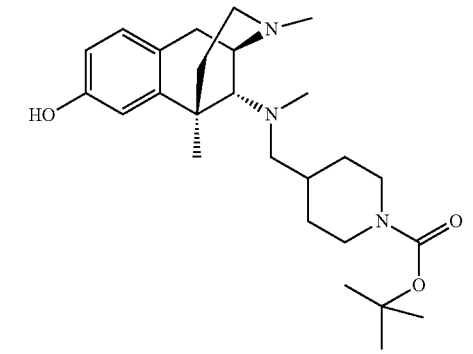 |
| 109 | 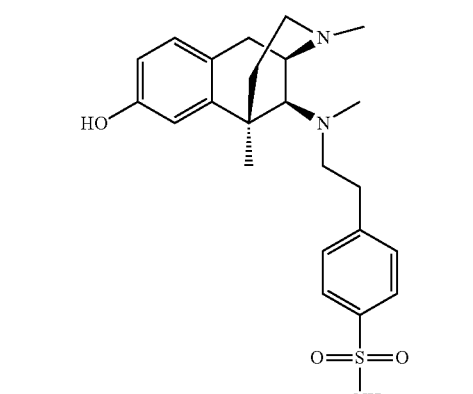 |
| 110 | 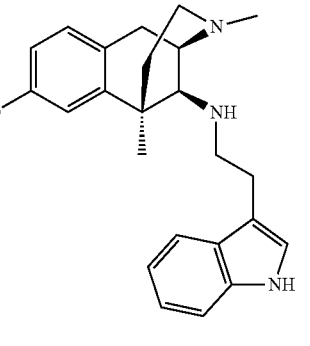 |
| 111 | 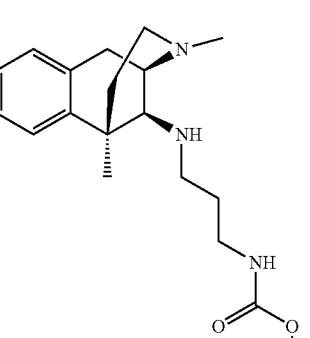 |
| 112 | 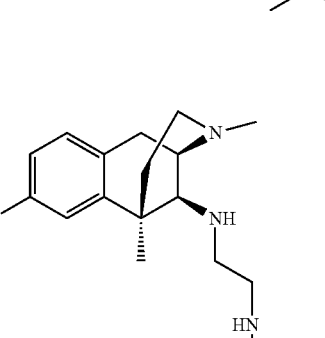 |
| 113 | 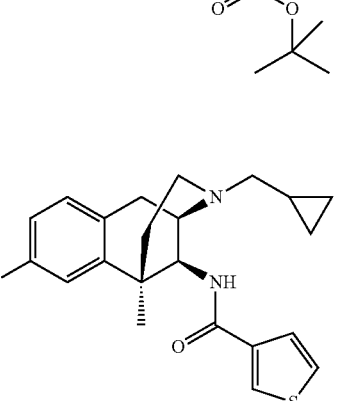 |

TABLE 3-continued

Structure of Exemplified Compounds

| Ref. No. | Compound |
|---|---|
| 114 | *(chemical structure)* |
| 115 | *(chemical structure)* |
| 116 | *(chemical structure)* |
| 117 | *(chemical structure)* |
| 118 | *(chemical structure)* |
| 119 | *(chemical structure)* |
| 120 | *(chemical structure)* |
| 121 | *(chemical structure)* |
| 122 | *(chemical structure)* |
| 123 | *(chemical structure)* |

TABLE 3-continued

Structure of Exemplified Compounds

| Ref. No. | Compound |
|---|---|
| 124 | (structure) |
| 125 | (structure) |
| 126 | (structure) |
| 127 | (structure) |
| 128 | (structure) |
| 129 | (structure) |
| 130 | (structure) |
| 131 | (structure) |
| 132 | (structure) |

TABLE 3-continued

Structure of Exemplified Compounds

| Ref. No. | Compound |
|---|---|
| 133 | |
| 134 | |
| 135 | |
| 136 | |
| 137 | |
| 138 | |
| 139 | |
| 140 | |

The in vitro test results of Tables 1, 2, and 2A show that representative Compounds of the Invention generally have high binding affinity for opioid receptors, and that these compounds activate these receptors as partial to full agonists. Compounds of the Invention are therefore expected to be useful to treat Conditions, particularly pain, that are responsive to the activation of one or more opioid receptors.

Example 52

4-(3-((((6R,11S)-3-(cyclopropylmethyl)-8-methoxy-6-methyl-1,2,3,4,5,6-hexahydro-2,6-methanobenzo[d]azocin-11-yl)-3-methylureido)benzamide (Compound 82)

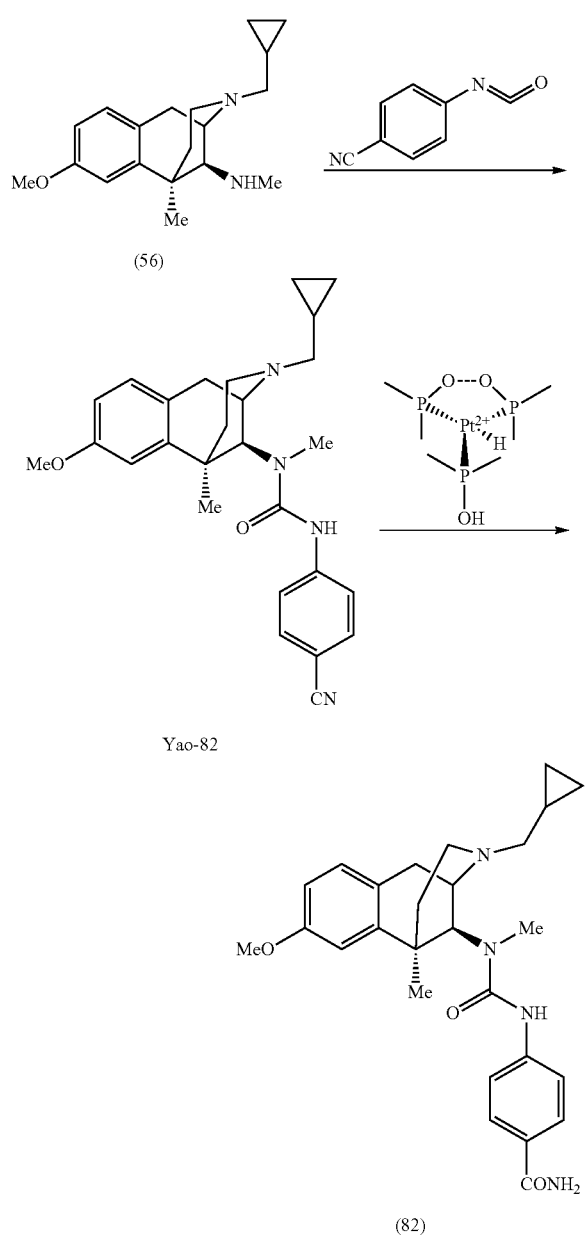

4-isocyanatobenzonitrile (0.4 g, 1.67 mmol, Aldrich) was added to a solution of Compound 56 (0.5 g, 1.67 mmol) in CHCl$_3$ (4 mL) at 0° C. The reaction mixture was warmed to RT, and stirred at RT for 24 h. The reaction was quenched with 2 mL of water and 0.2 mL of conc. NH$_4$OH, and extracted with CHCl$_3$. The CHCl$_3$ layer was separated, concentrated, and purified by flash chromatography (SiO$_2$, 10% CHCl$_3$/hexanes) to give Compound Yao-82 as a colorless oil (0.6 g, 81%).

LC/MS, m/z=445.4 [M+H]$^+$ (Calc: 444.6).

A mixture of Compound Yao-82 (50 mg, 0.09 mmol) and bis(dimethyloxidophosphoranyl) (hydroxydimethylphosphoranyl)platinum(VI) hydride (5 mg, STREM CHEM. Inc.) in 1 mL of EtOH/water (3/1) was shaken at 85° C. for 3 h. The reaction was quenched with water, and extracted with CHCl$_3$. The CHCl$_3$ layer was separated, concentrated, and purified by reverse-phase prep HPLC (C18, 0-100% 0.1% TFA in water/0.1% TFA in ACN) to yield Compound 82 as a TFA-salt (white solid, 15 mg, 36%).

$^1$H NMR $\delta_H$ (400 MHz, CD$_3$OD) 7.87 (d, J=8.0 Hz, 2H) 6.98 (d, J=8.8 Hz, 1H), 6.71 (d, J=2.8 Hz, 1H), 6.62 (dd, J=2.8 and 7.6 Hz, 1H), 4.24 (d, J=5.6 Hz, 1H), 3.27-3.40 (m, 1H), 3.23 (s, 3H), 3.00-3.11 (m, 1H), 2.62-2.70 (m, 1H), 2.28-2.37 (m, 1H), 1.47 (s, 3H), 1.44 (d, J=14.8 Hz, 1H), 1.04-1.13 (m, 1H), 0.66-0.71 (m, 2H), 0.38-0.44 (m, 2H).

LC/MS, m/z=431.3 [M+H]$^+$ (Calc: 430.5).

Example 53

4-((2R,6R,11S)-11-(3-(4-cyanophenyl)-1-methylureido)-8-hydroxy-6-methyl-1,2,5,6-tetrahydro-2,6-methanobenzo[d]azocin-3(4H)-yl)-N,N-dimethyl-2,2-diphenylbutanamide (Compound 84)

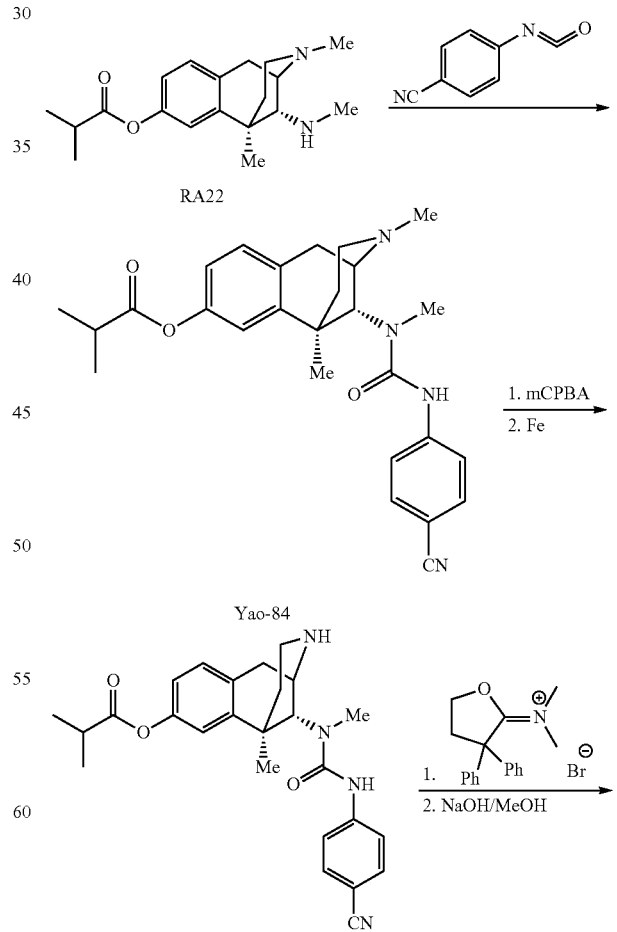

-continued

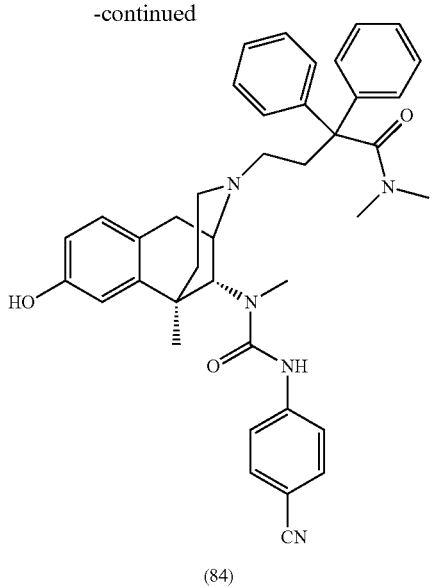

(84)

4-isocyanatobenzonitrile (0.40 g, 2.8 mmol) was added to a solution of Compound RA22 (0.8 g, 2.53 mmol) in CHCl₃ (4 mL) at 0° C. The reaction mixture was warmed to RT, and stirred at RT for 24 h. The reaction was quenched with 2 mL of water and 0.2 mL of conc. NH₄OH, and extracted with CHCl₃. The CHCl₃ layer was separated, concentrated, and purified by flash chromatography (SiO₂, 10% CHCl₃/hexanes) to give Compound Yao-84 as an orange solid (0.85 g, 73%).

LC/MS, m/z=461.3 [M+H]⁺ (Calc: 460.5).

mCPBA (80 mg, 85%) was added to a solution of Compound Yao-084 (0.20 g, 0.43 mmol) in CHCl₃ (4 mL) at 0° C. After 10 min, 30 μL of HCl (5N) and 100 mg of iron powder were added. The reaction mixture was warmed to RT, and stirred at RT for 16 h. The reaction was filtered through a layer of Na₂SO₄, then quenched with water and extracted with CHCl₃. The CHCl₃ layer was washed with saturated aq. sodium sulfite (1 mL), and concentrated to give the crude product Compound Yao-85 (0.20 g).

LC/MS, m/z=447.2 [M+H]⁺ (Calc: 446.5).

Dihydro-N,N-dimethyl-3,3-diphenyl-2(3H)-furan-aminium bromide (60 mg, 0.17 mmol) was added to a solution of Compound Yao-085 (0.15 g, 0.34 mmol) in DCM (15 mL) and TEA (30 μL) at 0° C. The reaction mixture was warmed to 36° C., and shaken at 36° C. for 2 h. The reaction was quenched with 1 mL of water and 1 mL of saturated NaHCO₃. The organic layer was separated, and concentrated under vacuum. The residue was re-dissolved in 2 mL of MeOH, then 0.1 mL of NaOH (2N) was added. The mixture was shaken at 36° C. for 2 h. The reaction mixture was concentrated under vacuum, and purified by reverse-phase prep HPLC (C18, 0-100% 0.1% TFA in water/0.1% TFA in ACN) to yield Compound 84 as a TFA-salt (white solid, 15 mg).

$^1$H NMR $\delta_H$ (400 MHz, CD₃OD) 7.52-7.60 (m, 4H), 7.28-7.42 (m, 10H), 6.88 (d, J=8.8 Hz, 1H), 6.71 (s, 1H), 6.59 (d, J=7.6 Hz, 1H), 4.52 (s, 0.8H), 4.34 (s, 0.2H), diastereoisomers of TFA-salt), 3.49 (br, 1H), 2.90-3.10 (m, 6H), 2.82-2.84 (m, 2H), 2.58-2.71 (m, 4H), 2.35-2.48 (m, 2H), 2.25 (s, 3H), 2.00-2.08 (m, 1H), 1.58 (d, J=15.6 Hz), 1.41 (s, 2.4H), 1.36 (3, 0.6H).

LC/MS, m/z=642.3 [M+H]⁺ (Calc: 641.8).

In a similar manner the following compounds were prepared.

3-(4-cyanophenyl)-1-((2R,6R,11S)-8-hydroxy-6-methyl-3-phenethyl-1,2,3,4,5,6-hexahydro-2,6-methanobenzo[d]azocin-11-yl)-1-methylurea (Compound 87)

$^1$H NMR $\delta_H$ (400 MHz, CD₃OD) 7.55-7.60 (m, 4H), 7.18-7.28 (m, 5H), 7.02 (d, J=8.8 Hz, 1H), 6.71 (s, 1H), 6.64 (d, J=7.6 Hz, 1H), 4.75 (s, 0.2H), 4.59 (s, 0.8H, diastereoisomers of TFA-salt), 3.94 (s, 1H), 3.23-3.59 (m, 3H), 2.92-3.14 (m, 4H), 2.62-2.73 (m, 4H), 1.91-2.08 (m, 1H), 1.64 (d, J=12.4 Hz, 1H), 1.46 (s, 3H).

LC/MS, m/z=481.2 [M+H]⁺ (Calc: 480.6).

3-(4-cyanophenyl)-1-((6R,11R)-3-(cyclobutylmethyl)-8-hydroxy-6-methyl-1,2,3,4,5,6-hexahydro-2,6-methanobenzo[d]azocin-11-yl)-1-methylurea (Compound 88)

$^1$H NMR $\delta_H$ (400 MHz, CD₃OD) 7.52-7.60 (m, 4H), 6.95-7.02 (m, 2H), 6.74 (d, J=2.8 Hz, 1H), 6.64 (dd, J=2.8 and 8.8 Hz, 1H), 4.54 (s, 1H), 3.74 (s, 1H), 3.56-3.58 (m, 1H), 3.44-3.47 (m, 1H), 3.22-3.28 (m, 1H), 3.05-3.13 (m, 1H), 2.92-3.04 (m, 2H), 2.58-2.73 (m, 5H), 1.73-2.18 (m, 7H), 1.43-1.61 (m, 4H).

LC/MS, m/z=445.2 [M+H]⁺ (Calc: 444.6).

3-(4-cyanophenyl)-1-((6R,11R)-3-(2,3-difluorobenzyl)-8-hydroxy-6-methyl-1,2,3,4,5,6-hexahydro-2,6-methanobenzo[d]azocin-11-yl)-1-methylurea (Compound 89)

$^1$H NMR $\delta_H$ (400 MHz, CD₃OD) 7.50-7.57 (m, 4H), 7.30-7.39 (m, 2H), 7.16-7.24 (m, 1H), 7.00-7.08 (m, 1H), 6.77 (d, J=3.2 Hz, 1H), 6.64 (dd, J=2.4 and 8.8 Hz, 1H), 4.50-4.56 (m, 2H), 3.84-3.91 (m, 1H), 3.56-3.58 (m, 1H), 3.44-3.47 (m, 1H), 3.05-3.19 (m, 2H), 2.76-2.85 (m, 1H), 2.68 (s, 3H), 1.98-2.11 (m, 1H), 1.62 (d, J=12.4 Hz, 1H), 1.44 (s, 3H).

LC/MS, m/z=503.3 [M+H]⁺ (Calc: 502.6).

3-(4-cyanophenyl)-1-((2R,6R,11S)-3-(furan-3-ylmethyl)-8-hydroxy-6-methyl-1,2,3,4,5,6-hexahydro-2,6-methanobenzo[d]azocin-11-yl)-1-methylurea (Compound 90)

$^1$H NMR $\delta_H$ (400 MHz, CD₃OD) 7.67-7.73 (m, 4H), 7.58 (d, J=8.4 Hz, 2H), 7.03 (d, J=9.2 Hz, 1H), 6.73 (d, J=2.4 Hz, 1H), 6.63 (dd, J=2.8 and 8.4 Hz, 1H), 6.51 (s, 1H), 4.23 (br, 1H), 3.46-3.56 (m, 3H), 3.05-3.12 (m, 2H), 2.67 (s, 3H), 2.46-2.52 (m, 1H), 1.85-2.05 (m, 2H), 1.38 (s, 3H), 1.31 (d, J=12.4 Hz, 1H).

LC/MS, m/z=457.2 [M+H]⁺ (Calc: 456.5).

Example 54

3-(((2R,6R,11S)-8-hydroxy-3,6-dimethyl-1,2,3,4,5,6-hexahydro-2,6-methanobenzo[d]azocin-11-yl)-3,4-dihydroquinazolin-2(1H)-one (Compound 91)

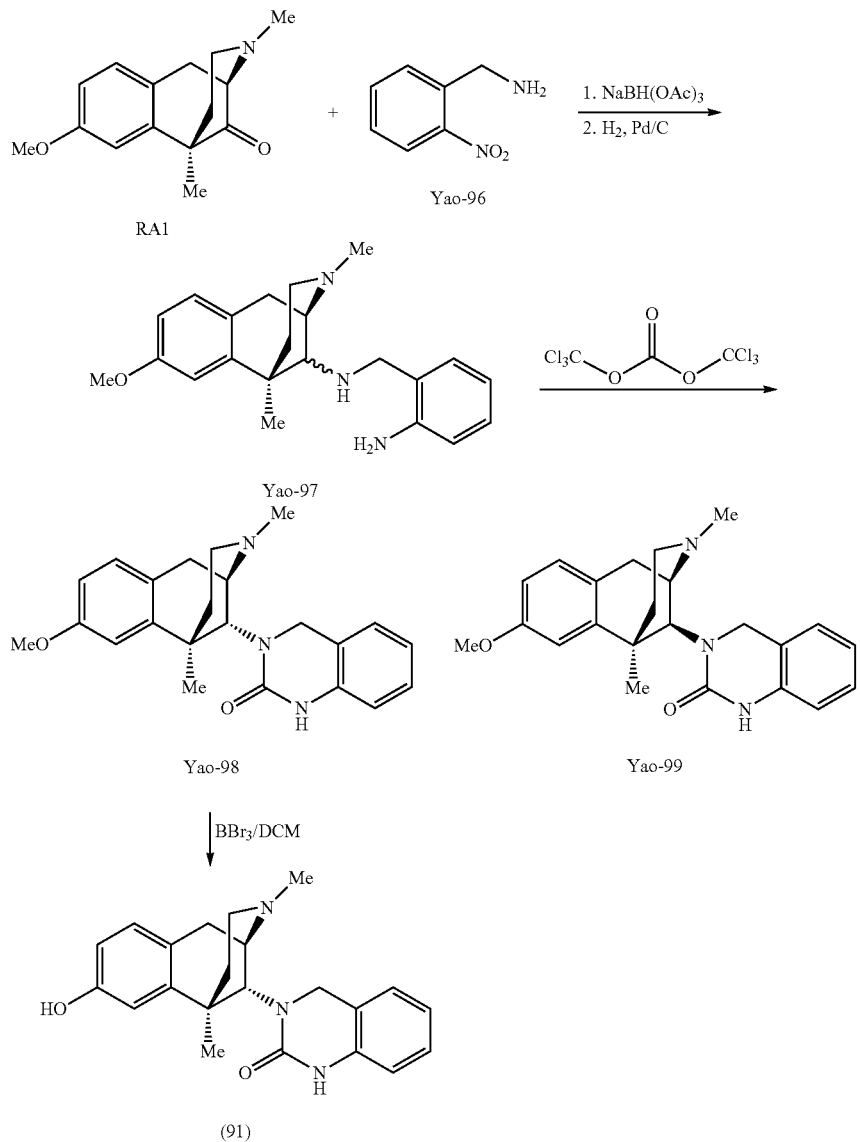

A mixture of Compound RA1 (0.36 g, 1.47 mmol), (2-nitrophenyl)methanamine, HCl (Compound Yao-96, 0.48 g, 2.5 mmol), TEA (0.4 g, 4 mmol) and Na$_2$SO$_4$ (0.5 g) in 4 mL of ACN was shaken at 40° C. for 16 h, then added NaBH(OAc)$_3$ (0.6 g, 2.9 mmol). The reaction mixture was shaken at RT for 2 h. The reaction was quenched with water (3 mL), and extracted with 20 mL of CHCl$_3$. The organic layer was washed with 1N NaOH (6 mL), and concentrated to give an oil, which was dissolved in MeOH (50 mL) and AcOH (2 mL). The MeOH/AcOH solution was passed through H-cube (5 atm, 7.5 mL/min, Pd/C 10%) at RT for 1 h. The solvent was removed under vacuum. The residue was dissolved in CHCl$_3$ (50 mL), cooled with ice-water, and neutralized to pH ~9 with 2N NaOH. The CHCl$_3$ layer was dried over Na$_2$SO$_4$, and filtered to afford crude Compound Yao-97 in chloroform (~50 mL).

LC/MS, m/z=352.4 [M+H]$^+$ (Calc: 351.5).

Triphosgene (0.75 g in 5 mL of CHCl$_3$) was added to a solution of the crude Compound Yao-97 (in 50 mL of CHCl$_3$ and 0.5 mL of TEA at 0° C. The reaction mixture was warmed to RT over 2 h. The reaction was quenched with water at 0° C., and neutralized with 1N NaOH. The organic layer was concentrated and purified by flash chromatography (SiO$_2$, 5% MeOH/DCM) to give Compound Yao-98 (120 mg) and Compound Yao-99 (55 mg). The structures of Compound Yao-98 and Compound Yao-99 were confirmed by 2D NMR.

Compound Yao-098:
$^1$H NMR δ$_H$ (400 MHz, CD$_3$OD) 7.14 (d, J=8.4 Hz, 1H), 7.04 (dd, J=7.0 and 8.4 Hz, 1H), 6.88 (d, J=2.8 Hz, 1H), 6.85 (dd, J=2.8 and 8.8 Hz, 1H), 6.74-6.78 (m, 1H), 6.71 (d, J=8.0

Hz, 1H), 6.53 (d, J=6.8 Hz, 1H), 4.56 (s, 1H), 3.86-3.98 (m, 3H), 3.75 (s, 3H), 3.44-3.58 (m, 1H), 3.30 (d, J=19.8 Hz, 1H), 3.10-3.15 (m, 3H), 2.87 (s, 3H), 2.60-2.66 (m, 1H), 1.97-2.06 (m, 1H), 1.66 (d, J=14.8 Hz, 1H), 1.42 (s, 3H).

BBr₃ (1M in DCM, 2 mL, 2 mmol) was added to a solution of Compound Yao-098 (0.10 g, 0.26 mmol) in DCM (4 mL) at −78° C. After 2 h at −78° C., the reaction mixture was warmed to 0° C. for 30 min. The reaction was quenched with water (2 mL), neutralized with saturated aq. NaHCO₃. The organic layer was separated, and purified by reverse-phase prep HPLC (C18, 0-100% 0.1% TFA in water/0.1% TFA in ACN) to yield Compound 91 as a TFA-salt (white solid, 25 mg).

¹H NMR δ$_H$ (400 MHz, CD₃OD) 7.03-7.07 (m, 2H), 6.75-6.79 (m, 2H), 6.71 (d, J=8.0 Hz, 2H), 6.55 (d, J=7.6 Hz, 1H), 4.53 (s, 1H), 3.82-4.00 (m, 4H), 3.04-3.14 (m, 2H), 2.55 (s, 3H), 2.60-2.66 (m, 1H), 1.97-2.03 (m, 1H), 1.63 (d, J=14.8 Hz, 1H), 1.38 (s, 3H).

LC/MS, m/z=364.2 [M+H]⁺ (Calc: 363.4).

Example 55

(Z)—N-((2R,6R,11S)-3-(cyclopropylmethyl)-8-methoxy-6-methyl-1,2,3,4,5,6-hexahydro-2,6-methanobenzo[d]azocin-11-yl)-3-(furan-3-yl)-N-methyl-acrylamide (Compound 86)

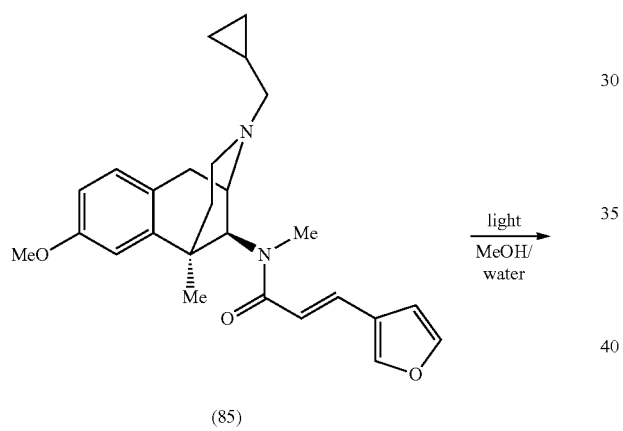

(85)

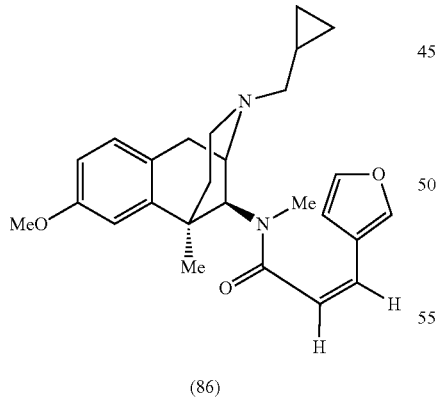

(86)

A solution of Compound 85 (50 mg, 0.12 mmol) in 16 mL of MeOH/water (7/1) was stirred under ambient fluorescent light in a Quartz flask at RT for 24 h. After the solvent was removed under vacuum, the residue was purified by reverse-phase prep HPLC (C18, 0-100% 0.1% TFA in water/0.1% TFA in ACN) to yield Compound 86 as a TFA-salt (white solid, 25 mg).

¹H NMR δ$_H$ (400 MHz, CD₃OD) 7.79 (s, 1H), 7.44 (s, 1H), 7.08 (d, J=7.8 Hz, 1H), 6.82 (d, J=3.6 Hz, 1H), 6.79 (dd, J=3.2 and 9.2 Hz, 1H), 6.65 (d, 1H, J=12.4 Hz, 1H), 6.61 (s, 1H), 6.15 (d, J=12.4 Hz, 1H), 4.31 (s, 1H), 3.90 (s, 1H), 3.38 (s, 3H), 3.07-3.18 (m, 5H), 2.61-2.68 (m, 1H), 2.28-2.37 (m, 1H), 1.54 (d, J=15.2 Hz, 1H), 1.49 (s, 3H), 1.01-1.13 (m, 1H), 0.62-0.73 (m, 2H), 0.35-0.41 (m, 2H).

LC/MS, m/z=421.2 [M+H]⁺ (Calc: 420.5).

Example 56

Resolution of Racemic Intermediates by Chiral Column Chromatography

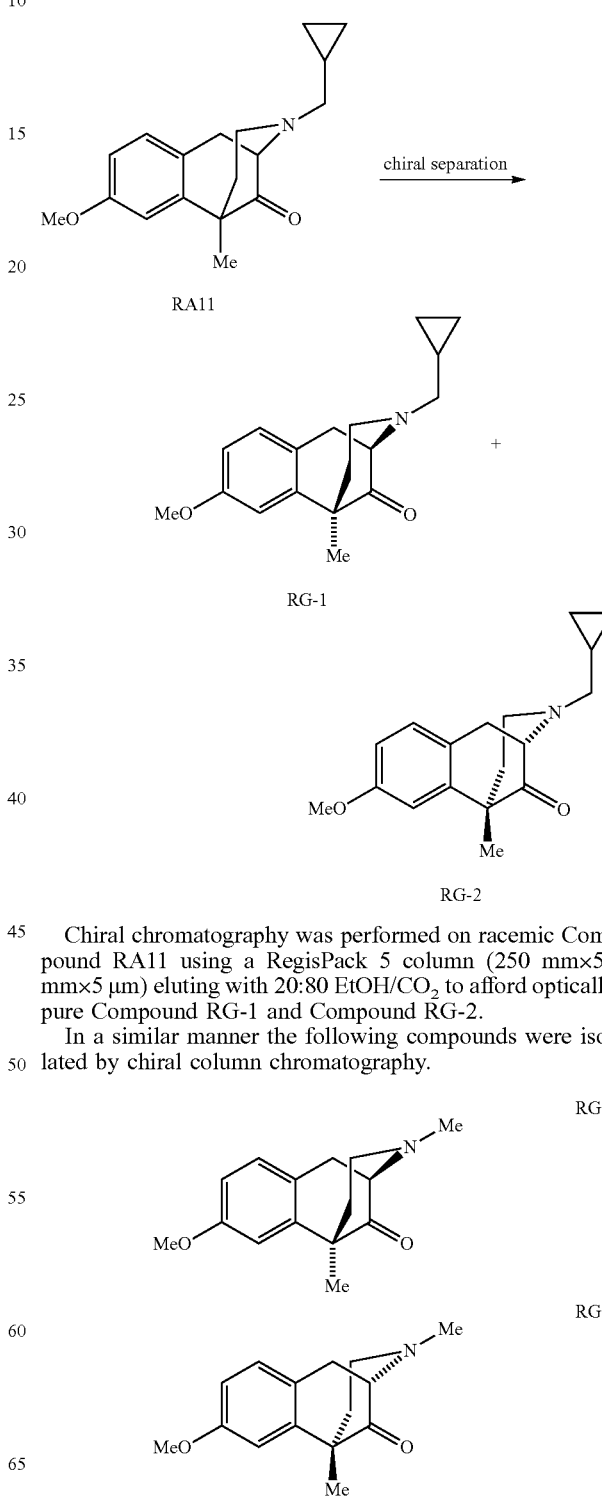

Chiral chromatography was performed on racemic Compound RA11 using a RegisPack 5 column (250 mm×50 mm×5 μm) eluting with 20:80 EtOH/CO₂ to afford optically pure Compound RG-1 and Compound RG-2.

In a similar manner the following compounds were isolated by chiral column chromatography.

-continued

| | |
|---|---|
| 92 | 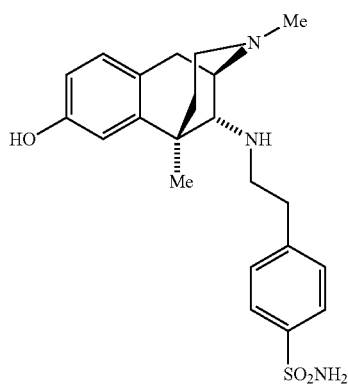 |
| 93 | 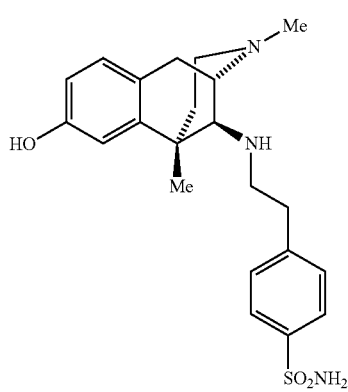 |
| 94 | 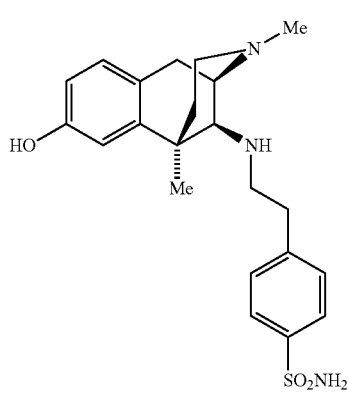 |
| 95 | 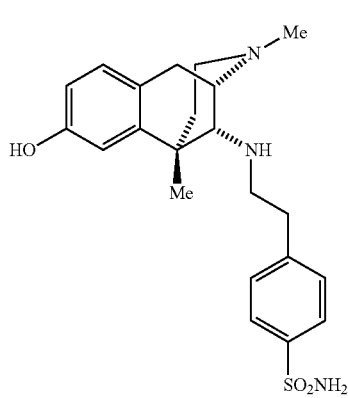 |

(2R,6S)-8-methoxy-3,6-dimethyl-1,2,3,4,5,6-hexa-hydro-2,6-methanobenzo[d]azocin-11-one (Compound RG-3)

LC/MS, m/z=246.1 [M+H]$^+$ (Calc: 245.3).

(2S,6R)-8-methoxy-3,6-dimethyl-1,2,3,4,5,6-hexa-hydro-2,6-methanobenzo[d]azocin-11-one (Compound RG-4)

LC/MS, m/z=246.1 [M+H]$^+$ (Calc: 245.3).

4-(2-(((2R,6S,11R)-8-hydroxy-3,6-dimethyl-1,2,3,4,5,6-hexahydro-2,6-methanobenzo[d]azocin-11-yl)amino)ethyl)benzenesulfonamide (Compound 92)

$^1$H NMR $\delta_H$ (400 MHz, DMSO-d$_6$) 8.85 (s, 1H, —OH), 7.62 (d, J=8.4 Hz, 2H), 7.30 (d, J=8.4 Hz, 2H), 7.19 (s, 2H, —NH$_2$), 6.76 (d, J=8.4 Hz, 1H), 6.50 (d, J=2.4 Hz, 1H), 6.41 (dd, J=8.1, 2.4 Hz, 1H), 2.94-3.04 (m, 1H), 2.77-2.91 (m, 1H), 2.56-2.76 (m, 4H), 2.44-2.54 (m, 2H), 2.09-2.32 (m, 4H), 1.82 (td, J=11.9, 2.8 Hz, 1H), 1.64 (td, J=12.5, 4.7 Hz, 1H), 1.23 (s, 3H), 1.12 (d, J=12.1 Hz, 1H), 0.99 (br. s., 1H). LC/MS, m/z=416.1 [M+H]$^+$ (Calc: 415.6).

4-(2-(((2S,6R,11S)-8-hydroxy-3,6-dimethyl-1,2,3,4,5,6-hexahydro-2,6-methanobenzo[d]azocin-11-yl)amino)ethyl)benzenesulfonamide (Compound 93)

$^1$H NMR $\delta_H$ (400 MHz, DMSO-d$_6$) 8.86 (s, 1H), 7.62 (d, J=8.4 Hz, 2H), 7.30 (d, J=8.1 Hz, 2H), 7.19 (s, 2H), 6.76 (d, J=8.1 Hz, 1H), 6.50 (d, J=2.4 Hz, 1H), 6.42 (dd, J=8.1, 2.4 Hz, 1H), 3.00 (br., 1H), 2.76-2.90 (m, 1H), 2.46-2.75 (m, 6H), 2.21 (br. s., 4H), 1.83 (t, J=10.8 Hz, 1H), 1.64 (td, J=12.5, 4.4 Hz, 1H), 1.24 (s, 3H), 1.13 (d, J=11.9 Hz, 1H), 0.99 (br. s., 1H). LC/MS, m/z=416.2 [M+H]$^+$ (Calc: 415.6).

4-(2-(((2R,6S,11S)-8-hydroxy-3,6-dimethyl-1,2,3,4,5,6-hexahydro-2,6-methanobenzo[d]azocin-11-yl)amino)ethyl)benzenesulfonamide (Compound 94)

$^1$H NMR $\delta_H$ (400 MHz, DMSO-d$_6$) 8.88 (s, 1H), 7.66 (d, J=8.4 Hz, 2H), 7.37 (d, J=8.4 Hz, 2H), 7.20 (s, 2H), 6.79 (d, J=8.1 Hz, 1H), 6.59 (d, J=2.4 Hz, 1H), 6.38-6.50 (m, 1H), 2.86-3.16 (m, 3H), 2.73 (d, J=7.3 Hz, 3H), 2.45-2.58 (m, 1H), 2.31 (br. s., 1H), 2.09-2.20 (m, 4H), 1.61-1.98 (m, 3H), 1.22 (s, 3H), 0.84 (d, J=11.7 Hz, 1H).

LC/MS, m/z=416.2 [M+H]$^+$ (Calc: 415.6).

4-(2-(((2S,6R,11R)-8-hydroxy-3,6-dimethyl-1,2,3,4,5,6-hexahydro-2,6-methanobenzo[d]azocin-11-yl)amino)ethyl)benzenesulfonamide (Compound 95)

$^1$H NMR $\delta_H$ (400 MHz, DMSO-d$_6$) 8.96 (s, 1H), 7.73 (d, J=8.4 Hz, 2H), 7.44 (d, J=8.4 Hz, 2H), 7.27 (s, 2H), 6.86 (d, J=8.4 Hz, 1H), 6.66 (d, J=2.4 Hz, 1H), 6.51 (dd, J=8.1, 2.4 Hz, 1H), 2.95-3.21 (m, 3H), 2.66-2.89 (m, 3H), 2.58 (dd, J=17.8, 5.7 Hz, 1H), 2.38 (br. s., 1H), 2.11-2.27 (m, 4H), 1.69-2.01 (m, 3H), 1.29 (s, 3H), 0.92 (d, J=11.9 Hz, 1H).

LC/MS, m/z=416.2 [M+H]$^+$ (Calc: 415.6).

Example 57

(2R,6S,11S)-3-(cyclopropylmethyl)-8-methoxy-6-methyl-1,2,3,4,5,6-hexahydro-2,6-methanobenzo[d]azocin-11-amine (Compound RG-5) and (2R,6S,11S)-3-(cyclopropylmethyl)-8-methoxy-6-methyl-1,2,3,4,5,6-hexahydro-2,6-methanobenzo[d]azocin-11-amine (Compound RG-6)

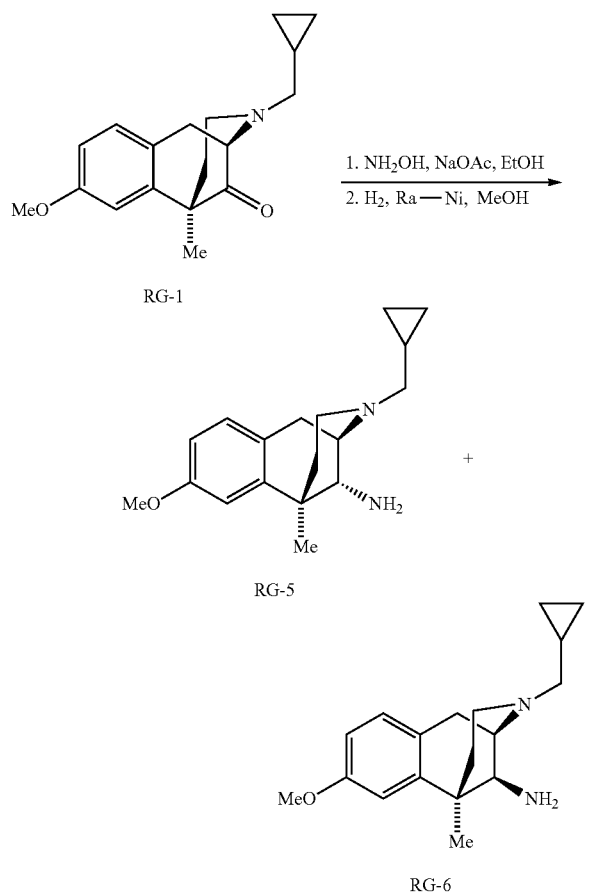

A mixture of Compound RG-1 (0.942 g, 3.30 mmol), sodium acetate (0.54 g, 6.59 mmol) and hydroxylamine hydrochloride (0.46 g, 6.59 mmol) in EtOH (10 mL) was heated at 45° C. for 16 h. The mixture was concentrated and then quenched by the addition of water (15 mL). The mixture was extracted with EtOAc (40 mL) and the organic extracts concentrated to give the crude oxime as a sticky solid, which was used directly in the next step.

The crude oxime was dissolved in MeOH (200 mL) and hydrogenated over Ra-Ni at 40 atm and 40° C. for 4 h. The mixture was filtered and the filtrate concentrated to give a residue that was purified by flash chromatography (SiO$_2$, 10% (10% NH$_4$OH in MeOH) in DCM) to give Compound RG-5 as a colorless oil (0.30 g, 32%) and Compound RG-6 as a colorless oil (0.25 g, 27%).

(2R,6S,11S)-3-(cyclopropylmethyl)-8-methoxy-6-methyl-1,2,3,4,5,6-hexahydro-2,6-methanobenzo[d]azocin-11-amine (Compound RG-5)

LC/MS, m/z=287.4 [M+H]$^+$ (Calc: 286.4).

(2R,6S,11S)-3-(cyclopropylmethyl)-8-methoxy-6-methyl-1,2,3,4,5,6-hexahydro-2,6-methanobenzo[d]azocin-11-amine(2R,6S,11S)-3-(cyclopropylmethyl)-8-methoxy-6-methyl-1,2,3,4,5,6-hexahydro-2,6-methanobenzo[d]azocin-11-amine (Compound RG-6)

LC/MS, m/z=287.4 [M+H]$^+$ (Calc: 286.4).

Example 58

(2R,6S,11S)-3-(cyclopropylmethyl)-8-methoxy-N,6-dimethyl-1,2,3,4,5,6-hexahydro-2,6-methanobenzo[d]azocin-11-amine (Compound RG-7) and (2R,6S,11S)-3-(cyclopropylmethyl)-8-methoxy-N,6-dimethyl-1,2,3,4,5,6-hexahydro-2,6-methanobenzo[d]azocin-11-amine (Compound RG-8)

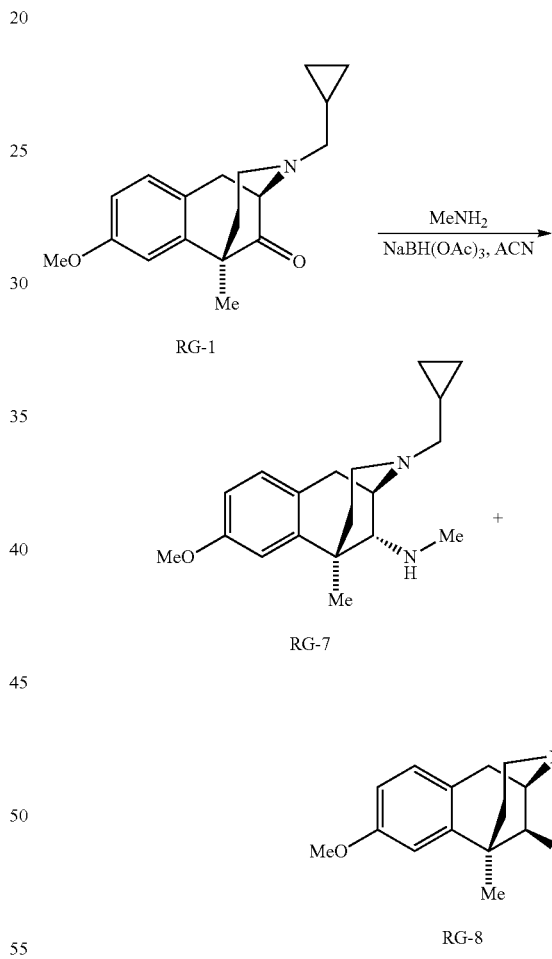

Chiral ketone Compound RG-1 was converted to chiral amines Compound RG-7 and Compound RG-8 according to the same procedure described in Example 41 for racemic Compound RA11.

(2R,6S,11S)-3-(cyclopropylmethyl)-8-methoxy-N,6-dimethyl-1,2,3,4,5,6-hexahydro-2,6-methanobenzo[d]azocin-11-amine (Compound RG-7)

LC/MS, m/z=301.4 [M+H]$^+$ (Calc: 300.4).

(2R,6S,11S)-3-(cyclopropylmethyl)-8-methoxy-N,6-dimethyl-1,2,3,4,5,6-hexahydro-2,6-methanobenzo[d]azocin-11-amine (Compound RG-8)

LC/MS, m/z=301.4 [M+H]$^+$ (Calc: 300.4).

Example 59

4-(2-(((2R,6S,11R)-3-(cyclopropylmethyl)-8-hydroxy-6-methyl-1,2,3,4,5,6-hexahydro-2,6-methanobenzo[d]azocin-11-yl)amino)ethyl)benzenesulfonamide (Compound 96) and 4-(2-(((2R,6S,11S)-3-(cyclopropylmethyl)-8-hydroxy-6-methyl-1,2,3,4,5,6-hexahydro-2,6-methanobenzo[d]azocin-11-yl)amino)ethyl)benzenesulfonamide (Compound 97)

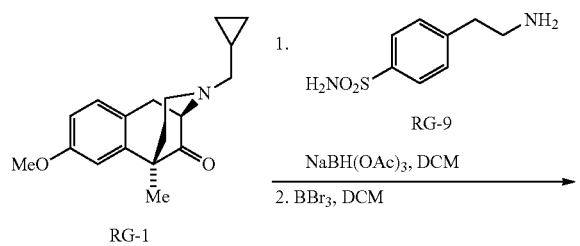

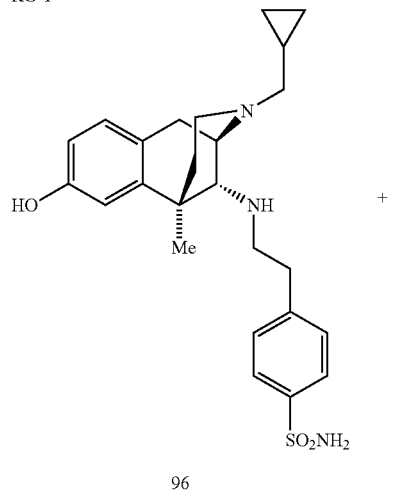

A mixture of Compound RG-1 (0.50 g, 1.65 mmol), Compound RG-9 (0.50 g, 2.47 mmol) and pTSA (0.03 g) in toluene (40 mL) was heated to reflux for 4 h and concentrated to give a brown oil. To this oil was added ACN (20 mL) followed by NaBH(OAc)$_3$ (1.05 g, 4.94 mmol). The reaction mixture was stirred at RT for 24 h, MeOH (1 mL) was added and the mixture concentrated. Water (10 mL) and EtOAc (100 mL) were added and the pH adjusted to ca 9 with conc. NH$_4$OH. The layers were separated and the organic layer was concentrated and purified by flash chromatography (SiO$_2$, 10% (10% NH$_4$OH in MeOH) in DCM) to give the product as a mixture of isomers.

This material was dissolved in DCM (4 mL), cooled to −78° C. and 1 M BBr$_3$ in DCM (2.0 mL, 2.0 mmol) was added. The mixture was stirred at −78° C. for 1 h allowed to warm to 0° C. and stirred an additional 30 min. The reaction was quenched by the addition of water (2 mL) and the pH adjusted to ca 8 with conc. NH$_4$OH. The layers were separated, the organic layer was concentrated and purified by flash chromatography (SiO$_2$, 10% (10% NH$_4$OH in MeOH) in DCM) to give Compound 96 as a white solid (0.020 g, 3%) and Compound 97 as a white solid (0.050 g, 7%).

4-(2-(((2R,6S,11R)-3-(cyclopropylmethyl)-8-hydroxy-6-methyl-1,2,3,4,5,6-hexahydro-2,6-methanobenzo[d]azocin-11-yl)amino)ethyl)benzenesulfonamide (Compound 96)

$^1$H NMR δ$_H$ (400 MHz, CD$_3$OD) 7.77 (d, J=8.36 Hz, 2H), 7.40 (d, J=7.92 Hz, 2H), 7.01 (d, J=7.92 Hz, 1H), 6.70-6.76 (m, 2H), 3.18-3.52 (m, 6H), 2.84-3.04 (m, 4H), 1.98-2.03 (m, 1H), 1.60-1.64 (m, 1H), 1.53 (s, 3H), 1.04-1.12 (m, 1H), 0.62-0.69 (m, 2H), 0.36-0.41 (m, 2H).

LC/MS, m/z=456.1 [M+H]$^+$ (Calc: 455.6).

4-(2-(((2R,6S,11S)-3-(cyclopropylmethyl)-8-hydroxy-6-methyl-1,2,3,4,5,6-hexahydro-2,6-methanobenzo[d]azocin-11-yl)amino)ethyl)benzenesulfonamide (Compound 97)

$^1$H NMR δ$_H$ (400 MHz, DMSO-d$_6$) 8.90 (s, 1H), 7.67 (d, J=8.1 Hz, 2H), 7.39 (d, J=8.4 Hz, 2H), 7.21 (s, 2H), 6.79 (d, J=8.4 Hz, 1H), 6.61 (d, J=2.4 Hz, 1H), 6.45 (dd, J=8.1, 2.4 Hz, 1H), 2.88-3.08 (m, 2H), 2.62-2.84 (m, 3H), 2.53 (dd, J=17.9, 5.8 Hz, 1H), 2.29-2.40 (m, 2H), 2.21 (ddt, J=19.5, 12.8, 6.4 Hz, 2H), 1.91-2.05 (m, 1H), 1.66-1.89 (m, 2H), 1.25 (s, 3H), 0.87 (d, J=12.1 Hz, 1H), 0.52-0.69 (m, 1H), 0.28-0.47 (m, 2H), −0.15-0.10 (m, 2H).

LC/MS, m/z=456.1 [M+H]$^+$ (Calc: 455.6).

In a similar manner the following chiral compounds were prepared from the appropriate chiral ketones.

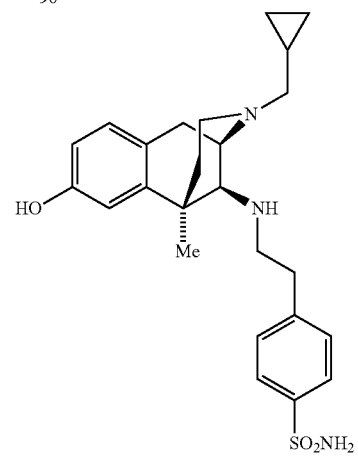

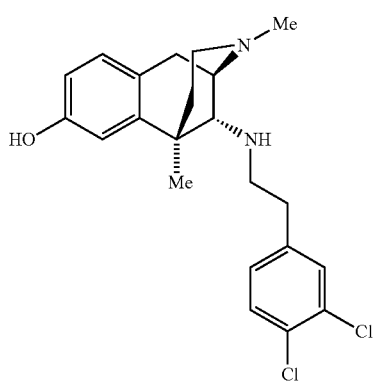

213 -continued
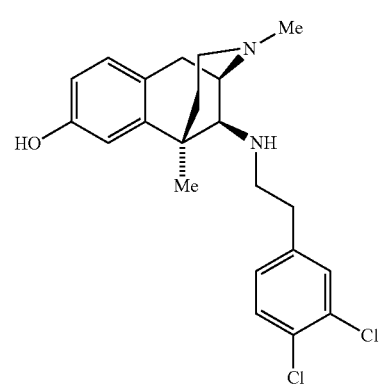
99
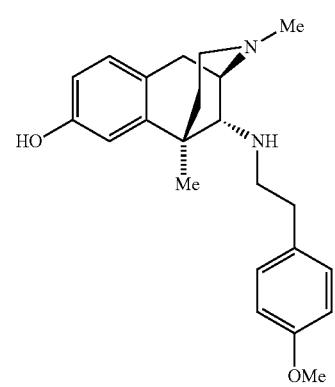
100
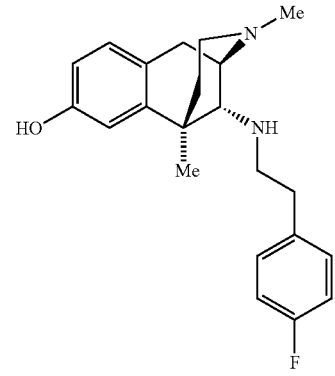
101
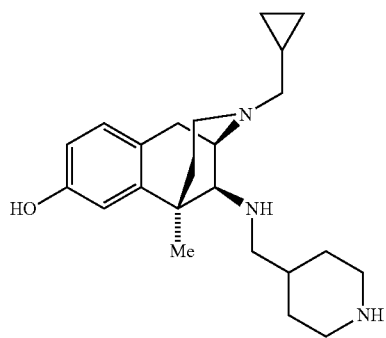
102
214 -continued
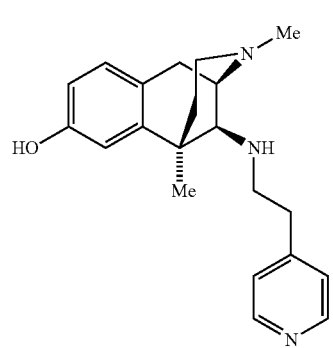
103
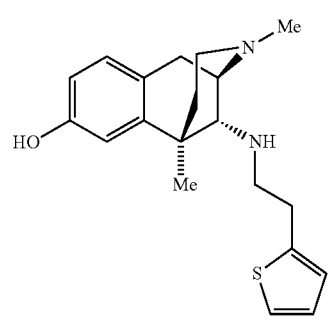
104
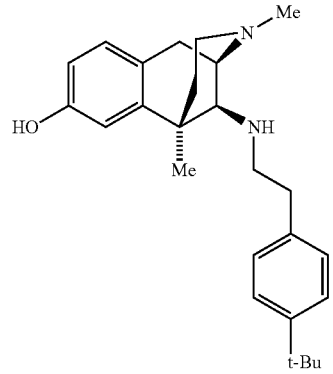
105
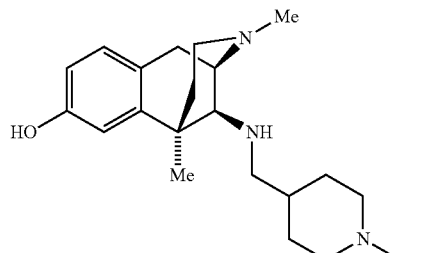
106
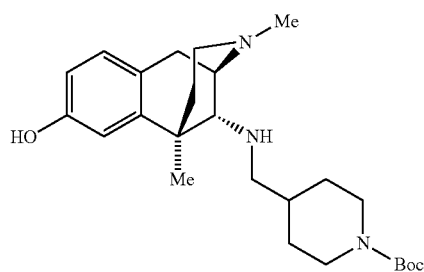
107

-continued

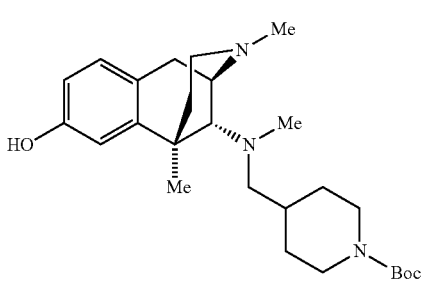

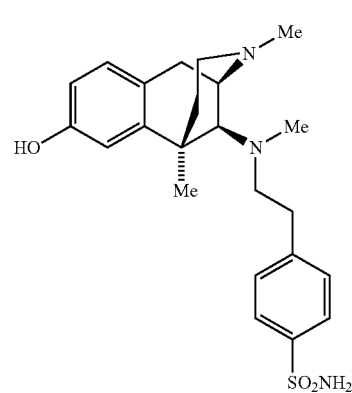

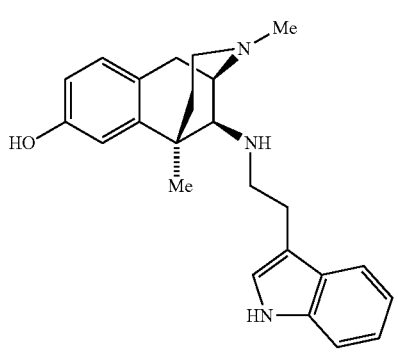

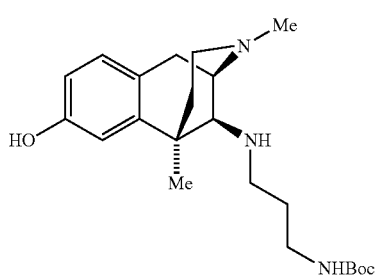

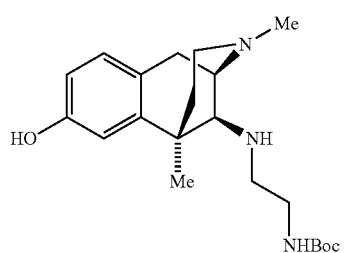

(2R,6S,11R)-11-((3,4-dichlorophenethyl)amino)-3,6-dimethyl-1,2,3,4,5,6-hexahydro-2,6-methanobenzo[d]azocin-8-ol (Compound 98)

$^1$H NMR $\delta_H$ (400 MHz, CD$_3$OD) 7.22-7.33 (m, 2H), 7.01 (dd, J=8.1, 1.8 Hz, 1H), 6.77 (d, J=8.1 Hz, 1H), 6.56 (d, J=2.2 Hz, 1H), 6.47 (dd, J=8.3, 2.3 Hz, 1H), 3.11 (br. s., 1H), 2.79-2.93 (m, 2H), 2.70-2.77 (m, 1H), 2.62 (d, J=3.5 Hz, 4H), 2.32 (s, 3H), 2.23-2.31 (m, 1H), 1.96-2.08 (m, 1H), 1.73 (td, J=12.9, 4.7 Hz, 1H), 1.28 (s, 3H), 1.18-1.26 (m, 1H).
LC/MS, m/z=405.1/407.1 [M/M+2]$^+$ (Calc: 405.4).

(2R,6S,11S)-11-((3,4-dichlorophenethyl)amino)-3,6-dimethyl-1,2,3,4,5,6-hexahydro-2,6-methanobenzo[d]azocin-8-ol (Compound 99)

$^1$H NMR $\delta_H$ (400 MHz, CD$_3$OD) 7.36 (s, 1H), 7.31 (d, J=8.3 Hz, 1H), 7.10 (dd, J=8.3, 1.9 Hz, 1H), 6.80 (d, J=8.4 Hz, 1H), 6.64 (d, J=2.4 Hz, 1H), 6.45 (dd, J=8.3, 2.5 Hz, 1H), 3.03-3.18 (m, 2H), 2.90-3.00 (m, 1H), 2.54-2.75 (m, 4H), 2.42 (br. s., 1H), 2.19-2.27 (m, 4H), 1.90-2.00 (m, 1H), 1.81 (td, J=12.9, 4.6 Hz, 1H), 1.25 (s, 3H), 0.97 (d, J=12.8 Hz, 1H).
LC/MS, m/z=405.1/407.1 [M/M+2]$^+$ (Calc: 405.4).

(2R,6S,11R)-11-((4-methoxyphenethyl)amino)-3,6-dimethyl-1,2,3,4,5,6-hexahydro-2,6-methanobenzo[d]azocin-8-ol (Compound 100)

$^1$H NMR $\delta_H$ (400 MHz, CD$_3$OD) 6.96 (d, J=8.6 Hz, 2H), 6.76 (d, J=8.1 Hz, 1H), 6.69 (d, J=8.6 Hz, 2H), 6.54 (d, J=2.6 Hz, 1H), 6.43-6.50 (m, 1H), 3.65 (s, 3H), 2.99-3.16 (m, 1H), 2.39-2.92 (m, 7H), 2.22-2.35 (m, 4H), 1.89-2.11 (m, 1H), 1.72 (d, J=4.8 Hz, 1H), 1.10-1.33 (m, 4H).
LC/MS, m/z=367.2 [M+H]$^+$ (Calc: 366.5).

(2R,6S,11R)-11-((4-fluorophenethyl)amino)-3,6-dimethyl-1,2,3,4,5,6-hexahydro-2,6-methanobenzo[d]azocin-8-ol (Compound 101)

$^1$H NMR $\delta_H$ (400 MHz, CD$_3$OD) 7.17 (dd, J=8.6, 5.5 Hz, 2H), 7.00 (d, J=8.4 Hz, 1H), 6.94 (t, J=8.8 Hz, 2H), 6.72 (d, J=2.4 Hz, 1H), 6.67 (dd, J=8.4, 2.4 Hz, 1H), 4.07 (br. s., 1H), 3.47 (br. s., 1H), 3.05-3.20 (m, 5H), 2.85-2.97 (m, 4H), 2.65-2.8 (m, 2H), 1.94-2.11 (m, 1H), 1.58-1.70 (m, 1H), 1.52 (s, 3H).
LC/MS, m/z=355.2 [M+H]$^+$ (Calc: 354.5).

(2R,6S,11S)-3-(cyclopropylmethyl)-6-methyl-11-((piperidin-4-ylmethyl)amino)-1,2,3,4,5,6-hexahydro-2,6-methanobenzo[d]azocin-8-ol (Compound 102)

$^1$H NMR $\delta_H$ (400 MHz, CD$_3$OD) 7.04 (d, J=8.4 Hz, 1H), 6.85 (d, J=2.4 Hz, 1H), 6.69 (dd, J=8.4, 2.4 Hz, 1H), 4.20 (br. s., 1H), 3.32-3.51 (m, 3H), 3.27 (br. s., 1H), 2.93-3.11 (m, 4H), 2.85 (dd, J=13.4, 8.1 Hz, 1H), 2.75 (d, J=5.3 Hz, 1H), 2.56-2.71 (m, 2H), 2.24 (br., 2H), 1.97-2.09 (m, 1H), 1.79-1.95 (m, 1H), 1.49-1.57 (m, 3H), 1.34-1.48 (m, 3H), 1.05-1.19 (m, 1H), 0.81 (d, J=4.2 Hz, 1H), 0.72 (br. s., 1H), 0.40-0.58 (m, 2H).
LC/MS, m/z=370.4 [M+H]$^+$ (Calc: 369.5).

(2R,6S,11S)-3,6-dimethyl-11-((2-(pyridin-4-yl)ethyl)amino)-1,2,3,4,5,6-hexahydro-2,6-methanobenzo[d]azocin-8-ol (Compound 103)

$^1$H NMR $\delta_H$ (400 MHz, CD$_3$OD) 8.78 (d, J=5.7 Hz, 2H), 8.03 (d, J=6.4 Hz, 2H), 7.08 (d, J=8.4 Hz, 1H), 6.87 (d, J=2.4

Hz, 1H), 6.72 (dd, J=8.3, 2.3 Hz, 1H), 3.87-3.96 (m, 1H), 3.35-3.41 (m, 1H), 3.20-3.25 (m, 4H), 3.07-3.16 (m, 3H), 2.91 (s, 3H), 2.65-2.76 (m, 1H), 2.23-2.39 (m, 1H), 1.50 (s, 3H), 1.44 (d, J=12.8 Hz, 1H).

LC/MS, m/z=338.3 [M+H]$^+$ (Calc: 337.5).

(2R,6S,11R)-3,6-dimethyl-11-((2-(thiophen-2-yl)ethyl)amino)-1,2,3,4,5,6-hexahydro-2,6-methanobenzo[d]azocin-8-ol (Compound 104)

$^1$H NMR $\delta_H$ (400 MHz, CD$_3$OD) 7.15 (d, J=5.2 Hz, 1H), 6.98 (d, J=8.4 Hz, 1H), 6.84 (d, J=8.5 Hz, 1H), 6.80 (s, 1H), 6.70 (s, 1H), 6.65 (d, J=8.5 Hz, 1H), 4.02 (d, J=2.9 Hz, 1H), 3.35 (br. s., 1H), 2.98-3.17 (m, 7H), 2.90 (s, 3H), 2.64 (br. s., 1H), 1.89-2.10 (m, 1H), 1.61 (d, J=13.4 Hz, 1H), 1.49 (s, 3H).

LC/MS, m/z=343.2 [M+H]$^+$ (Calc: 342.5).

(2R,6S,11S)-11-((4-(tert-butyl)phenethyl)amino)-3,6-dimethyl-1,2,3,4,5,6-hexahydro-2,6-methanobenzo[d]azocin-8-ol (Compound 105)

$^1$H NMR $\delta_H$ (400 MHz, CD$_3$OD) 7.20-7.24 (m, J=8.1 Hz, 2H), 7.05-7.09 (m, J=8.1 Hz, 2H), 6.79 (d, J=8.4 Hz, 1H), 6.64 (d, J=2.4 Hz, 1H), 6.46 (dd, J=8.4, 2.4 Hz, 1H), 3.07 (d, J=18.0 Hz, 1H), 2.99 (br. s., 1H), 2.86-2.95 (m, 1H), 2.63-2.77 (m, 3H), 2.56 (dd, J=17.9, 5.4 Hz, 1H), 2.43 (br. s., 1H), 2.15-2.26 (m, 4H), 1.79-2.01 (m, 2H), 1.26 (s, 3H), 1.20 (s, 9H), 0.97 (d, J=12.5 Hz, 1H).

LC/MS, m/z=393.3 [M+H]$^+$ (Calc: 392.6).

tert-butyl 4-((((2R,6S,11S)-8-hydroxy-3,6-dimethyl-1,2,3,4,5,6-hexahydro-2,6-methanobenzo[d]azocin-11-yl)amino)methyl)piperidine-1-carboxylate (Compound 106)

$^1$H NMR $\delta_H$ (400 MHz, CD$_3$OD) 6.94 (d, J=8.4 Hz, 1H), 6.74 (d, J=2.4 Hz, 1H), 6.59 (dd, J=8.3, 2.5 Hz, 1H), 4.01 (d, J=13.4 Hz, 2H), 3.66 (d, J=4.6 Hz, 1H), 3.26 (s, 1H), 3.13 (d, J=6.2 Hz, 1H), 2.85-2.95 (m, 2H), 2.74 (s, 3H), 2.49-2.71 (m, 5H), 2.14 (td, J=13.9, 5.1 Hz, 1H), 1.60-1.88 (m, 3H), 1.41 (s, 3H), 1.35 (s, 9H), 1.31 (d, J=13.0 Hz, 1H), 0.96-1.13 (m, 2H).

LC/MS, m/z=430.2 [M+H]$^+$ (Calc: 429.6).

tert-butyl 4-((((2R,6S,11R)-8-hydroxy-3,6-dimethyl-1,2,3,4,5,6-hexahydro-2,6-methanobenzo[d]azocin-11-yl)amino)methyl)piperidine-1-carboxylate (Compound 107)

$^1$H NMR $\delta_H$ (400 MHz, CD$_3$OD) 7.00 (d, J=8.6 Hz, 1H), 6.71 (d, J=2.4 Hz, 1H), 6.66 (dd, J=8.4, 2.4 Hz, 1H), 3.91-4.07 (m, 3H), 3.34 (br. s., 1H), 3.18 (br. s., 1H), 3.10 (d, J=10.1 Hz, 1H), 2.91 (s, 3H), 2.58-2.84 (m, 5H), 1.95-2.11 (m, 1H), 1.58-1.79 (m, 4H), 1.53 (s, 3H), 1.3-1.36 (m, 10H), 0.92-1.10 (m, 2H).

LC/MS, m/z=430.4 [M+H]$^+$ (Calc: 429.6).

tert-butyl 4-((((2R,6S,11R)-8-hydroxy-3,6-dimethyl-1,2,3,4,5,6-hexahydro-2,6-methanobenzo[d]azocin-11-yl)(methyl)amino)methyl)piperidine-1-carboxylate (Compound 108)

$^1$H NMR $\delta_H$ (400 MHz, CDCl$_3$) 6.82 (d, J=8.4 Hz, 1H), 6.65 (d, J=2.4 Hz, 1H), 6.51 (dd, J=8.1, 2.4 Hz, 1H), 3.95 (br. s., 2H), 3.08 (dd, J=5.4, 2.3 Hz, 1H), 3.00 (d, J=18.5 Hz, 1H), 2.69-2.75 (m, 1H), 2.45-2.64 (m, 3H), 2.24-2.37 (m, 6H), 1.90-2.06 (m, 4H), 1.79 (td, J=12.7, 5.1 Hz, 2H), 1.44-1.67 (m, 1H), 1.34-1.39 (m, 12H), 1.06-1.29 (m, 2H), 0.75-0.94 (m, 2H).

LC/MS, m/z=444.3 [M+H]$^+$ (Calc: 443.6).

4-(2-(((2R,6S,11S)-8-hydroxy-3,6-dimethyl-1,2,3,4,5,6-hexahydro-2,6-methanobenzo[d]azocin-11-yl)(methyl)amino)ethyl)benzenesulfonamide (Compound 109)

$^1$H NMR $\delta_H$ (400 MHz, CD$_3$OD) 7.75-7.79 (m, J=8.4 Hz, 2H), 7.36-7.40 (m, J=8.4 Hz, 2H), 6.90 (d, J=8.4 Hz, 1H), 6.70 (d, J=2.4 Hz, 1H), 6.57 (dd, J=8.4, 2.4 Hz, 1H), 3.65 (d, J=5.1 Hz, 1H), 3.23-3.44 (m, 4H), 3.03-3.11 (m, 5H), 2.86 (dd, J=18.4, 5.8 Hz, 1H), 2.60 (dd, J=11.7, 3.5 Hz, 1H), 2.45 (s, 3H), 2.11-2.32 (m, 2H), 1.48 (s, 3H), 1.32 (d, J=13.9 Hz, 1H).

LC/MS, m/z=430.2 [M+H]$^+$ (Calc: 429.6).

(2R,6S,11S)-11-((2-(1H-indol-3-yl)ethyl)amino)-3,6-dimethyl-1,2,3,4,5,6-hexahydro-2,6-methanobenzo[d]azocin-8-ol (Compound 110)

$^1$H NMR $\delta_H$ (400 MHz, CD$_3$OD) 7.54 (d, J=7.9 Hz, 1H), 7.28 (d, J=8.1 Hz, 1H), 6.86-7.10 (m, 4H), 6.68 (d, J=2.4 Hz, 1H), 6.56 (dd, J=8.4, 2.4 Hz, 1H), 3.40 (br. s., 1H), 3.12-3.20 (m, 2H), 3.03-3.10 (m, 4H), 2.85-2.93 (m, 1H), 2.62 (d, J=8.4 Hz, 1H), 2.26-2.36 (m, 4H), 1.95-2.05 (m, 1H), 1.21-1.32 (m, 4H).

LC/MS, m/z=376.2 [M+H]$^+$ (Calc: 375.5).

tert-butyl (3-(((2R,6S,11S)-8-hydroxy-3,6-dimethyl-1,2,3,4,5,6-hexahydro-2,6-methanobenzo[d]azocin-11-yl)amino)propyl)carbamate (Compound 111)

$^1$H NMR $\delta_H$ (400 MHz, CD$_3$OD) 7.06 (d, J=8.4 Hz, 1H), 6.86 (d, J=2.4 Hz, 1H), 6.71 (dd, J=8.4, 2.4 Hz, 1H), 3.81 (br. s., 1H), 3.39 (s, 1H), 3.12-3.29 (m, 4H), 2.87-3.05 (m, 3H), 2.81 (s, 3H), 2.58 (td, J=12.7, 3.4 Hz, 1H), 2.21-2.30 (m, 1H), 1.82 (quin, J=6.6 Hz, 2H), 1.52-1.59 (m, 3H), 1.46 (s, 9H), 1.42-1.45 (m, 1H).

LC/MS, m/z=390.3 [M+H]$^+$ (Calc: 389.5).

tert-butyl (2-(((2R,6S,11S)-8-hydroxy-3,6-dimethyl-1,2,3,4,5,6-hexahydro-2,6-methanobenzo[d]azocin-11-yl)amino)ethyl)carbamate (Compound 112)

$^1$H NMR $\delta_H$ (400 MHz, CD$_3$OD) 7.06 (d, J=8.4 Hz, 1H), 6.86 (d, J=2.4 Hz, 1H), 6.71 (dd, J=8.3, 2.5 Hz, 1H), 3.77-3.82 (m, 1H), 3.32-3.38 (m, 1H), 3.27-3.31 (m, 1H), 3.13-3.26 (m, 2H), 2.98-3.07 (m, 2H), 2.87-2.92 (m, 2H), 2.86 (s, 3H), 2.61-2.71 (m, 1H), 2.21-2.31 (m, 1H), 1.50 (s, 3H), 1.48 (s, 9H), 1.41 (d, J=14.3 Hz, 1H).

LC/MS, m/z=376.2 [M+H]$^+$ (Calc: 375.5).

Example 60

N-((2R,6S,11S)-3-(cyclopropylmethyl)-8-hydroxy-6-methyl-1,2,3,4,5,6-hexahydro-2,6-methanobenzo[d]azocin-11-yl)thiophene-3-carboxamide (Compound 113)

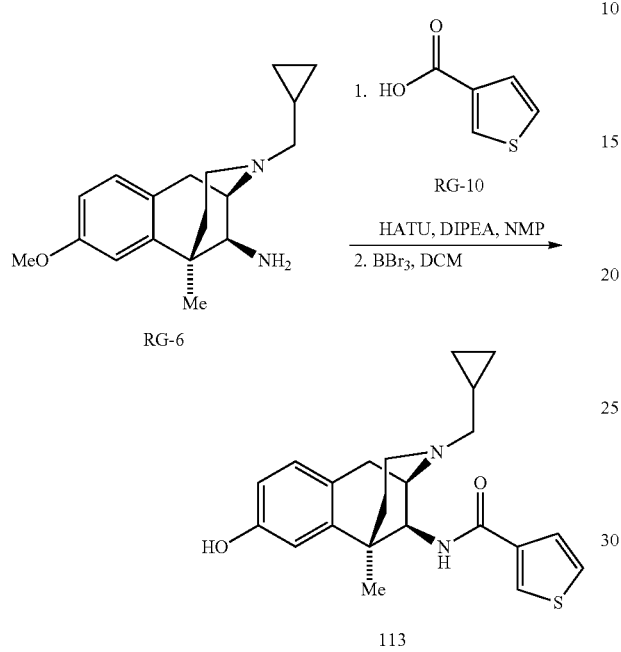

To a mixture of Compound RG-6 (0.10 g, 0.35 mmol), Compound RG-10 (0.054 g, 0.42 mmol) and DIPEA (0.045 g, 0.35 mmol) in NMP (1 mL) was added HATU (0.16 g, 0.42 mmol) at RT. The reaction mixture was stirred at RT for 16 h, quenched by the addition of water and the mixture extracted with EtOAc. The organic layer was concentrated and purified by flash chromatography (SiO$_2$, 10% (10% NH$_4$OH in MeOH) in DCM) to give the desired product.

This material was dissolved in DCM (8 mL), cooled to −78° C. and 1 M BBr$_3$ in DCM (2.0 mL, 2.0 mmol) was added. The mixture was stirred at −78° C. for 2 h allowed to warm to 0° C. and stirred an additional 30 min. The reaction was quenched by the addition of water (2 mL) and the pH adjusted to ca 8 with conc. NH$_4$OH. The layers were separated, the organic layer was concentrated and purified by flash chromatography (SiO$_2$, 10% (7% NH$_4$OH in MeOH) in DCM) to give Compound 113 as a white solid (0.040 g, 29%).

$^1$H NMR δ$_H$ (400 MHz, DMSO-d$_6$) 8.95 (s, 1H), 8.13 (dd, J=2.6, 1.1 Hz, 1H), 7.47-7.57 (m, 2H), 7.38 (d, J=5.1 Hz, 1H), 6.81 (d, J=8.4 Hz, 1H), 6.59 (d, J=2.4 Hz, 1H), 6.46 (dd, J=8.3, 2.3 Hz, 1H), 4.00 (d, J=7.3 Hz, 1H), 3.14-3.20 (m, 1H), 2.91 (d, J=18.0 Hz, 1H), 2.62 (dd, J=18.0, 6.2 Hz, 1H), 2.47 (d, J=7.0 Hz, 1H), 2.15-2.34 (m, 2H), 1.86-2.01 (m, 2H), 1.10 (s, 3H), 0.99 (d, J=10.1 Hz, 1H), 0.73 (t, J=6.2 Hz, 1H), 0.27-0.39 (m, 2H), 0.01 (d, J=4.6 Hz, 2H).

LC/MS, m/z=383.1 [M+H]$^+$ (Calc: 382.5).

In a similar manner the following chiral compounds were prepared from the appropriate chiral amines.

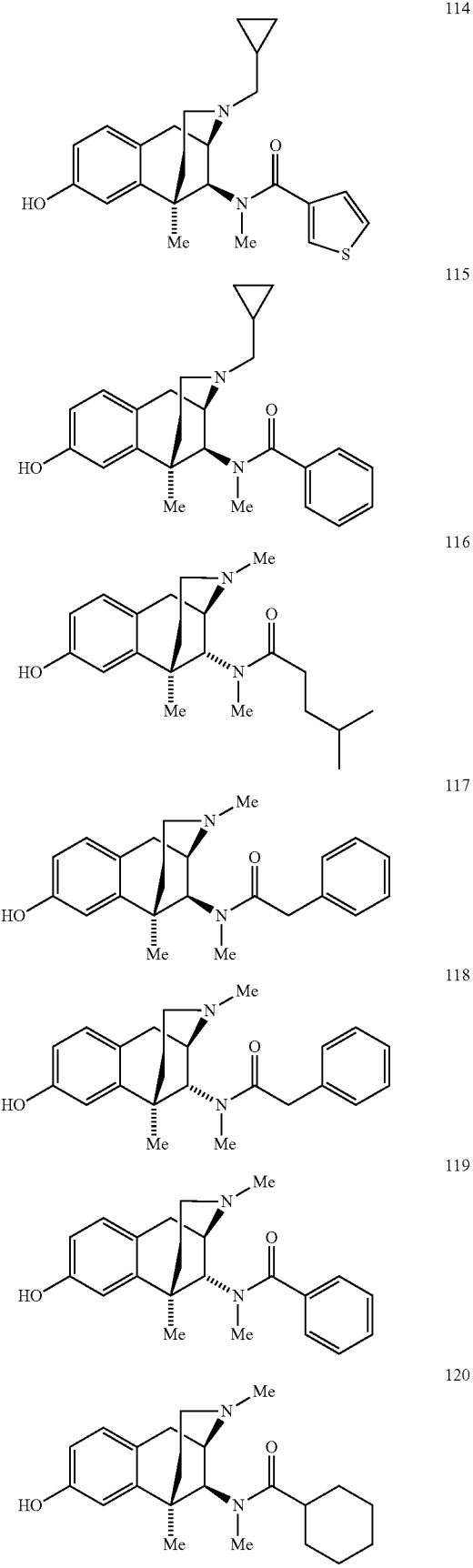

-continued

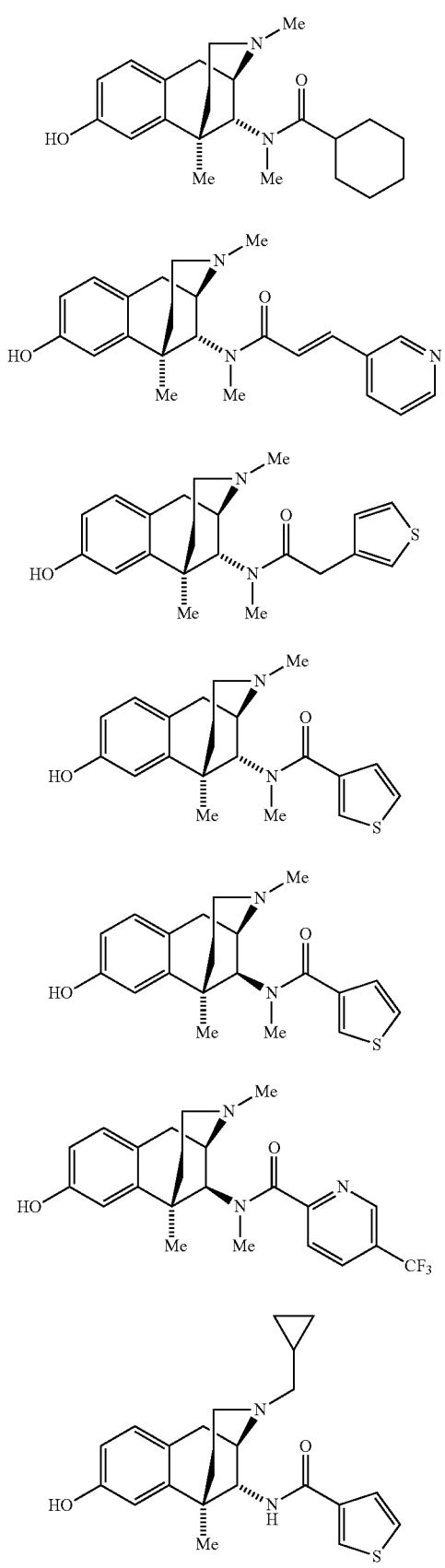

N-((2R,6S,11S)-3-(cyclopropylmethyl)-8-hydroxy-6-methyl-1,2,3,4,5,6-hexahydro-2,6-methanobenzo[d]azocin-11-yl)-N-methylthiophene-3-carboxamide (Compound 114)

$^1$H NMR $\delta_H$ (400 MHz, CD$_3$OD) 6.90-7.70 (m, 3H), 6.37-6.82 (m, 3H), 4.88 (s, 0.6H), 3.99 (s, 0.4H), 3.58-3.60 (m, 3H), 3.41-3.52 (m, 1H), 2.95-3.1 (m, 1H), 2.34-2.72 (m, 3H), 2.08-2.22 (m, 3H), 1.09-1.29 (m, 4H), 0.72-0.82 (m, 1H), 0.35-0.42 (m, 2H), −0.04-0.04 (m, 2H).
LC/MS, m/z=397.2 [M+H]$^+$ (Calc: 396.6).

N-((2R,6S,11S)-3-(cyclopropylmethyl)-8-hydroxy-6-methyl-1,2,3,4,5,6-hexahydro-2,6-methanobenzo[d]azocin-11-yl)-N-methylbenzamide (Compound 115)

$^1$H NMR $\delta_H$ (400 MHz, CD$_3$OD) 7.16-7.35 (m, 5H), 6.82 (d, J=8.1 Hz, 0.6H), 6.63-6.65 (m, 1H), 6.33-6.49 (m, 1.4H), 4.9 (s, 0.6H), 3.85 (s, 0.4H), 3.45-3.65 (m, 4H), 2.92-3.1 (m, 1H), 2.63-2.74 (m, 1.6H), 2.34-2.42 (m, 1.4H), 2.0-2.22 (m, 3H), 1.08-1.34 (m, 4H), 0.65-0.8 (m, 1H), 0.35-0.43 (m, 2H), −0.04-0.04 (m, 2H).
LC/MS, m/z=391.2 [M+H]$^+$ (Calc: 390.5).

N-((2R,6S,11R)-8-hydroxy-3,6-dimethyl-1,2,3,4,5,6-hexahydro-2,6-methanobenzo[d]azocin-11-yl)-N,4-dimethylpentanamide (Compound 116)

$^1$H NMR $\delta_H$ (400 MHz, CD$_3$OD) 6.86 (d, J=7.7 Hz, 1H), 6.64 (d, J=2.4 Hz, 1H), 6.50-6.54 (m, 1H), 4.65 (d, J=2.6 Hz, 0.6H), 3.85 (d, J=2.6 Hz, 0.4H), 2.93-3.11 (m, 2H), 2.39-2.64 (m, 4H), 2.23-2.40 (m, 6H), 1.99-2.13 (m, 1H), 1.81-1.91 (m, 1H), 1.34-1.56 (m, 3H), 1.24-1.32 (m, 4H), 0.79-0.89 (m, 6H).
LC/MS, m/z=345.3 [M+H]$^+$ (Calc: 344.5).

N-((2R,6S,11S)-8-hydroxy-3,6-dimethyl-1,2,3,4,5,6-hexahydro-2,6-methanobenzo[d]azocin-11-yl)-N-methyl-2-phenylacetamide (Compound 117)

$^1$H NMR $\delta_H$ (400 MHz, DMSO-d$_6$) 8.97 (s, 1H), 6.92-7.32 (m, 5H), 6.83 (d, J=8.4 Hz, 1H), 6.40-6.62 (m, 2H), 4.66 (s, 1H), 3.70 (d, J=2.9 Hz, 2H), 3.51 (s, 3H), 2.69-3.10 (m, 2H), 2.51-2.64 (m, 1H), 2.30-2.40 (m, 1H), 2.10-2.23 (m, 3H), 1.82-2.07 (m, 2H), 0.92-1.16 (m, 4H).
LC/MS, m/z=365.2 [M+H]$^+$ (Calc: 364.5).

N-((2R,6S,11R)-8-hydroxy-3,6-dimethyl-1,2,3,4,5,6-hexahydro-2,6-methanobenzo[d]azocin-11-yl)-N-methyl-2-phenylacetamide (Compound 118)

$^1$H NMR $\delta_H$ (400 MHz, DMSO-d$_6$) 9.04 (d, J=2.4 Hz, 1H), 7.00-7.39 (m, 5H), 6.76-6.90 (m, 1H), 6.36-6.63 (m, 2H), 4.52 (d, J=2.6 Hz, 0.6H), 3.86 (d, J=2.6 Hz, 0.4H), 3.57-3.74 (m, 2H), 2.87-2.92 (m, 1H), 2.76-2.78 (m, 1H), 2.52 (s, 1.8H), 2.38 (s, 1.2H), 2.30-2.35 (m, 1H), 2.20-2.26 (m, 1H), 2.18 (s, 3H), 1.55-1.91 (m, 2H), 1.18 (s, 1.8H), 1.03-1.15 (m, 1H), 0.94 (s, 1.2H).
LC/MS, m/z=365.2 [M+H]$^+$ (Calc: 364.5).

N-((2R,6S,11R)-8-hydroxy-3,6-dimethyl-1,2,3,4,5,6-hexahydro-2,6-methanobenzo[d]azocin-11-yl)-N-methylbenzamide (Compound 119)

$^1$H NMR $\delta_H$ (400 MHz, DMSO-d$_6$) 8.94-9.19 (m, 1H), 7.15-7.54 (m, 5H), 6.86 (t, J=8.0 Hz, 1H), 6.55-6.69 (m, 1H), 6.36-6.53 (m, 1H), 4.70 (br. 0.5H), 3.68 (br., 0.5H), 2.88-3.09 (m, 2H), 2.59-2.66 (m, 1H), 2.55 (s, 1.5H), 2.39 (s, 1.5H), 2.24 (br., 2H), 2.05 (br., 2H), 1.80-1.87 (m, 1.5H), 1.06-1.43 (m, 4.5H).

LC/MS, m/z=351.1 [M+H]⁺ (Calc: 350.5).

N-((2R,6S,11S)-8-hydroxy-3,6-dimethyl-1,2,3,4,5,6-hexahydro-2,6-methanobenzo[d]azocin-11-yl)-N-methylcyclohexanecarboxamide (Compound 120)

¹H NMR $\delta_H$ (400 MHz, DMSO-d₆) 8.96 (s, 1H), 6.83 (d, J=8.4 Hz, 1H), 6.55 (d, J=2.4 Hz, 1H), 6.47 (dd, J=8.4, 2.4 Hz, 1H), 4.67 (s, 1H), 3.52 (s, 3H), 3.05 (d, J=17.4 Hz, 1H), 2.96 (d, J=5.3 Hz, 1H), 2.50-2.69 (m, 2H), 2.33-2.41 (m, 1H), 2.15-2.28 (m, 3H), 1.90-2.05 (m, 2H), 1.55-1.85 (m, 5H), 1.06-1.36 (m, 6H), 1.03 (s, 3H).

LC/MS, m/z=357.1 [M+H]⁺ (Calc: 356.5).

N-((2R,6S,11R)-8-hydroxy-3,6-dimethyl-1,2,3,4,5,6-hexahydro-2,6-methanobenzo[d]azocin-11-yl)-N-methylcyclohexanecarboxamide (Compound 121)

¹H NMR $\delta_H$ (400 MHz, CD₃OD) 6.87-7.08 (m, 1H), 6.72 (d, J=2.2 Hz, 1H), 6.63 (dd, J=8.3, 2.3 Hz, 1H), 4.87 (br. s., 0.3H), 4.66 (br., 0.7H), 3.58 (br. s., 1H), 2.90-3.14 (m, 3H), 2.84 (s, 3H), 2.43-2.74 (m, 5H), 1.90-2.00 (m, 1H), 1.49-1.79 (m, 6H), 1.06-1.45 (m, 8H).

LC/MS, m/z=357.3 [M+H]⁺ (Calc: 356.5).

(E)-N-((2R,6S,11R)-8-hydroxy-3,6-dimethyl-1,2,3,4,5,6-hexahydro-2,6-methanobenzo[d]azocin-11-yl)-N-methyl-3-(pyridin-3-yl)acrylamide (Compound 122)

¹H NMR $\delta_H$ (400 MHz, DMSO-d₆) 8.94-9.31 (m, 1H), 8.69-8.87 (m, 1H), 8.47 (dd, J=4.7, 1.4 Hz, 1H), 8.05 (d, J=7.9 Hz, 1H), 7.10-7.55 (m, 3H), 6.87 (d, J=8.4 Hz, 1H), 6.60 (d, J=2.4 Hz, 1H), 6.49 (dd, J=8.1, 2.4 Hz, 1H), 4.63 (d, J=2.6 Hz, 0.7H), 4.11 (d, J=2.4 Hz, 0.3H), 2.79-3.11 (m, 2H), 2.72 (s, 2H), 2.50 (s, 1H), 2.18-2.30 (m, 4H), 1.72-1.95 (m, 2H), 1.23-1.35 (m, 3H), 1.19 (d, J=11.7 Hz, 1H).

LC/MS, m/z=378.1 [M+H]⁺ (Calc: 377.5).

N-((2R,6S,11R)-8-hydroxy-3,6-dimethyl-1,2,3,4,5,6-hexahydro-2,6-methanobenzo[d]azocin-11-yl)-N-methyl-2-(thiophen-3-yl)acetamide (Compound 123)

¹H NMR $\delta_H$ (400 MHz, DMSO-d₆) 9.05 (s, 1H), 7.39 (dd, J=5.0, 3.0 Hz, 1H), 7.12 (d, J=1.8 Hz, 1H), 6.87-6.98 (m, 1H), 6.83 (d, J=7.9 Hz, 1H), 6.56 (d, J=2.0 Hz, 1H), 6.46 (dd, J=8.3, 1.9 Hz, 1H), 4.51 (br. s., 0.6H), 3.88 (br. s., 0.4H), 3.62-3.81 (m, 1H), 3.61 (s, 1H), 2.89-2.95 (m, 1H), 2.72-2.84 (m, 1H), 2.53 (s, 2H), 2.38 (s, 2H), 2.15-2.29 (m, 4H), 1.63-1.93 (m, 2H), 0.94-1.26 (m, 4H).

LC/MS, m/z=371.1 [M+H]⁺ (Calc: 370.5).

N-((2R,6S,11R)-8-hydroxy-3,6-dimethyl-1,2,3,4,5,6-hexahydro-2,6-methanobenzo[d]azocin-11-yl)-N-methylthiophene-3-carboxamide (Compound 124)

¹H NMR $\delta_H$ (400 MHz, DMSO-d₆) 9.07 (s, 1H), 7.41-7.80 (m, 2H), 7.13 (dd, J=5.0, 1.0 Hz, 1H), 6.87 (t, J=7.6 Hz, 1H), 6.36-6.68 (m, 2H), 4.66 (br. s., 0.5H), 3.84 (br. s., 0.5H), 2.90-2.95 (m, 1H), 2.56-2.6 (m, 1H), 2.53 (s, 3H), 2.05-2.35 (m, 4H), 1.69-1.96 (m, 1.5H), 1.34-1.48 (m, 0.5H), 1.03-1.33 (m, 4H).

LC/MS, m/z=357.1 [M+H]⁺ (Calc: 356.5).

N-((2R,6S,11S)-8-hydroxy-3,6-dimethyl-1,2,3,4,5,6-hexahydro-2,6-methanobenzo[d]azocin-11-yl)-N-methylthiophene-3-carboxamide (Compound 125)

¹H NMR $\delta_H$ (400 MHz, CD₃OD) 7.78-7.93 (m, 1H), 7.48 (dd, J=5.1, 2.9 Hz, 1H), 7.29 (dd, J=5.1, 1.1 Hz, 1H), 7.00 (d, J=8.4 Hz, 1H), 6.73 (d, J=2.4 Hz, 1H), 6.64 (dd, J=8.4, 2.4 Hz, 1H), 4.07-4.27 (m, 1H), 3.92 (br. s., 1H), 3.38 (d, J=3.5 Hz, 2H), 3.21-3.21 (m, 4H), 2.89 (s, 3H), 2.74 (td, J=13.0, 3.4 Hz, 1H), 2.38 (td, J=13.9, 4.7 Hz, 1H), 1.57 (s, 3H), 1.47 (d, J=14.3 Hz, 1H).

LC/MS, m/z=357.1 [M+H]⁺ (Calc: 356.5).

N-((2R,6S,11S)-8-hydroxy-3,6-dimethyl-1,2,3,4,5,6-hexahydro-2,6-methanobenzo[d]azocin-11-yl)-N-methyl-5-(trifluoromethyl)picolinamide (Compound 126)

¹H NMR $\delta_H$ (400 MHz, CD₃OD) 8.92 (s, 1H), 8.25 (dd, J=8.3, 1.9 Hz, 1H), 7.82 (d, J=8.4 Hz, 1H), 7.01 (d, J=8.4 Hz, 1H), 6.75 (d, J=2.4 Hz, 1H), 6.65 (dd, J=8.1, 2.4 Hz, 1H), 4.21 (br. s., 1H), 4.00 (br. s., 1H), 3.41 (d, J=3.5 Hz, 2H), 3.24-3.30 (m, 1H), 3.07 (s, 3H), 2.93 (s, 3H), 2.76 (td, J=13.0, 3.5 Hz, 1H), 2.40 (td, J=13.9, 4.6 Hz, 1H), 1.62 (s, 3H), 1.51 (d, J=14.5 Hz, 1H).

LC/MS, m/z=420.1 [M+H]⁺ (Calc: 419.4).

N-((2R,6R,11R)-3-(cyclopropylmethyl)-8-hydroxy-6-methyl-1,2,3,4,5,6-hexahydro-2,6-methanobenzo[d]azocin-11-yl)thiophene-3-carboxamide (Compound 127)

¹H NMR $\delta_H$ (400 MHz, CD₃OD) 7.96 (t, J=2.0 Hz, 1H), 7.33 (d, J=2.0 Hz, 2H), 7.01 (d, J=8.4 Hz, 1H), 6.77 (d, J=2.4 Hz, 1H), 6.67 (dd, J=8.4, 2.4 Hz, 1H), 4.49 (d, J=3.3 Hz, 1H), 4.12 (br. s., 1H), 3.25-3.70 (m, 2H), 3.07-3.21 (m, 2H), 2.81-3.06 (m, 1H), 2.60 (td, J=13.3, 3.4 Hz, 1H), 2.07 (td, J=13.9, 4.5 Hz, 1H), 1.70 (dd, J=14.5, 1.5 Hz, 1H), 1.47 (s, 3H), 0.96-1.26 (m, 1H), 0.64-0.78 (m, 2H), 0.28-0.62 (m, 2H).

LC/MS, m/z=383.3 [M+H]⁺ (Calc: 382.5).

Example 61

N-((2R,6S,11S)-3-(cyclopropylmethyl)-8-hydroxy-6-methyl-1,2,3,4,5,6-hexahydro-2,6-methanobenzo[d]azocin-11-yl)-3-(trifluoromethyl)benzenesulfonamide (Compound 128)

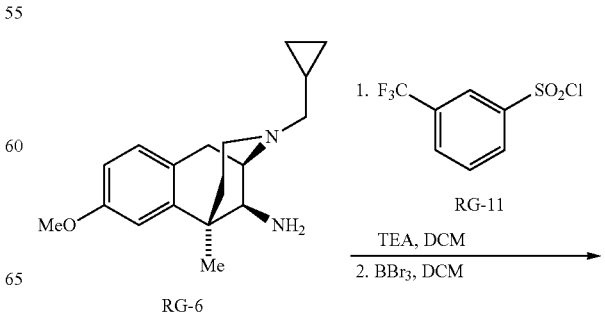

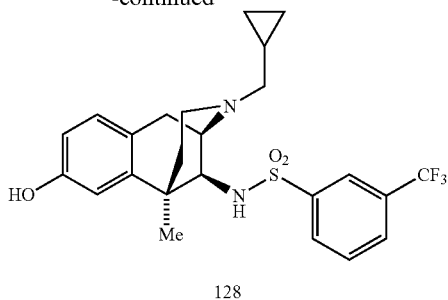

128

To a mixture of Compound RG-6 (0.10 g, 0.35 mmol) and TEA (0.035 g, 0.35 mmol) in DCM (2 mL) was added Compound RG-11 (0.102 g, 0.42 mmol) at 0° C. The reaction mixture was stirred at RT for 16 h, quenched by the addition of water and the mixture extracted with CHCl$_3$. The organic layer was concentrated to give the crude product which was used directly in the next step.

This material was dissolved in DCM (8 mL), cooled to −78° C. and 1 M BBr$_3$ in DCM (2.0 mL, 2.0 mmol) was added. The mixture was stirred at −78° C. for 2 h allowed to warm to 0° C. and stirred an additional 30 min. The reaction was quenched by the addition of water (2 mL) and the pH adjusted to ca 8 with conc. NH$_4$OH. The layers were separated and the organic layer was concentrated and purified by flash chromatography (SiO$_2$, 10% (10% NH$_4$OH in MeOH) in DCM) to give Compound 128 as a white solid (0.100 g, 60%).

$^1$H NMR δ$_H$ (400 MHz, DMSO-d$_6$) 9.12 (br. s., 1H), 8.30 (s, 1H), 8.25 (d, J=7.9 Hz, 1H), 8.09 (d, J=7.7 Hz, 1H), 7.79-7.95 (m, 1H), 7.56-7.80 (m, 1H), 6.89 (d, J=8.4 Hz, 1H), 6.72 (d, J=2.2 Hz, 1H), 6.59 (dd, J=8.1, 2.4 Hz, 1H), 3.46 (br. s., 1H), 2.87 (d, J=17.8 Hz, 1H), 2.77 (dd, J=5.5, 2.9 Hz, 1H), 2.45 (td, J=17.0, 5.4 Hz, 3H), 1.86-2.03 (m, 3H), 1.27 (s, 3H), 1.09 (d, J=9.7 Hz, 1H), 0.44-0.63 (m, 1H), 0.25-0.39 (m, 1H), −0.15-0.16 (m, 3H).

LC/MS, m/z=481.2 [M+H]$^+$ (Calc: 480.5).

In a similar manner the following chiral compounds were prepared from the appropriate chiral amines.

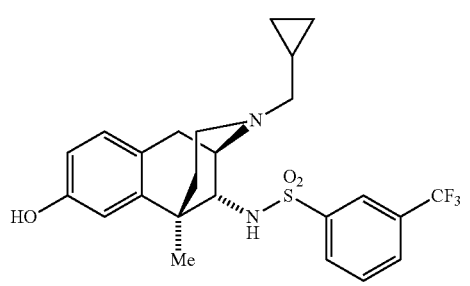

129

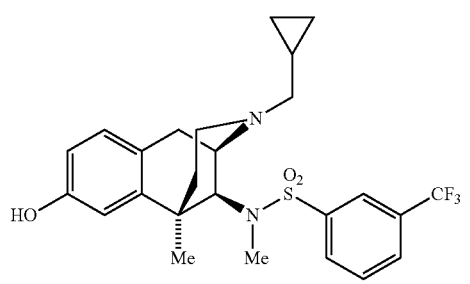

130

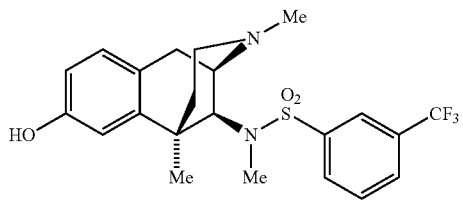

131

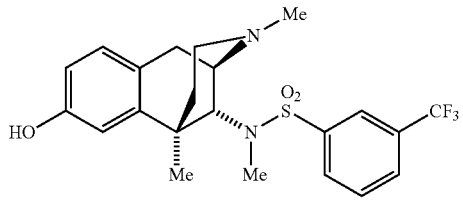

132

N-((2R,6S,11R)-3-(cyclopropylmethyl)-8-hydroxy-6-methyl-1,2,3,4,5,6-hexahydro-2,6-methanobenzo[d]azocin-11-yl)-3-(trifluoromethyl)benzenesulfonamide (Compound 129)

$^1$H NMR δ$_H$ (400 MHz, CD$_3$OD) 8.25 (s, 1H), 8.21 (d, J=7.9 Hz, 1H), 8.02 (d, J=7.7 Hz, 1H), 7.75-7.93 (m, 1H), 7.01-7.21 (m, 1H), 6.65-6.87 (m, 2H), 3.88-4.18 (m, 1H), 3.54-3.85 (m, 2H), 3.38 (d, J=6.8 Hz, 1H), 2.99-3.31 (m, 3H), 2.36-2.73 (m, 1H), 1.93 (td, J=14.0, 4.6 Hz, 1H), 1.43-1.73 (m, 1H), 0.93-1.26 (m, 5H), 0.67-0.87 (m, 2H), 0.34-0.62 (m, 2H).

LC/MS, m/z=481.2 [M+H]$^+$ (Calc: 480.5).

N-((2R,6S,11S)-3-(cyclopropylmethyl)-8-hydroxy-6-methyl-1,2,3,4,5,6-hexahydro-2,6-methanobenzo[d]azocin-11-yl)-N-methyl-3-(trifluoromethyl)benzenesulfonamide (Compound 130)

$^1$H NMR δ$_H$ (400 MHz, CD$_3$OD) 8.18 (d, J=7.9 Hz, 1H), 8.13 (s, 1H), 8.07 (d, J=7.7 Hz, 1H), 7.86-7.96 (m, 1H), 6.97 (d, J=8.4 Hz, 1H), 6.82 (d, J=2.4 Hz, 1H), 6.67 (dd, J=8.1, 2.4 Hz, 1H), 4.17 (s, 1H), 3.51 (s, 3H), 3.09 (d, J=17.6 Hz, 1H), 2.99 (br. s., 1H), 2.53-2.70 (m, 2H), 2.08-2.41 (m, 4H), 1.53 (s, 3H), 1.27-1.41 (m, 1H), 0.58 (br. s., 1H), 0.18-0.42 (m, 2H), −0.10-0.10 (m, 2H).

LC/MS, m/z=495.1 [M+H]$^+$ (Calc: 494.6).

N-((2R,6S,11S)-8-hydroxy-3,6-dimethyl-1,2,3,4,5,6-hexahydro-2,6-methanobenzo[d]azocin-11-yl)-N-methyl-3-(trifluoromethyl)benzenesulfonamide (Compound 131)

$^1$H NMR δ$_H$ (400 MHz, CD$_3$OD) 7.93-8.11 (m, 2H), 7.82-7.91 (m, 1H), 7.72 (t, J=7.7 Hz, 1H), 7.32-7.55 (m, 1H), 6.90 (d, J=8.1 Hz, 1H), 6.75 (br. s., 1H), 6.62 (dd, J=8.4, 2.4 Hz, 1H), 4.10 (s, 1H), 3.36 (s, 3H), 3.09 (d, J=15.6 Hz, 1H), 2.46-2.71 (m, 2H), 2.39 (d, J=9.9 Hz, 1H), 1.97-2.24 (m, 5H), 1.43 (s, 3H), 1.25 (d, J=10.6 Hz, 1H).

LC/MS, m/z=455.1 [M+H]$^+$ (Calc: 454.5).

N-((2R,6S,11R)-8-hydroxy-3,6-dimethyl-1,2,3,4,5,6-hexahydro-2,6-methanobenzo[d]azocin-11-yl)-N-methyl-3-(trifluoromethyl)benzenesulfonamide (Compound 132)

$^1$H NMR δ$_H$ (400 MHz, CD$_3$OD) 7.99-8.16 (m, 2H), 7.90 (d, J=7.9 Hz, 1H), 7.64-7.80 (m, 1H), 6.84 (d, J=8.1 Hz, 1H), 6.34-6.59 (m, 2H), 3.90 (d, J=2.6 Hz, 1H), 2.86-3.08 (m, 2H), 2.57 (dd, J=18.9, 5.9 Hz, 1H), 2.51 (s, 3H), 2.19-2.38 (m, 4H), 1.97 (td, J=12.5, 3.4 Hz, 1H), 1.70 (td, J=12.8, 4.7 Hz, 1H), 1.20 (d, J=11.7 Hz, 1H), 0.87 (s, 3H).

LC/MS, m/z=455.1 [M+H]$^+$ (Calc: 454.5).

Example 62

Using methods similar to those described in the previous examples, the following compounds were also made:

3-(4-(tert-butyl)phenyl)-1-((2R,6S,11S)-3-(cyclopropylmethyl)-8-hydroxy-6-methyl-1,2,3,4,5,6-hexahydro-2,6-methanobenzo[d]azocin-11-yl)-1-methylurea (Compound 133)

$^1$H NMR (400 MHz, DMSO-d$_6$) δ: 8.93 (br. s., 1H), 8.01 (br. s., 1H), 7.26 (d, J=8.8 Hz, 2H), 7.12 (d, J=8.8 Hz, 2H), 6.80 (d, J=8.1 Hz, 1H), 6.54 (d, J=2.4 Hz, 1H), 6.44 (dd, J=8.1, 1.8 Hz, 1H), 4.44 (br. s., 1H), 3.57 (br. s., 3H), 3.34 (br. s., 1H), 2.97 (d, J=17.4 Hz, 1H), 2.53-2.59 (m, 2H), 2.33 (dd, J=12.2, 6.5 Hz, 1H), 2.13-2.25 (m, 1H), 1.94-2.07 (m, 2H), 1.00-1.22 (m, 13H), 0.64-0.87 (m, 1H), 0.26-0.49 (m, 2H), −0.09-0.11 (m, 2H).

LC/MS, m/z=462.3 [M+H]$^+$ (Calc: 461.64)

1-((2R,6S,11S)-3-(cyclopropylmethyl)-8-hydroxy-6-methyl-1,2,3,4,5,6-hexahydro-2,6-methanobenzo[d]azocin-11-yl)-3-(5-fluorobenzo[d]thiazol-2-yl)-1-methylurea (Compound 134)

$^1$H NMR (400 MHz, METHANOL-d$_4$) δ: 7.73 (dd, J=8.6, 5.5 Hz, 1H), 7.27 (dd, J=10.1, 2.4 Hz, 1H), 6.90-7.07 (m, 2H), 6.77 (d, J=2.4 Hz, 1H), 6.66 (dd, J=8.4, 2.4 Hz, 1H), 4.10 (d, J=5.5 Hz, 1H), 3.84 (s, 1H), 3.21 (s, 3H), 3.02-3.14 (m, 2H), 2.77 (d, J=6.8 Hz, 2H), 2.28-2.52 (m, 2H), 1.47 (s, 3H), 1.3-1.35 (m, 2H), 1.17-1.29 (m, 1H), 0.42-0.71 (m, 2H), 0.11-0.33 (m, 2H).

LC/MS, m/z=481.2 [M+H]$^+$ (Calc: 480.6)

1-((6R,11R)-6-allyl-8-methoxy-3-methyl-1,2,3,4,5,6-hexahydro-2,6-methanobenzo[d]azocin-11-yl)-3-(4-cyanophenyl)-1-methylurea (Compound 135)

$^1$H NMR (400 MHz, METHANOL-d$_4$, TFA-salt) δ: 7.45-7.65 (m, 4H), 7.13 (d, J=8.4 Hz, 1H), 6.90 (d, J=2.2 Hz, 1H), 6.82 (dd, J=8.4, 2.4 Hz, 1H), 5.74-5.94 (m, 1H), 5.20 (d, J=17.2 Hz, 1H), 5.15 (d, J=10.1 Hz, 1H), 4.56 (br. s., 1H), 3.67-3.81 (m, 4H), 3.24-3.35 (m, 1H), 3.03-3.16 (m, 2H), 2.81-2.94 (m, 4H), 2.72 (s, 3H), 2.47-2.66 (m, 2H), 2.27 (td, J=13.9, 4.6 Hz, 1H), 1.50 (d, J=14.3 Hz, 1H).

LC/MS, m/z=431.3 [M+H]$^+$ (Calc: 430.54)

3-(4-cyanophenyl)-1-((6R,11R)-8-methoxy-3-methyl-6-propyl-1,2,3,4,5,6-hexahydro-2,6-methanobenzo[d]azocin-11-yl)-1-methylurea (Compound 136)

$^1$H NMR (400 MHz, METHANOL-d$_4$, TFA-salt) δ: 7.44-7.65 (m, 4H), 7.11 (d, J=8.6 Hz, 1H), 6.89 (d, J=2.2 Hz, 1H), 6.81 (dd, J=8.4, 2.4 Hz, 1H), 4.63 (d, J=2.0 Hz, 1H), 3.65-3.81 (m, 4H), 3.24-3.33 (m, 1H), 3.03-3.16 (m, 2H), 2.86 (s, 3H), 2.69 (s, 3H), 2.60 (td, J=13.2, 3.5 Hz, 1H), 2.28 (td, J=13.8, 4.6 Hz, 1H), 2.08 (td, J=13.1, 3.9 Hz, 1H), 1.75 (td, J=13.3, 4.4 Hz, 1H), 1.35-1.56 (m, 2H), 1.17-1.33 (m, 1H), 0.92-1.03 (m, 3H).

LC/MS, m/z=433.2 [M+H]$^+$ (Calc: 432.56)

3-(4-cyanophenyl)-1-((6R,11S)-8-hydroxy-3-methyl-6-propyl-1,2,3,4,5,6-hexahydro-2,6-methanobenzo[d]azocin-11-yl)-1-methylurea (Compound 137)

$^1$H NMR (400 MHz, METHANOL-d$_4$, TFA-salt) δ: 7.47-7.68 (m, 4H), 6.98 (d, J=8.4 Hz, 1H), 6.52-6.70 (m, 2H), 4.05 (d, J=5.1 Hz, 1H), 3.92 (s, 1H), 3.29-3.45 (m, 2H), 3.26 (s, 3H), 3.13 (dd, J=12.3, 4.0 Hz, 1H), 2.85 (s, 3H), 2.63 (td, J=12.9, 3.7 Hz, 1H), 2.40 (td, J=13.8, 4.8 Hz, 1H), 1.85-2.01 (m, 1H), 1.58-1.73 (m, 1H), 1.12-1.49 (m, 3H), 0.95 (t, J=7.3 Hz, 3H).

LC/MS, m/z=419.2 [M+H]$^+$ (Calc: 418.53)

3-(4-(aminomethyl)phenyl)-1-((6R,11S)-8-methoxy-3-methyl-6-propyl-1,2,3,4,5,6-hexahydro-2,6-methanobenzo[d]azocin-11-yl)-1-methylurea (Compound 138)

$^1$H NMR (400 MHz, METHANOL-d$_4$, TFA-salt) δ: 7.48 (d, J=8.6 Hz, 2H), 7.32 (d, J=8.6 Hz, 2H), 7.09 (d, J=8.6 Hz, 1H), 6.77 (dd, J=8.5, 2.3 Hz, 1H), 6.69 (d, J=2.2 Hz, 1H), 4.04 (d, J=5.1 Hz, 1H), 3.99 (s, 2H), 3.93 (s, 1H), 3.69 (s, 3H), 3.28-3.45 (m, 2H), 3.25 (s, 3H), 3.11 (dd, J=12.4, 4.3 Hz, 1H), 2.84 (s, 3H), 2.60 (td, J=12.9, 3.5 Hz, 1H), 2.40 (td, J=13.6, 4.7 Hz, 1H), 1.89-2.10 (m, 1H), 1.55-1.75 (m, 1H), 1.31-1.48 (m, 2H), 1.15-1.29 (m, 1H), 0.96 (t, J=7.3 Hz, 3H).

LC/MS, m/z=437.2 [M+H]$^+$ (Calc: 436.59)

1-(5-fluorobenzo[d]thiazol-2-yl)-3-((2R,6S,11R)-8-hydroxy-3,6-dimethyl-1,2,3,4,5,6-hexahydro-2,6-methanobenzo[d]azocin-11-yl)urea (Compound 139)

$^1$H NMR (400 MHz, METHANOL-d$_4$, TFA-salt) δ: 7.66 (dd, J=8.6, 5.3 Hz, 1H), 7.24 (dd, J=9.8, 2.3 Hz, 1H), 6.92 (td, J=9.0, 2.5 Hz, 1H), 6.86 (d, J=8.4 Hz, 1H), 6.68 (d, J=2.4 Hz, 1H), 6.51 (dd, J=8.1, 2.4 Hz, 1H), 3.88 (s, 1H), 3.12 (d, J=18.0 Hz, 1H), 2.99 (br. s., 1H), 2.70 (dd, J=17.9, 5.8 Hz, 1H), 2.33-2.41 (m, 1H), 2.31 (s, 3H), 2.06 (td, J=12.1, 3.1 Hz, 1H), 1.86 (td, J=12.9, 4.8 Hz, 1H), 1.23 (s, 3H), 1.13 (d, J=13.2 Hz, 1H).

LC/MS, m/z=427.2 [M+H]$^+$ (Calc: 426.51)

3-(5-fluorobenzo[d]thiazol-2-yl)-1-((2R,6S,11R)-8-hydroxy-3,6-dimethyl-1,2,3,4,5,6-hexahydro-2,6-methanobenzo[d]azocin-11-yl)-1-methylurea (Compound 140)

$^1$H NMR (CD$_3$OD) δ: 7.60 (m, 1H), 7.16 (d, J=8.0 Hz, 1H), 6.89 (m, 2H), 6.66 (m, 1H), 6.53 (m, 1H), 4.47 (br, 1H), 3.07 (m, 2H), 2.73-2.56 (m, 4H), 2.43-2.33 (m, 4H), 2.10 (m, 1H), 1.91 (m, 1H), 1.39-1.28 (m, 4H) ppm LC/MS, m/z=441.1 [M+H]$^+$ (Calc: 440.53)

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

All patents and publications cited herein are fully incorporated by reference in their entirety.

What is claimed is:

1. A compound of Formula I':

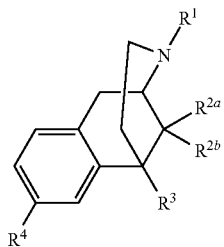

wherein $R^1$ is selected from the group consisting of —$(C_1$-$C_{10})$alkyl, $(C_3$-$C_{12})$cycloalkyl-$(C_1$-$C_6)$alkyl-, ((6- to 14-membered)aryl)-$(C_1$-$C_6)$alkyl-, diphenyl$(C_1$-$C_6)$alkyl-, each of which is optionally substituted by 1, 2 or 3 independently selected $R^9$ groups;

$R^{2a}$ is absent, H or OH;

$R^{2b}$ is —Z-G-$R^{10}$;

Z is absent;

G is selected from the group consisting of: =CH, $NR^8$, =N—O, and =N—NH; provided that when $R^{2a}$ is absent, G is not $NR^8$;

$R^{10}$ is selected from the group consisting of —$(C_1$-$C_{10})$alkyl, —$(C_2$-$C_{12})$alkenyl, —C(=O), —C(=O)—$(C_1$-$C_6)$alkyl, —C(=O)—$(C_2$-$C_6)$alkenyl, —C(=O)-(6- to 14-membered)aryl, —C(=O)—$(C_1$-$C_6)$alkyl-(6- to 14-membered)aryl, —$(C_2$-$C_{12})$alkynyl, —$(C_1$-$C_{10})$alkoxy, —$(OCH_2CH_2)_s$—O$(C_1$-$C_6)$alkyl, —$(CH_2CH_2O)_s$—$(C_1$-$C_6)$alkyl, —$NH_2$, —NH$(C_1$-$C_6)$alkyl, CN, $NR^5R^6$, —$(C_1$-$C_6)$alkyl-$NR^5R^6$, —$CONR^5R^6$, —$(C_1$-$C_6)$alkyl-CO—$NR^5R^6$, —$COOR^7$, —$(C_1$-$C_6)$alkyl-CO—$OR^7$, —$(C_1$-$C_6)$alkoxy-$COOR^7$, —CO—$(CH_2)_n$—$COOR^7$, —CO—$(CH_2)_n$—CO—$NR^5R^6$, —$(C_3$-$C_{12})$cycloalkyl, (($C_3$-$C_{12}$)cycloalkyl)-$(C_1$-$C_6)$alkyl-, —$(C_4$-$C_{12})$cycloalkenyl, (($C_4$-$C_{12}$)cycloalkenyl)-$(C_1$-$C_6)$alkyl-, —$(C_6$-$C_{14})$bicycloalkyl, (($C_6$-$C_{14}$)bicycloalkyl)-$(C_1$-$C_6)$alkyl-, —$(C_8$-$C_{20})$tricycloalkyl, (($C_8$-$C_{20}$)tricycloalkyl)-$(C_1$-$C_6)$alkyl-, —$(C_7$-$C_{14})$bicycloalkenyl, (($C_7$-$C_{14}$)bicycloalkenyl)-$(C_1$-$C_6)$alkyl-, —$(C_8$-$C_{20})$tricycloalkenyl, (($C_8$-$C_{20}$)tricycloalkenyl)-$(C_1$-$C_6)$alkyl-, -(6- to 14-membered)aryl, ((6- to 14-membered)aryl)-$(C_1$-$C_6)$alkyl-, -(7- to 12-membered)bicyclic ring system, ((7- to 12-membered)bicyclic ring system)-$(C_1$-$C_6)$alkyl-, -(7- to 12-membered)bicyclic aryl, ((7- to 12-membered)bicyclic aryl)-$(C_1$-$C_6)$alkyl-, -(5- to 12-membered)heteroaryl, ((5- to 12-membered)heteroaryl)-$(C_1$-$C_6)$alkyl-, -(3- to 12-membered)heterocycle, ((3- to 12 membered)heterocycle)-$(C_1$-$C_6)$alkyl-, -(7- to 12-membered)bicycloheterocycle, ((7- to 12-membered)bicycloheterocycle)-$(C_1$-$C_6)$alkyl-, phenyl, benzyl and naphthyl; each of which is optionally substituted with one, two, or three substituents independently selected from the group consisting of —OH, (=O), halo, —C(halo)$_3$, —CH(halo)$_2$, —CH$_2$(halo), —$(C_1$-$C_6)$alkyl, halo$(C_1$-$C_6)$alkyl-, —$(C_2$-$C_6)$alkenyl, —$(C_2$-$C_6)$alkynyl, hydroxy$(C_1$-$C_6)$alkyl-, dihydroxy$(C_1$-$C_6)$alkyl-, —$(C_1$-$C_6)$alkoxy, (($C_1$-$C_6)$alkoxy)CO$(C_1$-$C_6)$alkoxy-, phenyl, benzyl, —$NH_2$, —NH$(C_1$-$C_6)$alkyl, —$(C_1$-$C_6)$alkyl-NH$(C_1$-$C_6)$alkyl-$R^{14}$, —CN, —SH, —$OR^{11}$, —$CONR^5R^6$, —$(C_1$-$C_6$alkyl)-CO—$NR^5R^6$, —$COOR^7$, —$(C_1$-$C_6)$alkyl-CO—$OR^7$, —$(C_1$-$C_6)$alkoxy-$COOR^7$, —$(OCH_2CH_2)_s$—O$(C_1$-$C_6)$alkyl, —$(CH_2CH_2O)_s$—$(C_1$-$C_6)$alkyl, $(C_1$-$C_6$alkyl)sulfonyl, (($C_1$-$C_6)$alkyl)sulfonyl$(C_1$-$C_6)$alkyl-, —NH—SO$_2$$(C_1$-$C_6)$alkyl, $NH_2$—SO$_2$$(C_1$-$C_6)$alkyl-, —N(SO$_2$$(C_1$-$C_6)$alkyl)$_2$, —C(=NH)NH$_2$, —NH—CO—$(C_1$-$C_6)$alkyl, —NH—CO—NH$_2$, —NH—C(=O)—NH—$(C_1$-$C_6)$alkyl, —NH—C(=O)-(6- to 14-membered)aryl, —NH—C(=O)—$(C_1$-$C_6)$alkyl-(6- to 14-membered)aryl, —NH—$(C_1$-$C_6)$alkyl-CO—$OR^7$, —NH—C(=O)—$(C_1$-$C_6)$alkyl-CO—$OR^7$, —NH—C(=O)—CH(NH$_2$)—$(C_1$-$C_6)$alkyl-CO—$OR^7$, —$(C_3$-$C_{12})$cycloalkyl, (($C_3$-$C_{12}$)cycloalkyl)-$(C_1$-$C_6)$alkyl-, -(6- to 14-membered)aryl, -(6- to 14-membered)aryloxy, —$(C_1$-$C_6)$alkoxy-C(O)$NR^5R^6$, —NH—$(C_1$-$C_6)$alkyl-C(O)—$NR^5R^6$, —C(O)NH—$(C_1$-$C_6)$alkyl-$COOR^7$, ((6- to 14-membered)aryl)-$(C_1$-$C_6)$alkyl-, -(5- to 12-membered)heteroaryl, ((5- to 12-membered)heteroaryl)-$(C_1$-$C_6)$alkyl-, -(3- to 12-membered)heterocycle, ((3- to 12-membered)heterocycle)-$(C_1$-$C_6)$alkyl-, -(7- to 12-membered)bicycloheterocycle, and ((7- to 12-membered)bicycloheterocycle)-$(C_1$-$C_6)$alkyl-;

$R^3$ is —$(C_1$-$C_6)$alkyl, —$(C_2$-$C_6)$alkenyl, or —$(C_2$-$C_6)$alkynyl;

$R^4$ is —OH or —$(C_1$-$C_5)$alkoxy;

$R^5$ and $R^6$ are each independently
a) hydrogen, —OH, halo, —C(halo)$_3$, —CH(halo)$_2$, —CH$_2$(halo);
b) —$(C_2$-$C_5)$alkenyl, —$(C_2$-$C_5)$alkynyl, —$(CH_2)_n$—O—$(CH_2)_n$—CH$_3$, —$(C_1$-$C_6)$alkoxy, each of which is optionally substituted with 1, 2, or 3 substituents independently selected from —OH, halo, —$(C_1$-$C_{10})$alkyl, —$(C_2$-$C_{10})$alkenyl, —$(C_2$-$C_{10})$alkynyl, —$(C_1$-$C_{10})$alkoxy, —$(C_3$-$C_{12})$cycloalkyl, —CHO, —C(O)OH, —C(halo)$_3$, —CH(halo)$_2$, CH$_2$(halo), —$(CH_2)_n$—O—$(CH_2)_n$—CH$_3$, phenyl, or $CONR^5R^6$;
c) —$(C_3$-$C_8)$cycloalkyl, (($C_3$-$C_8$)cycloalkyl)-$(C_1$-$C_6)$alkyl-, —$COOR^7$, —$(C_1$-$C_6)$alkyl-$COOR^7$, —$CONH_2$, or $(C_1$-$C_6)$alkyl-CONH—;
d) ((6- to 14-membered)aryl) optionally substituted with 1, 2, or 3 independently selected $R^{30}$ groups; or
e) $R^5$ and $R^6$ together with the nitrogen atom to which they are attached form a (4- to 8-membered)heterocycle optionally substituted with 1, 2, or 3 independently selected $R^{30}$ groups;

$R^{5a}$ and $R^{6a}$ are each independently selected from the group consisting of:
a) hydrogen, —OH, halo, —C(halo)$_3$, —CH(halo)$_2$, and —CH$_2$(halo);
b) —$(C_2$-$C_6)$alkenyl, —$(C_2$-$C_6)$alkynyl, —$(CH_2)_n$—O—$(CH_2)_n$—CH$_3$, and —$(C_1$-$C_6)$alkoxy, each of which is optionally substituted with 1, 2, or 3 substituents independently selected from —OH, halo, —$(C_1$-$C_{10})$alkyl, —$(C_2$-$C_{12})$alkenyl, —$(C_2$-$C_{12})$alkynyl, —$(C_1$-$C_{10})$alkoxy, —$(C_3$-$C_{12})$cycloalkyl, —CHO, —COOH, —C(halo)$_3$, —CH(halo)$_2$, CH$_2$(halo), —$(CH_2)_n$—O—$(CH_2)_n$—CH$_3$, and phenyl;
c) —$(C_3$-$C_8)$cycloalkyl, (($C_3$-$C_8$)cycloalkyl)-$(C_1$-$C_6)$alkyl-, —$COOR^7$, —$(C_1$-$C_6)$alkyl-$COOR^7$, —$CONH_2$, and $(C_1$-$C_6)$alkyl-CONH—;
d) -(6- to 14-membered)aryl optionally substituted with 1, 2, or 3 independently selected $R^{30}$ groups; or
e) $R^{5a}$ and $R^{6a}$ together with the nitrogen atom to which they are attached form a (4- to 8-membered)heterocycle optionally substituted with 1, 2, or 3 independently selected $R^{30}$ groups;

each $R^7$ is independently selected from the group consisting of hydrogen, —$(C_1$-$C_6)$alkyl, —$(C_2$-$C_6)$alkenyl, —$(C_2$-$C_6)$alkynyl, —$(C_3$-$C_{12})$cycloalkyl, —$(C_4$-$C_{12})$cycloalkenyl, (($C_3$-$C_{12}$)cycloalkyl)-$(C_1$-$C_6)$alkyl-, and (($C_4$-$C_{12}$)cycloalkenyl)-$(C_1$-$C_6)$alkyl-;

each R[8] is methyl or ethyl;
each R[9] is independently phenyl, or CONR[5a]R[6a];
each R[11] is independently selected from —C(halo)$_3$, —CH(halo)$_2$, —CH$_2$(halo), —(C$_2$-C$_5$)alkenyl, —(C$_2$-C$_5$)alkynyl, —(CH$_2$)$_n$—O—(CH$_2$)$_n$—CH$_3$, (6- to 14-membered)aryl, ((6- to 14-membered)aryl)-(C$_1$-C$_6$)alkyl-, (5- to 12-membered)heteroaryl, and ((5- to 12-membered)heteroaryl)-(C$_1$-C$_6$)alkyl-;
each R[14] is independently selected from —COOR[7], —(C$_1$-C$_6$)alkyl-COOR[7], —C(=O)—(C$_1$-C$_6$)alkyl-COOR[7], —(C$_1$-C$_6$)alkyl-C(=O)—(C$_1$-C$_6$)alkyl-COOR[7], CONH$_2$, or —(C$_1$-C$_6$)alkyl-CONH;
each R[30] is independently selected from COOR[7], CONR[5a]R[6a], —C(=O), CN, -(3- to 12-membered)heteroaryl, ((3- to 12-membered)heteroaryl)-(C$_1$-C$_6$)alkyl-, NH$_2$, halo, and ((6- to 14-membered)aryl)-(C$_1$-C$_6$)alkoxy-;
m is an integer 1, 2, 3, 4, 5, or 6;
n is an integer 0, 1, 2, 3, 4, 5, or 6;
s in an integer 1, 2, 3, 4, 5, or 6;
provided that when R[4] is —(C$_1$-C$_5$)alkoxy then:
R[2a] and R[2b] cannot be taken together to form =O;
or a pharmaceutically acceptable salt thereof.

2. A compound of claim 1 having Formula IA':

or a pharmaceutically acceptable salt thereof.

3. A compound of claim 1 having Formula IB':

or a pharmaceutically acceptable salt thereof.

4. A compound of claim having Formula IC':

or a pharmaceutically acceptable salt thereof.

5. A compound of claim 1 having Formula ID':

or a pharmaceutically acceptable salt thereof.

6. A compound of claim 1, wherein R[2a] is hydrogen.
7. A compound of claim 1, wherein R[2a] is OH.
8. A compound of claim 1, wherein G is NR[8].
9. A compound of claim 1, wherein G is NR[8], and R[8] is methyl.
10. A compound of claim 1, wherein G is =CH.
11. A compound of claim 1, wherein G is =N—O.
12. A compound of claim 1, wherein R[10] is a -(6 to 14-membered)aryl or ((6- to 14-membered)aryl)-(C$_1$-C$_6$)alkyl-, optionally substituted with —(C$_1$-C$_6$)alkyl-CO—NR[5]R[6], or NH$_2$—SO$_2$(C$_1$-C$_6$)alkyl-.
13. A compound of claim 1, wherein R[10] is optionally substituted phenyl or benzyl.
14. A compound of claim 1, wherein R[10] is piperidinyl optionally substituted with COOR[7] or NH$_2$.
15. A compound of claim 1, wherein R[10] is pyrrolidinyl.
16. A compound of claim 1, wherein R[10] is -(5- to 12-membered)heteroaryl.
17. A compound of claim 1, wherein R[10] is optionally substituted pyridinyl.
18. A compound of claim 1, wherein R[10] is furanyl.
19. A compound of claim 1, wherein R[10] is —C(=O) or —C(=O)—(C$_2$-C$_6$)alkenyl, optionally substituted with a -(6- to 14-membered)aryl or -(5- to 12-membered)heteroaryl.
20. A compound of claim 1, wherein R[10] is —C(=O)—(C$_1$-C$_6$)alkyl-(6- to 14-membered)aryl, optionally substituted with halo.
21. A compound of claim 1, wherein R[10] is NR[5]R[6].
22. A compound of claim 21, wherein at least one of R[5] and R[6] is hydrogen.
23. A compound of claim 21, wherein one of R[5] and R[6] is hydrogen, and the other is —(C$_1$-C$_6$)alkyl-COOR[7].
24. A compound of claim 1, wherein R[10] is CONR[5]R[6].
25. A compound of claim 24, wherein at least one of R[5] and R[6] is -(6- to 14-membered)aryl substituted with one R[30].
26. A compound of claim 25, wherein said R[30] is COOR[7].
27. A compound of claim 26, wherein R[7] is hydrogen.
28. A compound of claim 1, wherein R[2a] is hydrogen, and R[2b] is —Z-G-R[10], wherein Z is absent, G is NR[8], R[8] is methyl or ethyl, and R[10] is ((6- to 14-membered)aryl)-(C$_1$-C$_6$)alkyl-.
29. A compound of claim 1, wherein R[2a] is hydrogen, and R[2b] is —Z-G-R[10], wherein Z is absent, G is NR[8] wherein R[8] is methyl or ethyl, and R[10] is —C(=O) substituted with a (6- to 14-membered)aryl.
30. A compound of claim 1, wherein R[2a] is hydrogen, and R[2b] is —Z-G-R[10], wherein Z is absent, G is NR[8] wherein R[8] is methyl or ethyl, and R[10] is -(6- to 14-membered)aryl substituted with NH$_2$—SO$_2$(C$_1$-C$_6$)alkyl-.
31. A compound of claim 1, wherein R[2a] is hydrogen, and R[2b] is —Z-G-R[10], wherein Z is absent, G is NR[8] wherein R[8]

is methyl or ethyl, and $R^{10}$ is —C(=O)—($C_2$-$C_6$)alkenyl substituted with -(5- to 12-membered)heteroaryl or -(3-to-12-membered)heterocycle.

32. A compound of claim 1, wherein $R^{2a}$ is hydrogen, and $R^{2b}$ is —Z-G-$R^{10}$, wherein Z is absent, G is $NR^8$ wherein $R^8$ is methyl or ethyl, and $R^{10}$ is $CONR^5R^6$ wherein one of $R^5$ or $R^6$ is hydrogen and the other is —($C_1$-$C_6$)alkyl-$COOR^7$.

33. A compound of claim 1, wherein $R^{2a}$ is hydrogen, and $R^{2b}$ is —Z-G-$R^{10}$, wherein Z is absent, G is $NR^8$ wherein $R^8$ is methyl or ethyl, and $R^{10}$ is $CONR^5R^6$ wherein one of $R^5$ or $R^6$ is hydrogen and the other is —($C_1$-$C_6$)alkyl-$COOR^7$.

34. A compound of claim 1, wherein $R^{2a}$ is hydrogen, and $R^{2b}$ is —Z-G-$R^{10}$, wherein Z is absent, G is $NR^8$ wherein $R^8$ is methyl or ethyl, and $R^{10}$ is —C(=O)—($C_2$-$C_6$)alkenyl substituted with -(3- to 12-membered)heterocycle.

35. A compound selected from the group consisting of:
2-(((8-methoxy-3,6-dimethyl-1,2,3,4,5,6-hexahydro-2,6-methanobenzo[d]azocin-11-ylidene)amino)oxy)acetic acid;
8-methoxy-3,6-dimethyl-1,2,3,4,5,6-hexahydro-2,6-methanobenzo[d]azocin-11-one oxime;
8-methoxy-3,6-dimethyl-1,2,3,4,5,6-hexahydro-2,6-methanobenzo[d]azocin-11-one-O-(2-(diethylamino)ethyl) oxime;
8-methoxy-3,6-dimethyl-11-propylidene-1,2,3,4,5,6-hexahydro-2,6-methanobenzo[d]azocine;
3-(cyclopropylmethyl)-8-methoxy-6-methyl-1,2,3,4,5,6-hexahydro-2,6-methanobenzo[d]azocin-11-one O-methyl oxime;
(Z)-ethyl 2-(8-methoxy-3,6-dimethyl-1,2,3,4,5,6-hexahydro-2,6-methanobenzo[d]azocin-11-ylidene)acetate;
(Z)-2-(8-methoxy-3,6-dimethyl-1,2,3,4,5,6-hexahydro-2,6-methanobenzo[d]azocin-11-ylidene)acetic acid;
ethyl 2-((6S,11R)-8-methoxy-3,6-dimethyl-1,2,3,4,5,6-hexahydro-2,6-methanobenzo[d]azocin-11-yl)acetate;
2-((6S,11R)-8-methoxy-3,6-dimethyl-1,2,3,4,5,6-hexahydro-2,6-methanobenzo[d]azocin-11-yl)acetic acid;
(E)-3-(furan-3-yl)-N-((6R,11R)-8-methoxy-3,6-dimethyl-1,2,3,4,5,6-hexahydro-2,6-methanobenzo[d]azocin-11-yl)-N-methylacrylamide;
8-hydroxy-3,6-dimethyl-1,2,3,4,5,6-hexahydro-2,6-methanobenzo[d]azocin-11-one oxime;
4-(11-(hydroxyimino)-8-methoxy-6-methyl-1,2,5,6-tetrahydro-2,6-methanobenzo[d]azocin-3(4H)-yl)-N,N-dimethyl-2,2-diphenylbutanamide;
(E)-3-(furan-3-yl)-N-((6R,11S)-8-methoxy-3,6-dimethyl-1,2,3,4,5,6-hexahydro-2,6-methanobenzo[d]azocin-11-yl)-N-methylacrylamide;
(E)-3-(furan-3-yl)-N-((2R,6R,11S)-8-hydroxy-3,6-dimethyl-1,2,3,4,5,6-hexahydro-2,6-methanobenzo[d]azocin-11-yl)-N-methylacrylamide;
(E)-N-ethyl-3-(furan-3-yl)-N-((2R,6R,11S)-8-methoxy-3,6-dimethyl-1,2,3,4,5,6-hexahydro-2,6-methanobenzo[d]azocin-11-yl)acrylamide;
4-fluoro-N'-((2S,6R)-8-methoxy-3,6-dimethyl-1,2,3,4,5,6-hexahydro-2,6-methanobenzo[d]azocin-11-ylidene)benzohydrazide;
N-((2R,6R,11S)-8-hydroxy-3,6-dimethyl-1,2,3,4,5,6-hexahydro-2,6-methanobenzo[d]azocin-11-yl)-N-methyl-2-(4-(methylsulfonyl)phenyl)acetamide;
4-(((2R,6R,11S)-8-hydroxy-3,6-dimethyl-1,2,3,4,5,6-hexahydro-2,6-methanobenzo[d]azocin-11-yl)(methyl)amino)-4-oxobutanoic acid;
(2R,6R,11S)-3,6-dimethyl-11-(methyl(phenethyl)amino)-1,2,3,4,5,6-hexahydro-2,6-methanobenzo[d]azocin-8-ol;
tert-butyl 4-((((2R,6S,11R)-8-hydroxy-3,6-dimethyl-1,2,3,4,5,6-hexahydro-2,6-methanobenzo[d]azocin-11-yl)(methyl)amino)methyl)piperidine-1-carboxylate;
N-((2R,6R,11R)-8-hydroxy-3,6-dimethyl-1,2,3,4,5,6-hexahydro-2,6-methanobenzo[d]azocin-11-yl)-N-methylbenzamide;
4-(3-((2R,6R,11S)-8-hydroxy-3,6-dimethyl-1,2,3,4,5,6-hexahydro-2,6-methanobenzo[d]azocin-11-yl)-3-methylureido)benzoic acid;
4-(3-((2R,6R,11R)-8-hydroxy-3,6-dimethyl-1,2,3,4,5,6-hexahydro-2,6-methanobenzo[d]azocin-11-yl)-3-methylureido)benzoic acid;
3-(((2R,6R,11S)-8-hydroxy-3,6-dimethyl-1,2,3,4,5,6-hexahydro-2,6-methanobenzo[d]azocin-11-yl)(methyl)carbamoyl)benzoic acid;
3-(((2R,6R,11R)-8-hydroxy-3,6-dimethyl-1,2,3,4,5,6-hexahydro-2,6-methanobenzo[d]azocin-11-yl)(methyl)carbamoyl)benzoic acid;
2-(((2R,6R,11S)-8-hydroxy-3,6-dimethyl-1,2,3,4,5,6-hexahydro-2,6-methanobenzo[d]azocin-11-yl)(methyl)carbamoyl)benzoic acid;
2-(4-(((2R,6R,11S)-8-hydroxy-3,6-dimethyl-1,2,3,4,5,6-hexahydro-2,6-methanobenzo[d]azocin-11-yl)(methyl)amino)phenyl)ethanesulfonamide;
(E)-N-((2R,6R,11S)-3-(cyclopropylmethyl)-8-methoxy-6-methyl-1,2,3,4,5,6-hexahydro-2,6-methanobenzo[d]azocin-11-yl)-3-(furan-3-yl)-N-methylacrylamide;
4-(((2R,6R,11R)-8-hydroxy-3,6-dimethyl-1,2,3,4,5,6-hexahydro-2,6-methanobenzo[d]azocin-11-yl)(methyl)carbamoyl)benzoic acid;
3-(3-((2R,6R,11S)-8-hydroxy-3,6-dimethyl-1,2,3,4,5,6-hexahydro-2,6-methanobenzo[d]azocin-11-yl)-3-methylureido)propanoic acid;
2-(((2R,6R,11S)-3-(cyclopropylmethyl)-8-methoxy-6-methyl-1,2,3,4,5,6-hexahydro-2,6-methanobenzo[d]azocin-11-yl)(methyl)amino)acetic acid;
2-(3-((2R,6S,11S)-8-hydroxy-3,6-dimethyl-1,2,3,4,5,6-hexahydro-2,6-methanobenzo[d]azocin-11-yl)-3-methylureido)-4-methylpentanoic acid;
(E)-N-((2R,6R,11S)-3-(cyclopropylmethyl)-8-hydroxy-6-methyl-1,2,3,4,5,6-hexahydro-2,6-methanobenzo[d]azocin-11-yl)-3-(furan-3-yl)-N-methylacrylamide;
3-(4-cyanophenyl)-1-((2R,6R,11S)-8-hydroxy-3,6-dimethyl-1,2,3,4,5,6-hexahydro-2,6-methanobenzo[d]azocin-11-yl)-1-methylurea;
3-(4-cyanophenyl)-1-((2R,6R,11S)-8-hydroxy-3,6-dimethyl-1,2,3,4,5,6-hexahydro-2,6-methanobenzo[d]azocin-11-yl)-1-methylurea; and
the pharmaceutically acceptable salts thereof.

36. A compound selected from the group consisting of:
3-(4-cyanophenyl)-1-((6R,11R)-3-(cyclopropylmethyl)-8-hydroxy-6-methyl-1,2,3,4,5,6-hexahydro-2,6-methanobenzo[d]azocin-11-yl)-1-methylurea;
3-(4-cyanophenyl)-1-((6R,11S)-3-(cyclopropylmethyl)-8-hydroxy-6-methyl-1,2,3,4,5,6-hexahydro-2,6-methanobenzo[d]azocin-11-yl)-1-methylurea;
4-(3-((6R,11S)-3-(cyclopropylmethyl)-8-methoxy-6-methyl-1,2,3,4,5,6-hexahydro-2,6-methanobenzo[d]azocin-11-yl)-3-methylureido)benzamide;
(E)-N-((6R,11R)-3-(cyclopropylmethyl)-8-hydroxy-6-methyl-1,2,3,4,5,6-hexahydro-2,6-methanobenzo[d]azocin-11-yl)-3-(furan-3-yl)-N-methylacrylamide;
4-((2R,6R,11S)-11-(3-(4-cyanophenyl)-1-methylureido)-8-hydroxy-6-methyl-1,2,5,6-tetrahydro-2,6-methanobenzo[d]azocin-3(4H)-yl)-N,N-dimethyl-2,2-diphenylbutanamide;

(E)-N-((2R,6R,11S)-3-(cyclopropylmethyl)-8-methoxy-6-methyl-1,2,3,4,5,6-hexahydro-2,6-methanobenzo[d]azocin-11-yl)-3-(furan-3-yl)-N-methylacrylamide;

(Z)—N-((2R,6R,11S)-3-(cyclopropylmethyl)-8-methoxy-6-methyl-1,2,3,4,5,6-hexahydro-2,6-methanobenzo[d]azocin-11-yl)-3-(furan-3-yl)-N-methylacrylamide;

3-(4-cyanophenyl)-1-((2R,6R,11S)-8-hydroxy-6-methyl-3-phenethyl-1,2,3,4,5,6-hexahydro-2,6-methanobenzo[d]azocin-11-yl)-1-methylurea;

3-(4-cyanophenyl)-1-((6R,11R)-3-(cyclobutylmethyl)-8-hydroxy-6-methyl-1,2,3,4,5,6-hexahydro-2,6-methanobenzo[d]azocin-11-yl)-1-methylurea;

3-(4-cyanophenyl)-1-((6R,11R)-3-(2,3-difluorobenzyl)-8-hydroxy-6-methyl-1,2,3,4,5,6-hexahydro-2,6-methanobenzo[d]azocin-11-yl)-1-methylurea;

3-(4-cyanophenyl)-1-((2R,6R,11S)-3-(furan-3-ylmethyl)-8-hydroxy-6-methyl-1,2,3,4,5,6-hexahydro-2,6-methanobenzo[d]azocin-11-yl)-1-methylurea; and the pharmaceutically acceptable salts thereof.

37. A pharmaceutical composition comprising an effective amount of a compound of claim 1, or a pharmaceutically salt thereof, and a pharmaceutically acceptable carrier or excipient.

38. A method for modulating opioid receptor function in a cell, comprising contacting a cell capable of expressing an opioid receptor with an effective amount of a compound of claim 1, or a pharmaceutically acceptable salt thereof, wherein the opioid receptor is an μ-opioid receptor, κ-opioid receptor, or ORL-1 receptor.

39. The method of claim 38, wherein the compound modulates μ-opioid receptor function.

40. The method of claim 38, wherein the compound acts as an agonist at the μ-opioid receptor.

41. The method of claim 38, wherein the compound acts as an antagonist at the μ-opioid receptor.

42. The method of claim 38, wherein the compound acts as an agonist at the κ-opioid receptor.

43. A method of treating a pain or constipation in a mammal, comprising administering to such mammal in need thereof an effective amount of a compound of claim 1, or a pharmaceutically acceptable salt thereof.

* * * * *